US010172874B2

(12) United States Patent
Hirst et al.

(10) Patent No.: US 10,172,874 B2
(45) Date of Patent: Jan. 8, 2019

(54) PHARMACEUTICAL COMPOSITIONS COMPRISING CYCLIC BORONIC ACID ESTER DERIVATIVES

(71) Applicant: Rempex Pharmaceuticals, Inc., Lincolnshire, IL (US)

(72) Inventors: Gavin Hirst, San Diego, CA (US); Raja Reddy, San Diego, CA (US); Scott Hecker, Del Mar, CA (US); Maxim Totrov, San Diego, CA (US); David C. Griffith, San Marcos, CA (US); Olga Rodny, Mill Valley, CA (US); Michael N. Dudley, San Diego, CA (US); Serge Boyer, San Diego, CA (US)

(73) Assignee: REMPEX PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 15/935,862

(22) Filed: Mar. 26, 2018

(65) Prior Publication Data
US 2018/0207183 A1    Jul. 26, 2018

Related U.S. Application Data

(60) Division of application No. 15/624,473, filed on Jun. 15, 2017, which is a continuation of application No. 15/015,002, filed on Feb. 3, 2016, now Pat. No. 9,694,025, which is a division of application No. 13/953,647, filed on Jul. 29, 2013, now Pat. No. 9,296,763, which is a division of application No. 13/205,112, filed on Aug. 8, 2011, now Pat. No. 8,680,136.

(60) Provisional application No. 61/488,655, filed on May 20, 2011, provisional application No. 61/372,296, filed on Aug. 10, 2010.

(51) Int. Cl.

| | |
|---|---|
| *A61K 31/69* | (2006.01) |
| *A61K 45/06* | (2006.01) |
| *C07F 5/02* | (2006.01) |
| *A61K 31/407* | (2006.01) |
| *A61K 31/4196* | (2006.01) |
| *A61K 31/427* | (2006.01) |
| *A61K 31/4439* | (2006.01) |
| *A61K 31/546* | (2006.01) |
| *A61K 9/00* | (2006.01) |

(52) U.S. Cl.
CPC ............ *A61K 31/69* (2013.01); *A61K 9/0019* (2013.01); *A61K 9/0053* (2013.01); *A61K 31/407* (2013.01); *A61K 31/4196* (2013.01); *A61K 31/427* (2013.01); *A61K 31/4439* (2013.01); *A61K 31/546* (2013.01); *A61K 45/06* (2013.01); *C07F 5/025* (2013.01); *Y02A 50/401* (2018.01); *Y02A 50/406* (2018.01); *Y02A 50/47* (2018.01); *Y02A 50/471* (2018.01); *Y02A 50/473* (2018.01); *Y02A 50/475* (2018.01); *Y02A 50/478* (2018.01); *Y02A 50/481* (2018.01); *Y02A 50/483* (2018.01)

(58) Field of Classification Search
CPC .............................. A61K 31/69; C07F 5/025
See application file for complete search history.

(56) References Cited

U.S. PATENT DOCUMENTS

| | | |
|---|---|---|
| 3,686,398 A | 8/1972 | Kohn et al. |
| 4,194,047 A | 3/1980 | Christensen et al. |
| 4,260,543 A | 4/1981 | Miller |
| 4,353,807 A | 10/1982 | Braid |
| 4,409,214 A | 10/1983 | Takaya et al. |
| 4,822,786 A | 4/1989 | Zama et al. |
| 5,442,100 A | 8/1995 | Bjorkquiest et al. |
| 5,888,998 A | 3/1999 | Maiti et al. |
| 6,184,363 B1 | 2/2001 | Shoichet et al. |
| 6,586,615 B1 | 7/2003 | Kettner et al. |
| 7,271,186 B1 | 9/2007 | Shoichet et al. |
| 7,439,253 B2 | 10/2008 | Lampilas et al. |
| 7,582,621 B2 | 9/2009 | Baker et al. |
| 7,612,087 B2 | 11/2009 | Aszodi et al. |
| 7,674,913 B2 | 3/2010 | Campbell et al. |
| 7,825,139 B2 | 11/2010 | Campbell et al. |
| 8,680,136 B2 | 3/2014 | Hirst et al. |
| 9,012,491 B2 | 4/2015 | Reddy et al. |
| 9,101,638 B2 | 8/2015 | Reddy et al. |
| 9,132,140 B2 | 9/2015 | Reddy et al. |
| 9,156,858 B2 | 10/2015 | Reddy et al. |
| 9,241,947 B2 | 1/2016 | Reddy et al. |
| 9,296,763 B2 | 3/2016 | Hirst et al. |
| 9,511,142 B2 | 12/2016 | Burns et al. |
| 9,642,869 B2 | 5/2017 | Reddy et al. |

(Continued)

FOREIGN PATENT DOCUMENTS

| | | |
|---|---|---|
| EP | 1550657 A1 | 7/2005 |
| EP | 2508506 A1 | 10/2012 |

(Continued)

OTHER PUBLICATIONS

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

(Continued)

*Primary Examiner* — Golam M Shameem
(74) *Attorney, Agent, or Firm* — Knobbe, Martens, Olson & Bear LLP

(57) ABSTRACT

Disclosed herein are antimicrobial compounds compositions, pharmaceutical compositions, the use and preparation thereof. Some embodiments relate to cyclic boronic acid ester derivatives and their use as therapeutic agents.

24 Claims, 4 Drawing Sheets

(56) References Cited

U.S. PATENT DOCUMENTS

| | | |
|---|---|---|
| 9,687,497 B1 | 6/2017 | Bis et al. |
| 9,694,025 B2 | 7/2017 | Hirst et al. |
| 10,004,758 B2 | 6/2018 | Hirst et al. |
| 2004/0019203 A1 | 1/2004 | Micetich et al. |
| 2004/0157826 A1 | 8/2004 | Lampilas et al. |
| 2005/0020572 A1 | 1/2005 | Aszodi et al. |
| 2005/0070719 A1 | 3/2005 | Belyakov et al. |
| 2006/0019116 A1 | 1/2006 | Conley et al. |
| 2006/0178357 A1 | 8/2006 | Buynak et al. |
| 2006/0210883 A1 | 9/2006 | Chen et al. |
| 2010/0056478 A1 | 3/2010 | Desarbre et al. |
| 2010/0120715 A1 | 5/2010 | Burns et al. |
| 2010/0256092 A1 | 10/2010 | Xia et al. |
| 2010/0292185 A1 | 11/2010 | Burns et al. |
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194284 A1 | 7/2014 | Reddy et al. |
| 2014/0194381 A1 | 7/2014 | Reddy et al. |
| 2014/0194382 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2014/0274954 A1 | 9/2014 | Chellappan et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |
| 2017/0057979 A1 | 3/2017 | Hecker et al. |
| 2017/0088561 A1 | 3/2017 | Reddy et al. |
| 2017/0136047 A1 | 5/2017 | Reddy et al. |
| 2017/0173055 A1 | 6/2017 | Bis et al. |
| 2018/0002351 A1 | 1/2018 | Hecker et al. |
| 2018/0051041 A1 | 2/2018 | Hecker et al. |
| 2018/0071325 A1 | 3/2018 | Hurst et al. |
| 2018/0214465 A1 | 8/2018 | Hirst et al. |

FOREIGN PATENT DOCUMENTS

| | | |
|---|---|---|
| FR | 2574070 A1 | 11/1984 |
| JP | 2003-229277 | 8/2003 |
| JP | 2004-291253 | 10/2004 |
| WO | WO 1987/05297 | 9/1987 |
| WO | WO 1989/10961 | 11/1989 |
| WO | WO 1998/56392 A1 | 12/1998 |
| WO | WO 2000/035904 A1 | 6/2000 |
| WO | WO 2000/035905 A1 | 6/2000 |
| WO | WO 2001/023374 A1 | 4/2001 |
| WO | WO 2001/030149 | 5/2001 |
| WO | WO 2002/022137 A1 | 3/2002 |
| WO | WO 2002/083884 | 10/2002 |
| WO | WO 2003/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2011/154953 | 12/2011 |
| WO | WO 2012/021455 A1 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/104897 A1 | 7/2013 |
| WO | WO 2013/122888 A2 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/144380 A1 | 9/2014 |
| WO | WO 2014/151958 A1 | 9/2014 |
| WO | WO 2015/171398 A1 | 11/2015 |
| WO | WO 2015/171430 A1 | 11/2015 |
| WO | WO 2015/179308 A1 | 11/2015 |
| WO | WO 2015/191907 A1 | 12/2015 |
| WO | WO 2016/003929 A1 | 1/2016 |
| WO | WO 2016/065282 A1 | 4/2016 |

OTHER PUBLICATIONS

Adediran et al., "A 'cephalosporin-like' cyclic depsipeptide: Synthesis and reaction with beta-lactam-recognizing enzymes", Bioorg Med Chem Lett. (1999) 9(3):341-346.

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

Allen et al., "Ansel's Pharmaceutical Dosage Forms and Drug Delivery Systems", 8th Edition (2004).

American Chemical Society. STN Chemical Database Registry RN: 1226917; Jun. 2010; 2 pages.

Arya et al., "Advances in asymmetric enolate methodology", Tetrahedron (2000) 56:917-947.

Babic et al., "What's new in antibiotic resistance? Focus on beta-lactamases", Drug Res Updates (2006) 9:142-156.

Bassetti et al., "New antibiotics for bad bugs: where are we?", Ann Clin Microbiol Antimicrob. (2013) 12:22-36.

Becker, Daniel E., "Antimicrobial Drugs", Anesth Prog (2013) 60:111-123.

Beenen et al., "Asymmetric copper-catalyzed synthesis of alpha-amino boronate esters from N-tert-butanesulfinyl aldimines", J Am Chem Soc. (2008) 130(22):6910-6911.

Biedrzycki et al., "Derivatives of tetrahedral boronic acids", J. Organomet. Chem. (1992) 431:255-270.

Bou et al., "Cloning, nucleotide sequencing, and analysis of the gene encoding an AmpC beta-lactamase in Acinetobacter baumannii", Antimicrob Agents Chemother (2000) 44(2):428-432.

Bou et al., "OXA-24, a novel class D beta-lactamase with carbapenemase activity in an Acinetobacter baumannii clinical strain", Antimicrob Agents Chemother (2000) 44(6):1556-1561, Erratum (2006) 50(6) 2280.

Brabez et al., "Design,synthesis, and biological studies of efficient multivalent melanotropin ligands: tools toward melanoma diagnosis and treament", J Med Chem. (2011) 54(20):7375-7384.

Brosz et al., "Resolution of alpha-aminoboronic esters by diastereoselective crystallization with pinanediols. Confirmation by x-ray analysis", Tetrahedron: Asymmetry (1997) 8(9):1435-1440.

(56) References Cited

OTHER PUBLICATIONS

Bush et al., "Minireview: Updated Functional Classification of beta-Lactamases," Antimicrob Agents Chemo. (2010) 54(3):969-976.

CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.

CAS Registry No. 105892-95-3 Boronic acid [1-(phenylsulfonyl)heptyl]-, dimethyl ester (2015); 2 pages.

Chemicalland21.com. "Meglumine", Jun. 7, 2011. Downloaded from </www.chemicalland21.com/lifescience/phar/N-METHYL-D-GLUCAMINE.htm>; 2 pages.

Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2).

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2).

Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", Oct. 6, 2014; retrieved online from URL:https://clinicaltrials.gov/archive/NCT02168946/20140_10_06.

Conte et al., "Intrapulmonary pharmacokinetics and pharmacodynamics of meropenem", Int J Antimicrob Agents (Dec. 2005) 26(6):449-456.

Coppa et al., "A Facile, Convenient and Selective Homolytic Carbamolylation of Heteroaromatic Bases", Heterocycles (1993) 36(12):2687-2696.

Coutts et al., "Two Efficient Methods for the Cleavage of Pinanediol Boronate Esters Yielding the Free Boronic Acids", Tetrahedron Ltt. (1994) 35(29):5109-5112.

Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.

Darses et al., "Potassium Organotrifluoroborates: New Perspectives in organic Synthesis", Chem Rev. (2008) 108:288-325.

Davoli et al., "Enantioselective total synthesis of (−)-microcarpalide", Tetrahedron (2005) 61:4427-4436.

de Meijere A. [Ed], Science of Synthesis—vol. 24; "Three Carbon-Heteroatom Bonds: Ketene Acetals and Yne-X Compounds", TOC 46 pages.

Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.

Drawz et al., "Three Decades of beta-Lactamase Inhibitors", Clin Microbiol Reviews (Jan. 2010) 23(1):160-201.

Eidam et al., "Design, synthesis, crystal structures and antimicrobial activity of sulfonamide boronic acids as beta-lactamase inhibitors", J Med Chem. (2010) 53(21):7852-7863.

Eissenstat et al., "Aminoalkylindoles: Structure-Activity Relationships of Novel Cannabinoid Mimetics", J Med Chem. (1995) 38(16):3094-3105.

El Nezhawy et al., "Synthesis and antioxidant activity of some thiazolidin-4-one derivatives", Springer; Chemical Monthly/Monatshefte für Chemie (2009) 140(5):531-539.

Endo et al., "Chemoselective Suzuki coupling of diborylmethane for facile synthesis of benzylboronates", Org Lett. (2011) 13(13):3368-3371.

Fan et al., STN International HCAPLUS database, Columbus, OH, Accession No. 2009: 425839, 2009.

Fan et al.(2009): STN International HCAPLUS database, Columbus (OH), accession No. 2009: 425839; 6 pages.

Farquhar et al., "Intensely potent doxorubicin analogues: structure—activity relationship", J. Med. Chem. (1998) 41(6):965-972.

Ghosh et al., "Enantioselective total synthesis of (+)-largazole, a potent inhibitor of histone deacetylase", Org Lett. (2008) 10(17):3907-3909.

Giroux, A., "Synthesis of benzylic boronates via palladium-catalyzed cross-coupling reaction of bis(pinacolato)diboron with benzylic halides", Tetrahedron Lett. (2003) 44:233-235.

Gorovoy et al., "Boron-Containing Peptidomimetics—A Novel Class of Selective Anti-tubercular Drugs", Chem Biol Drug Des. (Jan. 2013) 81:408-413.

Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.

Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.

Greene, et al., "*Greene's Protective Groups in Organic Synthesis*", 4th Edition, (2007); pp. 774, 785 & 787.

Hama et al., "Palladium-Catalyzed alpha-Arylation of Zinc Enolates of Esters: Reaction Conditions and Substrate Scope", J Org Chem. (2013) 78(17):8250-8266.

Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.

Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.

Inglis et al., "Observations on the Deprotection of Pinanediol andPpinacol Boronate Esters via Fluorinated Intermediates", J Org Chem. (2010) 75(2):468-471.

Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.

Ito et al., "An efficient constructive method for a tricyclic system: an important intermediate for the synthesis of tricycloclavulone", Tetrahedron Lett. (2003) 44:1259-1261.

Jadhav et al., "Direct synthesis of [alpha-[(tert-Butoxycarbonyl)amino]alkyl]-boronates from (alpha-Haloalkyl)boronates", Org Chem. (1996) 61(22):7951-7954.

Jagannathan et al., "Synthesis of Boronic Acid Analogues of alpha-Amino Acids by Introducing Side Chains as Electrophiles", J Org Chem. (2001) 66(19):6375-6380.

Jiang et al., "A Practical Synthesis of Cefcapene Pivoxil", Synthesis (2012) 44:207-214.

Johnson et al., "A drug targeting motif for glycosidase inhibitors: An iminosugar-boronate shows unexpectedly selective beta-galactosidase inhibition", Tetrahed Lttrs. (2002) 43(49):8905-8908.

Kabalka et al., "Synthesis of a series of bornonated unnatural cyclic amino acids as potential boron neutron capture therapy agents", Appl Organomet Chem. (2008) 22(9):516-522.

Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", (1993) 22(5):845-848.

Kawamorita et al., "Synthesis of Primary and Secondary Alkylboronates through Site-Selective C(sp3)-H Activation with Silica-supported Monophosphine-Ir Catalysts", J Am Chem Soc. (2013) 135:2947-2950.

Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Jul. 2009) 53(7):2799-2803.

Kint et al., "New-found fundamentals of bacterial persistance", Trends Microbiol. (2012) 20(12):577-585.

(56) References Cited

OTHER PUBLICATIONS

Kose et al. "Synthesis of photochromic 2,3-bis(5-methyl-2-phenyl-4-thiazolyl)-1,4-naphthoquinone derivatives",' J Photochem Photobiol. A: Chemistry. (2011) 219(1):58-61.

Kotha et al., "Recent applications of the suzuki-miyaura cross-coupling reaction in organic synthesis", Tetrahedron (2002) 58:9633-9695.

Kumar et al., "Synthesis of intermediates for the lactone moiety of mevinic acids via tellurium chemistry", J. Org. Chem., (1994) 59(17):4760-4764.

Kumar et al., "Development of Practical Methodologies for the Synthesis of Functionalized Benzoboroxoles", Tetrahedron Lett. (Aug. 25, 2010) 51(34):4482-4485.

Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.

Kuti et al., "Use of Monte Carlo simulation to design an optimized pharmacodynamic dosing strategy for meropenem", J Clin Pharmacol. (Oct. 2003) 43(10:1116-1123.

Laitar et al., "Catalytic diboration of aldehydes via insertion into the copper-boron bond", J Am Chem Soc. (2006) 128(34):11036-11037.

Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.

Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131(51):18234-18235.

Li et al, "Novel macrocyclic HCV NS3 protease inhibitors derived from α-amino cyclic boronates", Bioorganic Med Chem Lett. (2010) 20:5695-5700.

Li et al., "Stereoselective total synthesis of etnangien and etnangien methyl ester", J Org Chem. (2010) 75(8):2429-2444.

Li et al., "Synthesis and evaluation of novel alpha-amino cyclic boronates as inhibitors of HCV NS3 protease", Bioorg Med Chem Lett. (2010) 20:3550-3556.

Liang et al., "The Efficient Copper(I) (Hexabenzyl)tren Catalyst and Dendritic Analogues for Green "Click". Reactions between Azides and Alkynes in Organic Solvent and in Water: Positive Dendritic Effects and Monometallic Mechanism", Advance Syn Catal. (2011) 353(18): 3434-3450.

Lima et al., "Bioisosterism: A Useful Strategy for Molecular Modification and Drug Design", Curr Med Chem. (2005) 12:23-49.

Liu et al., "Application of Stereoselective Ether Transfer to the Synthesis of Isotactic Polyethers", J Org Chem. (2010) 75(12):3953-3957.

Liu et al. "Selective Protein tyrosine phosphatase 1B inhibitors: Targeting the second phosphotyrosine ! binding site with non-carboxylic acid-containing ligands", J Med Chem. (2003) 46(16):3437-3440.

Livermore et al., "Activities of NXL104 combinations with Ceftazidime and Aztreonam against Carbapenemase-producing Enterobacteriaceae", Antimicr Agents Chemother. (2011) 55(1):390-394.

Livermore et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.

Lodise et al., "Penetration of meropenem into epithelial lining fluid of patients with ventilator-associated pneumonia", Antimicrob Agents Chemother. (Apr. 2011) 55(4):1606-1610.

Malfertheiner et al., "Current concepts in the management of Helicobacter pylori infection: the Maastricht III Consensus Report", Gut (2007) 56(6):772-781.

Matteson et al., "Iodomethaneboronic Esters and Aminomethaneboronic Esters", J Organomet. Chem. (1979) 170:259-264.

Matteson et al., "A Directed Chiral Synthesis of Amino Acids from Boronic Esters", Tetrahedron Lett. (1987) 28(39):4499-4502.

Matteson, D.S., "Asymmetric Synthesis with Boronic Esters", Acc Chem Res. (1988) 21(8):294-300.

Matteson et al., "A stereospecific convergent coupling of nucleophilic and electrophilic chiral carbons", J. Am. Chem. Soc. (1989) 111:4399-4402.

Matteson, "Boronic esters in stereodirected synthesis", Tetrahedron (1989) 45(7):1859-1885.

Matteson et al., "Synthesis of asymmetrically deuterated glycerol and dibenzylglyceraldehyde via boronic esters", J. Am. Chem. Soc. (1990) 112:3964-3969.

Matteson et al., "(Alkoxyalkyl)boronic Ester Intermediates for Asymmetric Synthesis", Organometallics (1996) 15:152-163.

Matteson, "Alpha-Halo Baronic Esters in Asymmetric Synthesis", Tetrahedron (1998) 54(36):10555-10607.

Matteson et al., "Glass-Catalyzed Conversion of Boronic Esters of Asymmetric Diols to Diol Sulfites and Amine Complexes of Boron Halides", Oranometallics (2001) 20:2920-2923 & supporting Information (9 pages).

Matteson et al., "Cesium Alkyltrifluoroborates from Asymmetric Boronic Esters", Synlett (Jul. 2006) 20:3501-3502.

Matteson et al., "Synthesis of a (Beta-acetamido-alpha-acetoxyethyl) boronic ester via azido boronic esters", J Organomet Chem. (2008) 693:2258-2262.

Meanwell, "Synopsis of some recent tactical application of bioisosteres in drug design", J. Med. Chem. (2011) 54:2529-2591.

Mendoza et al., "Bis(phenylthio)methaneboronic Esters as Sources of Carbanions and Ketene Thioacetals", J Org Chem. (1979) 44(8):1352-1354.

Micalizio et al., "A Boronic Ester Annulation Strategy for Diversity-Oriented Organic Synthesis", Angew Chem Int Ed Engl. (2002) 41(1):152-154.

Montalbetti et al., "Amide bond formation and peptide coupling", Tetrahedron (2005) 61:10827-10852.

Montefour et al., "Acinetobacter baumannii: an emerging multidrug-resistant pathogen in critical care", Crit Care Nurse (2008) 28(1):15-25; quiz 26.

Morandi et al., "Structure-based optimization of cephalothin-analogue boronic acids as beta-lactamase inhibitors", Bioorg Med Chem. (2008) 16(3):1195-205. Epub Nov. 7, 2007.

Nema et al. "Excipients and Their Role in Approved Injectable Products: Current Usage and Future Directions", PDA J Pharm Sci Technol. (2011) 65(3):287-332.

Ness et al., "Structure-based design guides the improved efficacy of deacylation transition state analogue inhibitors of TEM-1 beta-Lactamase", Biochemistry (2000) 39(18):5312-5321.

Nordmann et al., How to Detect NDM-1 Producers, J. Clin. Micro. (2011) 49:718-721.

Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.

Patani et al., "Bioisosterism: A Rational Approach in Drug Design", Chem Rev. (1996) 96:3147-3176.

Paterson et al., "Extended-Spectrum beta-Lactamases: a Clinical Update", Clin Microbiol Rev. (2005) 18(4):657-686.

Perez et al., "Why are we afraid of Acinetobacter baumannii?", Expert Rev Anti Infect Ther. (2008) 6(3):269-71.

Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.

Powell et al., "Compendium of excipients for parenteral formulations", PDA J Pharm Sci Technol. (1998) 52(5):238-311.

Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.

Robak et al., "Synthesis and applications of tert-butanesulfinamide", Chem Rev. (2010) 110(6):3600-3740.

Rodriguez-Martinez et al., "VIM-19, a Metallo-beta-lactamase with increased Carbapenemase Activity from Escherichia coli and Klebsiella pneumoniae", Antimicro Agents Chemother. (2010) 54(1):471-476.

(56) References Cited

OTHER PUBLICATIONS

Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.
Sawyer et al., "Physical properties and synthetic utility of a-alkoxyorganolithium species as studied through ligand selectivity in tin-lithium exchange", J. Am. Chem. Soc. (1988) 110:842-853.
Selander et al., "Palladium-catalyzed allylic C—OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singh et al., "Assymetric Homologation of Boronic Esters Bearing Azido and Silyloxy Substituents", J Org Chem. (2000) 65(20):6650-6653 and Erratum: J Org Chem. (2001) 66(22):7560.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3S,5R,7R,10R,11R)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C—H insertion", Tetrahedron (2002) 58:6545-6554.
Sun et al., "Programmed Synthesis of a Contiguous Stereotriad Motif by Triple Stereospecific Reagent-controlled Homologation", Org Lttr. (Jul. 2013) 15(17):4500-4503.
Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
Vasil'Ev et al., (1977): STN International HCAPLUS database, Columbus, (OH), accession No. 1977: 72730; 1 page.
Vasil'Ev et al., STN International HCAPLUS database, Columbus, OH, accession No. 1977:72730.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Waley, Stephen G., "A quick method for the determination of inhibition constants", Biochem J. (1982) 205(3):631-633.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Webb et al., "Metal catalysed hydroboration of vinyl sulfides, sulfoxides, sulfones, and sulfonates", J Mol Cat A: Chem. (2007) 275:91-100.
Wohlrab et al., "Total synthesis of plusbacin A₃: a depsipeptide antibiotic active against vancomycin-resistant bacteria", J. Am. Chem. Soc. (2007) 129:4175-4177.
Xia et al., "Synthesis and SAR of novel benzoxaboroles as a new class of beta-lactamase inhibitors", Bioorg Med Chem Lett. (2011) 21:2533-2536.
Xie et al., "Group-assisted purification (GAP) chemistry for the synthesis of Velcade via asymmetric borylation of N-phosphinylimines", Beilstein J Org Chem (Mar. 2014) 10:746-751.
Yamamoto et al., "Iridium-catalyzed hydroboration of alkenes with pinacolborane", Tetrahedron (2004) 60:10695-10700.
Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.
Yuen et al., "Deprotection of pinacolyl boronate esters via hydrolysis of intermediate potassium trifluoroborates", Tetrahed Lttr. (2005)46(46):7899-7903.
International Search Report and Written Opinion dated Sep. 14, 2011 for International Patent Application No. PCT/US2011/046957, filed Aug. 8, 2011.
Banker G.S. et al. [Eds.], Modern Pharmaceutics, 4th Edition; Marcel Dekker, Inc. (2002); Chapters 9 and 10, 98 pages.
Buesking et al., "Asymmetric Synthesis of Protected alpha-Amino Boronic Acid Derivatives with an Air- and Moisture-stable Cu(II) Catalyst", J Org Chem. (Mar. 2014) 79(8): 3671-3677.
CAS Registry No. 2005:329437 CAPLUS; "Product subclass 28: Vinylboranes", Vaultier et al., (2004); XP-002764965; 1 page.
Cunha, "Meropenem in elderly and renally impaired patients", Int'l J Antimicro Agents (1998) 10: 107-117.
Hall D.G. [Ed], Boronic Acids [vol. 2]: Preparations and applications in Organic Synthesis, ' Medicine and Materials, Wiley-VCH, Weinheim, 2nd Edition (2011); TOC.
Hartung et al., "Highly Z-selective and Enantioselective Ring Opening/Cross Metathesis Catalyzed by Resolved Stereogenic-At-Ru Complex", J Am Chem Soc. (Jul. 2013) 135(28): 10183-10185.
Larock R. [Ed.] Comprehensive Organic Transformations, VCH Publishers 1989; TOC, 11 pages.
Lieberman H.A. [Ed] Pharmaceutical Dosage Forms—Tablets; Marcel Dekker, Inc. (1989) 2nd Ed; TOC.
Matteson, "Boronic Esters in Asymmetric Synthesis", J Org Chem. (Oct. 2013) 78(20): 10009-10023.
McOmie J.R.W. [Ed], *Protective Groups in Organic Chemistry*, Plenum Press, London & New York (1973); TOC, 3 pages.
Munar et al., "Drug Dosing Adjustments in Patients with Chronic Kidney Disease", Am Fam Physician (May 2007) 75(1): 1487-1496.
Overman et al., "Organic Synthesis—Working with Hazardous Chemicals", Org Synth. (1990) 68: 182; 5 pages.
Paquette L.A. [Ed.] Encyclopedia of Reagents for Organic Synthesis, vol. 1; J. Wiley & Sons (1995); Cover Only.
Sawant et al., "Synthesis of the C1-C13 Fragment of Biselyngbyaside", Synlett (2011) 20: 3002-3004.
Singer et al., "Catalytic, enantioselective acetate aldol additions to alpha-, beta-Ynals: Preparation of optically active propargylic alcohols", Tetrahedron (1998) 54(25): 7025-7032.
Ambrose et al., Pharmacokinetics-pharmacodynamics of antimicrobial therapy: it's not just for mice anymore. Clin Infect Dis. (2007) 44: 79-86.
Ambrose et al., "Pharmacokinetics-pharmacodynamics of CB-618 in combination with cefepime, ceftazidime, ceftolozane and meropenem: the pharmacological basis for a stand-alone beta-lactamase inhibitor", Antimicrob Agents Chemother. (Nov. 2017) 61(12): e00630-17; 7 pages.
Austad et al. "Development of a multi kilogram-scale, tandem cyclopropanation ring-expansion reaction en route to hedgehog antagonist IPI-926", Org Process Res Dev., (2016) 20(4):786-798; Supporting Information, 70 pages.
Berkhout et al., "Pharmacodynamics of Ceftazidime and Avibactam in Neutropenic Mice with Thigh or Lung Infection", Antimicrob Agents Chemother. (2015) 60 (1): 368-375.
Bhavnani et al., Pharmacokinetic-Pharmacodynamic (PK_PD) basis for CLSI carbapenem (CARB) susceptibility breakpoint changes. abstr Abstracts of Papers, 50th Interscience Conference on Antimicrobial Agents and Chemotherapy, Sep. 12-15, 2010; #A1-1382, Boston, MA; 3 pages.
Bilello et al., "Effect of 2',3'-8 didehydro-3'-deoxythymidine in an in vitro hollow-fiber pharmacodynamic model system correlates with results of dose-ranging clinical studies", Antimicrob Agents Chemother. (1994) 38(6): 1386-1391.
Bowker et al., Comparative pharmacodynamics of meropenem using an in-vitro model to simulate once, twice and three times daily dosing in humans. J Antimicrob Chemother (1998) 42: 461-467.
Braisted et al., "Discovery of a potent small molecule IL-2 inhibitor through fragment assembly", J Am Chem Soc., (2003) 125(13): 3714-3715; Supporting Information, 42 pages.

(56) References Cited

OTHER PUBLICATIONS

Bulik et al., "Comparison of the activity of a human simulated, high-dose, prolonged infusion of meropenem against *Klebsiella pneumoniae* producing the KPC carbapenemase versus that against *Pseudomonas aeruginosa* in an in vitro pharmacodynamic model", Antimicrob Agents Chemother (2010) 54(2): 804-810.

Bundgaard H. [Ed.], "Design of Prodrugs", Elsevier (1985); TOC, 2 pages.

CAS Registry No. 831209-98-4 6H-Dibenz[c,e][1,2]oxaborin, 6a,10a-dihydro-6-hydroxy; Entered STN: Feb. 15, 2005; 1 page.

CAS Registry No. 831210-03-8 6H-Dibenz[c,e][1,2]oxaborin, 2,4-dibromo-6a, 10a-dihydro-6-hydroxy; Feb. 15, 2005; 1 page.

Chandrasekhar et al., "The first Corey-Chaykovsky epoxidation and cyclopropanation in ionic liquids", Tetrahedron Letts. (2003) 44:3629-3630.

Charette et al., "Palladium-catalyzed Suzuki-type cross-couplings of iodocyclopropanes with boronic acids: Synthesis of trans-1,2-dicyclopropyl alkenes", J Org Chem. (1996) 61(25): 8718-8719; Supporting Information, 52 pages.

Chinchilla et al., "Recent advances in Sonogashira reactions", Chem Soc Rev., (2011) 40: 5084-5121.

Clark et al., "Concise synthesis of the C-1-C-12 fragment of amphidinolides T1-T5", Org Biomol Chem. (2011) 9(13): 4823-4830.

Clinical and Laboratory Standards Institute (formerly NCCLS, National Committee for Clinical Laboratory Standards). "Methods for Dilution of Antimicrobial Susceptibility Tests for Bacteria That Grow Aerobically; Approved Standard—9th Edition", CLSI (Jan. 2012) M07-A9 32(2): 88 pages.

Craig WA., "Pharmacokinetic/pharmacodynamic parameters: rationale for antibacterial dosing of mice and men", Clin Infect Dis. (1998) 26(1): 1-10.

Dörwald F.Z., *Side Reactions in Organic Synthesis—A guide to Successful Synthesis Design*, Wiley-VCH Verlag GmbH & Co. KGaA, Weinheim, Germany (2005); Preface in 4 pages.

Drusano et al., Meropenem: clinical response in relation to in vitro susceptibility. Clin Microbiol Infect. (2000) 6: 185-194.

Dunetz et al., "Large-scale applications of amide coupling reagents for the synthesis of pharmaceuticals", Org Process Res Develop. (2016) 20(2): 140-177.

Eggen et al., "Total synthesis of cryptophycin-24 (Arenastatin A) amenable to structural modifications in the C16 side chain", J Org Chem. (2000) 65(23): 7792-7799; and Supporting documents, 22 pages.

Goodman et al., [Eds.], "The Pharmacological Basis of Therapeutics", 8th. Edition, Pergamon Press (1990); TOC, 8 pages.

Gunanathan et al., "Ruthenium catalyzed hydroboration of terminal alkynes to Z vinylboronates", J Am Chem Soc. (2012) 134(35): 14349-14352; Supporting Information, 32 pages.

He et al., "Ligand-promoted borylation of C(sp3)—H bonds with palladium(II) catalysts", Angew Chem Int Ed., (2016) 55(2): 785-789.

Higuchi et al., [Eds.] "Pro-drugs as Novel Drug Delivery Systems", ACS Sumposium Series 14 (1975); TOC, 3 pages.

Hoveyda A., "Evolution of catalytic stereoselective olefin metathesis: From ancillary transformation to purveyor of stereochemical identity", J Org Chem. (Jun. 2014) 79(11): 4763-4792.

Hu et al., "Ag(I)-catalyzed C—H borylation of terminal alkynes", Tetrahedron (2014) 70: 5815-5819.

Jang et al., Copper-catalyzed trans-hydroboration of terminal aryl alkynes: Stereodivergent synthesis of alkenylboron compounds. Org Letts. (2016) 18(6): 1390-1393; Supporting Information in 37 pages.

Jordan V.C., "Tamoxifen: A most unlikely pioneering medicine", Drug Discovery (2003) 2:205-213.

Kuang et al., "Convenient and stereoselctive synthesis of (Z)-1-bromo-1-alkenes by microwave-induced reaction", Tetrahedron Letts. (2001) 42(23): 3893-3896.

Lebel et al., "Boc-protected amines via a mild and efficient one-pot Curtius rearrangement", Org Letts. (2005) 7(19): 4107-4110.

Lee et al., "Comparison of 30-min and 3-h infusion regimens for imipenem/cilastatin and for meropenem evaluated by Monte Carlo simulation", Diagn Microbiol Infect Dis. (2010) 68: 251-258.

Li et al., "Population Pharmacokinetic Analysis and Dosing Regimen Optimization of Meropenem in Adult Patients", J Clin Pharmacol. (2006) 46(10): 1171-1178.

Lin et al., "Enantioselective syn and anti homocrotylation of aldehydes: Application to the formal synthesis of spongidepsin", J Am Chem Soc. (2015) 137(40): 13176-13182; Supporting Information in 177 pages.

Louie et al., Impact of meropenem in combination with tobramycin in a murine model of Pseudomonas aeruginosa pneumonia. Antimicrob Agents Chemother (2013) 57: 2788-2792.

Luithle et al., "Synthesis of enantiomerically pure cis-cyclopropylboronic esters", Eur J Org Chem. (2000) 14: 2557-2562.

MacVane et al., Characterizing in vivo pharmacodynamics of carbapenems against *Acinetobacter baumannii* in a Murine thigh infection model to support breakpoint determinations. Antimicrob Agents Chemother (2014) 58: 599-601.

Maguire B. A., Inhibition of Bacterial Ribosome Assembly: a Suitable Drug Target? Microbiol Mol Biol Rev. (2009) 73(1):22-35.

McSharry et al., "Prediction of the pharmacodynamically linked variable of oseltamivir carboxylate for influenza A virus using an in vitro hollow-fiber infection model system", Antimicrob Agents Chemother (2009) 53(6): 2375-2381.

Mkhalid et al., "C—H activation for the construction of C—B bonds", Chem Rev. (2010) 110(2): 890-931.

Molander et al., "Highly stereoselective synthesis of cis-alkenyl pinacolboronates and potassium cis-alkenyltrifluoroborates via a hydroboration/protodeboronation approach", J Org Chem. (2008) 73(17): 6841-6844.

Mori et al., "Synthesis of 1,3-dienes from alkynes and ethylene: Acetic acid 2-methylene-3-phenethylbut-3-enyl ester", Org Synth. (2005) 81: 1-13.

Morrill et al., "Treatment Options for Carbapenem-Resistant *Enterobacteriaceae* Infections", Open Forum Infectious Diseases [OFID] Apr. 2015; 15 pages.

Nicasio et al., "Pharmacokinetics-Pharmacodynamics of Tazobactam in Combination with Piperacillin in an In Vitro Infection Model", Antimicrob Agents Chemother. (2016) 60: 2075-2080. doi: 10.1128/AAC.02747-15.

Nicolau DP., "Pharmacokinetic and pharmacodynamic properties of meropenem", Clin Infect Dis. (2008) 47 Suppl 1: S32-S40.

Noguchi et al., "Boron-masking strategy for the selective synthesis of oligoarenes via iterative Suzuki-Miyaura coupling", J Am Chem Soc. (2007) 129(4): 758-759; Supporting Information, 46 pages.

Pellissier, H., "Recent developments in asymmetric cyclopropanation", Tetrahedron (2008) 64(30-31): 7041-7095.

Pietruszka et al., "Enantiomerically pure cyclopropylamines from cyclopropylboronic esters", Eur J Org Chem. (2009) 34: 5998-6008.

Pine et al., "Resonance vs. Tautomerism" in *Organic Chemistry*; McGraw-Hill, New York 4th Ed. (1980), pp. 218-219.

Rehm et al., "*Staphylococcus aureus*: Methicillin-susceptible *S. aureus* to Methicillin-resistant *S. aureus* and VancomyMcin-resistant *S. aureus*", Clin Inf Diseases. (2010) 51(S2):S176-S182.

Roche, E.B. (Ed.)., Bioreversible Carriers in Drug Design: Theory and Application. New York: Pergamon Press (1987); pp. 14-21.

Rubino et al., "Phase 1 Study of the Safety, Tolerability, and Pharmacokinetics of Vaborbactam and Meropenem Alone and in Combination following Single and Multiple Doses in Healthy Adult Subjects", Antimicrob Agents Chemother. (Apr. 2018) 62(4): E02228-17; 12 pages.

Sabet et al., "Activity of Simulated Human Dosage Regimens of Meropenem and Vaborbactam against Carbapenem-Resistant Enterobacteriaceae in an In Vitro Hollow-Fiber Model", Antimicrob Agents Chemother (2017) 62. pii: e01969-17. doi: 10.1128/AAC.01969-17.

Sabet et al., "Activity of Meropenem-Vaborbactam in Mouse Models of Infection Due to KPC-Producing Carbapenem-Resistant Enterobacteriaceae", Antimicrob Agents Chemother. (2017) 62:1 10 e01446-379 17.

Scriven et al., "Azides: Their preparation and synthetic uses", Chem Rev. (1988) 88(2): 297-368.

(56) References Cited

OTHER PUBLICATIONS

Singh et al., "Confronting the challenges of discovery of novel antibacterial agents", Bioorg Med Chem Lett. (2014) 24*16):3683-3689.

Sumida et al., "Boron-selective biaryl coupling approach to versatile dibenzoxaborins and application to concise synthesis of defucogilvocarcin M", Org Ltt. (Dec. 2014) 16(23):6240-6243.

Sun et al., "A method for the deprotection of alkylpinacolyl boronate esters", J Org Chem. (2011) 76(9): 3571-3575; Supporting Information, 8 pages.

Tam et al., "Optimization of meropenem minimum concentration/MIC ratio to suppress in vitro resistance of *Pseudomonas aeruginosa*", Antimicrob Agents Chemother. (2005) 49(12): 4920-4927.

U.S. Department of Health and Human Resources, "Antibiotic Resistance Threats in the United States, 2013"; 114 pages.

Valters et al., "Ring-Chain Tautomerism", Plenum Press, New York and London, Softcover reprint of the hardcover 1st Ed. 1985, Chapter 1, 23 pages.

VanScoy et al., "Pharmacokinetics-pharmacodynamics of tazobactam in 386 combination with ceftolozane in an in vitro infection model", Antimicrob Agents Chemother. (2013) 57: 2809-2814. doi: 10.1128/AAC.02513-12.

Voituriez et al., "Preparation of a storable zinc carbenoid species and its application in cyclopropanation, chain extension, and [2,3]-sigmatropic rearrangement reactions", J Org Chem. (2010) 75(4): 1244-1250; Supporting Information, 20 pages.

Walker et al., "Pharmacodynamic activities of meropenem in an animal infection model", (1994), Abstracts of Papers #A91, 34th Interscience Conference on Antimicrobial Agents and Chemotherapy, Orlando , FL., 5 pages.

Wilson D.N., "The A-Z of bacterial translation inhibitors", Crit Rev Biochem Mol Biolog. (2009) 44(6):393-433.

Wong et al., "A chemoselective Reformatsky-Negishi approach to α-haloaryl esters", Tetrahedron (2014) 70(7): 1508-1515.

Zhu et al., "Design, preparation, x-ray crystal structure, and reactivity of o-alkoxyphenyliodonium bis(methoxycarbonyl)methanide, a highly soluble carbene precursor", Org Lett. (2012) 14(12): 3170-3173; Supporting Information, 76 pages.

PHARMACEUTICAL COMPOSITIONS COMPRISING CYCLIC BORONIC ACID ESTER DERIVATIVES

RELATED APPLICATIONS

This application is a division of U.S. application Ser. No. 15/624,473 filed Jun. 15, 2017 which is a continuation of U.S. application Ser. No. 15/015,002 filed Feb. 3, 2016 now U.S. Pat. No. 9,694,025 issued Jul. 4, 2017 which is a division of U.S. application Ser. No. 13/953,647 filed Jul. 29, 2013 now U.S. Pat. No. 9,296,763 which is a division of U.S. application Ser. No. 13/205,112 filed Aug. 8, 2011 entitled "CYCLIC BORONIC ACID ESTER DERIVATIVES AND THERAPEUTIC USES THEREOF" now U.S. Pat. No. 8,680,136 which claims the benefit of U.S. Prov. App. Nos. 61/372,296, filed Aug. 10, 2010, and 61/488,655, filed May 20, 2011, all of the foregoing are incorporated herein by reference in their entireties.

FIELD OF THE INVENTION

The present invention relates to antimicrobial compounds, compositions, their use and preparation as therapeutic agents. In particular, the present invention relates to cyclic boronic acid ester compounds.

BACKGROUND OF THE INVENTION

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactams. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Because there are three major molecular classes of serine-based β-lactamases, and each of these classes contains significant numbers of β-lactamase variants, inhibition of one or a small number of β-lactamases is unlikely to be of therapeutic value. Legacy β-lactamase inhibitors are largely ineffective against at least Class A carbapenemases, against the chromosomal and plasmid-mediated Class C cephalosporinases and against many of the Class D oxacillinases. Therefore, there is a need for improved β-lactamase inhibitors.

SUMMARY OF THE INVENTION

The present invention relates to antimicrobial agents and potentiators thereof. Some embodiments include compounds, compositions, pharmaceutical compositions, use and preparation thereof. In particular, some embodiments, relate to cyclic boronic acid ester derivatives.

Some embodiments include compounds having the structure of formula I:

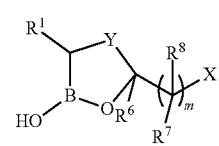

or a pharmaceutically acceptable salt thereof, wherein:

Y is a 1-4 atom alkylene or 2-4 atom alkenylene linker, optionally substituted by one or more substituents selected from the group consisting of Cl, F, CN, CF$_3$, —R$^9$, —OR$^9$, —C(=O)NR$^9$R$^{10}$, and —C(=O)OR$^9$, wherein said alkylene or alkenylene linker is optionally fused to an optionally substituted aryl, optionally substituted heteroaryl, optionally substituted carbocyclyl, or optionally substituted heterocyclyl;

R$^1$ is selected from a group consisting of —C$_{1-9}$alkyl, —C$_{2-9}$alkenyl, —C$_{2-9}$alkynyl, —NR$^9$R$^{10}$, —C$_{1-9}$alkylR$^{11}$, —C$_{2-9}$alkenylR$^{11}$, —C$_{2-9}$alkynylR$^{11}$, -carbocyclyl-R$^{11}$, —CH(OH)C$_{1-9}$alkylR$^9$, —CH(OH)C$_{2-9}$alkenylR$^9$, —CH(OH)C$_{2-9}$alkynylR$^9$, —CH(OH)carbocyclyl-R$^9$, —C(=O)R$^9$, —C(=O)C$_{1-9}$alkylR$^9$, —C(=O)C$_{2-9}$alkenylR$^9$, —C(=O)C$_{2-9}$alkynylR$^9$, —C(=O)C$_{2-9}$carbocyclyl-R$^9$, —C(=O)NR$^9$R$^{10}$, —N(R$^9$)C(=O)R$^9$, —N(R$^9$)C(=O)NR$^9$R$^{10}$, —N(R$^9$)C(=O)OR$^9$), —N(R$^9$)C(=O)C(=NR$^{10}$)R$^9$, —N(R$^9$)C(=O)C(=CR$^9$R$^{10}$)R$^9$, —N(R$^9$)C(=O)C$_{1-4}$alkylN(R$^9$)C(=O)R$^9$, N(R$^9$)C(=NR$^{10}$)R$^9$, —C(=NR$^{10}$NR$^9$R$^{10}$, —N=C(R$^9$)NR$^9$R$^{10}$, —N(R$^9$)SO$_2$R$^9$, —N(R$^9$)SO$_2$NR$^9$R$^{10}$, —N=CHR$^9$, substituted or unsubstituted aryl, substituted or unsubstituted heteroaryl, substituted or unsubstituted carbocyclyl, and substituted or unsubstituted heterocyclyl;

R$^6$ is selected from a group consisting of H, —C$_{1-9}$alkyl, C$_{2-9}$alkenyl, —C$_{2-9}$alkynyl, carbocyclyl, —C$_{1-9}$alkylR$^{11}$, —C$_{2-9}$alkenylR$^{11}$, —C$_{2-9}$alkynylR$^{11}$, carbocyclyl-R$^{11}$, —C(=O)OR$^9$, —C$_{1-9}$alkylCO$_2$R$^9$, —C$_{2-9}$alkenylCO$_2$R$^9$, —C$_{2-9}$alkynylCO$_2$R$^9$, and -carbocyclyl-CO$_2$R$^9$, or alternatively:

(i) R$^6$ and an R$^7$ are taken together with the atoms to which they are attached to form a substituted or unsubstituted carbocyclyl or substituted or unsubstituted heterocyclyl, (ii) R$^6$ and a carbon atom in Y are taken together with intervening atoms to form a substituted or unsubstituted carbocyclyl or substituted or unsubstitued heterocyclyl, or (iii) R$^6$ is absent when the carbon to which it is attached is a ring atom in an aryl or heteroaryl ring;

each R$^7$ is independently selected from a group consisting of H, halo, —C$_{1-9}$alkyl, —C$_{2-9}$alkenyl, —C$_{2-9}$alkynyl, —NR$^9$R$^{10}$, —OR$^9$, —C$_{1-9}$alkylCO$_2$R$^9$, —C$_{2-9}$alkenylCO$_2$R$^9$, —C$_{2-9}$alkynylCO$_2$R$^9$, and -carbocyclyl-CO$_2$R$^9$, or independently:

(i) R$^6$ and an R$^7$ are taken together with the atoms to which they are attached to form a substituted or unsubstituted carbocyclyl or substituted or unsubstituted heterocyclyl, (ii) R$^7$ and an R$^8$ are taken together with the atoms to which they are attached to form a substituted or unsubstituted carbocyclyl or substituted or unsubstituted heterocyclyl, (iii) an R$^7$ and a carbon atom in Y are taken together with intervening atoms to form a substituted or unsubstituted carbocyclyl or substituted or unsubstitued heterocyclyl, (iv) each of the following conditions are met:
(a) Y is a 3-4 atom alkylene or 3-4 atom alkenylene linker,
(b) R$^6$ is absent,
(c) R$^7$ and a carbon atom in Y are taken together with intervening atoms to form a substituted or unsubstituted aryl or a substituted or unsubstituted heteroaryl, and (d) each R$^8$ attached to a ring atom forming part of the substituted or unsubstituted aryl or a substituted or unsubstituted heteroaryl formed by R$^7$ and Y is absent;

each R$^8$ is independently selected from a group consisting of H, halo, —C$_{1-9}$alkyl, —C$_{2-9}$alkenyl, —C$_{2-9}$alkynyl, —NR$^9$R$^{10}$, —OR$^9$, —C$_{1-9}$alkylCO$_2$R$^9$, —C$_{2-9}$alkenylCO$_2$R$^9$, —C$_{2-9}$alkynylCO$_2$R$^9$, -carbocyclyl-CO$_2$R$^9$, or independently:

(i) an R$^7$ and an R$^8$ are taken together with the atoms to which they are attached to form a substituted or unsubstituted carbocyclyl or substituted or unsubstituted heterocyclyl, (ii) a geminal R$^7$ and R$^8$ together form —C$_{2-9}$alkenylenylCO$_2$R$^9$, or (iii) each R$^8$ attached to a ring atom forming part of a substituted or unsubstituted aryl is absent;

each R$^9$ is independently selected from a group consisting of H, —C$_{1-9}$alkyl, C$_{2-9}$alkenyl, —C$_{2-9}$alkynyl, carbocyclyl, —C$_{1-9}$alkylR$^{11}$, —C$_{2-9}$alkenylR$^{11}$, —C$_{2-9}$alkynylR$^{11}$, -carbocyclyl-R$^{11}$, substituted or unsubstituted aryl, substituted or unsubstituted heteroaryl, substituted or unsubstituted carbocyclyl, and substituted or unsubstituted heterocyclyl;

each R$^{10}$ is independently selected from a group consisting of H, —C$_{1-9}$alkyl, —OR$^9$, —CH(=NH), —C(=O)OR$^9$, substituted or unsubstituted aryl, substituted or unsubstituted heteroaryl, substituted or unsubstituted carbocyclyl, and substituted or unsubstituted heterocyclyl;

each R$^{11}$ is independently selected from a group consisting of substituted or unsubstituted aryl, substituted or unsubstituted heteroaryl, substituted or unsubstituted carbocyclyl, and substituted or unsubstituted heterocyclyl;

X is selected from a group consisting of H, —CO$_2$R$^{12}$, and carboxylic acid isosteres;

R$^{12}$ is selected from a group consisting of H, C$_{1-9}$alkyl, —(CH$_2$)$_{0-3}$—R$_{11}$, —C(R$^{13}$)$_2$OC(O)C$_{1-9}$alkyl, —C(R$^{13}$)$_2$OC(O)R$^{11}$, —C(R$^{13}$)$_2$OC(O)OC$_{1-9}$alkyl and —C(R$^{13}$)$_2$OC(O)OR$^{11}$;

each R$^{13}$ is independently selected from a group consisting of H and C$_{1-4}$alkyl; and m is independently zero or an integer from 1 to 2, wherein each C$_{1-9}$alkyl, C$_{2-9}$alkenyl, and C$_{2-9}$alkynyl is independently optionally substituted.

In some embodiments, the compound of formula I has the structure of formula II:

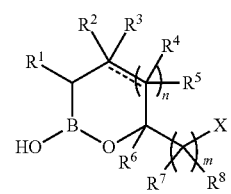

II or a pharmaceutically acceptable salt thereof, wherein:

the bond represented by a dashed and solid line represents a bond selected from the group consisting of a single bond and a double bond with the proviso that the dashed and solid line can only be a double bond when n is 1;

R$^2$ and R$^4$ are independently selected from a group consisting of Cl, F, CN, CF$_3$, —R$^9$, —OR$^9$, —C(=O)NR$^9$R$^{10}$, and —C(=O)OR$^9$; or alternatively, R$^2$ and R$^4$ are taken together with the atoms to which they are attached to form a substituted or unsubstituted aryl, substituted or unsubstituted heteroaryl, substituted or unsubstituted carbocyclyl or substituted or unsubstituted heterocyclyl;

$R^3$ and $R^5$ are independently selected from a group consisting of Cl, F, CN, $CF_3$, —$R^9$, —$OR^9$, —C(=O)$NR^9R^{10}$, and —C(=O)$OR^9$, with the proviso that if the bond represented by a dashed and solid line is a double bond then $R^3$ and $R^5$ are absent; and n is independently zero or an integer from 1 to 2.

In some embodiments, the compound of formula I the structure of formula IIIa or IIIb:

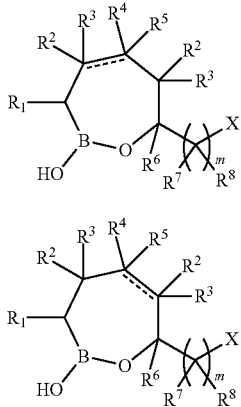

IIIa

IIIb or a pharmaceutically acceptable salt thereof, wherein:

the bond represented by a dashed and solid line represents a bond selected from the group consisting of a single bond and a double bond;

each $R^2$ and $R^4$ are independently selected from a group consisting of Cl, F, CN, $CF_3$, —$R^9$, —$OR^9$, —C(=O)$NR^9R^{10}$, and —C(=O)$OR^9$; or alternatively, an $R^2$ and $R^4$ are taken together with the atoms to which they are attached to form a substituted or unsubstituted aryl, substituted or unsubstituted heteroaryl, substituted or unsubstituted carbocyclyl or substituted or unsubstituted heterocyclyl;

each $R^3$ and $R^5$ are independently selected from a group consisting of Cl, F, CN, $CF_3$, —$R^9$, —$OR^9$, —C(=O)$NR^9R^{10}$, and —C(=O)$OR^9$, with the proviso that if the bond represented by a dashed and solid line is a double bond then $R^3$ and $R^5$ are absent.

In some embodiments, the compound of formula I has the structure of formula IVa, IVb, or IVc:

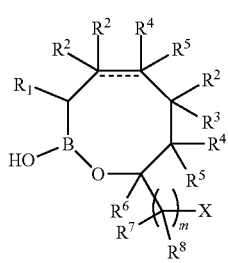

IVa

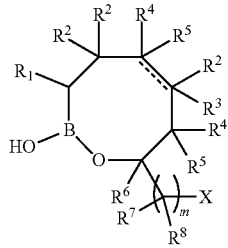

IVb

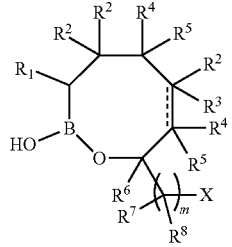

IVc or a pharmaceutically acceptable salt thereof, wherein:

the bond represented by a dashed and solid line represents a bond selected from the group consisting of a single bond and a double bond;

each $R^2$ and each $R^4$ are independently selected from a group consisting of Cl, F, CN, $CF_3$, —$R^9$, —$OR^9$, —C(=O)$NR^9R^{10}$, and —C(=O)$OR^9$; or alternatively, an $R^2$ and an $R^4$ are taken together with the atoms to which they are attached to form a substituted or unsubstituted aryl, substituted or unsubstituted heteroaryl, substituted or unsubstituted carbocyclyl or substituted or unsubstituted heterocyclyl;

each $R^3$ and each $R^5$ are independently selected from a group consisting of Cl, F, CN, $CF_3$, —$R^9$, —$OR^9$, —C(=O)$NR^9R^{10}$, and —C(=O)$OR^9$, with the proviso that if the bond represented by a dashed and solid line is a double bond then the $R^3$ and $R^5$ attached to the carbon atoms bonded that bond are absent.

Some embodiments include a pharmaceutical composition comprising a therapeutically effective amount of any one of the foregoing compounds and a pharmaceutically acceptable excipient.

Some embodiments include any one of the foregoing compounds or compositions for use in the treatment or prevention of a bacterial infection.

Some embodiments include methods for treating or preventing a bacterial infection comprising administering to a subject in need thereof, an effective amount of any one of the foregoing compounds or compositions.

Some embodiments include the use of any one of the foregoing compounds or compositions in the preparation of a medicament for the treatment or prevention of a bacterial infection.

Some embodiments further comprise administering an additional medicament, either is a separate composition or in the same composition.

In some embodiments, the additional medicament includes an antibacterial agent, antifungal agent, an antiviral agent, an anti-inflammatory agent or an anti-allergic agent.

In some embodiments, the additional medicament comprises an antibacterial agent such as a β-lactam.

In some embodiments, the β-lactam includes Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Biapenem, Doripenem, Ertapenem, Imipenem, Meropenem, Panipenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04,546, ME1036, BAL30072, SYN 2416, Ceftiofur, Cefquinome, Cefovecin, Aztreonam, Tigemonam, Carumonam, RWJ-442831, RWJ-333441, or RWJ-333442.

In some embodiments, the β-lactam includes Ceftazidime, Biapenem, Doripenem, Ertapenem, Imipenem, Meropenem, or Panipenem.

In some embodiments, the β-lactam is selected from Aztreonam, Tigemonam, BAL30072, SYN 2416, or Carumonam.

In some embodiments, the β-lactam Tigemonam, the composition is suitable for oral administration, X is —CO$_2$R$^{12}$, and R$^{12}$ is selected from a group consisting of C$_{1-9}$alkyl, —(CH$_2$)$_{0-3}$—R$_{11}$, —C(R$^{13}$)$_2$OC(O)C$_{1-9}$alkyl, —C(R$^{13}$)$_2$OC(O)R$^{11}$, —C(R$^{13}$)$_2$OC(O)OC$_{1-9}$alkyl and —C(R$^{13}$)$_2$OC(O)OR$^{11}$.

In some embodiments, the infection that is treated or prevented comprises a bacteria that includes *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis,* or *Staphylococcus saccharolyticus.*

In some embodiments, the infection that is treated or prevented comprises a bacteria that includes *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii,* or *Bacteroides splanchnicus.*

Some embodiments include a sterile container, comprising any one of the foregoing compounds in solid form and an antibacterial agent in solid form. In some embodiments, the antimicrobial agent is one of the additional medicaments described above. Some embodiments include a method of preparing a pharmaceutical composition for administration, comprising reconstituting the contents of the sterile container using a pharmaceutically acceptable diluent. In some embodiments, the reconstituted solution is administered intravenously to a patient.

DETAILED DESCRIPTION

Figure 1:
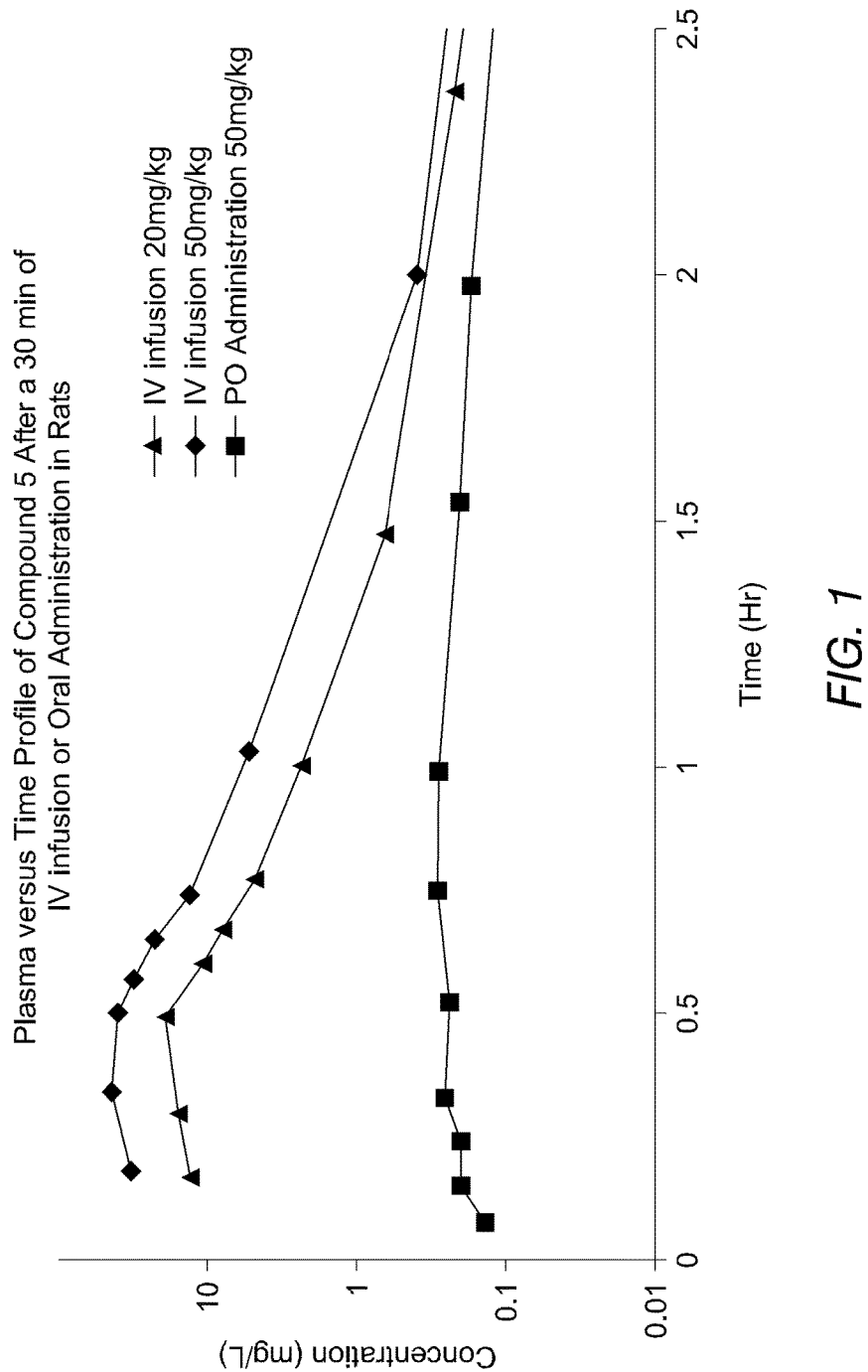
FIG. 1 is a graph depicting the plasma concentration profile of a cyclic boronic acid ester derivative as a function of time after administration to Sprague Dawley rats.

The present invention relates to antimicrobial agents and potentiators thereof. Some embodiments include compounds, compositions, pharmaceutical compositions, uses thereof, including methods of preparation, and methods of treatment. In particular, the present invention relates to cyclic boronic acid ester derivatives. In some embodiments, the cyclic boronic acid ester derivatives have the structure of formula I, II, IIIa, IIIb, IVa, IVb, or IVc as described above.

Some embodiments of the compound of formula II have the defined 3,6-cis-stereochemistry shown in formula IIa:

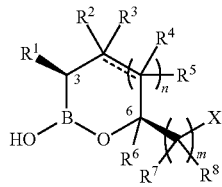

IIa or a pharmaceutically acceptable salt thereof.

Some embodiments of the compound of formula II have the defined 3,6-trans-stereochemistry shown in formula IIb:

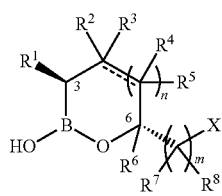

IIb or a pharmaceutically acceptable salt thereof.

In one embodiment of the compound of formula II:

$R^1$ is selected from a group consisting of —$C_{1-9}$alkyl, —$C_{2-9}$alkenyl, —$C_{2-9}$alkynyl, —$NR^9R^{10}$, —$C_{1-9}$alkyl$R^{11}$, —$C_{2-9}$alkenyl$R^{11}$, —$C_{2-9}$alkynyl$R^{11}$, —CH(OH)$C_{1-9}$alkyl$R^9$, —CH(OH)$C_{2-9}$alkenyl$R^9$, —CH(OH)$C_{2-9}$alkynyl$R^9$, —C(=O)$R^9$, —C(=O)$C_{1-9}$alkyl$R^9$, —C(=O)$C_{2-9}$alkenyl$R^9$, —C(=O)$C_{2-9}$alkynyl$R^9$, —C(=O)$NR^9R^{10}$, —$N(R^9)$C(=O)$R^9$, —$N(R^9)$C(=O)$NR^9R^{10}$, —$N(R^9)$C(=O)$OR^9$, —$N(R^9)$C(=O)C(=$NR^{10}$)$R^9$, —$N(R^9)$C(=O)$C_{1-4}$alkyl$N(R^9)$C(=O)$R^9$, —$N(R^9)$C(=$NR^{10}$)$R^9$, —C(=$NR^{10}$)$NR^9R^{10}$, —N=C($R^9$)$NR^9R^{10}$, —$N(R^9)$SO$_2R^9$, —$N(R^9)$SO$_2NR^9R^{10}$, substituted or unsubstituted aryl, substituted or unsubstituted heteroaryl, substituted or unsubstituted carbocyclyl, and substituted or unsubstituted heterocyclyl;

$R^6$ is selected from a group consisting of H, —$C_{1-9}$alkyl, $C_{2-9}$alkenyl, —$C_{2-9}$alkynyl, —$C_{1-9}$alkyl$R^{11}$, —$C_{2-9}$alkenyl$R^{11}$, —$C_{2-9}$alkynyl$R^{11}$, —C(=O)$OR^9$, and —$C_{1-9}$alkylCO$_2R^9$, —$C_{2-9}$alkenylCO$_2R^9$, and —$C_{2-9}$alkynylCO$_2R^9$, or alternatively $R^6$ and an $R^7$ are taken together with the atoms to which they are attached to form a substituted or unsubstituted carbocyclyl or substituted or unsubstituted heterocyclyl;

each $R^7$ is independently selected from a group consisting of H, —$NR^9R^{10}$, —$OR^9$, and —$C_{1-9}$alkylCO$_2R^9$, —$C_{2-9}$alkenylCO$_2R^9$, and —$C_{2-9}$alkynylCO$_2R^9$, or independently, $R^6$ and an $R^7$ or independently an IC and an $R^8$ are taken together with the atoms to which they are attached to form a substituted or unsubstituted carbocyclyl or substituted or unsubstituted heterocyclyl;

each $R^8$ is independently selected from a group consisting of H, —$NR^9R^{10}$, —$OR^9$, and —$C_{1-9}$alkylCO$_2R^9$, —$C_{2-9}$alkenylCO$_2R^9$, and —$C_{2-9}$alkynylCO$_2R^9$, or independently, an $R^7$ and an $R^8$ are taken together with the atoms to which they are attached to form a substituted or unsubstituted carbocyclyl or substituted or unsubstituted heterocyclyl;

each $R^9$ is independently selected from a group consisting of H, —$C_{1-9}$alkyl, $C_{2-9}$alkenyl, —$C_{2-9}$alkynyl, —$C_{1-9}$alkyl$R^{11}$, —$C_{2-9}$alkenyl$R^{11}$, —$C_{2-9}$alkynyl$R^{11}$, substituted or unsubstituted aryl, substituted or unsubstituted heteroaryl, substituted or unsubstituted —(CH$_2$)$_{0-3}$carbocyclyl, and substituted or unsubstituted heterocyclyl;

each $R^{10}$ is independently selected from a group consisting of H, —$C_{1-9}$alkyl, —$OR^9$, —CH(=NH), substituted or unsubstituted aryl, substituted or unsubstituted heteroaryl, substituted or unsubstituted carbocyclyl, and substituted or unsubstituted heterocyclyl; and X is selected from a group consisting of H, —CO$_2$H and carboxylic acid isosteres.

In some embodiments of compounds of formulas II, IIa, or IIb, n is 1.

In some embodiments of compounds of formulas II, IIa, or IIb, n is zero.

In some embodiments of compounds of formulas II, IIa, or IIb, n is 2.

Some embodiments of the compounds of formula IIIa or IIIb have the 3,7-cis-stereochemistry shown in formula IIIc and IIId:

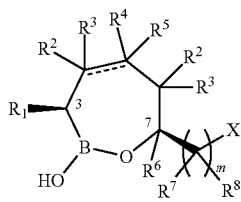

IIIc

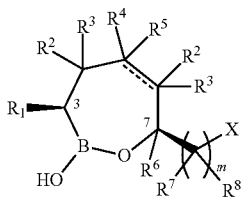

IIId or a pharmaceutically acceptable salt thereof.

Some embodiments of the compounds of formula Ma or Mb have the 3,7-trans-stereochemistry shown in formula IIIe and IIIf:

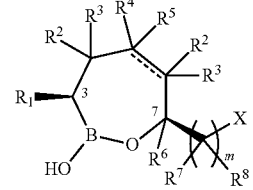

IIIe

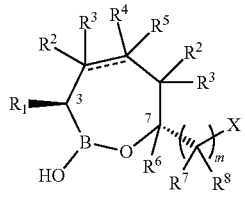

IIIf or a pharmaceutically acceptable salt thereof.

Some embodiments of the compounds of formulas IVa, IVb, or IVc have the 3,8-cis-stereochemistry shown in formula IVd, IVe, and IVf:

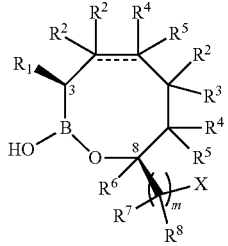
IVd

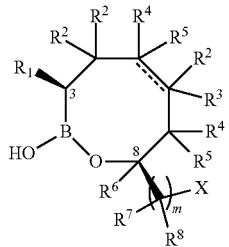
IVe

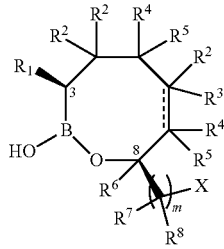
IVf or a pharmaceutically acceptable salt thereof.

Some embodiments of the compounds of formulas IVa, IVb, or IVc have the 3,8-trans-stereochemistry shown in formula IVg, IVh, and IVi:

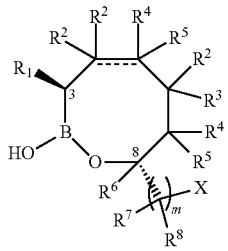
IVg

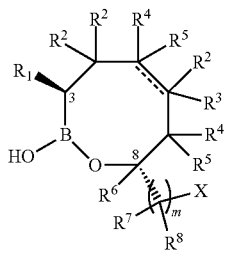
IVh

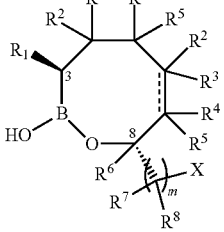
IVi or a pharmaceutically acceptable salt thereof.

In some embodiments of the compounds of formulas II, IIa, IIIa, IIIb, IIIc, IVa, IVb, IVc, IVd, IVe, IVf, IVg, IVh, and IVi, each $R^2$, $R^3$, $R^4$, and $R^5$ are hydrogen.

In some embodiments of the compounds of formulas II, IIa, IIIa, IIIb, IIIc, IVa, IVb, IVc, IVd, IVe, IVf, IVg, IVh, and IVi, at least one $R^2$ is substituted or unsubstituted aryl.

In some embodiments of the compounds of formulas II, IIa, IIIa, IIIb, IIIc, IVa, IVb, IVc, IVd, IVe, IVf, IVg, IVh, and IVi, at least one $R^4$ is substituted or unsubstituted aryl.

In some embodiments of the compounds of formulas II, IIa, IIIa, IIIb, IIIc, IVa, IVb, IVc, IVd, IVe, IVf, IVg, IVh, and IVi, at least one $R^2$ and $R^4$ are taken together with the atoms to which they are attached to form a substituted or unsubstituted aryl.

In some embodiments of the compounds of formulas II, IIa, IIIa, IIIb, IIIc, IVa, IVb, IVc, IVd, IVe, IVf, IVg, IVh, and IVi, the bond represented by a dashed and solid line is a single bond. In other embodiments, the bond represented by a dashed and solid line is a double bond.

In some embodiments of the compounds of formulas I, II, IIa, IIIa, IIIb, IIIc, IVa, IVb, IVc, IVd, IVe, IVf, IVg, IVh, and IVi, $R^6$ and each $R^7$ and $R^8$ is hydrogen.

In some embodiments of the compounds of formulas I, II, IIa, IIIa, IIIb, IIIc, IVa, IVb, IVc, IVd, IVe, IVf, IVg, IVh, and IVi, $R^1$ is —NHC(=O)$C_{1-9}$alkyl$R^{11}$. In some such embodiments, $R^{11}$ is substituted or unsubstituted aryl or substituted or unsubstituted heteroaryl. In some such embodiments, $R^{11}$ is thien-2-yl.

In some embodiments of the compounds of formulas I, II, IIa, IIIa, IIIb, IIIc, IVa, IVb, IVc, IVd, IVe, IVf, IVg, IVh, and IVi, $R^1$ is —NHC(=O)C(=NOR$^9$)R$^{9'}$, wherein R$^{9'}$ is selected from the group consisting of $C_{1-9}$alkyl, substituted or unsubstituted aryl, substituted or unsubstituted heteroaryl, substituted or unsubstituted carbocyclyl and substituted or unsubstituted heterocyclyl.

In some embodiments of the compounds of formulas I, II, IIa, IIIa, IIIb, IIIc, IVa, IVb, IVc, IVd, IVe, IVf, IVg, IVh, and IVi, $R^1$ is —NHC(=O)$C_{1-9}$alkyl$R^{11}$. In some such embodiments, $R^{11}$ is substituted or unsubstituted aryl, substituted or unsubstituted heteroaryl, substituted or unsubstituted carbocyclyl, or substituted or unsubstituted heterocyclyl.

In some embodiments of the compounds of formulas I, II, IIa, IIIa, IIIb, IIIc, IVa, IVb, IVc, IVd, IVe, IVf, IVg, IVh, and IVi, $R^1$ is —NHC(=O)R$^{9'}$, wherein R$^{9'}$ is substituted or unsubstituted aryl, substituted or unsubstituted heteroaryl, substituted or unsubstituted carbocyclyl, or substituted or unsubstituted heterocyclyl.

In some embodiments of the compounds of formulas I, II, IIa, IIIa, IIIb, IIIc, IVa, IVb, IVc, IVd, IVe, IVf, IVg, IVh, and IVi, $R^1$ is —NR$^9$R$^{10}$.

In some embodiments of the compounds of formulas I, II, IIa, IIIa, IIIb, IIIc, IVa, IVb, IVc, IVd, IVe, IVf, IVg, IVh, and IVi, $R^1$ is —$C_{1-9}$alkyl$R^{11}$.

In some embodiments of the compounds of formulas I, II, IIa, IIIa, IIIb, IIIc, IVa, IVb, IVc, IVd, IVe, IVf, IVg, IVh, and IVi, $R^1$ is —CH(OH)$C_{1-9}$alkyl$R^9$.

In some embodiments of the compounds of formulas I, II, IIa, IIIa, IIIb, IIIc, IVa, IVb, IVc, IVd, IVe, IVf, IVg, IVh, and IVi, $R^1$ is —C(=O)$C_{1-9}$alkyl $R^9$.

In some embodiments of the compounds of formulas I, II, IIa, IIIa, IIIb, IIIc, IVa, IVb, IVc, IVd, IVe, IVf, IVg, IVh, and IVi, $R^1$ is —C(=O)N$R^9R^{10}$.

In some embodiments of the compounds of formulas I, II, IIa, IIIa, IIIb, IIIc, IVa, IVb, IVc, IVd, IVe, IVf, IVg, IVh, and IVi, $R^1$ is —N($R^8$)C(=O)N$R^9R^{10}$.

In some embodiments of the compounds of formulas I, II, IIa, IIIa, IIIb, IIIc, IVa, IVb, IVc, IVd, IVe, IVf, IVg, IVh, and IVi, $R^1$ is —N($R^9$)C(=O)O$R^9$.

In some embodiments of the compounds of formulas I, II, IIa, IIIa, IIIb, IIIc, IVa, IVb, IVc, IVd, IVe, IVf, IVg, IVh, and IVi, $R^1$ is —N($R^9$)C(=O)$C_{1-4}$alkylN($R^9$)C(=O) $R^9$.

In some embodiments of the compounds of formulas I, II, IIa, IIIa, IIIb, IIIc, IVa, IVb, IVc, IVd, IVe, IVf, IVg, IVh, and IVi, $R^1$ is —N($R^9$)C(=N$R^{10}$)$R^9$.

In some embodiments of the compounds of formulas I, II, IIa, IIIa, IIIb, IIIc, IVa, IVb, IVc, IVd, IVe, IVf, IVg, IVh, and IVi, $R^1$ is —C(=N$R^{10}$)N$R^9R^{10}$.

In some embodiments of the compounds of formulas I, II, IIa, IIIa, IIIb, IIIc, IVa, IVb, IVc, IVd, IVe, IVf, IVg, IVh, and IVi, $R^1$ is —N=C($R^9$)N$R^9R^{10}$.

In some embodiments of the compounds of formulas I, II, IIa, IIIa, IIIb, IIIc, IVa, IVb, IVc, IVd, IVe, IVf, IVg, IVh, and IVi, $R^1$ is —C(=O)C(=N$R^{10}$)$R^9$.

In some embodiments of the compounds of formulas I, II, IIa, IIIa, IIIb, IIIc, IVa, IVb, IVc, IVd, IVe, IVf, IVg, IVh, and IVi, $R^1$ is —N($R^9$)SO$_2R^9$.

In some embodiments of the compounds of formulas I, II, IIa, IIIa, IIIb, IIIc, IVa, IVb, IVc, IVd, IVe, IVf, IVg, IVh, and IVi, $R^1$ is —N($R^9$)SO$_2$N$R^9R^{10}$.

In some embodiments of the compounds of formulas I, II, IIa, IIIa, IIIb, IIIc, IVa, IVb, IVc, IVd, IVe, IVf, IVg, IVh, and IVi, X is —CO$_2$H.

In some embodiments of the compounds of formulas I, II, IIa, IIIa, IIIb, IIIc, IVa, IVb, IVc, IVd, IVe, IVf, IVg, IVh, and IVi, X is a carboxylic acid isostere. In some such embodiments, the carboxylic acid isostere is selected from the group consisting of —P(O)(O$R^9$)$_2$, —P(O)($R^9$)(O$R^9$), —P(O)(O$R^{12'}$)$_2$, —P(O)($R^9$)(O$R^{12'}$), —CON($R^9$)OH, —SO$_3$H, —SO$_2$N($R^9$)OH, and

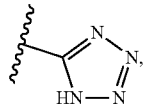

wherein $R^{12'}$ is selected from the group consisting of H, $R_{11}$, —C($R^{13}$)$_2$OC(O)$C_{1-9}$alkyl, —C($R^{13}$)$_2$OC(O)$R^{11}$, —C($R^{13}$)$_2$OC(O)O$C_{1-9}$alkyl and —C($R^{13}$)$_2$OC(O)O$R^{11}$.

In some embodiments of the compounds of formulas I, II, IIa, IIIa, IIIb, IIIc, IVa, IVb, IVc, IVd, IVe, IVf, IVg, IVh, and IVi, m is 1.

In some embodiments of the compounds of formulas I, II, IIa, IIIa, IIIb, IIIc, IVa, IVb, IVc, IVd, IVe, IVf, IVg, IVh, and IVi, $R^6$, $R^7$ and $R^8$ are H.

In some embodiments of the compounds of formulas I, II, IIa, IIIa, IIIb, IIIc, IVa, IVb, IVc, IVd, IVe, IVf, IVg, IVh, and IVi, $R^7$ is H; $R^8$ is —$C_{1-9}$alkylCO$_2R^9$; and $R^9$ is H.

Some embodiments include a compound selected from the group consisting of:

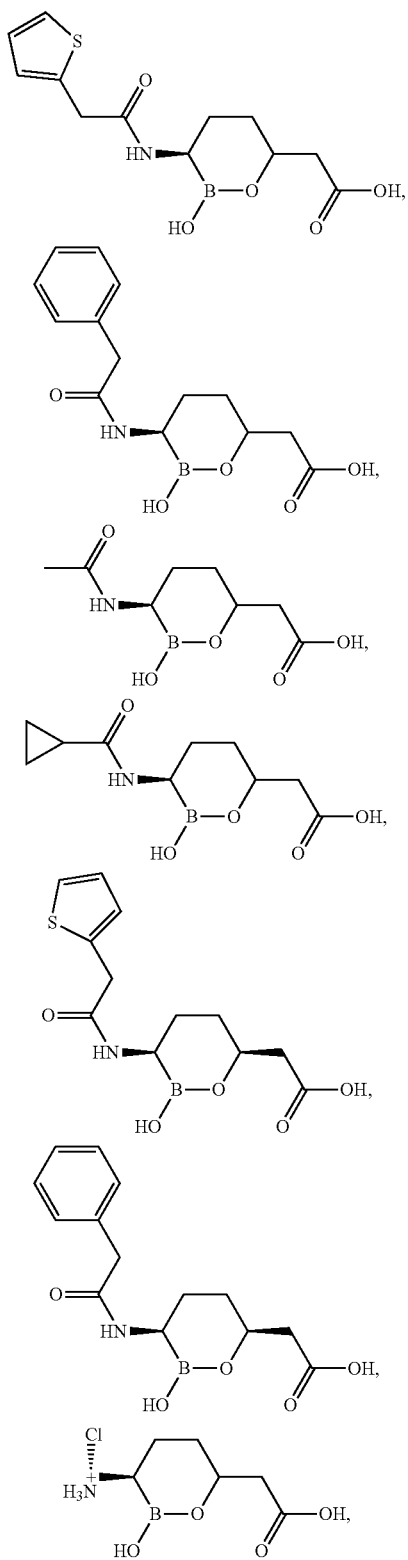

-continued
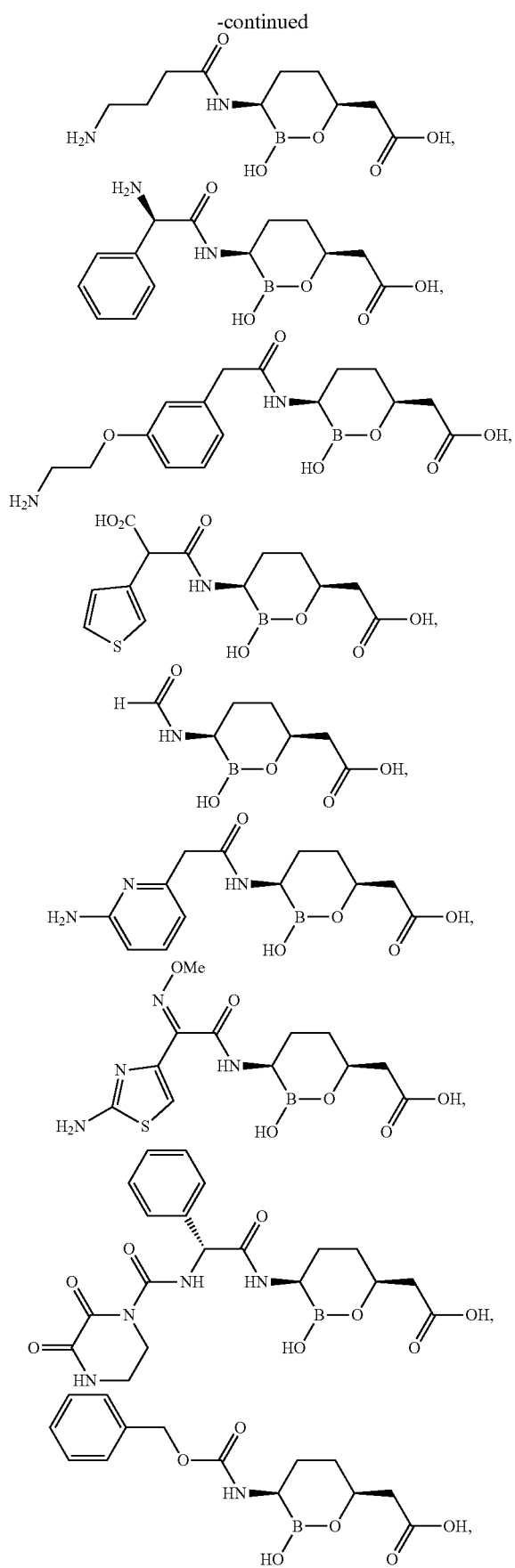
-continued
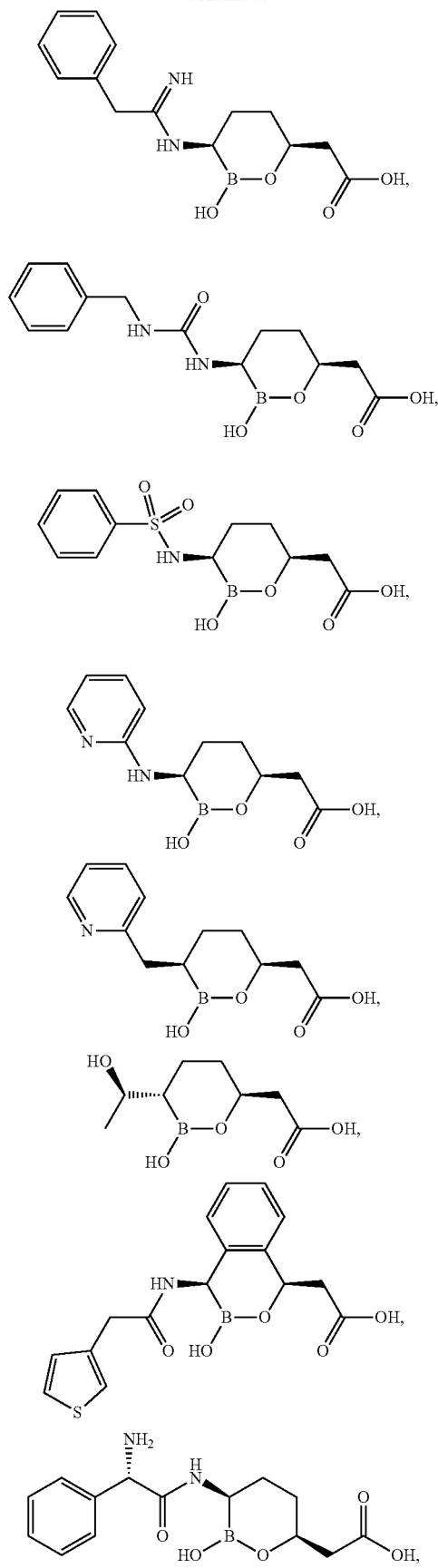

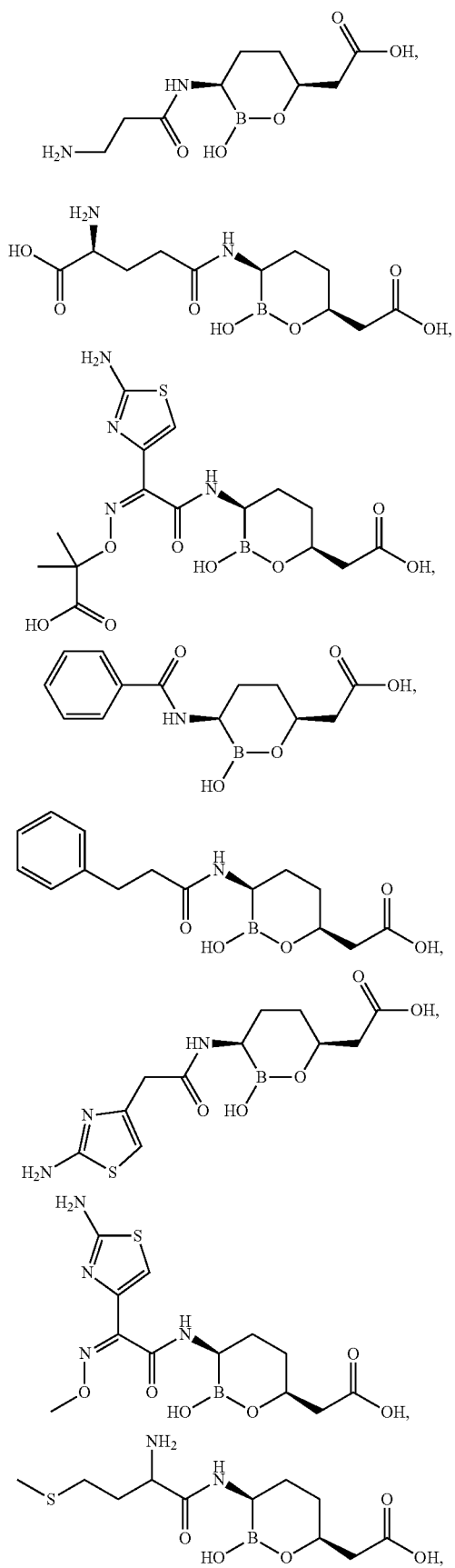
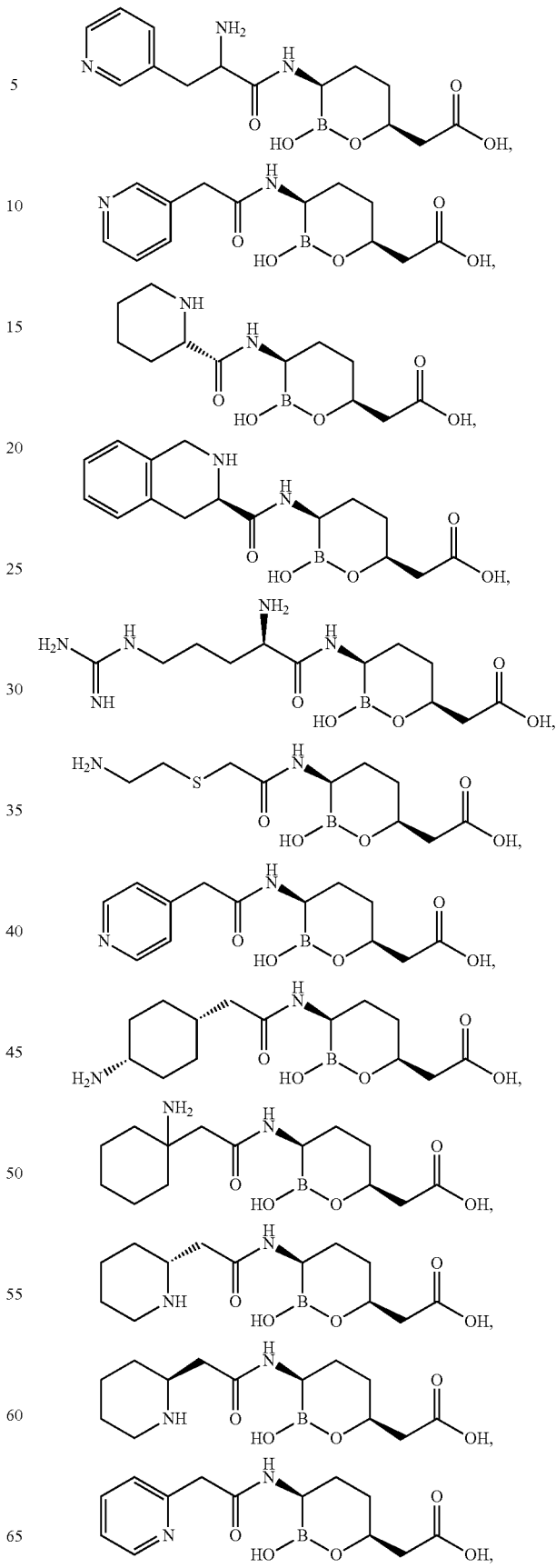

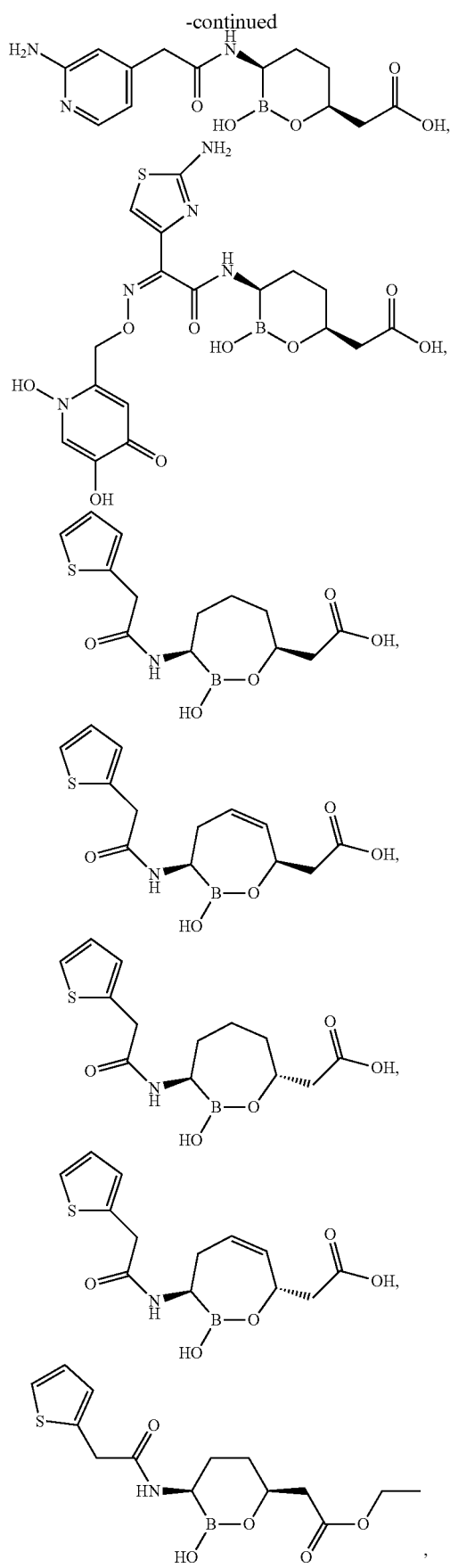

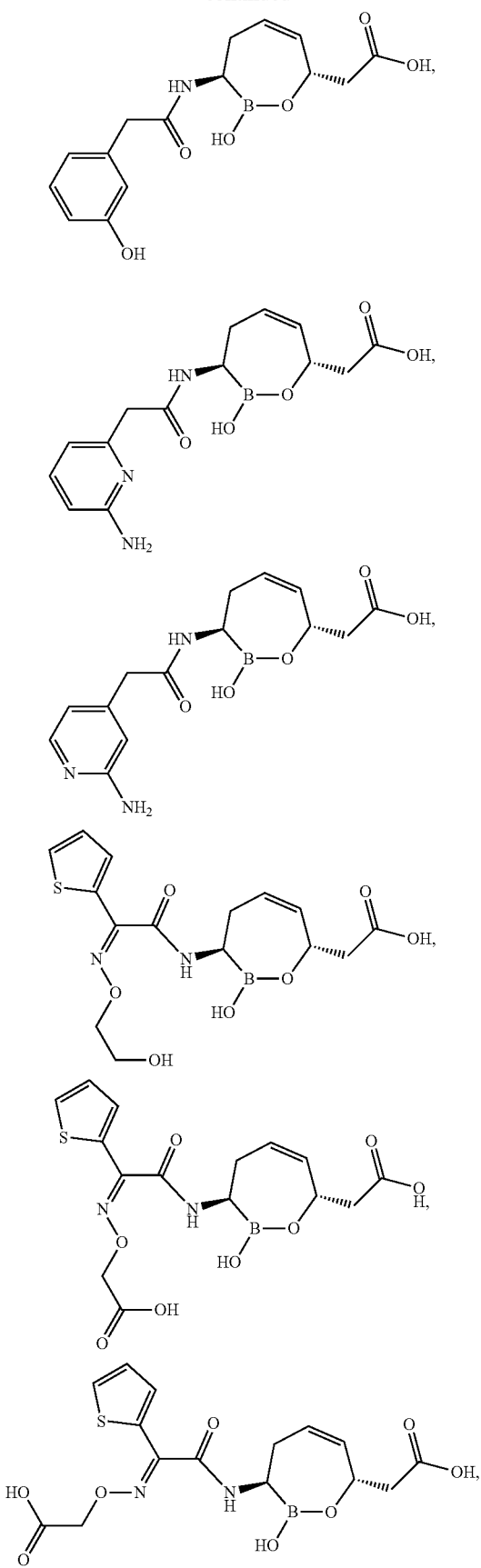
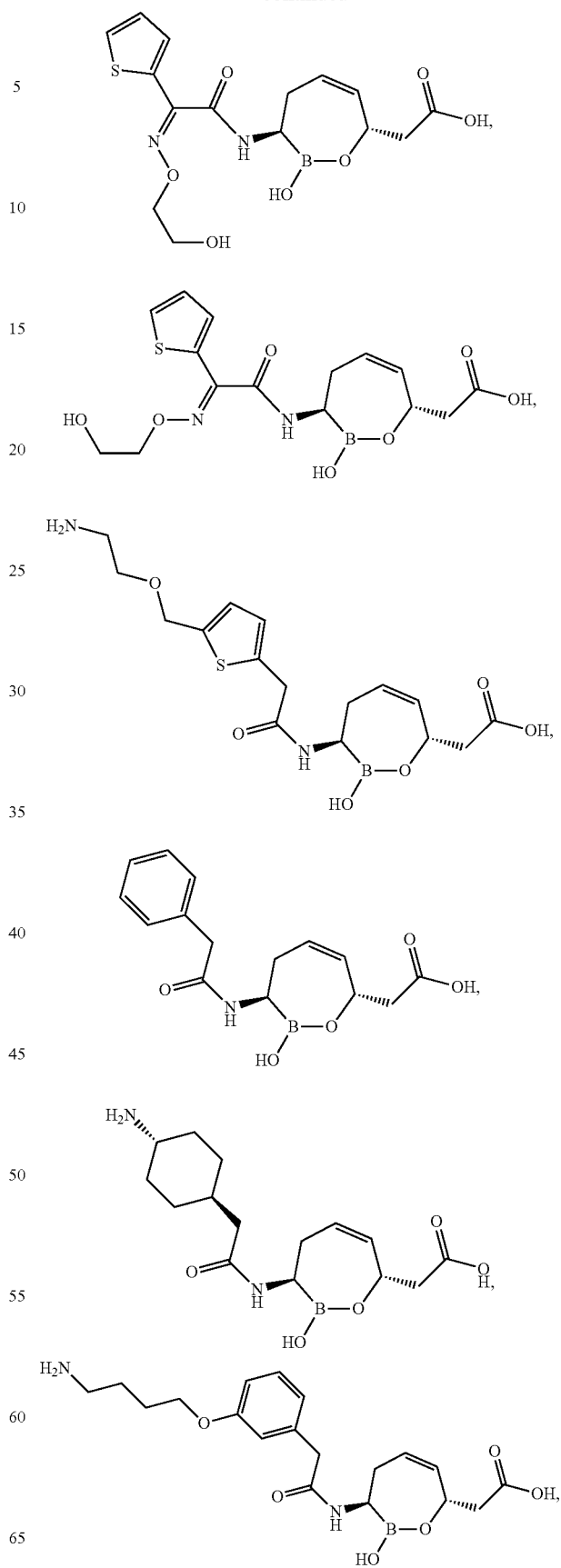

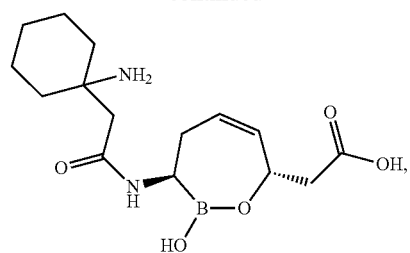
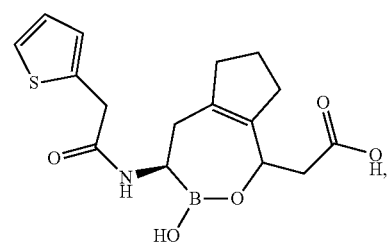
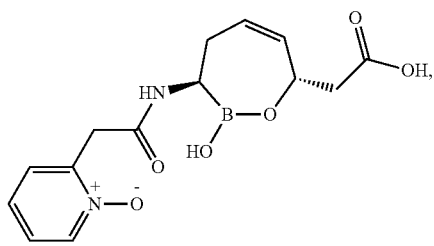
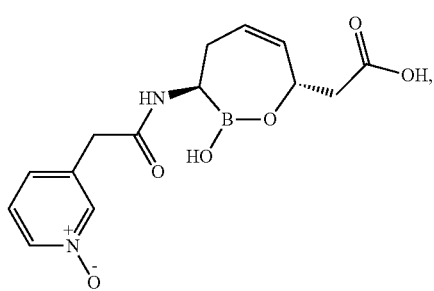
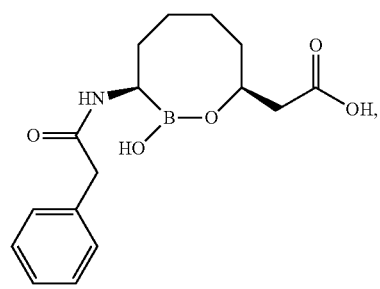
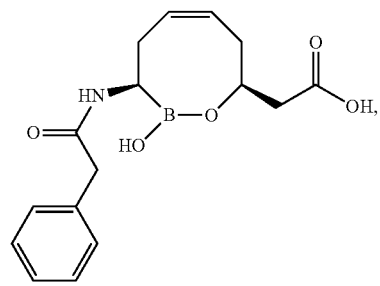
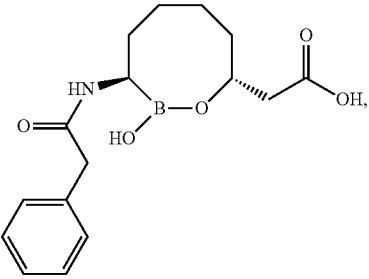
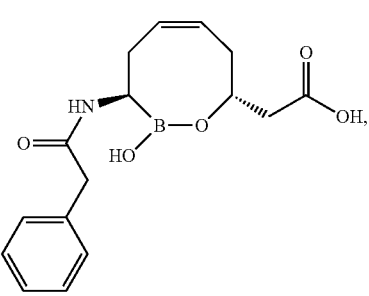
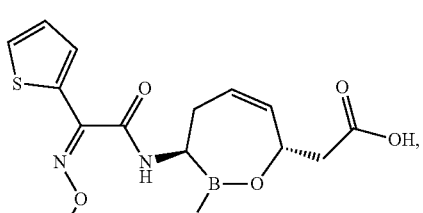
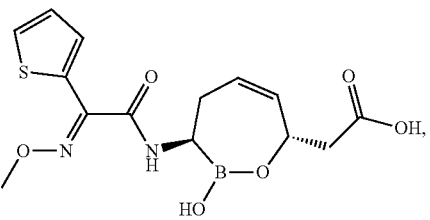
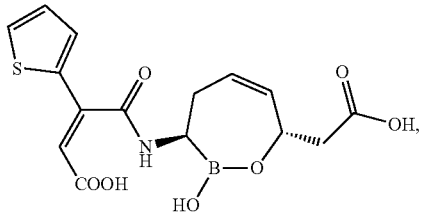
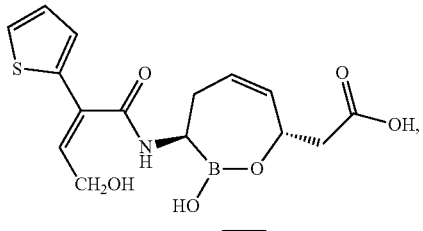
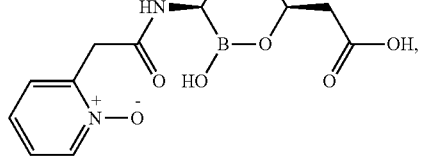

-continued
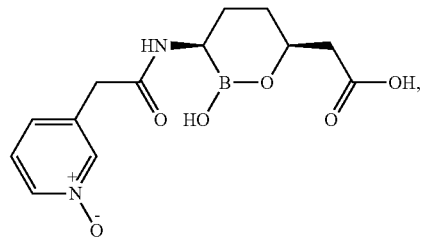
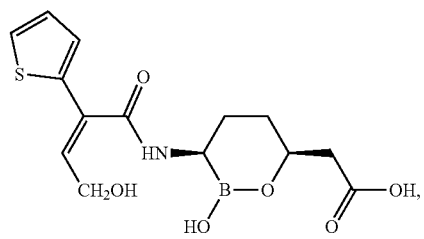
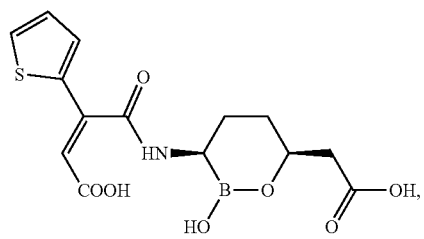
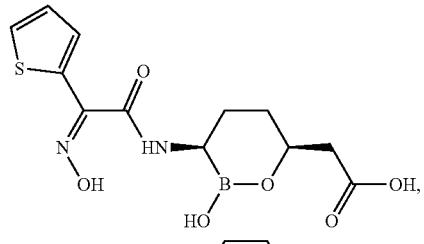
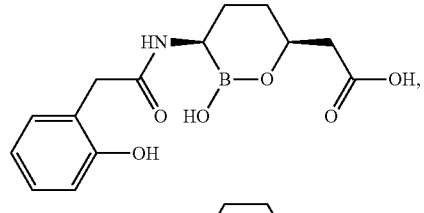
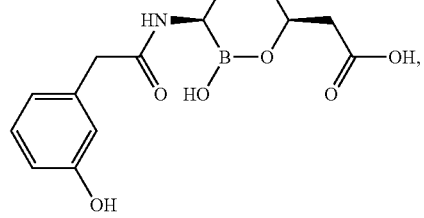
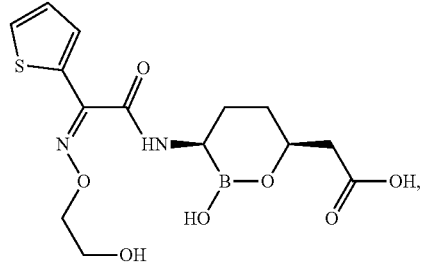
-continued
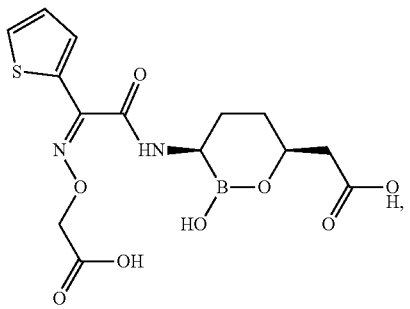
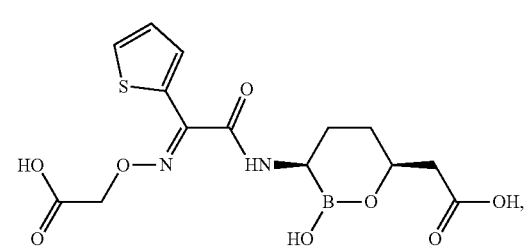
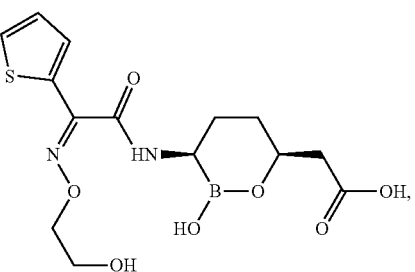
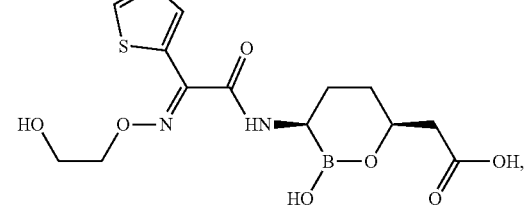
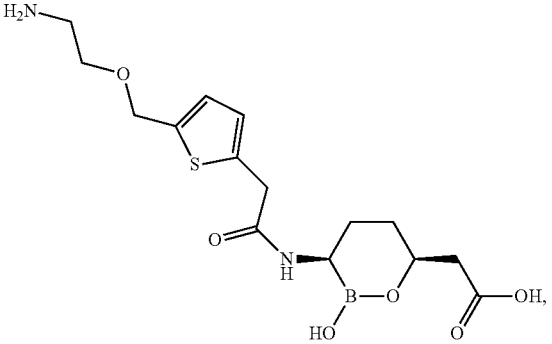
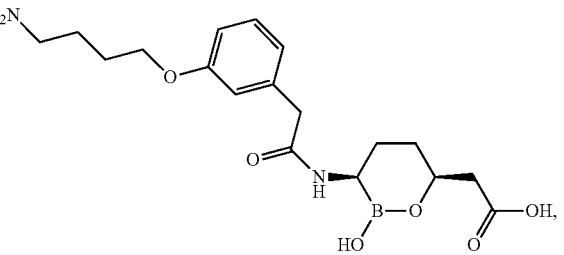

27
-continued
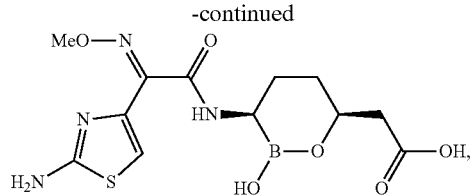
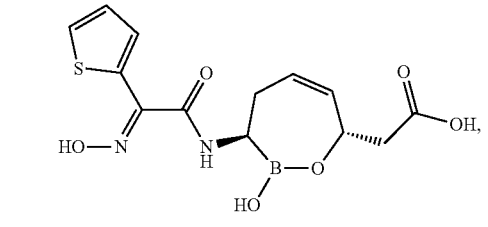
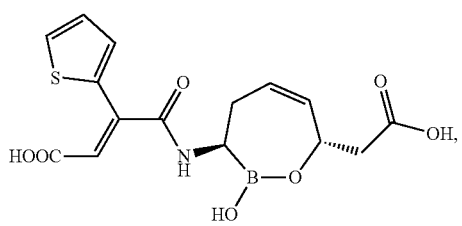
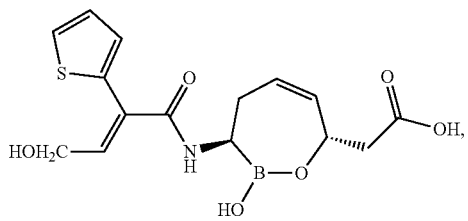
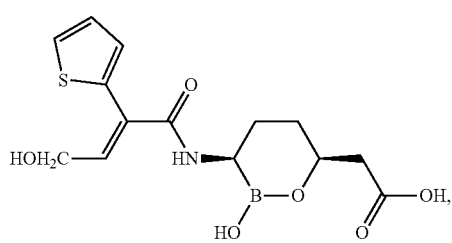
28
-continued
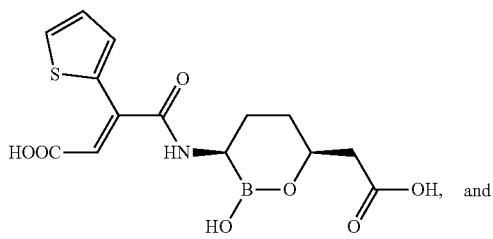
or a pharmaceutically acceptable salt thereof.
Some embodiments include compounds selected from the group consisting of:
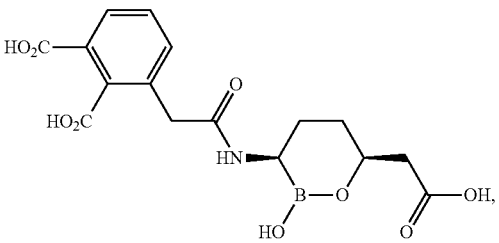
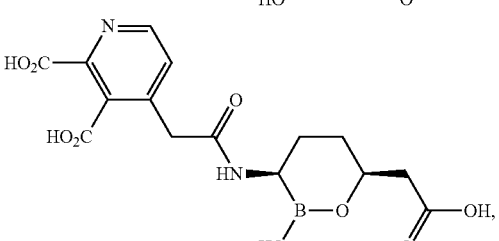
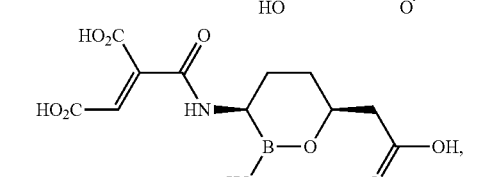
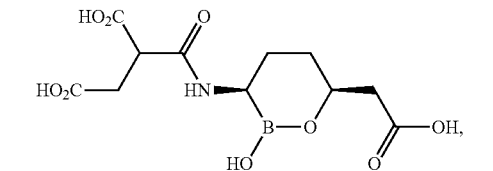
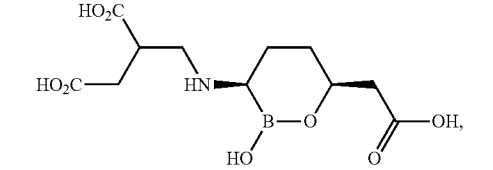

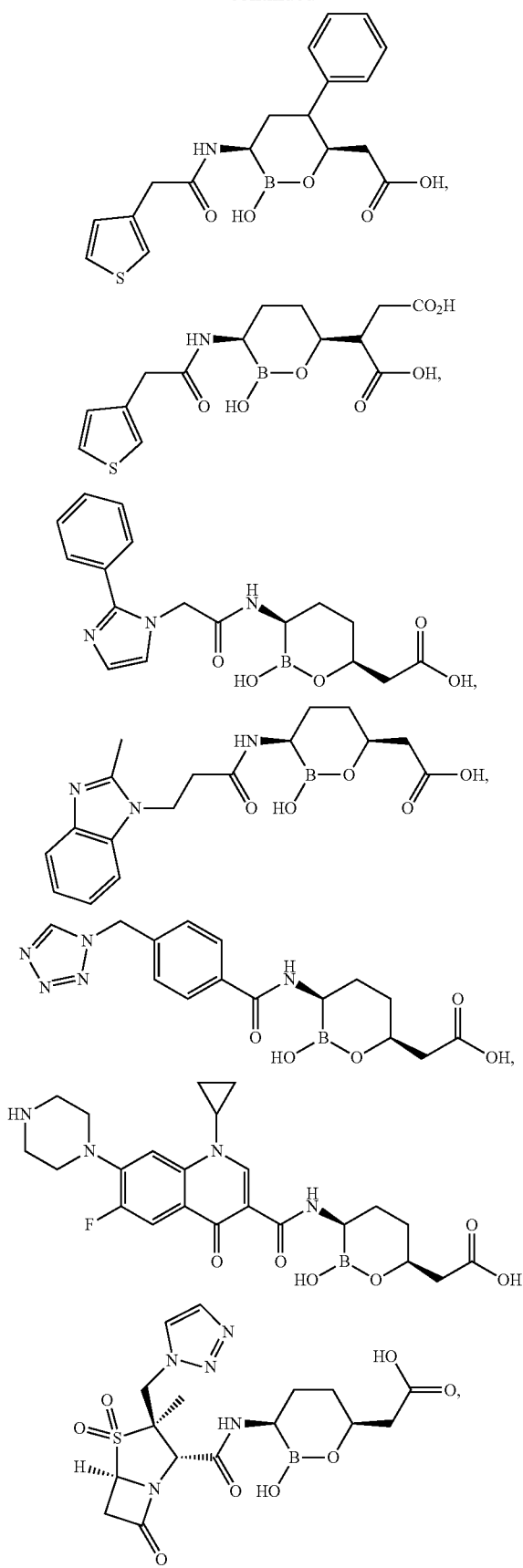
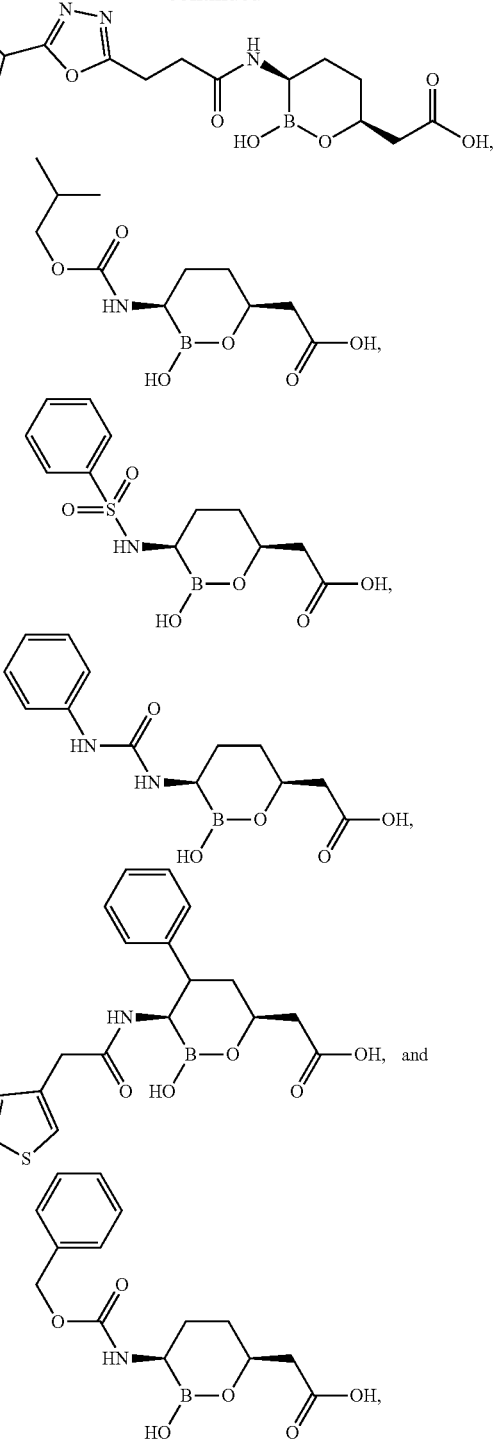
or a pharmaceutically acceptable salt thereof.
Definitions
Terms and substituents are given their ordinary meaning unless defined otherwise, and may be defined when introduced and retain their definitions throughout unless otherwise specified, and retain their definitions whether alone or as part of another group unless otherwise specified.

As used herein, "alkyl" means a branched, or straight chain saturated chemical group containing only carbon and hydrogen, such as methyl, isopropyl, isobutyl, sec-butyl and pentyl. In various embodiments, alkyl groups can either be unsubstituted or substituted with one or more substituents, e.g., halogen, hydroxyl, substituted hydroxyl, acyloxy, amino, substituted amino, amido, cyano, nitro, guanidino, amidino, mercapto, substituted mercapto, carboxy, sulfonyloxy, carbonyl, benzyloxy, aryl, heteroaryl, carbocyclyl, heterocyclyl, or other functionality that may be suitably blocked with a protecting group. Typically, alkyl groups will comprise 1 to 20 carbon atoms, 1 to 9 carbon atoms, preferably 1 to 6, and more preferably 1 to 5 carbon atoms.

As used herein, "alkenyl" means a straight or branched chain chemical group containing only carbon and hydrogen and containing at least one carbon-carbon double bond, such as 1-propenyl, 2-propenyl, 2-methyl-1-propenyl, 1-butenyl, 2-butenyl, and the like. In various embodiments, alkenyls can either be unsubstituted or substituted with one or more substituents, e.g., halogen, hydroxyl, substituted hydroxyl, acyloxy, amino, substituted amino, amido, cyano, nitro, guanidino, amidino, mercapto, substituted mercapto, carboxy, sulfonyloxy, carbonyl, benzyloxy, aryl, heteroaryl, carbocyclyl, heterocyclyl, or other functionality that may be suitably blocked with a protecting group. Typically, alkenyl groups will comprise 2 to 20 carbon atoms, 2 to 9 carbon atoms, preferably 2 to 6, and more preferably 2 to 5 carbon atoms.

As used herein, "alkynyl" means a straight or branched chain chemical group containing only carbon and hydrogen and containing at least one carbon-carbon triple bond, such as 1-propynyl, 1-butynyl, 2-butynyl, and the like. In various embodiments, alkynyls can either be unsubstituted or substituted with one or more substituents, e.g., halogen, hydroxyl, substituted hydroxyl, acyloxy, amino, substituted amino, amido, cyano, nitro, guanidino, amidino, mercapto, substituted mercapto, carboxy, sulfonyloxy, carbonyl, benzyloxy, aryl, heteroaryl, carbocyclyl, heterocyclyl, or other functionality that may be suitably blocked with a protecting group. Typically, alkynyl groups will comprise 2 to 20 carbon atoms, 2 to 9 carbon atoms, preferably 2 to 6, and more preferably 2 to 5 carbon atoms.

As used herein, "carbocyclyl" means a non-aromatic cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. In various embodiments, carbocyclyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked with a protecting group. Typically, carbocyclyl groups will comprise 3 to 10 carbon atoms, preferably 3 to 6.

As used herein, "cycloalkyl" means a fully saturated carbocyclyl ring system. Examples include cyclopropyl, cyclobutyl, cyclopentyl, and cyclohexyl.

As used herein, "cycloalkenyl" means a carbocyclyl ring system having at least one double bond. An example is cyclohexenyl.

As used herein, "lower alkyl" means a subset of alkyl, and thus is a hydrocarbon substituent, which is linear, or branched. Preferred lower alkyls are of 1 to about 4 carbons, and may be branched or linear. Examples of lower alkyl include butyl, propyl, isopropyl, ethyl, and methyl. Likewise, radicals using the terminology "lower" refer to radicals preferably with 1 to about 4 carbons in the alkyl portion of the radical.

As used herein, "aryl" means an aromatic radical having a single-ring (e.g., phenyl) or multiple condensed rings (e.g., naphthyl or anthryl) with only carbon atoms present in the ring backbone. In various embodiments, aryl groups can either be unsubstituted or substituted with one or more substituents, e.g., amino, cyano, hydroxyl, lower alkyl, haloalkyl, alkoxy, nitro, halo, mercapto, carboxy, carbonyl, benzyloxy, aryl, heteroaryl, and other substituents. Some embodiments include substitution with an alkoxy group, which may be further substituted with one or more substituents, e.g., amino, cyano, hydroxyl, lower alkyl, haloalkyl, alkoxy, nitro, halo, mercapto, and other substituents. A preferred aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). In various embodiments, heteroaryl groups can either be unsubstituted or substituted with one or more substituents, e.g., amino, cyano, hydroxyl, lower alkyl, haloalkyl, alkoxy, nitro, halo, mercapto, carboxy, carbonyl, benzyloxy, aryl, heteroaryl, and other substituents. Examples of heteroaryl include thienyl, pyridyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl, quinolinyl, quinazolinyl and others.

In these definitions it is contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl ring. Though many substituents will be useful, preferred substituents include those commonly found in aryl compounds, such as alkyl, cycloalkyl, hydroxy, alkoxy, cyano, halo, haloalkyl, mercapto and the like.

As used herein, "amide" or "amido" includes both RNR'CO— (in the case of R=alkyl, alkaminocarbonyl-) and RCONR'— (in the case of R=alkyl, alkyl carbonylamino-). "Amide" or "amido" includes a H—CON—, alkyl-CON—, carbocyclyl-CON—, aryl-CON—, heteroaryl-CON— or heterocyclyl-CON— group, wherein the alkyl, carbocyclyl, aryl or heterocyclyl group is as herein described.

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO—, alkyl-CO—, carbocyclyl-CO—, aryl-CO—, heteroaryl-CO— or heterocyclyl-CO— group wherein the alkyl, carbocyclyl, aryl or heterocyclyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo or halide" is a chloro, bromo, fluoro or iodo atom radical. Chloro and fluoro are preferred halides. The term "halo" also contemplates terms sometimes referred to as "halogen", or "halide".

As used herein, "heterocyclyl" means a non-aromatic cyclic ring system comprising at least one heteroatom in the ring system backbone. Heterocyclyls may include multiple fused rings. Heterocyclyls may have any degree of saturation provided that at least one ring in the ring system is not aromatic. The heteroatom(s) may be present in either a non-aromatic or aromatic ring in the ring system. In various embodiments, heterocyclyls may be substituted or unsubstituted with one or more substituents, e.g., halogen, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. Preferred heterocycles are of 5-7 members. In six membered monocyclic heterocycles, the heteroatom(s) are selected from one up to three of O, N or S, and when the heterocycle is five membered, preferably it has one or two heteroatoms selected from O, N, or S. Examples of heterocyclyl include pyrrolidinyl, piperidinyl, azepanyl, tetrahydrofuranyl, tetrahydropyranyl, oxepanyl, tetrahydrothiophenyl, tetrahydrothiopyranyl, thiepanyl, indolinyl and dihydrobenzofuranyl.

As used herein, "substituted amino" means an amino radical which is substituted by one or two alkyl, cycloalkyl, aryl, heteroaryl or heterocyclyl groups, wherein the alkyl, aryl, heteroaryl, cycloalkyl or heterocyclyl are defined as above.

As used herein, "substituted hydroxyl" means RO— group wherein R is an alkyl, an aryl, heteroaryl, cycloalkyl or a heterocyclyl group, wherein the alkyl, cycloalkyl, aryl, heteroaryl or heterocyclyl are defined as above.

As used herein, "substituted thiol" means RS— group wherein R is an alkyl, an aryl, heteroaryl, cycloalkyl or a heterocyclyl group, wherein the alkyl, cycloalkyl, aryl, heteroaryl or heterocyclyl are defined as above.

As used herein, "sulfonyl" means an alkylSO$_2$, arylSO$_2$, heteroarylSO$_2$, carbocyclylSO$_2$, or heterocyclyl-SO$_2$ group wherein the alkyl, carbocyclyl, aryl, heteroaryl or heterocyclyl are defined as above.

As used herein, "sulfamido" means an alkyl-N—S(O)$_2$N—, aryl-NS(O)$_2$N—, heteroaryl-NS(O)$_2$N—, carbocyclyl-NS(O)$_2$N or heterocyclyl-NS(O)$_2$N— group wherein the alkyl, carbocyclyl, aryl, heteroaryl or heterocyclyl group is as herein described.

As used herein, "sulfonamido" means an alkyl-S(O)$_2$N—, aryl-S(O)$_2$N—, heteroaryl-S(O)$_2$N—, carbocyclyl-S(O)$_2$N— or heterocyclyl-S(O)$_2$N— group wherein the alkyl, carbocyclyl, aryl, heteroaryl or heterocyclyl group is as herein described.

As used herein, "ureido" means an alkyl-NCON—, aryl-NCON—, heteroaryl-NCON—, carbocyclyl-NCON—, heterocyclyl-NCON— group or heterocyclyl-CON— group wherein the heterocyclyl group is attached by a ring nitrogen, and wherein the alkyl, carbocyclyl, aryl, heteroaryl or heterocyclyl group is as herein described.

As used herein, "guanidino" means an alkyl-NC(=NR')N—, aryl-NC(=NR')N—, heteroaryl-NC(=NR')N—, carbocyclyl-NC(=NR')N— or heterocyclyl-NC(=NR')N— group wherein R' is an H, substituted or unsubstituted hydroxyl, CN, alkyl, aryl, heteroaryl or a heterocyclyl group, wherein the alkyl, carbocyclyl, aryl, heteroaryl or heterocyclyl group is as herein described.

As used herein, a substituted group is derived from the unsubstituted parent group in which there has been an exchange of one or more hydrogen atoms for another atom or group. When substituted, the substituent group(s) is (are) substituted with one or more substituent(s) individually and independently selected from $C_1$-$C_6$ alkyl, $C_1$-$C_6$ alkenyl, $C_1$-$C_6$ alkynyl, $C_3$-$C_7$ carbocycle (optionally substituted with halo, alkyl, alkoxy, carboxyl, haloalkyl, CN, —SO$_2$-alkyl, —CF$_3$, and —OCF$_3$), $C_1$-$C_6$ heteroalkyl, 5-7 membered heterocyclyl (e.g., tetrahydrofuryl) (optionally substituted with halo, alkyl, alkoxy, carboxyl, CN, —SO$_2$-alkyl, —CF$_3$, and —OCF$_3$), aryl (optionally substituted with halo, alkyl, aryl optionally substituted with $C_1$-$C_6$ alkyl, arylalkyl, alkoxy, carboxyl, CN, —SO$_2$-alkyl, —CF$_3$, and —OCF$_3$), arylalkyl (optionally substituted with halo, alkyl, alkoxy, aryl, carboxyl, CN, —SO$_2$-alkyl, —CF$_3$, and —OCF$_3$), heteroaryl (optionally substituted with halo, alkyl, alkoxy, aryl, aralkyl, carboxyl, CN, —SO$_2$-alkyl, —CF$_3$, and —OCF$_3$), heteroarylalkyl (optionally substituted with halo, alkyl, alkoxy, aryl, carboxyl, CN, —SO$_2$-alkyl, —CF$_3$, and —OCF$_3$), halo (e.g., chloro, bromo, iodo and fluoro), cyano, hydroxy, $C_1$-$C_6$ alkoxy, $C_1$-$C_6$ alkoxyalkyl (i.e., ether), aryloxy, sulfhydryl (mercapto), halo($C_1$-$C_6$)alkyl (e.g., —CF$_3$), $C_1$-$C_6$ alkylthio, arylthio, amino (—NH$_2$), mono- and di-($C_1$-$C_6$)alkyl amino, quaternary ammonium salts, amino($C_1$-$C_6$)alkoxy (e.g, —O(CH$_2$)$_4$NH$_2$), amino($C_1$-$C_6$)alkoxyalkyl (e.g., —CH$_2$O(CH$_2$)$_2$NH$_2$), hydroxy($C_1$-$C_6$)alkylamino, amino($C_1$-$C_6$)alkylthio (e.g, —S(CH$_2$)$_2$NH$_2$), cyanoamino, nitro, carbamyl, oxo (=O), carboxy, glycolyl, glycyl, hydrazino, guanidinyl, sulfamyl, sulfonyl, sulfinyl, thiocarbonyl, thiocarboxy, C-amide, N-amide, N-carbamate, O-carbamate, and urea. Wherever a group is described as "optionally substituted" that group can be substituted with the above substituents.

In some embodiments, substituted group(s) is (are) substituted with one or more substituent(s) individually and independently selected from $C_1$-$C_6$ alkyl, $C_3$-$C_7$ carbocycle, amino (—NH$_2$), amino($C_1$-$C_6$)alkoxy, carboxyl, oxo (=O), $C_1$-$C_6$ alkylthio, amino($C_1$-$C_6$)alkylthio, guanidinyl, aryl, 5-7 membered heterocyclyl, heteroarylalkyl, hydroxy, halo, amino($C_1$-$C_6$)alkoxy, and amino($C_1$-$C_6$)alkoxyalkyl.

In some embodiments, substituted group(s) is (are) substituted with one or more substituent(s) individually and independently selected from $C_1$-$C_6$ alkyl, amino (—NH$_2$), amino($C_1$-$C_6$)alkoxy, carboxyl, oxo (=O), $C_1$-$C_6$ alkylthio, amino($C_1$-$C_6$)alkylthio, guanidinyl, hydroxy, halo, amino ($C_1$-$C_6$)alkoxy, and amino($C_1$-$C_6$)alkoxyalkyl.

In some embodiments, substituted group(s) is (are) substituted with one or more substituent(s) individually and independently selected from $C_1$-$C_6$ alkyl, amino (—NH$_2$), carboxyl, oxo (=O), guanidinyl, hydroxy, and halo.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical. For example, as used herein, "alkylene" means a branched, or straight chain saturated di-radical chemical group containing only carbon and hydrogen, such as methylene, isopropylene, isobutylene, sec-butylene, and pentylene, that is attached to the rest of the molecule via two points of attachment. As used herein, "alkenylene" means a straight or branched chain di-radical chemical group containing only carbon and hydrogen and containing at least one carbon-carbon double bond, such as 1-propenylene, 2-propenylene, 2-methyl-1-propenylene, 1-butenylene, and 2-butenylene, that is attached to the rest of the molecule via two points of attachment.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —SO$_3$H, —SO$_2$HNR$^9$, —PO$_2$(R$^9$)$_2$, —PO$_3$(R$^9$)$_2$, —CONHNHSO$_2$R$^9$, —COHNSO$_2$R$^9$, and —CONR⁹CN, where R⁹ is as defined above. In addition, carboxylic acid isosteres can include 5-7 membered carbocycles or heterocycles containing any combination of $CH_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with $R^9$ as defined above.

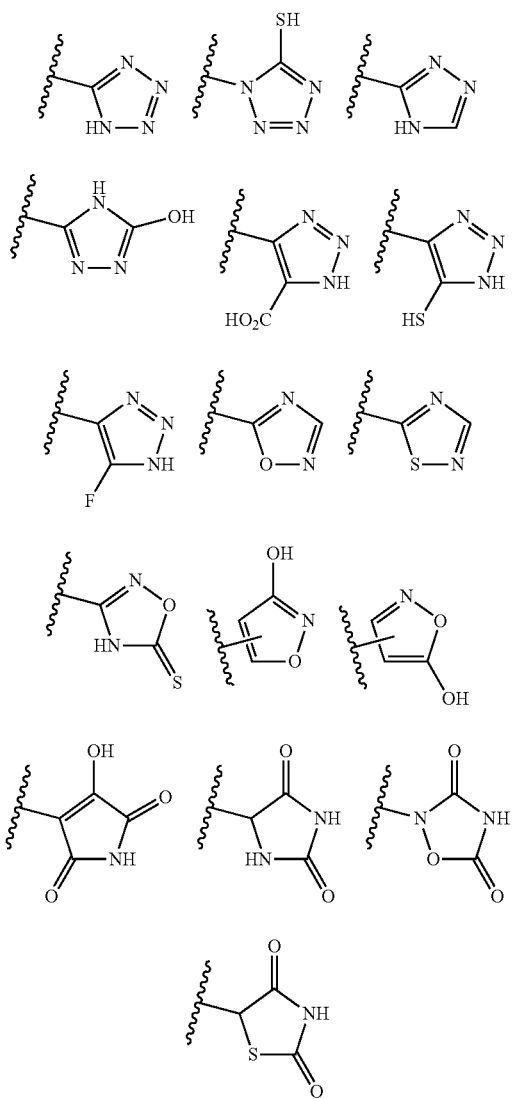

It is also contemplated that when chemical substituents are added to a carboxylic isostere, the compound retains the properties of a carboxylic isostere. It is contemplated that when a carboxylic isostere is optionally substituted with one or more moieties selected from $R^9$ as defined above, then the substitution and substitution position is selected such that it does not eliminate the carboxylic acid isosteric properties of the compound. Similarly, it is also contemplated that the placement of one or more $R^9$ substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

The skilled artisan will recognize that some structures described herein may be resonance forms or tautomers of compounds that may be fairly represented by other chemical structures, even when kinetically; the artisan recognizes that such structures are only a very small portion of a sample of such compound(s). Such compounds are considered within the scope of the structures depicted, though such resonance forms or tautomers are not represented herein.

In some embodiments, due to the facile exchange of boron esters, the compounds described herein may convert to or exist in equilibrium with alternate forms. Accordingly, in some embodiments, the compounds described herein may exist in combination with one or more of these forms. For example, Compound 5 may exist in combination with one or more open-chain form (5a), dimeric form (5b), cyclic dimeric form (5c), trimeric form (5d), cyclic trimeric form (5e), and the like.

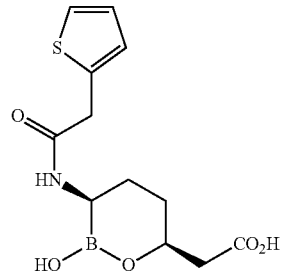

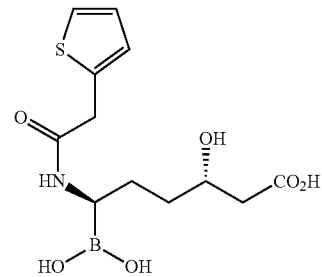

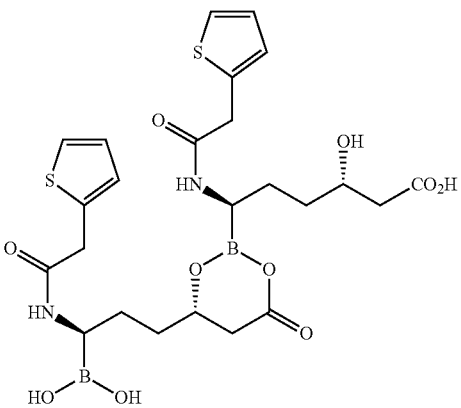

-continued

5c

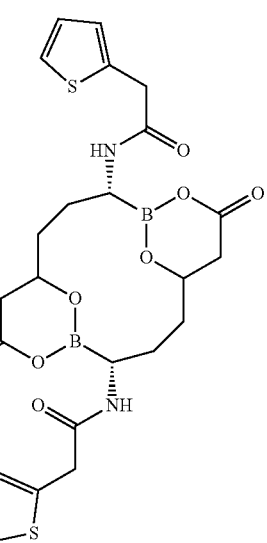

5d

5e

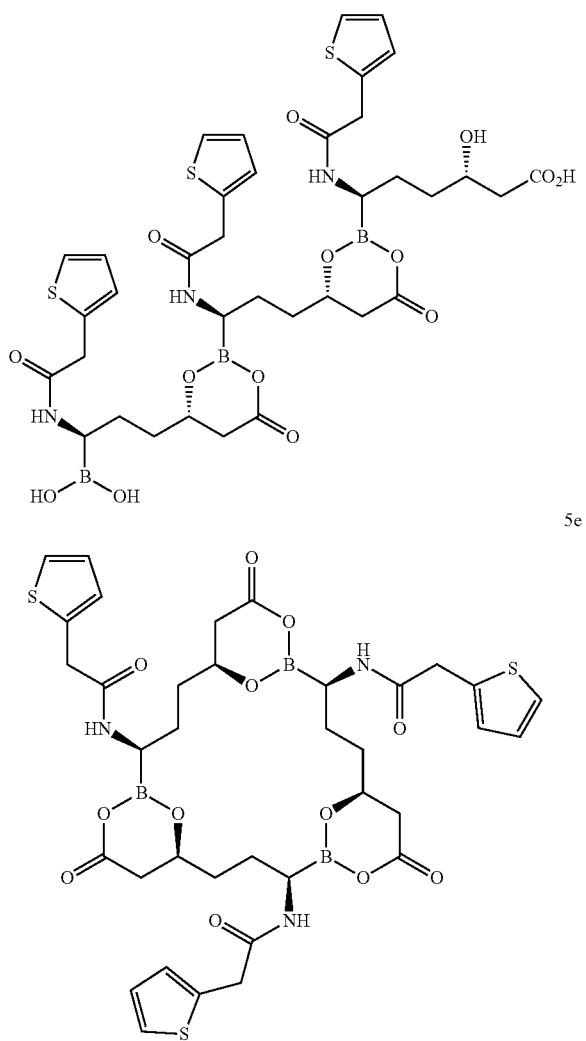

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes humans, cattle, horses, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

"Solvate" refers to the compound formed by the interaction of a solvent and an EPI, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection, whereby the treatment reduces the likelihood that the patient will develop an infection. The term "therapeutic treatment" refers to administering treatment to a patient already suffering from an infection.

Administration and Pharmaceutical Compositions

Some embodiments include pharmaceutical compositions comprising: (a) a safe and therapeutically effective amount of the cyclic boronic acid ester derivative, or its corresponding enantiomer, diastereoisomer or tautomer, or pharmaceutically acceptable salt; and (b) a pharmaceutically acceptable carrier.

The cyclic boronic acid ester derivatives are administered at a therapeutically effective dosage, e.g., a dosage sufficient to provide treatment for the disease states previously described. While human dosage levels have yet to be optimized for the compounds of the preferred embodiments, generally, a daily dose for most of the cyclic boronic acid ester derivatives described herein is from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonary, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety.

In addition to the selected compound useful as described above, come embodiments include compositions containing a pharmaceutically-acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents;

tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. These oral forms comprise a safe and effective amount, usually at least about 5%, with a maximum of about 90%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The resulting composition may be infused into the patient over a period of time. In various embodiments, the infusion time ranges from 5 minutes to continuous infusion, from 10 minutes to 8 hours, from 30 minutes to 4 hours, and from 1 hour to 3 hours. In one embodiment, the drug is infused over a 3 hour period. The infusion may be repeated at the desired dose interval, which may include, for example, 6 hours, 8 hours, 12 hours, or 24 hours.

The compositions for intravenous administration may be provided to caregivers in the form of one more solids that are reconstituted with a suitable diluent such as sterile water, saline or dextrose in water shortly prior to administration. Reconstituted concentrated solutions may be further diluted into a parenteral solutions haing a volume of from about 25 to about 1000 ml, from about 30 ml to about 500 ml, or from about 50 ml to about 100 ml. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Kits for Intravenous Administration

Some embodiments include a kit comprising a compound described herein and an additional agent, such as an antimicrobial agent. In one embodiment, both components are provided in a single sterile container. In the case of solids for reconstitution, the agents may be pre-blended and added to the container simultaneously or may be dry-powder filled into the container in two separate steps. In some embodiments, the solids are sterile crystalline products. In other embodiment, the solids are lyophiles. In one embodiment, both components are lyophilized together. Non-limiting examples of agents to aid in lyophilization include sodium or potassium phosphates, citric acid, tartaric acid, gelatin, and carbohydrates such as dextrose, mannitol, and dextran. One embodiment includes non-sterile solids that are irradiated either before or after introduction into the container.

In the case of a liquid, the agents may be dissolved or dispersed in a diluent ready for administration. In another embodiment, the solution or dispersion may be further diluted prior to administration. Some embodiments include providing the liquid in an IV bag. The liquid may be frozen to improve stability.

In one embodiment, the container includes other ingredients such as a pH adjuster, a solubilizing agent, or a dispersing agent. Non-limiting examples of pH adjusters include NaOH, sodium carbonate, sodium acetate, HCl, and citric acid.

The molar ratio of compound described herein to additional agent (e.g., antibacterial agent) may be from about 10:1 to 1:10, 8:1 to 1:8, 5:1 to 1:5, 3:1 to 1:3, 2:1 to 1:2, or about 1:1. In various embodiments the amount of compound described herein may be from 100 mg to 5 g, 500 mg to 2 g, or about 1 g. Similarly, in various embodiments the amount of additional agent may be from 100 mg to 5 g, 500 mg to 2 g, or about 1 g.

In an alternative embodiment, the two components may be provided in separate containers. Each container may include a solid, solution, or dispersion. In such embodiments, the two containers may be provided in a single package or may be provided separately. In one embodiment, the compound described herein is provided as a solution while the additional agent (e.g., antibacterial agent) is provided as a solid ready for reconstitution. In one such embodiment, the solution of the compound described herein is used as the diluent to reconstitute the other agent.

Methods of Treatment

Some embodiments of the present invention include methods of treating bacterial infections with the compounds and compositions comprising cyclic boronic acid ester derivatives described herein. Some methods include administering a compound, composition, pharmaceutical composition described herein to a subject in need thereof. In some embodiments, a subject can be an animal, e.g., a mammal, a human. In some embodiments, the bacterial infection comprises a bacteria described herein. As will be appreciated from the foregoing, methods of treating a bacterial infection include methods for preventing bacterial infection in a subject at risk thereof.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. When combining the agents in a single dosage form, they may be physically mixed (e.g, by co-dissolution or dry mixing) or may form an adduct or be covalently linked such that they split into the two or more active ingredients upon administration to the patient. In another embodiment, the agents are administered sequentially. In one embodiment the agents are administered through the same route, such as orally. In another embodiment, the agents are administered through different routes, such as one being administered orally and another being administered i.v.

Examples of additional medicaments include an antibacterial agent, antifungal agent, an antiviral agent, an anti-inflammatory agent and an anti-allergic agent.

Some embodiments include co-administration of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04, 546, ME1036, BAL30072, SYN 2416, Ceftiofur, Cefquinome, Cefovecin, Aztreonam, Tigemonam, Carumonam, RWJ-442831, RWJ-333441, and RWJ-333442.

Preferred embodiments include β-lactams such as Ceftazidime, Biapenem, Doripenem, Ertapenem, Imipenem, Meropenem, ME1036, Tomopenem, Razupenem, and Panipenem.

Some embodiments include co-administration of the compounds, compositions and/or pharmaceutical compositions described herein with an additional agent, wherein the additional agent comprises a monobactam. Examples of monobactams include aztreonam, tigemonam, BAL 30072, SYN 2416 (BAL19764), and carumonam.

Some embodiments include co-administration of the compounds, compositions and/or pharmaceutical compositions described herein with an additional agent, wherein the additional agent comprises a Class A, B, C, or D beta-lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Other examples of beta-lactamase inhibitors administred as an additional agent include clavulanic acid, tazobactam, sulbactam, avibactam (NXL-104), WK-7655, and BAL29880. MK-7655 has the following structure:

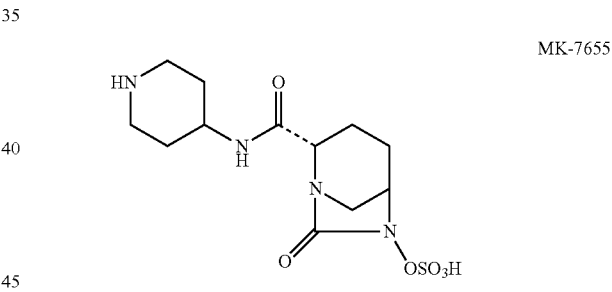

MK-7655

Indications

The compounds and compositions comprising cyclic boronic acid ester derivatives described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Neisseria, Bacillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysente-* riae, *Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtherias, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

The following examples will further describe the present invention, and are used for the purposes of illustration only, and should not be considered as limiting.

EXAMPLES

General Procedures

Materials used in preparing the cyclic boronic acid ester derivatives described herein may be made by known methods or are commercially available. It will be apparent to the skilled artisan that methods for preparing precursors and functionality related to the compounds claimed herein are generally described in the literature including, for example, procedures described in U.S. Pat. No. 7,271,186 and WO2009064414, each of which is incorporated by reference in its entirety. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

($^1$H) nuclear magnetic resonance spectra (NMR) were measured in the indicated solvents on either a Bruker NMR spectrometer (Avance TM DRX500, 500 MHz for 1H) or Varian NMR spectrometer (Mercury 400BB, 400 MHz for 1H). Peak positions are expressed in parts per million (ppm) downfield from tetramethylsilane. The peak multiplicities are denoted as follows, s, singlet; d, doublet; t, triplet; q, quartet; quin, quintet; sex, sextet; sep, septet; non, nonet; dd, doublet of doublets; td, triplet of doublets; m, multiplet.

The following abbreviations have the indicated meanings:
n-BuLi=n-butyllithium
t-Bu=tert-butyl
DCM=dichloromethane
DMF=N,N-dimethylformamide
DIPEA=diisopropylethylamine
EDCI=1-ethyl-3-(3-dimethylaminopropyl) carbodiimide
ESBL=extended-spectrum β-lactamase
ESIMS=electron spray mass spectrometry
EtOAc=ethyl acetate
EtOH=ethanol
HATU=2-(7-aza-1H-benzotriazole-1-yl)-1,1,3,3-tetramethyluronium hexafluorophosphate
HCl=hydrochloric acid
HOBt=hydroxybenzotriazole
Im=imidazole
LiHMDS=lithium bis(trimethylsilyl)amide
MeCN=acetonitrile
NaHCO$_3$=sodium bicarbonate
Na$_2$SO$_4$=sodium sulfate
NMM=N-methylmorpholine
NMR=nuclear magnetic resonance
Pd/C=palladium on carbon
TBDMSCl=tert-butyldimethylsilyl chloride
TBS=tert-butyldimethylsilyl
TFA=trifluoroacetic acid
THF=tetrahydrofuran TLC=thin layer chromatography
TMS=trimethylsilyl
TPPB=tris(pentafluorophenyl)borane monohydrate The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

Compounds of formula I where $R^1$ is an acylamino group and X is a carboxylic acid can be prepared as depicted in Scheme 1.

Scheme 1

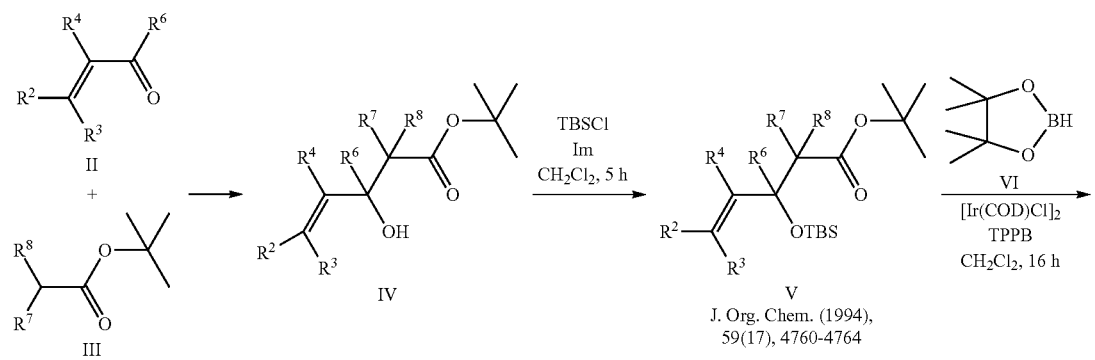

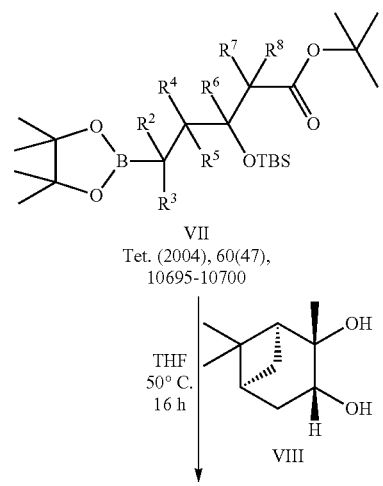

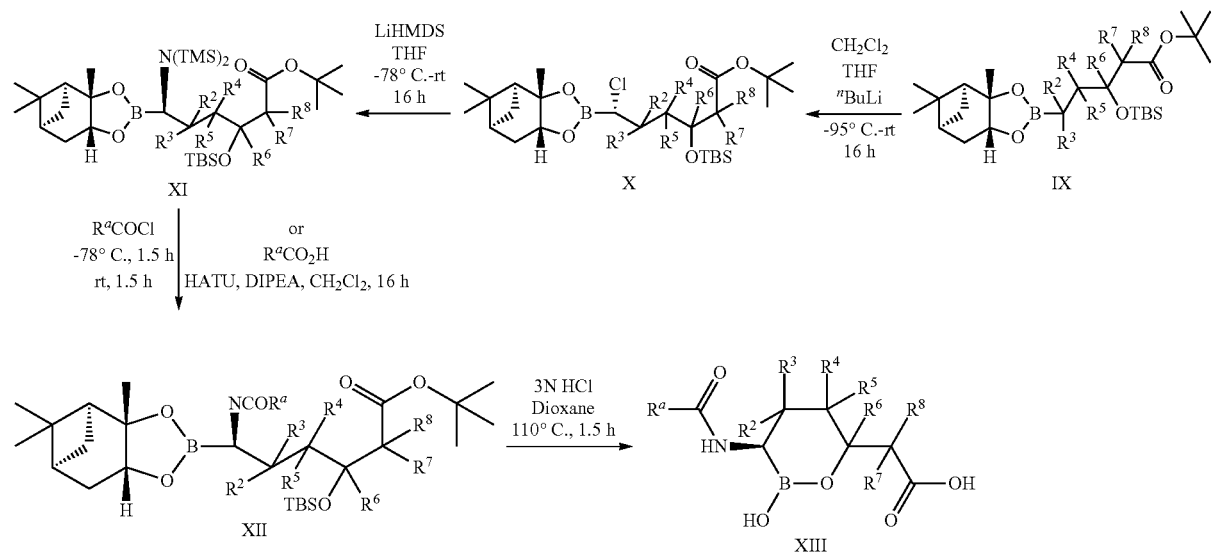

The addition of enolates to substituted α,β-unsaturated ketones or aldehydes to form β-hydroxy esters is a well-known reaction (Scheme 1). Substituents $R^7$ and $R^8$ of formula I may be controlled by use of the appropriate α-mono or di-substituted ester III. Similarly, substituents $R^2$, $R^3$, and $R^4$ may be controlled by use of the appropriate substituted substituted α,β-unsaturated ketones or aldehydes analog II. Precursors of structure IV, where $R^6$ and $R^7$ or $R^8$ are combined together, may be made following the known procedures [*J. Am. Chem. Soc.* (1982), 104, 1735-7, *Tetrahedron Lett.* (2003), 44, 1259-62]. The β-hydroxy ester of structure IV is protected with an acid-sensitive protecting group, affording V; this selection allows simultaneous deprotection of the boronate ester and hydroxyl protecting group in the final step, resulting in a cyclized product. The pinacol boronate VII is formed from substituted V using iridium catalysis [*Tetrahedron* (2004), 60, 10695-700]. Trans-esterification was readily achieved with optically active pinane diol VIII to result in IX [*Tetrahedron: Asymmetry*, (1997), 8, 1435-40]. Transesterification may also be achieved from the catechol ester analog of VII. Such catechol esters can be made by reaction of V with commercially available catechol borane [*Tetrahedron* (1989), 45, 1859-85]. Homologation of IX to give chloromethylene addition product X with good stereocontrol may be achieved via Matteson reaction conditions (WO0946098). The chloro derivative X can be utilized to introduce a substituted amine group at the C3-position of the oxaborinane-2-ol. Stereospecific substitution with hexamethyldisilazane gives the corresponding bis(trimethylsilyl) amide XI which may be reacted in situ with an acid chloride to result directly in analogs of structure XII Such analogs of XII can also be made via coupling of the bis-TMS amine with commercially available carboxylic acids under typical amide coupling conditions (e.g., carbodiimide or HATU coupling). Compounds of Formula 1 where $R^1$ is substituted with —N($R^9$)C(=O)C(=NO$R^9$)$R^9$ may be synthesized from corresponding carboxylic acids via coupling of XI to XII as in scheme 1. Such carboxylic acids can be made by following the procedures described U.S. Pat. No. 5,888,998, U.S. Application Publication No. 2004/0019203, and U.S. Pat. No. 4,822,786, all of which are incorporated herein by reference in their entirety. Simultaneous deprotection of the pinane ester, the tert-butyldimethylsilyloxy group and the tert-butyl ester group and concomitant cyclization are achieved by heating with dilute HCl, affording the desired oxaborinane derivatives of structure XIII This transformation may also be achieved by treatment with $BCl_3$ or $BBr_3$. Alternatively, the deprotection may be attained via trans-esterification with isobutyl boronic acid in presence of dilute HCl (WO09064413).

Scheme 2

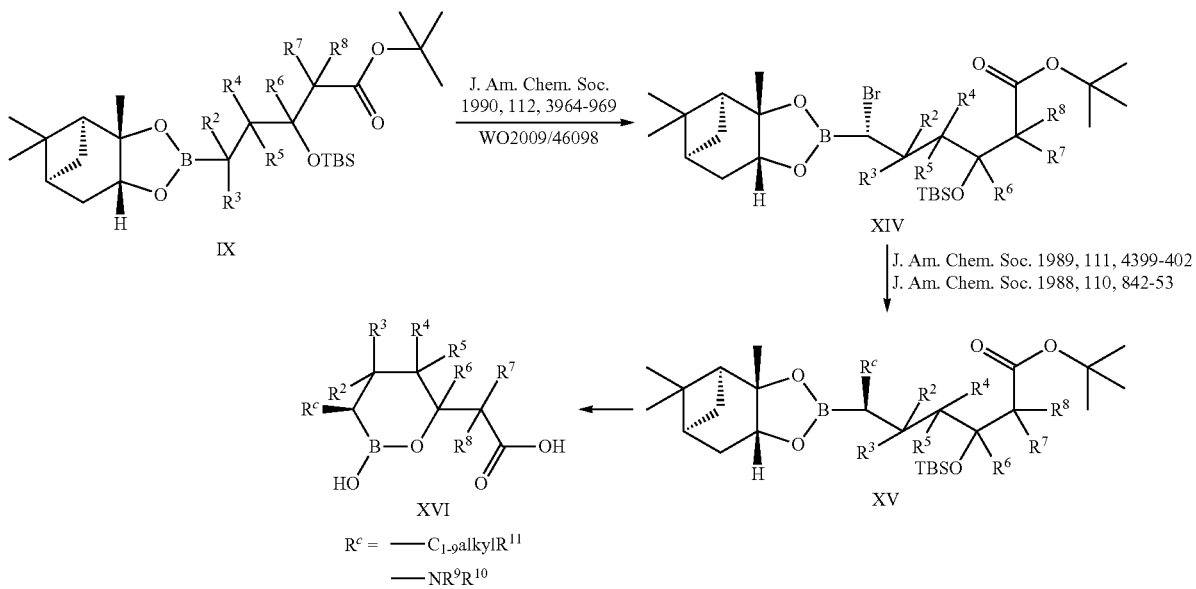

Compounds of structure XVI where $R^1$ of Formula I is an alkyl, aralkyl or aminoaryl group may be made from bromo intermediate XIV as shown in Scheme 2 [*J. Organomet. Chem.* (1992), 431, 255-70]. Such bromo derivatives may be made as analogously to the chloro compounds of Scheme 1, utilizing dibromomethane [*J Am. Chem. Soc.* (1990), 112, 3964-969]. Displacement of the bromo group in XIV can be achieved by α-alkoxy substituted alkyllithium agents [*J. Am. Chem. Soc.* (1989), 111, 4399-402; *J. Am. Chem. Soc.* (1988), 110, 842-53] or organomagnesium reagents (WO0946098) or by the sodium salt of alkyl or aryl carbamate derivatives [*J. Org. Chem.* (1996), 61, 7951-54], resulting in XV. Cyclization of XV to afford XVI may be achieved under the conditions described in Scheme 1.

Scheme 3

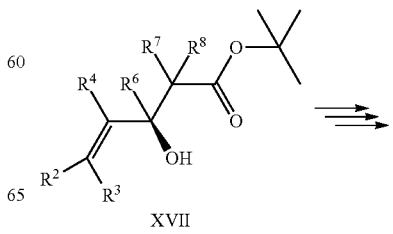

Scheme 4

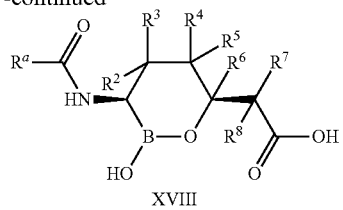

XVIII

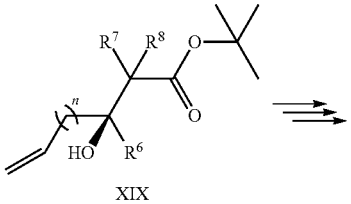

XIX

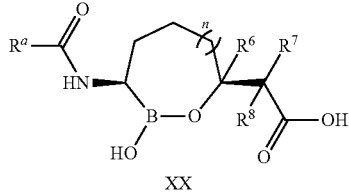

XX

Compounds of formula XIII and XVI are mixtures of 3,6-cis- and 3,6-trans-isomers. These analogs can be made in enantiomerically pure form as single isomers by starting (as in Scheme 1) with a single enantiomer (XVII), as shown in Scheme 3. A variety of methods to prepare such enantiomerically pure β-hydroxy esters are known in literature, for example via resolution [*Org. Lett.*, (2008), 10, 3907-09] or stereoselective synthesis [*Tetrahedron*, (2000), 56, 917-47]. Such single isomers result in enantiomerically pure cis-compounds XIII or XVI when used in the sequences depicted in Schemes 1 and 2.

The sequence shown in Scheme 1 also allows for varied ring sizes in formula I such as 7- and 8-membered rings. For example, a seven-membered analog XX where n=1 can be achieved by using the corresponding allyl intermediate (XIX) as a starting material (Scheme 4). Such allyl derivatives as XIX can be made utilizing one of several well known β-hydroxy ester preparations [*Tetrahedron* (2007), 63, 8336-50]. Intermediate XIX where n=2 can be prepared as described in Scheme 1 to give corresponding 8-membered compound of structure XX starting from pent-4-ene-1-al [*J. Med. Chem.* (1998), 41(6), 965-972].

Scheme 5

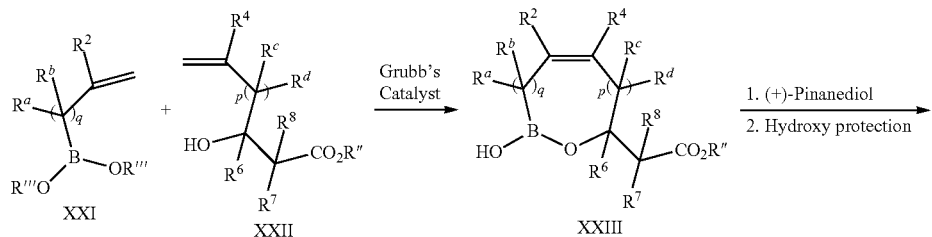

XXI + XXII →(Grubb's Catalyst)→ XXIII →(1. (+)-Pinanediol; 2. Hydroxy protection)→

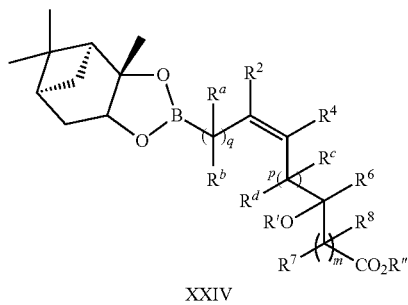

XXIV

Matteson Homologation-Amide formation:
1. DCM n-BuLi, THF
2. LiHMDS
3. R⁹COCl or R⁹CO₂H, EDCI HOBt

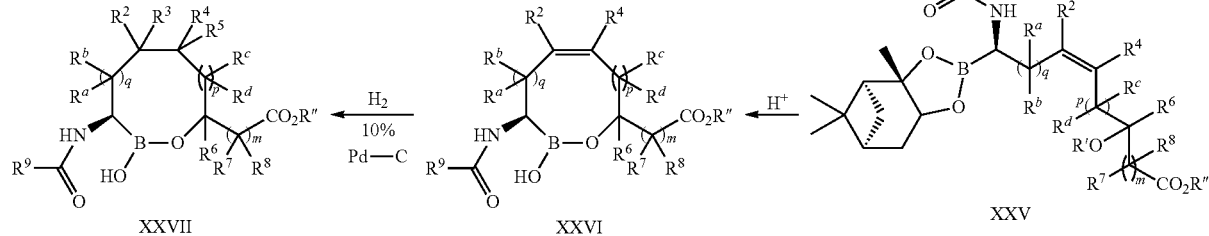

Compounds of formula XXVI and XXVII can be made following the sequence depicted in Scheme 5. Ring-Closing Metathesis reaction with boronated olefins (XXI) and olefin substituted β-hydroxy esters (XXII) result in cyclic boronates of formula XXIII Such cyclic boronates (XXIII) undergo ready esterification with (+)-pinane diol to give required Matteson reaction precursors upon protection of the resulting alcohol with groups such as t-butyldimethylsilyl- or benzyl or trityl. Matteson homologation followed by amide formation result in compounds of formula XXV with high stereoselectivity, as described above. Acid mediated hydrolysis of compounds of XXV upon deprotection give cyclic boronate (XXVI). Double bond substitution of XXVI can be further modified to other analogs such as saturated cyclic boronate (XXVII) by catalytic hydrogenation. The above sequence can be utilized to make 7- or 8-membered rings with double bond at a desired position by varying p and q of XXI and XXII.

Scheme 6

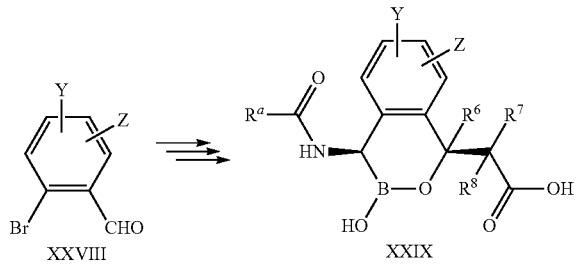

Compounds of formula I where $R^2$ and $R^4$ taken together form an aryl ring can be made from commercially available substituted aryl precursors as XXVIII. Substitution of the bromine atom by a boronate ester may be done under palladium catalyzed conditions [*Tetrahedron* (2002), 58, 9633-95]. The steps of hydroxy ester formation, α-amidoboronate preparation and cyclization can be attained by synthetic steps analogous to those in Scheme 1 to give compounds XXIX.

Scheme 7

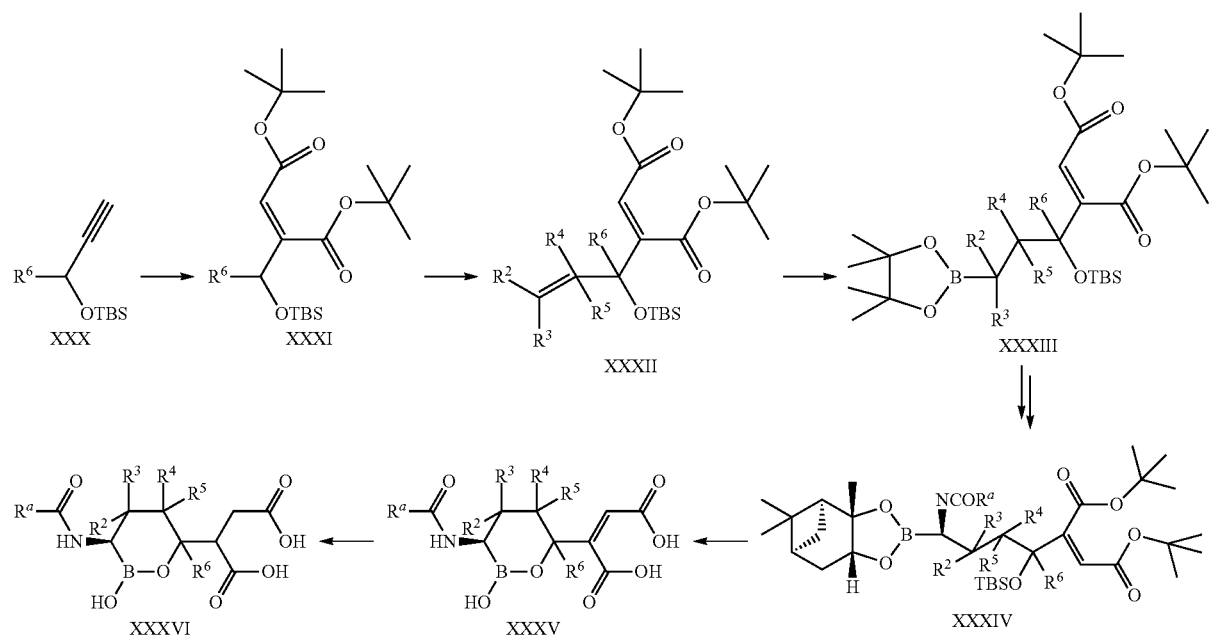

Compounds of formula I where $R^7$ and $R^8$ are substituted as maleate (XXXV) or succinate (XXXVI) may be made following the sequence shown in Scheme 7. Maleate intermediates such as XXXII can be transformed to analogs XXXV analogously to the steps in Scheme 1. Analogs of XXXV can be further transformed to the corresponding succinic acids of structure XXXVI by catalytic hydrogenation. Maleate intermediate XXXII may be assembled from intermediate XXXI by successive deprotection of the TBS group, oxidation to the aldehyde, addition of vinyl Grignard and reprotection as a TBS ether. Intermediate XXXI may be formed from a protected propargylic alcohol XXX following methods known in the literature [*Tetrahedron*, (2002), 58, 6545-54].

Compounds of Formula I where X is a carboxylic acid isostere can be prepared following the protocols described in the literature (see *J. Med. Chem.* 2011, 54, 2529-2591, which is incorporated herein by reference in its entirety).

Illustrative Compound Examples

Synthesis of 2-((3R)-2-hydroxy-3-(2-(thiophen-2-yl)acetamido)-1,2-oxaborinan-6-yl)acetic acid An example synthesis of 1 is depicted in Scheme 8 and Example 1.

Example 1

Step 1

A round-bottom flask charged with [Ir(cod)Cl]$_2$ (350 mg, 0.52 mmol) and 1,4-bis(diphenylphosphanyl)butane (446 mg, 1.04 mmol) was flushed with argon. DCM (60 mL), pinacolborane (3 mL, 21 mmol) and tert-butyl-3-(tert-butyldimethylsilyloxy)pent-4-enoate XXXVII [*J. Org. Chem.*, (1994), 59(17), 4760-4764] (5 g, 17.48 mmol) in 5 mL of DCM were added successively at room temperature. The mixture was then stirred at room temperature for 16 h. The reaction was quenched with MeOH (3 mL) and water (10 mL), the product was extracted with ether, and dried. Chromatography on silica gel (100% DCM→50% EtOAc/DCM gave tert-butyl 3-(tert-butyldimethylsilyloxy)-5-(4,4,5,5-tetramethyl-1,3,2-dioxaborolan-2-yl)pentanoate XXXVIII (5.5 g, 13.2 mmol, 75.5% yield).

Step 2

To a solution of tert-butyl 3-(tert-butyldimethylsilyloxy)-5-(4,4,5,5-tetramethyl-1,3,2-dioxaborolan-2-yl)pentanoate XXXVIII (5.4 g, 13 mmol) in THF (25 mL) was added (1S,2S,3R,5S)-2,6,6-trimethylbicyclo[3.1.1]heptane-2,3-diol (2.4 g, 14.3 mol) at room temperature. The reaction mixture was stirred for 16 h and then was concentrated under

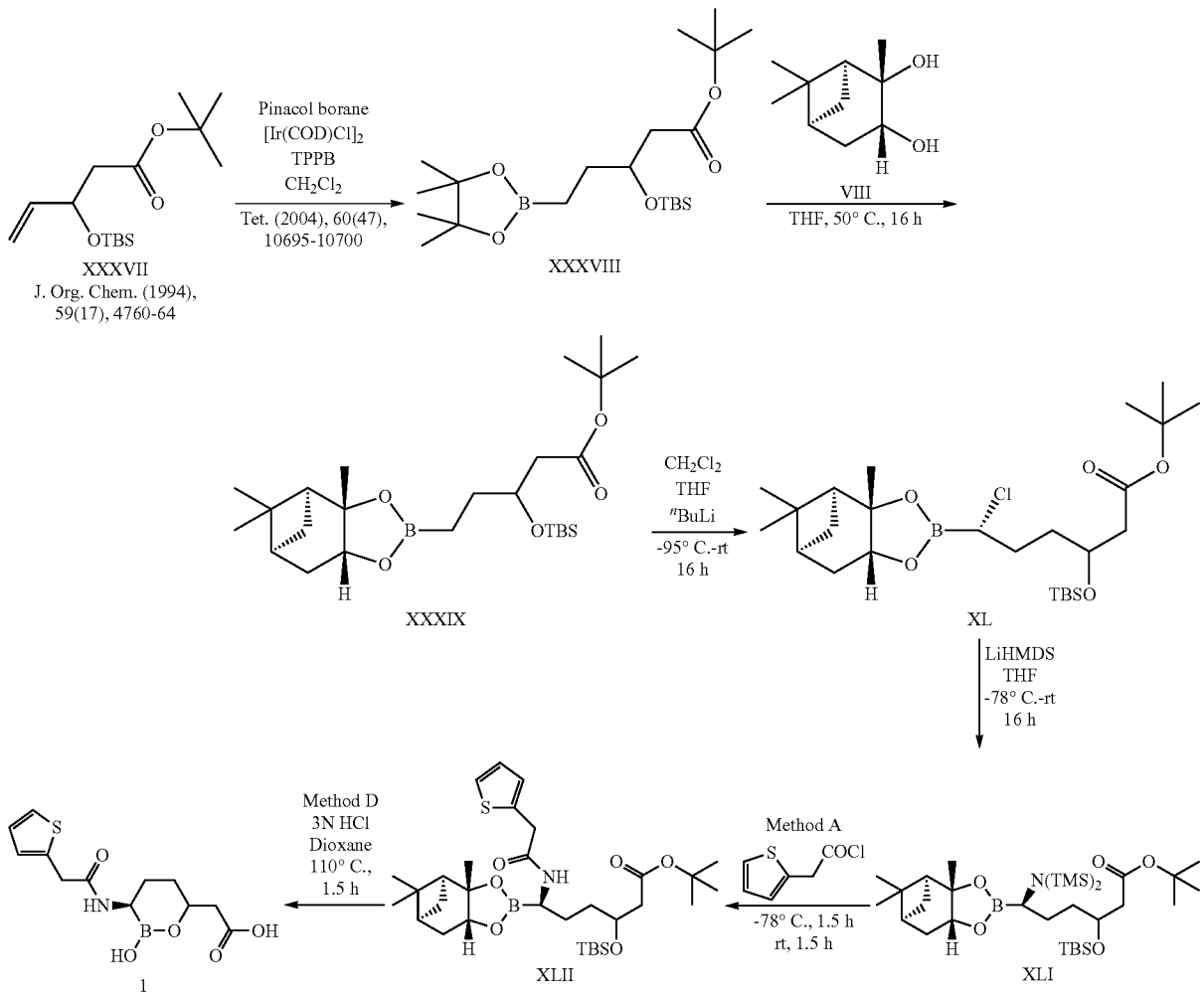

Scheme 8 vacuum. The residue was purified by column chromatography (100% hexane→40% EtOAc/hexane) on silica gel to give 1-(tert-butoxy)-3-[(tert-butyldimethylsilyl)oxy]-1-oxo-6-[(2S,6R)-2,9,9-trimethyl-3,5-dioxa-4-boratricyclo[6.1.1.0$^{2,6}$]decan-4-yl]hexan-3-yl XXXIX (5.5 g, 11 mmol, 84.6% yield).

Step 3

To a solution of DCM (1.5 mL, 23.6 mmol) in THF (30 mL) at −100° C. was added 2.5 M n-butyl lithium in hexane (5.19 mL, 12.98 mmol) slowly under nitrogen and down the inside wall of the flask whilst maintaining the temperature below −90° C. The resulting white precipitate was stirred for 30 minutes before the addition of 1-(tert-butoxy)-3-[(tert-butyldimethyl silyl)oxy]-1-oxo-6-[(2S,6R)-2,9,9-trimethyl-3,5-dioxa-4-boratricyclo[6.1.1.0$^{2,6}$]decan-4-yl]hexan-3-yl XXXIX (5.5 g, 11 mmol) in THF (10 mL) at −90° C. Zinc chloride (23.6 mL, 0.5 M in diethyl ether, 11.86 mmol) was then added to the reaction mixture at −90° C. and then the reaction was allowed to warm to room temperature where it was stirred for 16 h. The reaction was quenched with a saturated solution of ammonium chloride and the phases were separated. The aqueous phase was then extracted with diethyl ether (3×50 mL) and the combined organic extracts were dried over Na$_2$SO$_4$, filtered and concentrated under reduced pressure. The concentrated material was then chromatographed (100% hexane→50% EtOAc/hexane) to obtain 6-(tert-butoxy)-4-[(tert-butyl dimethyl silyl)oxy]-1-chloro-6-oxo-1-[(2S,6R)-2,9,9-trimethyl-3,5-dioxa-4-boratricyclo[6.1.1.0$^{2,6}$]decan-4-yl]hexyl XL (5.6 g, 10.5 mmol, 95.4% yield).

Step 4-5

Chloro intermediate XL (1.2 g, 2.33 mmol) in THF (10 mL) was cooled to −78° C. under nitrogen. A solution of LiHMDS (2.33 mL, 1.0 M in THF, 2.33 mmol) was added slowly and the reaction flask was then allowed to warm to room temperature where it was stirred for 16 h. Method A: The resulting was cooled to −78° C. and 5-thiopheneacetyl chloride was added and the solution stirred at −78° C. for 1.5 h. Then, the cooling bath was removed and the solution stirred at ambient temperature for 1.5 h. The reaction was quenched with water and extracted twice with EtOAc. The organic layers were combined, washed with water, brine, dried (Na$_2$SO$_4$) and concentrated in vacuo to afford a pale yellow solid as crude product. The residue was chromatographed on a silica column (100% DCM→40% EtOAc/DCM) to afford 570 mg of 6-(tert-butoxy)-4-[(tert-butyldimethylsilyl)oxy]-6-oxo-1-(thiophen-2-ylacetamido)-1-[(2S,6R)-2,9,9-trimethyl-3,5-dioxa-4-boratricyclo[6.1.1.0$^{2,6}$]decan-4-yl]hexylidyne XLII as a white solid (570 mg, 0.92 mmol, 39.5% yield).

Step 6

Method D:

To a solution of amide XLII (250 mg, 0.40 mmol) in 1,4-dioxane (10 mL) was added 10 mL of 3 N HCl. The mixture was heated to 110° C. for 90 min. The solution was cooled and diluted with 10 mL of water and extracted twice with 10 mL of diethyl ether. The aqueous layer was concentrated to afford a sticky residue as crude product. The residue was rinsed with 5 mL of water, dissolved in 10% MeCN-water and lyophilized to afford 2-((3R)-2-hydroxy-3-(2-(thiophen-2-yl)acetamido)-1,2-oxaborinan-6-yl)acetic acid 1 as white powder (100 mg, 0.337 mmol, 84.1% yield). $^1$H NMR (CD$_3$OD) δ ppm 0.94-1.35 (m, 1H), 1.35-1.54 (m, 1H), 1.54-1.68 (m, 1H), 1.68-2.00 (m, 1H), 2.20-2.67 (m, 3H), 3.93 (s, 1H), 3.98 (s, 1H), 4.02-4.23 (m, 2H), 6.98-7.05 (m, 2H), 7.32-7.36 (m, 1H); ESIMS found for C$_{12}$H$_{16}$BNO$_5$S m/z 280 (100%) (M−H$_2$O)+.

Alternative procedures for Steps 5 and 6 are shown in Scheme 9.

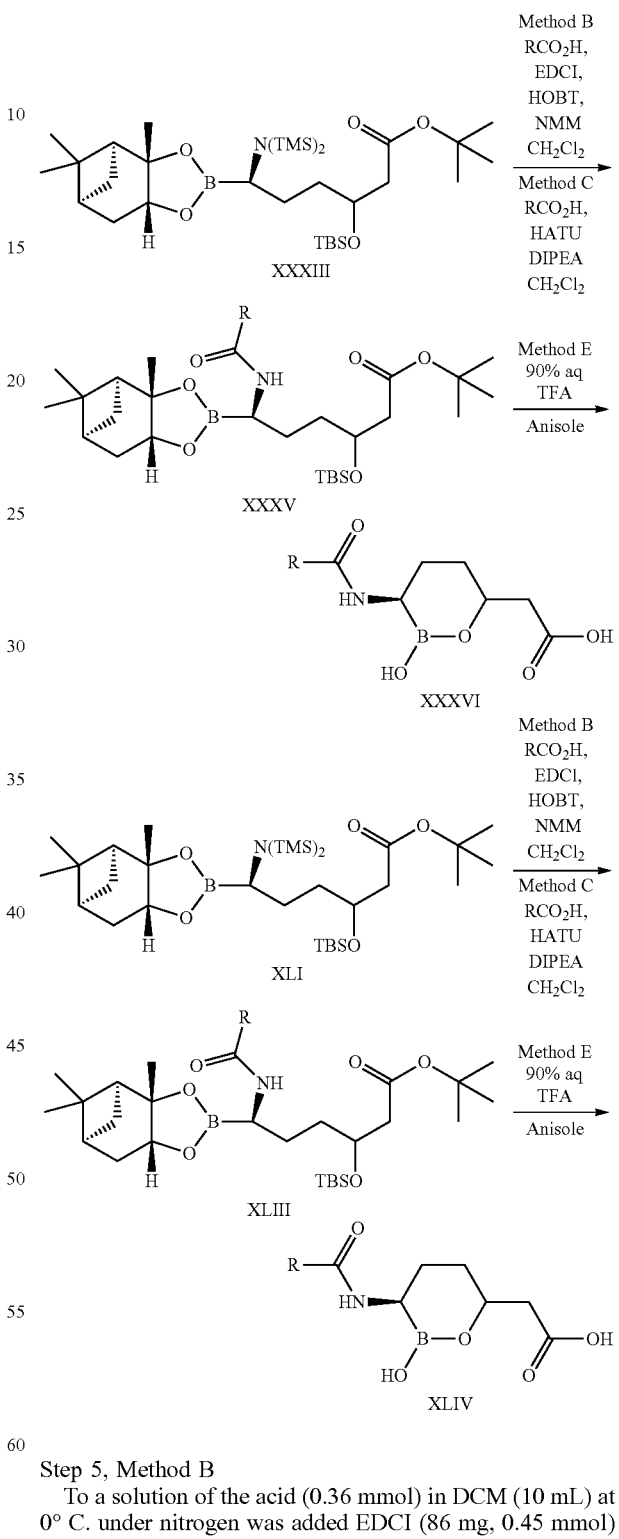

Scheme 9

Step 5, Method B

To a solution of the acid (0.36 mmol) in DCM (10 mL) at 0° C. under nitrogen was added EDCI (86 mg, 0.45 mmol) and HOBT (48 mg, 0.36 mmol). After stirring at 0° C. for 30 minutes, a solution of the bis-silyl amide intermediate XLI (0.3 mmol) in DCM (2 mL) followed by N-methyl-morpholine (65 μL, 0.6 mmol) were sequentially added at 0° C. The reaction flask was then allowed to warm to room temperature. After stirring at room temperature overnight, the reaction mixture was washed with water, then brine, dried ($Na_2SO_4$), filtered and concentrated under vacuum. The residue was purified by column chromatography to produce intermediate XLIII Step 5, Method C A solution of bis-silyl amide XLI (0.5 mmol) and acid in dry DCM (10 mL) were cooled to 0° C. Then DIPEA (1.5 mmol) was added drop wise followed HATU (0.75 mmol). The mixture was then allowed to warm to room temperature. After TLC has indicated complete conversion (~3 h) of the starting materials, the reaction was diluted with additional DCM (20 mL). The reaction mixture was washed with water (3×5 mL), brine (10 mL), and dried over $Na_2SO_4$. After removal of the solvent, the residue was subjected to flash column chromatography to produce intermediate XLIII Step 6, Method E To a solution of amide (XLIII) (0.1 mmol) in dichloroethane (2 mL) at 0° C. was treated with pre-cooled 90% aq. TFA (4 mL) and stirred at room temperature for 3 hrs. The reaction mixture was evaporated in vacuo, azeotroped with MeCN (3×5 mL) and the residue was triturated with ether (5 mL). The product separated was filtered, dissolved in dioxane-water mixture and freeze dried to give the final product XLIV as a fluffy solid.

The following compounds are prepared in accordance with the procedure described in the above Example 1 using methods A and D.

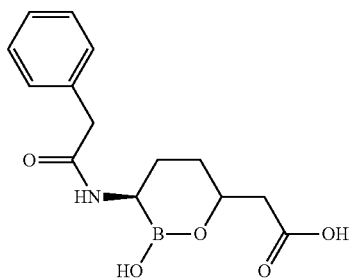 [SMILES: O=C(O)CC1CC[C@H](NC(=O)Cc2ccccc2)B(O)O1]

2-((3R)-2-hydroxy-3-(2-phenylacetamido)-1,2-oxaborinan-6-yl)acetic acid 2

$^1$H NMR ($CD_3OD$) δ ppm 0.82-1.33 (m, 1H), 1.33-1.51 (m, 1H), 1.51-1.68 (m, 1H), 1.69-2.00 (m, 1H), 2.14-2.34 (m, 1H), 2.34-2.69 (m, 2H), 3.74-3.76 (m, 2H), 3.98-4.20 (m, 1H), 7.22-7.41 (m, 5H); ESIMS found for C14H18BNO5 m/z 274 (100%) $(M-H_2O)^+$.

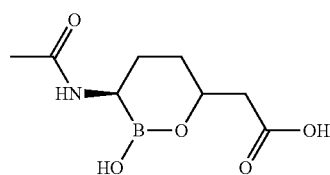

2-((3R)-3-acetamido-2-hydroxy-1,2-oxaborinan-6-yl)acetic acid 3

$^1$H NMR ($CD_3OD$) δ ppm 1.07-1.36 (m, 1H), 1.36-1.59 (m, 1H), 1.59-1.73 (m, 1H), 1.73-2.09 (m, 2H), 2.15-2.16 (d, 3H), 2.35-2.69 (m, 3H), 4.01-4.23 (m, 1H); ESIMS found for $C_8H_{14}BNO_5$ m/z 198 (100%) $(M-H_2O)^+$.

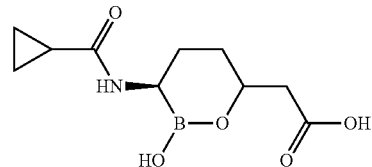 [SMILES: O=C(O)CC1CC[C@H](NC(=O)C2CC2)B(O)O1]

2-((3R)-3-(cyclopropanecarboxamido)-2-hydroxy-1,2-oxaborinan-6-yl)acetic acid 4

$^1$H NMR ($CD_3OD$) δ ppm 0.98-1.32 (m, 5H), 1.32-1.67 (m, 2H), 1.67-2.06 (m, 2H), 2.27-2.66 (m, 3H), 3.98-4.16 (m, 1H); ESIMS found for $C_{10}H_{16}BNO_5$ m/z 224 (100%) $(M-H_2O)^+$.

The following compounds are prepared starting from enantiomerically pure (R)-tert-butyl 3-hydroxypent-4-enoate (J. Am. Chem. Soc. 2007, 129, 4175-4177) in accordance with the procedure described in the above Example 1.

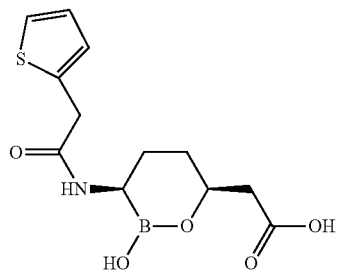

2-((3R,6 S)-2-hydroxy-3-(2-(thiophen-2-yl)acetamido)-1,2-oxaborinan-6-yl)acetic acid 5

$^1$H NMR ($CD_3OD$) δ ppm 0.97-1.11 (q, 1H), 1.47-1.69 (m, 2H), 1.69-1.80 (m, 1H), 2.21-2.33 (td, 1H), 2.33-2.41 (dd, 1H), 2.58-2.67 (m, 1H), 3.97 (s, 2H), 4.06-4.14 (m, 1H), 6.97-7.04 (m, 1H), 7.04-7.08 (m, 1H), 7.34-7.38 (dd, 1H); ESIMS found for $C_{12}H_{16}BNO_5S$ m/z 280 (100%) $(M-H_2O)^+$.

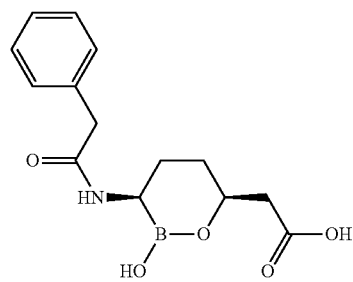 [SMILES: O=C(O)C[C@@H]1CC[C@H](NC(=O)Cc2ccccc2)B(O)O1]

2-((3R,6 S)-2-hydroxy-3-(2-phenylacetamido)-1,2-oxaborinan-6-yl)acetic acid 6

$^1$H NMR ($CD_3OD$) δ ppm 0.86-1.02 (m, 1H), 1.44-1.53 (dd, 1H), 1.53-1.66 (td, 1H), 1.68-1.78 (m, 1H), 2.17-2.26

(dd, 1H), 2.26-2.36 (dd, 2H), 3.75 (s, 2H), 4.02-4.12 (m, 1H), 7.22-7.40 (m, 5H); ESIMS found for $C_{14}H_{18}BNO_5$ m/z 274 (100%) $(M-H_2O)^+$.

The following compounds are prepared in accordance with the procedure described in the above Example 1 starting from enantiomerically pure (R)-tert-butyl 3-hydroxypent-4-enoate (J. Am. Chem. Soc. 2007, 129, 4175-4177) using methods B and D.

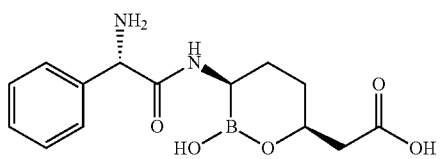

33

2-((3R,6S)-3-((S)-2-amino-2-phenylacetamido)-2-hydroxy-1,2-oxaborinan-6-yl)acetic acid 33 was isolated as the HCl salt. $^1$H NMR (CD$_3$OD) δ ppm 1.24-1.27 (m, 1H), 1.51-1.72 (m, 3H), 2.45-2.50 (dd, J=5 Hz, J=5 Hz, 1H), 2.55-2.63 (dd, J=2 Hz, J=3 Hz, 1H), 3.66-3.71 (m, 1H), 4.38-4.53 (m, 1H), 4.99-5.09 (d, 1H), 7.48-7.56 (m, 5H); ESIMS found for $C_{14}H_{19}BN_2O_5$ m/z 289 $(M-H_2O)^+$.

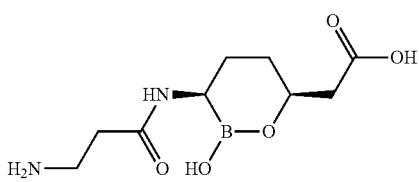

34

2-((3R,6S)-3-(3-aminopropanamido)-2-hydroxy-1,2-oxaborinan-6-yl)acetic acid 34 was isolated as the HCl salt. $^1$H NMR (CD$_3$OD) δ ppm 1.24-1.29 (td, J=13 Hz. J=3 Hz, 1H), 1.55-1.62 (td, J=14 Hz, J=4 Hz, 1H), 1.68-1.72 (m, 1H), 1.79-1.82 (m, 1H), 2.43-2.47 (dd, J=6 Hz, J=6 Hz, 2H), 2.70-2.74 (m, 2H), 2.83-2.86 (t, J=7 Hz, 2H), 3.26-3.29 (t, J=7 Hz, 1H), 4.10-4.16 (m, 1H); ESIMS found for $C_9H_{17}BN_2O_5$ m/z 227 $(M-H_2O)^+$.

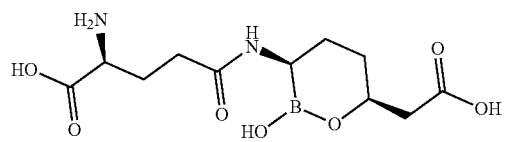

35

(S)-2-amino-5-((3R,6S)-6-(carboxymethyl)-2-hydroxy-1,2-oxaborinan-3-ylamino)-5-oxopentanoic acid 35 was isolated as the HCl salt. $^1$H NMR (CD$_3$OD) δ ppm 1.50-1.66 (m, 2H), 1.66-1.84 (m, 2H), 2.10-2.20 (sex, J=8 Hz 1H), 2.20-2.29 (m, 1H), 2.40-2.47 (m, 2H), 2.55-2.59 (q, J=7 Hz 1H), 2.69-2.75 (m, 1H), 2.94-2.98 (td, J=9 Hz, J=2 Hz 1H), 3.99-4.12 (m, 2H); ESIMS found for $C_{11}H_{19}BN_2O_7$ m/z 302.8 (M+H).

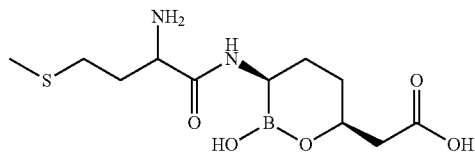

41

2-((3R,6S)-3-(2-amino-4-(methylthio)butanamido)-2-hydroxy-1,2-oxaborinan-6-yl)acetic acid 41 was isolated as the HCl salt. $^1$H NMR (CD$_3$OD) δ ppm 1.45-1.65 (m, 1H), 1.65-1.75 (m, 1H), 1.75-1.86 (m, 1H), 1.86-2.05 (m, 1H), 2.09-2.20 (m, 4H), 2.46-2.73 (m, 6H), 2.84-2.86 (t, J=6 Hz, 1H), 3.99-4.02 (t, J=7 Hz, 1H), 4.38-4.46 (m, 1H); ESIMS found for $C_{11}H_{21}BN_2O_5S$ m/z 287 $(M-H_2O)^+$.

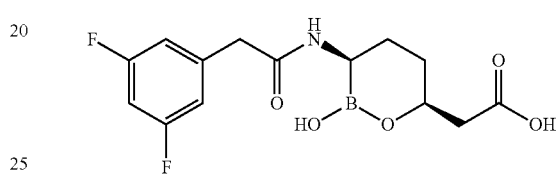

66

2-((3R,6S)-3-(2-(3,5-difluorophenyl)acetamido)-2-hydroxy-1,2-oxaborinan-6-yl)acetic acid 66 was isolated as the HCl salt. $^1$H NMR (CD$_3$OD) δ ppm 0.98-1.07 (q, J=13 Hz, 1H), 1.55-1.68 (m, 2H), 1.73-1.79 (dd, J=6 Hz, J=3 Hz, 1H), 2.22-2.26 (dd, J=15 Hz, J=6 Hz, 1H), 2.33-2.38 (dd, J=13 Hz, J=7 Hz, 1H), 2.62-2.63 (m, 1H), 3.78 (s, 2H), 4.05-4.12 (m, 1H), 6.88-5.93 (tt, J=5 Hz, J=2 Hz, 1H), 6.97-7.01 (dd, J=5 Hz, J=2 Hz, 2H); ESIMS found for $C_{14}H_{16}BF_2NO_5$ m/z 310.1 $(M-H_2O)^+$.

The following compounds are prepared in accordance with the procedure described in the above Example 1 starting from enantiomerically pure (R)-tert-butyl 3-hydroxypent-4-enoate (J. Am. Chem. Soc. 2007, 129, 4175-4177) using methods A and E.

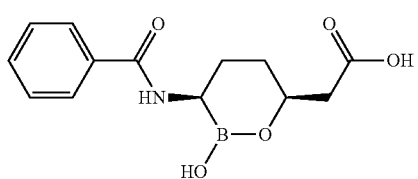

37

2-((3R,6S)-3-benzamido-2-hydroxy-1,2-oxaborinan-6-yl)acetic acid 37

$^1$H NMR (CD$_3$OD) δ ppm 1.10-1.19 (q, J=11 Hz, 1H), 1.60-1.65 (dd, J=14 Hz, J=3 Hz, 1H), 1.71-1.80 (td, J=9 Hz, J=3 Hz, 1H), 1.91-1.96 (d, J=14 Hz, 1H), 2.32-2.38 (dd, J=15 Hz, J=6 Hz, 1H), 2.44-2.49 (dd, J=15 Hz, J=7 Hz, 1H), 2.82-2.84 (d, J=4 Hz, 1H), 4.10-4.17 (m, 1H), 7.57-7.60 (t, J=8 Hz, 2H), 7.70-7.73 (t, J=8 Hz, 1H), 8.00-8.02 (d, J=8 Hz 2H); ESIMS found for $C_{13}H_{16}BNO_5$ m/z 260 $(M-H_2O)^+$.

The following compounds are prepared in accordance with the procedure described in the above Example 1 starting from enantiomerically pure (R)-tert-butyl 3-hydroxypent-4-enoate (J. Am. Chem. Soc. 2007, 129, 4175-4177) using methods B and E.

36

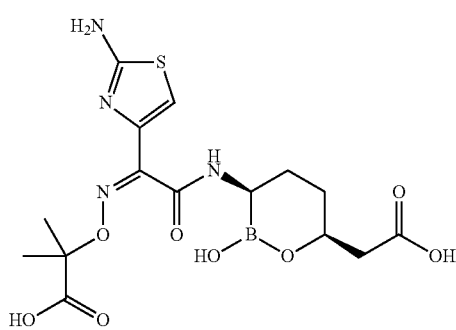

2-((Z)-1-(2-aminothiazol-4-yl)-2-((3R,6S)-6-(carboxymethyl)-2-hydroxy-1,2-oxaborinan-3-ylamino)-2-oxoethylideneaminooxy)-2-methylpropanoic acid 36 was isolated as the TFA salt. $^1$H NMR (CD$_3$OD) δ ppm 1.60 (s, 3H), 1.61 (s, 3H), 1.62-1.75 (m, 2H), 1.77-1.82 (m, 1H), 1.86-1.91 (m, 1H), 2.55-2.58 (t, J=6 Hz, 2H), 2.90-2.94 (t, J=6 Hz, 2H), 4.37-4.42 (m, 1H), 7.11 (s, 1H); ESIMS found for C$_{15}$H$_{21}$BN$_4$O$_8$S m/z 411 (M–H$_2$O)$^+$.

38

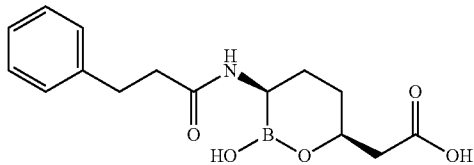

2-((3R,6S)-2-hydroxy-3-(3-phenylpropanamido)-1,2-oxaborinan-6-yl)acetic acid 38

$^1$H NMR (CD$_3$OD) δ ppm 0.78-0.87 (q, J=13 Hz, 1H), 1.40-1.46 (dd, J=10 Hz, J=3 Hz, 1H), 1.54-1.62 (dt, J=8 Hz, J=4 Hz, 1H), 1.63-1.70 (d, J=13 Hz, 1H), 2.24-2.29 (dd, J=15 Hz, J=6 Hz, 1H), 2.36-2.40 (dd, J=8 Hz, J=3 Hz, 1H), 2.53-2.56 (d, J=3.2 Hz, 1H), 2.74-2.78 (t, J=7 Hz, 2H), 2.98-3.01 (t, J=6 Hz, 2H), 3.90-4.03 (m, 1H), 7.18-7.23 (m, 1H), 7.25-7.33 (m, 4H); ESIMS found for C$_{15}$H$_{20}$BNO$_5$ m/z 288 (M–H$_2$O)$^+$.

39

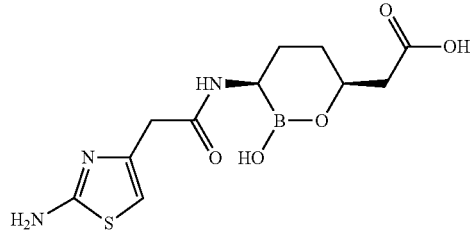

2-((3R,6S)-3-(2-(2-aminothiazol-4-yl)acetamido)-2-hydroxy-1,2-oxaborinan-6-yl)acetic acid 39 was isolated as the TFA salt. $^1$H NMR (CD$_3$OD) δ ppm 1.25-1.36 (m, 1H), 1.63-1.76 (m, 3H), 2.40-2.43 (d, J=6 Hz 2H), 2.68-2.70 (m, 1H), 3.72 (s, 2H), 4.17-4.21 (m, 1H), 6.69 (s, 1H); ESIMS found for C$_{11}$H$_{16}$BN$_3$O$_5$S m/z 296.1 (M–H$_2$O)$^+$.

40

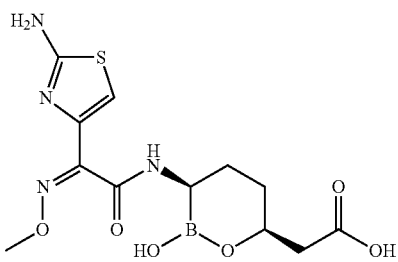

2-((3R,6S)-3-((Z)-2-(2-aminothiazol-4-yl)-2-(methoxyimino)acetamido)-2-hydroxy-1,2-oxaborinan-6-yl)acetic acid 40 was isolated as the TFA salt. $^1$H NMR (CD$_3$OD) δ ppm 1.56-1.67 (m, 2H), 1.76-1.81 (m, 1H), 1.86-1.90 (m, 1H), 2.50-2.54 (dd, J=17 Hz, J=6 Hz, 1H), 2.59-2.64 (dd, J=16 Hz, J=7 Hz, 1H), 2.86-2.90 (t, J=7 Hz, 1H), 4.22 (s, 3H), 4.34-4.37 (m, 1H), 7.86 (s, 1H); ESIMS found for C$_{12}$H$_{17}$BN$_4$O$_6$S m/z 339.1 (M–H$_2$O)$^+$.

42

2-((3R,6S)-3-(2-amino-3-(pyridin-3-yl)propanamido)-2-hydroxy-1,2-oxaborinan-6-yl)acetic acid 42 was isolated as the TFA salt. $^1$H NMR (CD$_3$OD/CF$_3$O$_2$D) δ ppm 1.43-1.56 (m, 2H), 1.72-1.83 (m, 2H), 2.37-2.42 (m, 1H), 2.53-2.57 (t, J=6 Hz, 1H), 2.89-2.93 (t, J=7 Hz, 1H), 3.37-3.43 (m, 2H), 4.17-4.21 (t, J=7 Hz, 1H), 4.41-4.46 (m, 1H), 8.06-8.10 (dd, J=6 Hz, J=3 Hz, 1H), 8.53-8.57 (t, J=17 Hz, 1H), 8.80-8.81 (brd, J=4 Hz, 1H), 8.84-8.87 (brd, J=6 Hz, 1H); ESIMS found for C$_{14}$H$_{20}$BN$_3$O= m/z 304.2 (M–H$_2$O)$^+$.

43

2-((3R,6S)-2-hydroxy-3-(2-(pyridin-3-yl)acetamido)-1,2-oxaborinan-6-yl)acetic acid 43 was isolated as the TFA salt. $^1$H NMR (CD$_3$OD) δ ppm 1.15-1.20 (m, 1H), 1.59-1.63 (m, 1H), 1.68-1.74 (m, 2H), 2.29-2.34 (dd, J=15 Hz, J=6 Hz, 2H), 2.66-2.68 (m, 1H), 3.94 (s, 2H), 4.11-4.18 (m, 1H), 7.82-7.85 (dd, J=8 Hz, J=6 Hz, 1H), 8.30-8.32 (d, J=8 Hz, 1H), 8.68-8.70 (brd, J=5 Hz, 1H), 8.72-8.75 (brs, 1H); ESIMS found for C$_{13}$H$_{17}$BN$_2$O$_5$ m/z 275 (M–H$_2$O)$^+$.

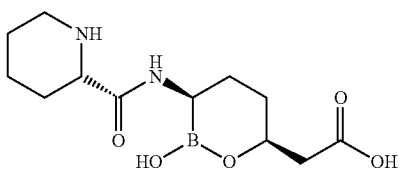

45

2-((3R,6S)-2-hydroxy-3-((S)-piperidine-2-carboxamido)-1,2-oxaborinan-6-yl)acetic acid 45 was isolated as the TFA salt. $^1$H NMR (CD$_3$OD) δ ppm 1.44-1.51 (m, 1H), 1.54-1.80 (m, 5H), 1.80-1.91 (m, 2H), 1.91-1.98 (brd, J=12 Hz, 1H), 2.16-2.21 (dd, J=13 Hz, J=2 Hz, 1H), 2.49-2.57 (non, J=7 Hz, 2H), 2.75-2.78 (t, J=6 Hz, 1H), 2.98-3.03 (dt, J=13 Hz, J=3 Hz, 1H), 3.36-3.39 (d, J=13 Hz, 1H), 3.79-3.82 (dd, J=12 Hz, J=4 Hz, 1H), 4.34-4.38 (m, 1H); ESIMS found for C$_{12}$H$_2$BN$_2$O$_5$ m/z 267 (M–H$_2$O)$^+$.

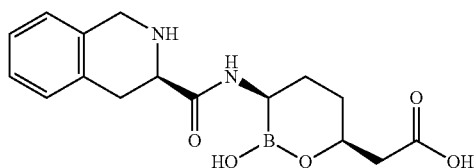

46

2-((3R,6S)-2-hydroxy-3-((R)-1,2,3,4-tetrahydroisoquinoline-3-carboxamido)-1,2-oxaborinan-6-yl)acetic acid 46 was isolated as the TFA salt. $^1$H NMR (CD$_3$OD) δ ppm 1.43-1.51 (m, 1H), 1.56-1.63 (m, 1H), 1.75-1.83 (m, 1H), 1.86-1.94 (m, 1H), 2.46-2.57 (dq, J=16 Hz, J=6 Hz, 2H), 2.82-2.86 (t, J=7 Hz, 1H), 3.18-3.24 (dd, J=17 Hz, J=12 Hz, 1H), 3.36-3.41 (dd, J=17 Hz, J=5 Hz, 1H), 4.21-4.24 (dd, J=18 Hz, J=13 Hz, 1H), 4.36-4.40 (m, 1H), 4.42 (s, 2H), 7.23-7.25 (m, 1H), 7.27-7.33 (m, 3H); ESIMS found for C$_{16}$H$_{21}$BN$_2$O$_5$ m/z 315 (M–H$_2$O)$^+$.

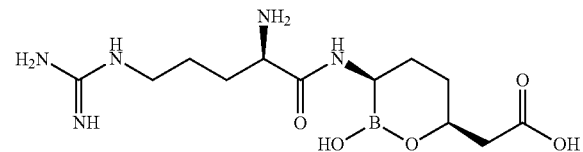

47

Following method E while the compound is still in 90% aq. trifluoroacetic acid (10 mL), 10% Pd/C (50 mg) was added. The reaction mixture was stirred under hydrogen for 6 h, filtered through Celite and rinsed with dichloroethane (10 mL). The filtrate was concentrated under vacuum and azeotroped with dichloroethane (2×10 mL). Triturating with ether resulted in a precipitate which was filtered and washed with ether (5 mL) and dried to give 2-((3R,6S)-3-((R)-2-amino-5-guanidinopentanamido)-2-hydroxy-1,2-oxaborinan-6-yl)acetic acid 47 as the TFA salt (50 mg) as an off-white solid. $^1$H NMR (CD$_3$OD) δ ppm 1.39-1.46 (m, 1H), 1.52-1.58 (m, 1H), 1.66-1.77 (m, 2H), 1.77-1.84 (m, 1H), 1.87-1.95 (m, 3H), 2.34-2.38 (dd, J=17 Hz, J=3 Hz, 1H), 2.63-2.68 (dd, J=17 Hz, J=7 Hz, 1H), 2.94-2.97 (dd, J=10 Hz, J=6 Hz, 1H), 3.20-3.24 (dt, J=7 Hz, J=2 Hz, 2H), 3.86-3.88 (t, J=6 Hz, 1H), 4.27-4.31 (m, 1H); ESIMS found for C$_{12}$H$_{24}$BN$_5$O$_5$ m/z 312.2 (M–H$_2$O)$^+$.

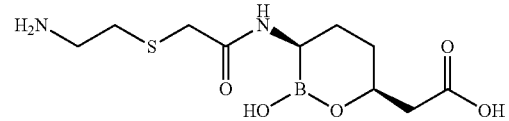

48

2-((3R,6S)-3-(2-(2-aminoethylthio)acetamido)-2-hydroxy-1,2-oxaborinan-6-yl)acetic acid 48 was isolated as the TFA salt. $^1$H NMR (CD$_3$OD) δ ppm 1.38-1.46 (m, 1H), 1.46-1.54 (m, 1H), 1.71-1.78 (m, 1H), 1.84-1.92 (m, 1H), 2.30-2.34 (dd, J=16 Hz, J=4 Hz, 1H), 2.56-2.61 (dd, J=16 Hz, J=6 Hz, 1H), 2.80-2.83 (t, J=6 Hz, 1H), 2.89-2.97 (non, J=7 Hz, 2H), 3.17-3.24 (non, J=5 Hz, 2H), 3.37 (s, 2H), 4.15-4.20 (m, 1H); ESIMS found for C$_{10}$H$_{19}$BN$_2$O$_5$S m/z 273 (M–H$_2$O)$^+$.

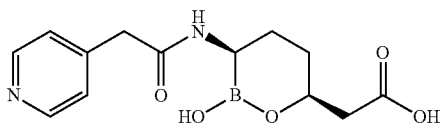

49

2-((3R,6S)-2-hydroxy-3-(2-(pyridin-4-yl)acetamido)-1,2-oxaborinan-6-yl)acetic acid 49 was isolated as the TFA salt. $^1$H NMR (CD$_3$OD) δ ppm 1.17-1.27 (m, 1H), 1.60-1.67 (m, 1H), 1.67-1.76 (m, 2H), 2.32-2.43 (m, 2H), 2.68-2.70 (t, J=4 Hz, 2H), 3.22-3.26 (t, J=7 Hz, 1H), 4.15-4.21 (m, 1H), 7.94-7.96 (d, J=7 Hz, 2H), 8.75-8.79 (d, J=6 Hz, 2H); ESIMS found for C$_{13}$H$_{17}$BN$_2$O$_5$ m/z 275.1 (M–H$_2$O)$^+$.

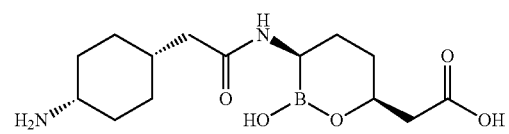

50

2-((3R,6S)-3-(2-(4-aminocyclohexyl)acetamido)-2-hydroxy-1,2-oxaborinan-6-yl)acetic acid 50 was isolated as the TFA salt. $^1$H NMR (CD$_3$OD) δ ppm 1.15-1.25 (m, 1H), 1.44-1.88 (m, 10H), 2.05-2.13 (m, 1H), 2.19-2.21 (d, J=8 Hz, 1H), 2.30-2.36 (dd, J=6 Hz, 1H), 2.38-2.47 (m, 3H), 2.61-2.63 (brd, J=3 Hz, 1H), 3.18-3.22 (t, J=7 Hz, 1H), 4.04-4.11 (m, 1H); ESIMS found for C$_{14}$H$_{25}$BN$_2$O$_5$ m/z 295.1 (M–H$_2$O)$^+$.

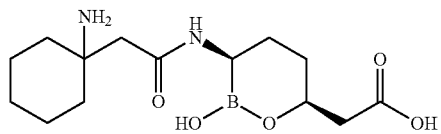

51

2-((3R,6S)-3-(2-(1-aminocyclohexyl)acetamido)-2-hydroxy-1,2-oxaborinan-6-yl)acetic acid 51 was isolated as the TFA salt. $^1$H NMR (CD$_3$OD) δ ppm 1.23-1.34 (m, 1H), 1.34-1.48 (m, 1H), 1.48-1.86 (m, 12H), 2.40-2.50 (m, 2H), 2.65-2.83 (m, 2H), 3.22-3.26 (t, J=7 Hz, 1H), 4.11-4.18 (m, 1H); ESIMS found for C$_{14}$H$_{25}$BN$_2$O$_5$ m/z 295 (M–H$_2$O)$^+$.

52

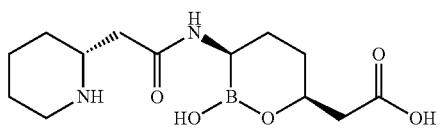

2-((3R,6S)-2-hydroxy-3-(2-((R)-piperidin-2-yl)acetamido)-1,2-oxaborinan-6-yl)acetic acid 52 was isolated as the TFA salt. $^1$H NMR (CD$_3$OD) δ ppm 1.27-1.37 (m, 1H), 1.49-1.80 (m, 7H), 1.86-2.00 (brdd, J=11 Hz, 3H), 2.44-2.46 (d, J=6 Hz, 2H), 2.61-2.65 (m, 1H), 2.72-2.73 (d, J=6 Hz, 1H), 3.03-3.09 (t, J=13 Hz, 1H), 3.41-3.45 (d, J=13 Hz, 1H), 3.47-3.56 (m, 1H), 4.15-4.21 (m, 1H); ESIMS found for C$_{13}$H$_{23}$BN$_2$O$_5$ m/z 281 (M–H$_2$O)$^+$.

53

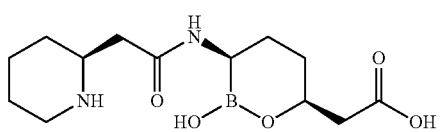

2-((3R,6S)-2-hydroxy-3-(2-((S)-piperidin-2-yl)acetamido)-1,2-oxaborinan-6-yl)acetic acid 53 was isolated as the TFA salt. $^1$H NMR (CD$_3$OD) δ ppm 1.26-1.35 (m, 1H), 1.48-1.59 (m, 1H), 1.59-1.68 (m, 2H), 1.68-1.81 (m, 3H), 1.87-2.00 (m, 3H), 2.45-2.47 (d, J=7 Hz, 2H), 2.65-2.67 (t, J=4 Hz, 1H), 2.74-2.76 (t, J=6 Hz, 2H), 3.03-3.08 (dt, J=13 Hz, J=3 Hz, 1H), 3.42-3.46 (brd, J=13 Hz, 1H), 3.47-3.55 (m, 1H), 4.12-4.19 (m, 1H); ESIMS found for C$_{13}$H$_{23}$BN$_2$O$_5$ m/z 298.1 (M+H).

54

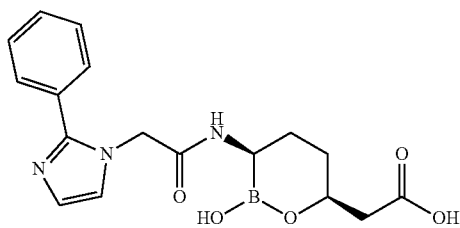

2-((3R,6S)-2-hydroxy-3-(2-(2-phenyl-1H-imidazol-1-yl)acetamido)-1,2-oxaborinan-6-yl)acetic acid 54 was isolated as the TFA salt. $^1$H NMR (CD$_3$OD) δ ppm 1.36-1.44 (m, 1H), 1.44-1.54 (m, 1H), 1.66-1.80 (m, 2H), 2.15 (s, 1H), 2.48-2.51 (m, J=6 Hz, 1H), 2.72-2.75 (t, J=7 Hz, 1H), 4.33-4.39 (m, 1H), 4.94-5.05 (m, 2H), 7.65-7.76 (m, 7H); ESIMS found for C$_{17}$H$_{20}$BN$_3$O$_5$ m/z 358.2 (M+H).

55

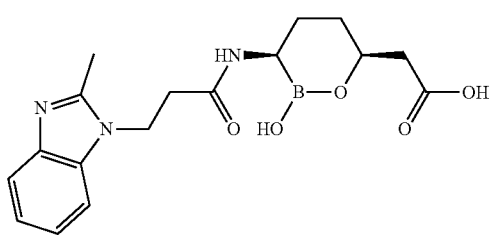

2-((3R,6S)-2-hydroxy-3-(3-(2-methyl-1H-benzo[d]imidazol-1-yl)propanamido)-1,2-oxaborinan-6-yl)acetic acid 55

$^1$H NMR (CD$_3$OD) δ ppm 0.92-1.00 (m, 1H), 1.47-1.53 (m, 1H), 1.58-1.62 (m, 2H), 2.31-2.33 (d, J=7 Hz, 2H), 2.50-2.52 (t, J=4 Hz, 1H), 2.97 (s, 3H), 3.08-3.20 (m, 2H), 4.04-4.10 (m, 1H), 4.77-4.81 (t, J=6 Hz, 2H), 7.61-7.68 (m, 2H), 7.75-7.78 (d, J=7 Hz, 1H), 7.93-7.95 (d, J=7 Hz, 1H); ESIMS found for C$_{17}$H$_{22}$BN$_3$O$_5$ m/z 342.2 (M–H$_2$O)$^+$.

56

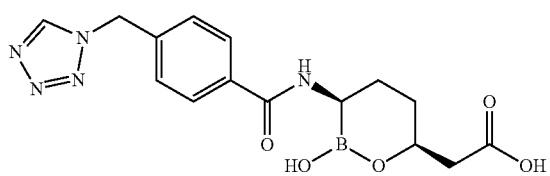

2-((3R,6S)-3-(4-((1H-tetrazol-1-yl)methyl)benzamido)-2-hydroxy-1,2-oxaborinan-6-yl)acetic acid 56

$^1$H NMR (CD$_3$OD) δ ppm 1.10-1.21 (m, 1H), 1.58-1.64 (m, 1H), 1.70-1.79 (m, 1H), 1.89-1.96 (m, 1H), 2.31-2.36 (dd, J=15 Hz, J=6 Hz, 1H), 2.41-2.47 (m, 1H), 2.80-2.83 (brd, J=4 Hz, 1H), 4.11-4.17 (m, 1H), 5.83 (s, 2H), 7.53-7.55 (d, J=8 Hz, 2H), 8.02-8.05 (d, J=8 Hz, 2H), 9.30 (s, 1H); ESIMS found for C$_{15}$H$_{18}$BN$_5$O$_5$ m/z 342.0 (M–H$_2$O)$^+$.

57

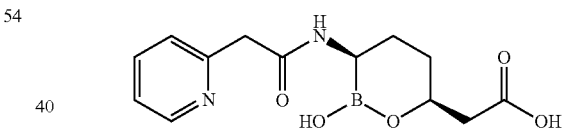

2-((3R,6S)-2-hydroxy-3-(2-(pyridin-2-yl)acetamido)-1,2-oxaborinan-6-yl)acetic acid 57 was isolated as the TFA salt. $^1$H NMR (CD$_3$OD) δ ppm 1.21-1.32 (m, 1H), 1.59-1.67 (m, 2H), 1.67-1.75 (m, 2H), 2.29-2.40 (m, 3H), 2.67-2.72 (m, 1H), 4.14-4.21 (m, 1H), 7.62-7.66 (t, J=6 Hz, 1H), 7.70-7.73 (d, J=8 Hz, 1H), 8.14-8.18 (t, J=8 Hz, 1H), 8.65-8.67 (d, J=5 Hz, 1H); ESIMS found for C$_{13}$H$_{17}$BN$_2$O$_5$ m/z 275.1 (M–H$_2$O)$^+$.

The following compounds are prepared in accordance with the procedure described in the above Example 1 using methods C and E.

58

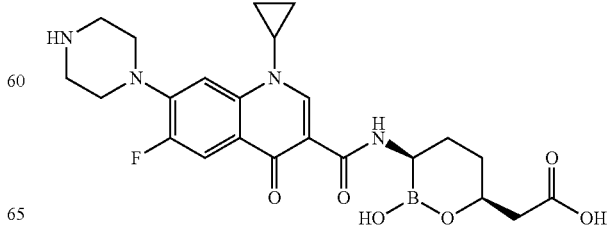

2-((3R,6S)-3-(1-cyclopropyl-6-fluoro-4-oxo-7-(piperazin-1-yl)-1,4-dihydroquinoline-3-carboxamido)-2-hydroxy-1,2-oxaborinan-6-yl)acetic acid 58 was isolated as the TFA salt. $^1$H NMR (CD$_3$OD) δ ppm 1.14-1.29 (m, 3H), 1.39-1.44 (brd, J=7 Hz, 2H), 1.56-1.63 (dd, J=14 Hz, J=3 Hz, 1H), 1.70-1.80 (m, 1H), 1.92-1.99 (d, J=14 Hz, 1H), 2.33-2.38 (dd, J=15 Hz, J=6 Hz, 1H), 2.43-2.48 (dd, J=15 Hz, J=7 Hz, 1H), 2.85-2.86 (d, J=3 Hz, 1H), 3.46-3.52 (m, 4H), 3.59-3.64 (m, 4H), 3.73-3.79 (m, 1H), 4.08-4.15 (m, 1H), 7.66-7.67 (d, J=7 Hz, 1H), 8.00-8.03 (d, J=13 Hz, 1H), 8.81 (s, 1H); ESIMS found for C$_{23}$H$_{28}$BFN$_4$O$_6$ m/z 469.2 (M–H$_2$O)$^+$.

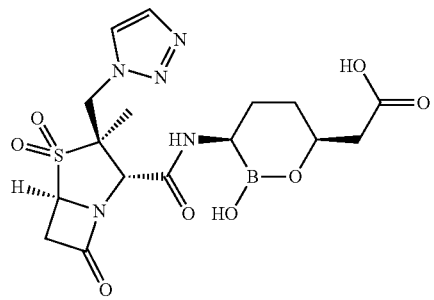

59

2-[(3R,6S)-2-hydroxy-3-[(2S,3S,5R)-3-methyl-4,4,7-trioxo-3-(1H-1,2,3-triazol-1-ylmethyl)-4λ$^6$-thia-1-azabicyclo[3.2.0]heptane-2-amido]-1,2-oxaborinan-6-yl]acetic acid 59

$^1$H NMR (CD$_3$OD) δ ppm 1.43 (s, 3H), 1.49-1.57 (m, 1H), 1.72-1.81 (m, 3H), 2.51-2.56 dd, J=15 Hz, J=6 Hz, 1H), 2.62-2.67 (dd, J=15 Hz, J=8 Hz, 1H), 2.80-2.84 (m, 1H), 3.41-3.44 (dd, J=17 Hz, J=2 Hz, 1H), 3.63-3.67 (dd, J=16 Hz, J=5 Hz, 1H), 4.37-4.44 (m, 1H), 4.61 (s, 1H), 4.90-4.94 (dd, J=5 Hz, J=2 Hz, 1H), 5.16-5.19 (d, J=15 Hz, 1H), 5.25-5.28 (d, J=15 Hz, 1H), 7.77 (s, 1H), 8.07 (s, 1H); ESIMS found for C$_{16}$H$_{22}$BN$_5$O$_8$S m/z 438 (M–H$_2$O)$^+$.

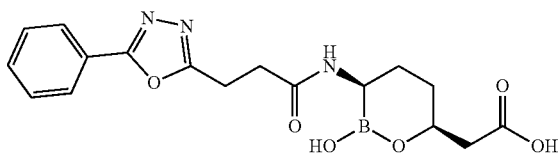

60

2-((3R,6S)-2-hydroxy-3-(3-(5-phenyl-1,3,4-oxadiazol-2-yl)propanamido)-1,2-oxaborinan-6-yl)acetic acid 60

$^1$H NMR (CD$_3$OD) δ ppm 1.10-1.21 (m, 1H), 1.50-1.58 (dd, J=14 Hz, J=3 Hz, 1H), 1.59-1.68 (dt, J=11 Hz, J=5 Hz, 1H), 1.74-1.81 (brd, J=13 Hz, 1H), 2.22-2.26 (dd, J=15 Hz, J=6 Hz, 1H), 2.30-2.34 (dd, J=15 Hz, J=7 Hz, 1H), 2.63-2.64 (d, J=4 Hz, 1H), 3.01-3.12 (sex, J=7 Hz, 2H), 3.33-3.43 (sex, J=7 Hz, 2H), 4.03-4.09 (m, 1H), 7.54-7.62 (m, 3H), 8.03-8.05 (d, J=8 Hz, 2H); ESIMS found for C$_{17}$H$_{20}$BN$_3$O$_6$ m/z 356.1 (M–H$_2$O)$^+$.

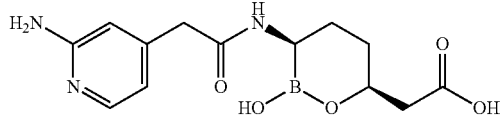

61

2-((3R,6S)-3-(2-(2-aminopyridin-4-yl)acetamido)-2-hydroxy-1,2-oxaborinan-6-yl)acetic acid 61 was isolated as the TFA salt. $^1$H NMR (CD$_3$OD) δ ppm 1.58-1.66 (m, 1H), 1.67-1.78 (m, 3H), 2.31-2.36 (dd, J=15 Hz, J=6 Hz, 1H), 2.39-2.44 (dd, J=15 Hz, J=7 Hz, 1H), 2.65-2.68 (t, J=4 Hz, 1H), 4.12-4.19 (m, 1H), 6.85-6.87 (d, J=7 Hz, 1H), 6.99 (s, 1H), 7.81-7.82 (d, J=7 Hz, 1H); ESIMS found for C$_{13}$H$_{18}$BN$_3$O$_5$ m/z 290.1 (M–H$_2$O)$^+$.

62

Following method E, the reaction mixture was evaporated in vacuo, azeotroped with MeCN (3×5 mL) and the residue was triturated with ether (5 mL). The precipitate was filtered, dissolved in dioxane-water mixture and freeze dried to get 2-((3R)-3-((Z)-2-(2-aminothiazol-4-yl)-2-((1,5-dihydroxy-4-oxo-1,4-dihydropyridin-2-yl) methoxyimino)acetamido)-2-hydroxy-1,2-oxaborinan-6-yl)acetic acid 62 as the TFA (25 mg) salt as a fluffy solid. ESIMS found for C$_{17}$H$_{20}$BN$_5$O$_9$S m/z 464.0 (M–H$_2$O)$^+$.

Synthesis of 2-((3R)-3-amino-2-hydroxy-1,2-oxaborinan-6-yl)acetic acid hydrochloride 7

An example synthesis of 7 is depicted in Scheme 10 and Example 2.

Scheme 10

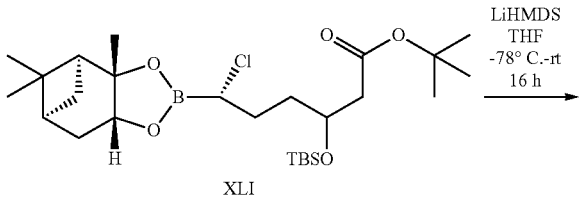

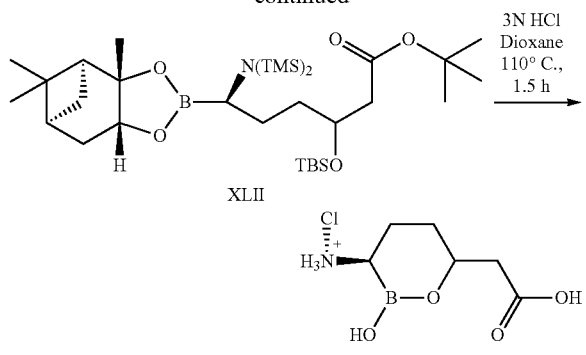

Example 2

Step 1

6-(tert-butoxy)-4-[(tert-butyldimethylsilyl)oxy]-1-chloro-6-oxo-1-[(2S,6R)-2,9,9-trimethyl-3,5-dioxa-4-boratricyclo[6.1.1.02,6]decan-4-yl]hexane XLI (515 mg, 0.97 mmol) in THF (5 mL) was cooled to −78° C. under nitrogen. A solution of LiHMDS (1 mL, 1.0 M in THF, 1 mmol, 1.0 eq) was added slowly and the reaction flask was then allowed to warm to room temperature where it was stirred for 16 h. The yellow solution was concentrated under reduced pressure to give an oil. After hexane (10 mL) was added to the oil, a precipitate formed. This was then filtered through Celite and the filtrate concentrated under reduced pressure to give 1-[bis(trimethylsilyl)amino]-6-(tert-butoxy)-4-[(tert-butyldimethylsilyl)oxy]-6-oxo-1-[(2S,6R)-2,9,9-trimethyl-3,5-dioxa-4-boratricyclo[6.1.1.02,6] decan-4-yl]hexyl XLII.

Step 2

The procedure is identical to that found in Example 1 method D. Compound 7 was isolated as a white powder (120 mg, 0.573 mmol, 59.1% yield). $^1$H NMR (CD$_3$OD) δ ppm 1.43-1.66 (m, 1H), 1.66-1.79 (m, 1H), 1.79-1.97 (m, 1H), 1.97-2.30 (m, 1H), 2.40-2.71 (m, 3H), 4.34-4.54 (m, 1H); ESIMS found for C$_6$H$_{12}$BNO$_4$ m/z 174 (63%) (M+H).

Synthesis of 2-((3R)-2-hydroxy-3-(2-(thiophen-2-yl)acetamido)-1,2-oxaborepan-7-yl)acetic acid 63

An example synthesis of 63 is depicted in Scheme 11 and Example 3.

Scheme 11

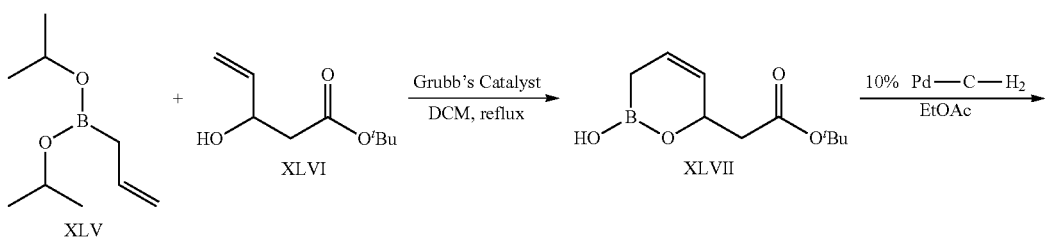

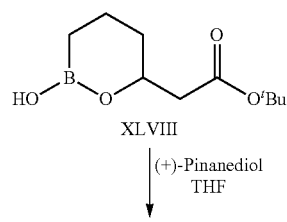

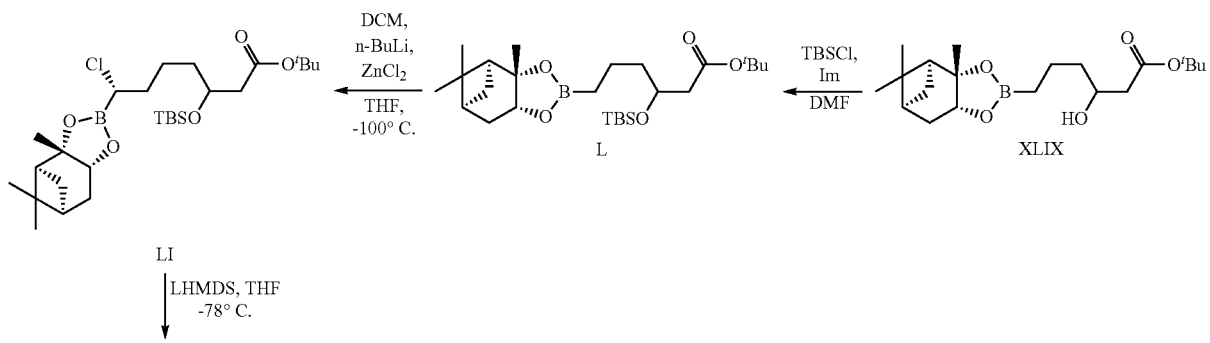

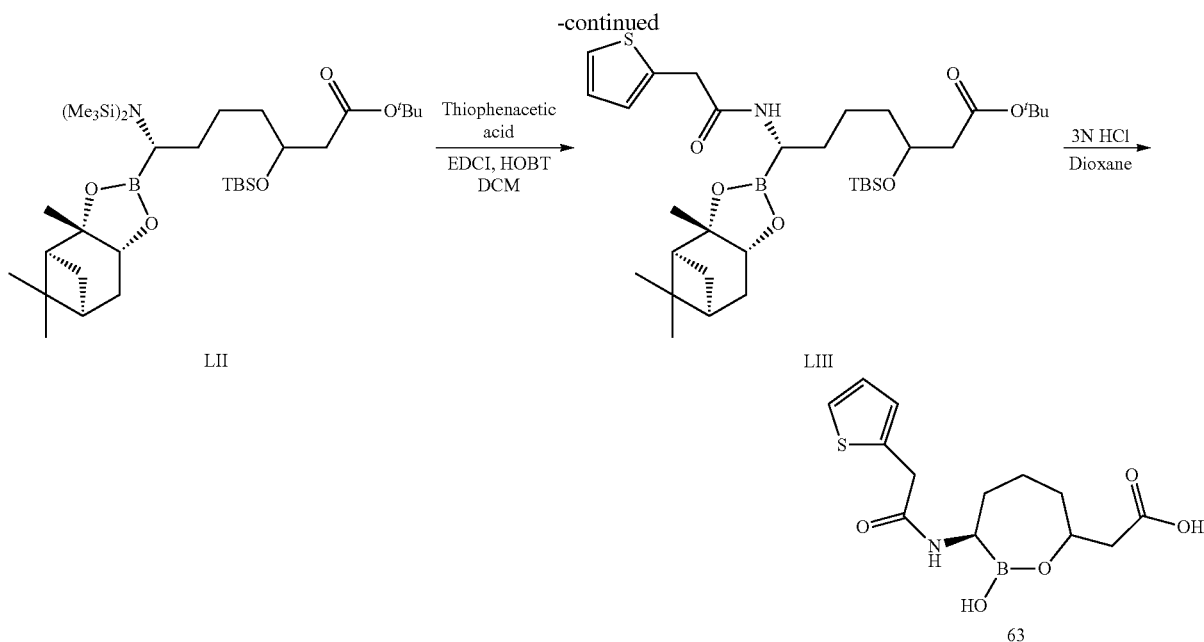

Example 3

Step 1

To a solution of tert-butyl 3-hydroxypent-4-enoate, XLVI (674 mg, 3.92 mmol) in DCM (15 mL) was added diisopropylallylboronate XLV (2 g, 11.76 mmol) via syringe. To the mixture was then added Grubbs' first generation catalyst (260 mg, 0.31 mmol, 7.5 mol %) and the vessel was purged with argon. The reaction was heated at 65° C. under nitrogen for 18 h. The mixture was concentrated under vacuum and the residue was purified by flash column chromatography (100% hexane→30% EtOAc/hexane) to afford tert-butyl 2-(2-hydroxy-3,6-dihydro-2H-1,2-oxaborinin-6-yl)acetate XLVII (770 mg, 3.63 mmol, 92.7% yield).

Step 2

To a solution of tert-butyl 2-(2-hydroxy-3,6-dihydro-2H-1,2-oxaborinin-6-yl)acetate XLVII (670 mg, 3.16 mmol) in EtOAc (45 mL) was added 10% Pd/C (135 mg). The vessel was evacuated by applying vacuum and flushed with hydrogen gas. The reaction was stirred under hydrogen for 2 h. The mixture was filtered through a Celite pad and which was washed with additional EtOAc (15 mL). Concentration of the filtrate gave pure tert-butyl 2-(2-hydroxy-1,2-oxaborinan-6-yl)acetate XLVIII (641 mg, 3.00 mmol, 94.8% yield).

Step 3

To a solution of tert-butyl 2-(2-hydroxy-1,2-oxaborinan-6-yl)acetate XLVIII (641 mg, 3.00 mmol) in THF (20 mL) was added (1S,2S,3R,5S)-2,6,6-trimethylbicyclo[3.1.1]heptane-2,3-diol (509 mg, 3 mol) at room temperature. The reaction mixture was stirred for 16 h and concentrated under vacuum. The residue was purified by column chromatography (100% hexane→40% EtOAc/hexane) on silica gel to give tert-butyl 3-hydroxy-6-[(1R,2R,6S,8R)-6,9,9-trimethyl-3,5-dioxa-4-boratricyclo[6.1.1.0$^{2,6}$]decan-4-yl] hexanoate XLIX (790 mg, 2.16 mmol, 71.9% yield).

Step 4

To a solution of alcohol XLIX (790 mg, 2.16 mmol) in DMF (7.5 mL) was added imidazole (548 mg, 8.06 mmol) followed by TBDMSCl (580 mg, 3.87 mol). The reaction mixture was stirred at room temperature for 16 h and concentrated under vacuum. The white slurry was dissolved in 100 mL of EtOAc and washed with saturated NaHCO$_3$ solution (20 mL), water (2×10 mL) and dried (Na$_2$SO$_4$). The organic extract was concentrated under vacuum and the residue was purified by column chromatography (100% hexane→30% EtOAc/hexane) on silica gel to give tert-butyl 3-[(tert-butyldimethylsilyl)oxy]-6-[(1R,2R,6S,8R)-6,9,9-trimethyl-3,5-dioxa-4-boratricyclo[6.1.1.0$^{2,6}$]decan-4-yl] hexanoate L (1 g, 2.08 mmol, 96.3% yield).

Step 5

To a solution of DCM (0.26 mL, 4.16 mmol) in THF (5 mL) at −100° C. was added 2.5 M n-butyl lithium in hexane (1 mL, 2.5 mmol) slowly under nitrogen and down the inside wall of the flask whilst maintaining the temperature below −90° C. The resulting white precipitate was stirred for 30 minutes before the addition of L (1 g, 2.08 mmol) in THF (3 mL) at −90° C. Zinc chloride (5 mL, 0.5 M in THF, 2.5 mmol) was then added to the reaction mixture at −90° C. and then the reaction was allowed to warm to room temperature where it was stirred for 16 h. The reaction was quenched with a saturated solution of ammonium chloride and the phases were separated. The aqueous phase was then extracted with diethyl ether (2×10 mL) and the combined organic extracts were dried over Na$_2$SO$_4$, filtered and concentrated under reduced pressure. The concentrated material was then chromatographed (100% hexane→20% EtOAc-hexane) to obtain tert-butyl (7S)-3-[(tert-butyldimethylsilyl)oxy]-7-chloro-7-[(1R,2R,6S,8R)-6,9,9-trimethyl-3,5-dioxa-4-boratricyclo[6.1.1.0$^{2,6}$]decan-4-yl]heptanoate LI (740 mg, 1.40 mmol, 67.2% yield).

Step 6

Chloro intermediate LI (727 mg, 1.37 mmol) in THF (7 mL) was cooled to −78° C. under nitrogen. A solution of 1M LiHMDS solution in THF (1.37 mL, 1.37 mmol) was added slowly at −78° C. Upon completion of the addition, the reaction flask was allowed to warm to room temperature. After stirring at room temperature for 16 h, the reaction mixture was concentrated under vacuum and hexane (20 mL) was added. The precipitated lithium salts were filtered off through a Celite pad, rinsed with additional hexane and the combined filtrates were concentrated under vacuum to give crude tert-butyl (7S)-7-[bis(trimethylsilyl)amino]-3-[(tert-butyl dimethyl silyl)oxy]-7-[(1R,2R,6S,8R)-6,9,9-trimethyl-3,5-dioxa-4-boratricyclo[6.1.1.0$^{2,6}$]decan-4-yl]heptanoate LII.

Step 7

To a stirred solution of 2-thiophenacetic acid (232 mg, 1.64 mmol) in DCM (45 mL) at 0° C. under nitrogen was added EDCI (391 mg, 2.05 mmol) and HOBT (221 mg, 1.64 mmol). After stirring at 0° C. for 30 minutes, a solution of the bis-silyl amide LII intermediate (1.37 mmol) in DCM (10 mL) followed by N-methyl-morpholine (0.3 mL, 2.74 mmol) were sequentially added at 0° C. Upon completion of the addition, the reaction flask was allowed to warm to room temperature. After stirring at room temperature overnight, the reaction mixture was washed with water, dried and concentrated under vacuum. The residue was purified by column chromatography (100% DCM-50% EtOAc/DCM) to afford tert-butyl (7S)-3-[(tert-butyl dimethyl silyl)oxy]-7-[2-(thiophen-2-yl)acetamido]-7-[(1R,2R,6S,8R)-6,9,9-trimethyl-3,5-dioxa-4-boratricyclo[6.1.1.0$^{2,6}$]decan-4-yl]heptanoate LIII (340 mg, 0.54 mmol, 39.4% yield for 2 steps).

Step 8

To a solution of amide LIII (300 mg, 0.47 mmol) in 1,4-dioxane (9 mL) was added 9 mL of 3 N HCl. The reaction mixture was heated at reflux for 90 minutes. The cooled reaction mixture was then diluted with water (10 mL) and extracted with diethyl ether (2×10 mL). The aqueous layer was concentrated to afford a sticky solid which was azeotroped with MeCN (3×10 mL). The residue was dissolved in 40% dioxane-water and lyophilized to afford 2-((3R)-2-hydroxy-3-(2-(thiophen-2-yl)acetamido)-1,2-oxaborepan-7-yl)acetic acid 63 as an off-white solid (100 mg, 32.1 mmol, 68.4% yield). $^1$H NMR (CD$_3$OD) δ ppm 1.21-1.38 (m, 2H), 1.42-1.60 (m, 2H), 1.60-1.72 (m, 1H), 1.80-1.94 (m, 1H), 2.32-2.47 (m, 2H), 2.54-2.58 (dd, J=15 Hz, J=6 Hz, 1H), 3.97-3.98 (d, J=8 Hz, 1H), 4.05 (s, 2H), 6.97-7.01 (m, 1H), 7.02-7.10 (m, 1H), 7.33-7.37 (m, 1H); ESIMS found for C$_{13}$H$_{18}$BNO$_5$S m/z 294.0 (M−H$_2$O)$^+$.

Synthesis of 2-((3R)-2-hydroxy-3-(2-(thiophen-2-yl)acetamido)-2,3,4,7-tetrahydro-1,2-oxaborepin-7-yl)acetic acid 64

An example synthesis of 64 is depicted in Scheme 12 and Example 4.

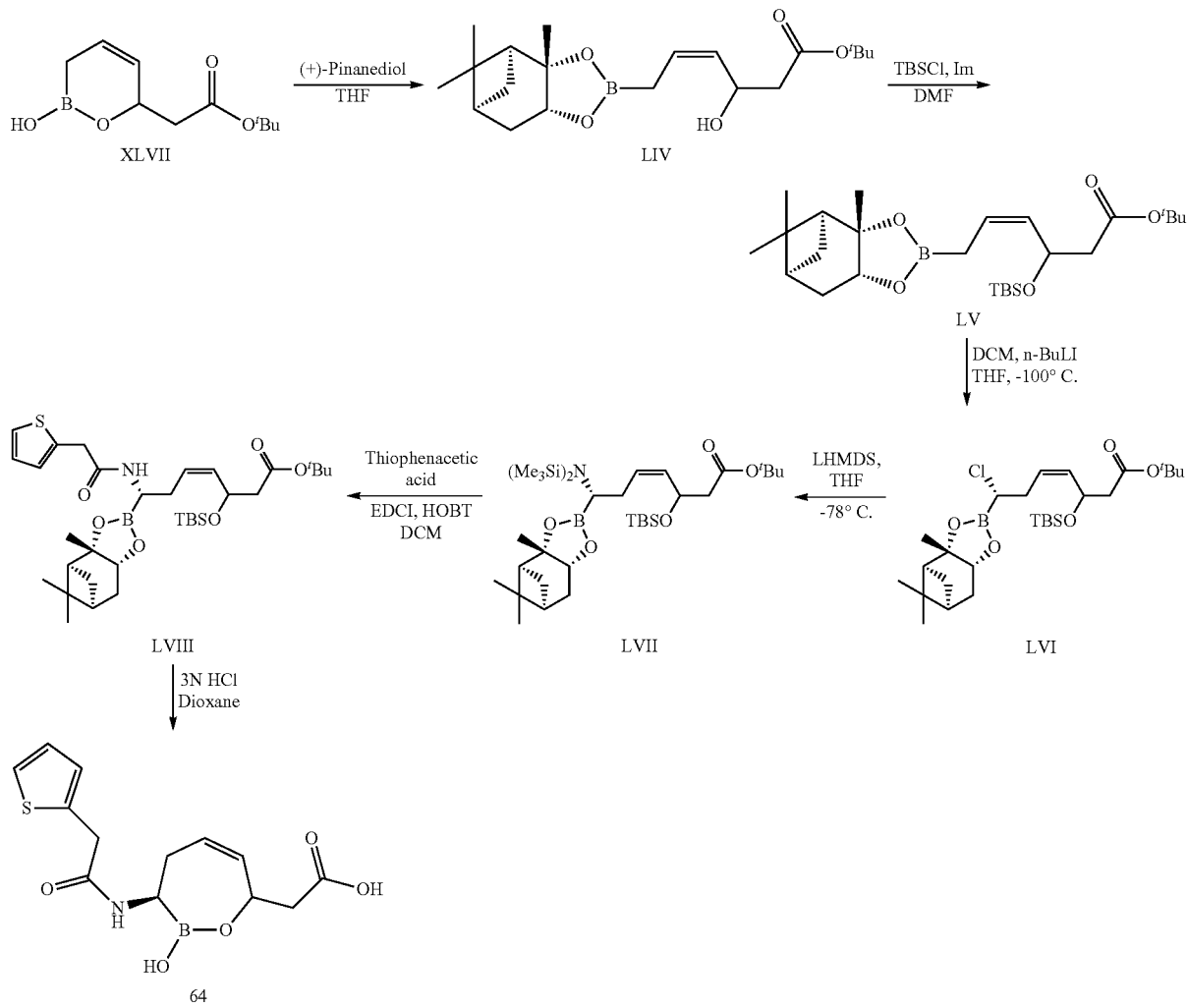

Example 4

Step 1

To a stirred solution of tert-butyl 2-(2-hydroxy-3,6-dihydro-2H-1,2-oxaborinin-6-yl)acetate XLVII (770 mg, 4.58 mmol) in THF (25 mL) was added (1S,2S,3R,5S)-2,6,6-trimethylbicyclo[3.1.1]heptane-2,3-diol (980 mg, 4.58 mmol) at room temperature. The reaction mixture was stirred for 16 h and concentrated under vacuum. The residue was purified by column chromatography (100% hexane→30% EtOAc/hexane) on silica gel to give tert-butyl (4Z)-3-hydroxy-6-[(1R,2R,6S,8R)-6,9,9-trimethyl-3,5-dioxa-4-boratricyclo[6.1.1.0$^{2,6}$]decan-4-yl]hex-4-enoate LIV (1 g, 2.75 mmol, 59.9% yield).

Step 2

To a solution of alcohol LIV (650 mg, 1.78 mmol) in DMF (10 mL) was added imidazole (484 mg, 7.12 mmol) followed by TBDMSCl (534 mg, 3.56 mol). The reaction mixture was stirred at room temperature for 16 h and concentrated under vacuum. The white slurry was dissolved in 100 mL of EtOAc and washed with water (2×10 mL), brine and dried (Na$_2$SO$_4$). The organic extract was concentrated under vacuum and the residue was purified by column chromatography (100% hexane→20% EtOAc/hexane) on silica gel to give tert-butyl (4Z)-3-[(tert-butyldimethylsilyl)oxy]-6-[(1R,2R,6S,8R)-6,9,9-trimethyl-3,5-dioxa-4-boratricyclo[6.1.1.0$^{2,6}$]decan-4-yl]hex-4-enoate LV (800 mg, 1.67 mmol, 93.9% yield).

Step 3

To a solution of DCM (0.3 mL, 4.68 mmol) in THF (8 mL) at −100° C. was added 2.5 M n-butyl lithium in hexane (1.12 mL, 2.8 mmol) slowly under nitrogen and down the inside wall of the flask whilst maintaining the temperature below −90° C. The resulting white precipitate was stirred for 30 minutes before the addition of LV (1.12 g, 2.34 mmol) in THF (3 mL) at −90° C. and the reaction was allowed to warm to room temperature where it was stirred for 16 h. The reaction was quenched with a saturated solution of ammonium chloride and the phases were separated. The aqueous phase was then extracted with diethyl ether (2×10 mL) and the combined organic extracts were dried over Na$_2$SO$_4$, filtered and concentrated under reduced pressure. The concentrated material was then chromatographed (100% hexane→20% EtOAc/hexane) to obtain tert-butyl (4Z,7S)-3-[(tert-butyldimethyl silyl)oxy]-7-chloro-7-[(1R,2R,6S,8R)-6,9,9-trimethyl-3,5-dioxa-4-boratricyclo[6.1.1.0$^{2,6}$]decan-4-yl]hept-4-enoate LVI (820 mg, 1.56 mmol, 66.5% yield).

Step 4

Chloro intermediate LVI (790 mg, 1.49 mmol) in THF (10 mL) was cooled to −78° C. under nitrogen. A solution of 1M LiHMDS solution in THF (1.5 mL, 1.5 mmol) was added slowly at −78° C. Upon completion of the addition, the reaction flask was allowed to warm to room temperature. After stirring at room temperature for 16 h, the reaction mixture was concentrated under vacuum and hexane (20 mL) was added. The precipitated lithium salts were filtered off through a Celite pad, rinsed with additional hexane and the combined filtrates were concentrated under vacuum to give crude tert-butyl (4Z,7S)-7-[bis(trimethylsilyl)amino]-3-[(tert-butyldimethylsilyl)oxy]-7-[(1R,2R,6S,8R)-6,9,9-trimethyl-3,5-dioxa-4-boratricyclo[6.1.1.0$^{2,6}$]decan-4-yl]hept-4-enoate LVII.

Step 5

To a stirred solution of 2-thiophenacetic acid (252 mg, 1.78 mmol) in DCM (35 mL) at 0° C. under nitrogen was added EDCI (426 mg, 2.23 mmol) and HOBT (240 mg, 1.78 mmol). After stirring at 0° C. for 30 minutes, a solution of the crude bis-silyl amide LVII intermediate in DCM (10 mL) followed by N-methyl-morpholine (0.32 mL, 3 mmol) were sequentially added at 0° C. Upon completion of the addition, the reaction flask was allowed to warm to room temperature. After stirring at room temperature overnight, the reaction mixture was washed with water, dried and concentrated under vacuum. The residue was purified by column chromatography (100% DCM-25% EtOAc/DCM) to afford tert-butyl (4Z,7S)-3-[(tert-butyldimethylsilyl)oxy]-7-[2-(thiophen-2-yl)acetamido]-7-[(1R,2R,6S,8R)-6,9,9-trimethyl-3,5-dioxa-4-boratricyclo[6.1.1.0$^{2,6}$]decan-4-yl]hept-4-enoate LVIII (600 mg, 0.95 mmol, 63.7% yield for 2 steps).

Step 6

A solution of amide LVIII (100 mg, 0.15 mmol) in anisole (5 mL) at 0° C. was treated with pre-cooled 90% aq trifluoroacetic acid (10 mL). The reaction mixture was warmed to room temperature and stirred for 16 h. The mixture was evaporated in vacuo, azeotroped with MeCN (3×5 mL). The residue was sonicated in water (10 mL) and ether (10 mL). The aqueous phase was separated, washed with ether (2×5 mL) and freeze dried to give fluffy solid 2-((3R)-2-hydroxy-3-(2-(thiophen-2-yl)acetamido)-2,3,4,7-tetrahydro-1,2-oxaborepin-7-yl)acetic acid 64 (15 mg, 0.05 mmol, 32.3% yield). $^1$H NMR (CD$_3$OD) δ ppm 2.23-2.35 (m, 2H), 2.40-2.61 (m, 2H), 2.76-2.83 (m, 1H), 3.96-4.03 (m, 1H), 4.10 (s, 2H), 5.34-5.40 (m, 1H), 5.53-5.74 (m, 1H), 6.97-7.08 (m, 2H), 7.32-7.39 (m, 1H); ESIMS found for C$_{13}$H$_{16}$BNO$_5$S m/z 292 (M−H$_2$O)$^+$.

Synthesis of ethyl 2-((3R,6S)-2-hydroxy-3-(2-(thiophen-2-yl)acetamido)-1,2-oxaborinan-6-yl)acetate 65

An example synthesis of 65 is depicted in Scheme 13 and Example 5.

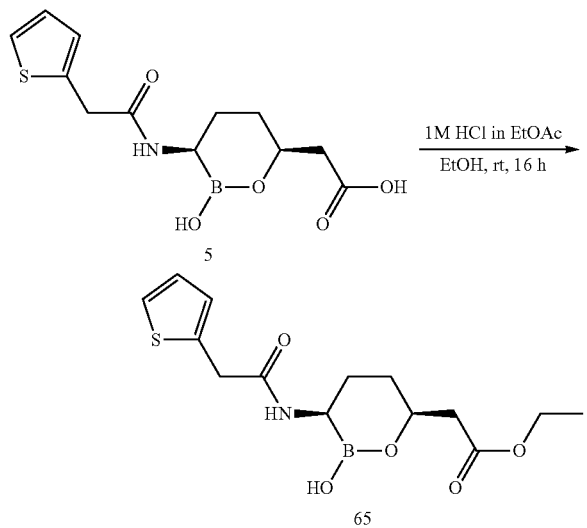

Scheme 13

Example 5

Step 1

To a solution of 5 (400 mg, 1.35 mmol) in 4 mL of absolute ethanol was added anhydrous 1M HCl in EtOAc (4 mL, 4 mmol). The reaction was stirred at room temperature for 16 h. The mixture was then concentrated and azeotroped with acetonitrile (3×10 mL) to give a sticky solid. Ether (10 mL) was added to the azeotroped sticky solid and the resulting precipitate was filtered. The filtered solid was rinsed with additional ether (5 mL) and dried to give ethyl 2-((3R,6S)-2-hydroxy-3-(2-(thiophen-2-yl)acetamido)-1,2-oxaborinan-6-yl)acetate 65 (300 mg, 0.92 mmol, 68.5% yield). $^1$H NMR (CD$_3$OD) δ ppm 0.98-1.09 (q, J=14 Hz, 1H), 1.23-1.26 (t, J=7 Hz, 3H), 1.49-1.54 (dd, J=14 Hz, J=3 Hz, 1H), 1.57-1.64 (dt, J=11 Hz, J=2 Hz, 1H), 1.72-1.78 (brd, J=14 Hz, 1H), 2.24-2.28 (dd, J=15 Hz, J=6 Hz, 1H), 2.34-2.39 (dd, J=15 Hz, J=8 Hz, 1H), 2.63 (brs, 1H), 3.99 (s, 2H), 4.07-4.13 (q, J=4 Hz, 3H), 6.99-7.01 (t, J=4 Hz, 1H), 7.05-7.06 (d, J=3 Hz, 1H), 7.35-7.36 (dd, J=5 Hz, J=1.3 Hz, 1H); ESIMS found for C$_{14}$H$_{20}$BNO$_5$S m/z 308.1 (M−H$_2$O)$^+$.

Synthesis of 2-((3R,7R)-2-hydroxy-3-(2-(thiophen-2-yl)acetamido)-2,3,4,7-tetrahydro-1,2-oxaborepin-7-yl)acetic acid 67

An example synthesis of 67 is depicted in Scheme 14 and Example 6.

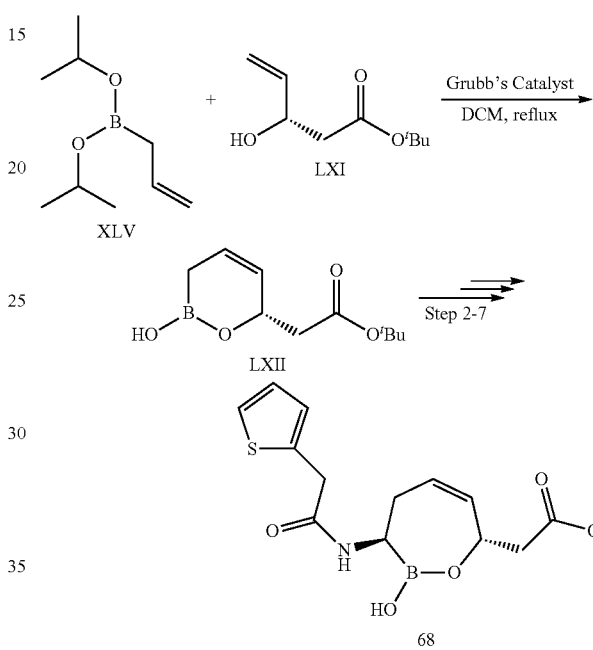

Example 6

Step 1
Prepared starting from enantiomerically pure (R)-tert-butyl 3-hydroxypent-4-enoate [*J. Am. Chem. Soc.* (2007), 129, 4175-4177] in accordance with the procedure described in the above Step 1 of Example 3.
Steps 2-7
Prepared in accordance with the procedure described in the above Steps 1-6 of Example 4.
White fluffy solid (23 mg, 0.074 mmol, 47% yield). $^1$H NMR (CD$_3$OD) δ ppm 2.29-2.31 (m, 1H), 2.40-2.68 (m, 4H), 4.10 (m, 2H), 4.74-4.82 (m, 1H), 5.35-5.38 (m, 1H), 5.53-5.58 (m, 1H), 6.98-7.05 (m, 2H), 7.32-7.36 (m, 1H); ESIMS found for C$_{13}$H$_{16}$BNO$_5$S m/z 292 (M−H$_2$O)$^+$.

Synthesis of 2-((3R,7S)-2-hydroxy-3-(2-(thiophen-2-yl)acetamido)-2,3,4,7-tetrahydro-1,2-oxaborepin-7-yl)acetic acid 68

An example synthesis of 68 is depicted in Scheme 15 and Example 7.

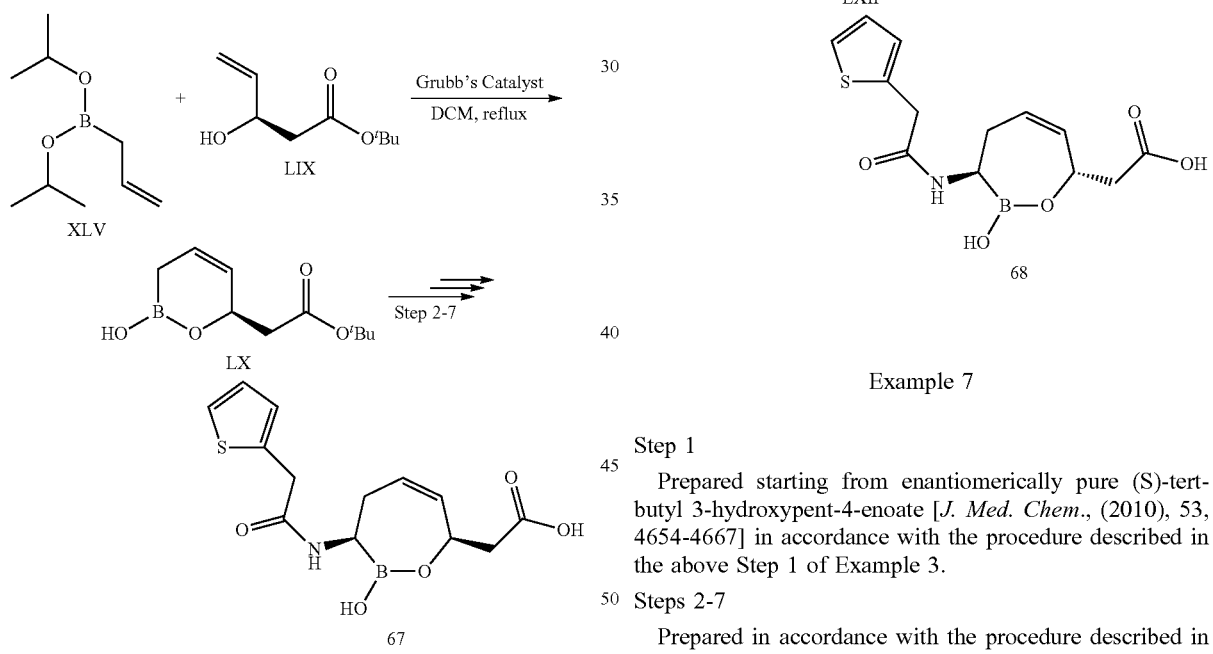

Example 7

Step 1
Prepared starting from enantiomerically pure (S)-tert-butyl 3-hydroxypent-4-enoate [*J. Med. Chem.*, (2010), 53, 4654-4667] in accordance with the procedure described in the above Step 1 of Example 3.
Steps 2-7
Prepared in accordance with the procedure described in the above Steps 1-6 of Example 4.
White fluffy solid (45 mg, 0.146 mmol, 39% yield). $^1$H NMR (CD$_3$OD) δ ppm 2.15-2.18 (m, 1H), 2.29-2.38 (m, 2H), 2.66-2.72 (m, 2H), 3.88-3.91 (m, 1H) 4.00 (s, 2H), 5.24-5.27 (m, 1H), 5.57-5.63 (m, 1H), 6.87-6.96 (m, 2H), 7.24-7.28 (m, 1H); ESIMS found for C$_{13}$H$_{16}$BNO$_5$S m/z 292 (M−H$_2$O)$^+$.

Synthesis of 2-((3R,6S)-3-(benzyloxycarbonylamino)-2-hydroxy-1,2-oxaborinan-6-yl)acetic acid 69

An example synthesis of 69 is depicted in Scheme 16 and Example 8.

Scheme 16

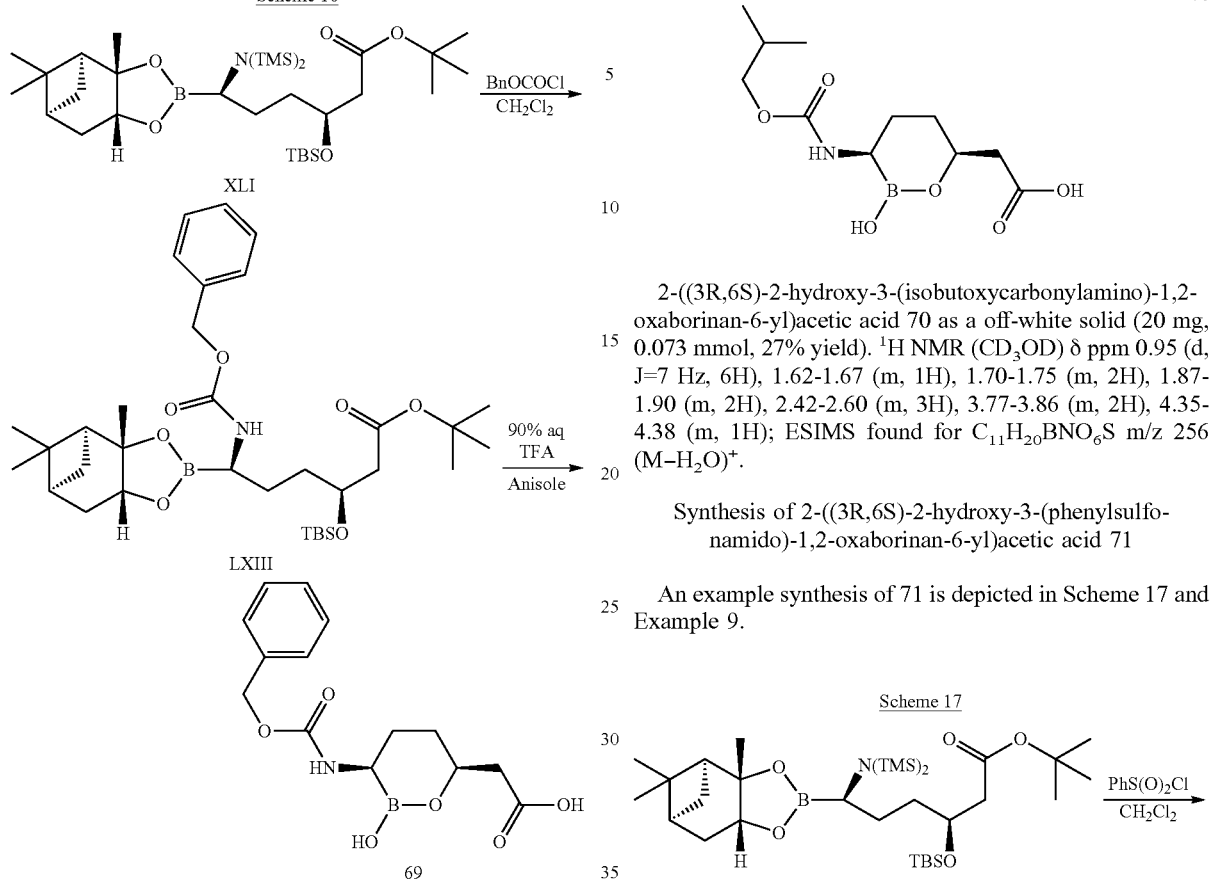

Example 8

Step 1

A solution of bis-silyl amide XLI (0.2 mmol) in DCM (5 mL) was cooled to 0° C. and benzyl chloroformate (0.056 mL, 0.4 mmol) was added. Then, the cooling bath was removed and the solution stirred at ambient temperature for 16 h. The reaction was quenched with water and extracted twice with EtOAc. The organic layers were combined, washed with water, brine, dried ($Na_2SO_4$) and concentrated in vacuo to afford a pale yellow oil as crude product. The residue was chromatographed on a silica column (100% DCM→40% EtOAc/DCM) to afford carbamate LXIII (90 mg, 0.143 mmol, 71.5% yield).

Step 2

A solution of carbamate LXIII (70 mg, 0.11 mmol) in anisole (5 mL) at 0° C. was treated with pre-cooled 90% aq trifluoroacetic acid (10 mL). The reaction mixture was warmed to room temperature and stirred for 16 h. The mixture was evaporated in vacuo, azeotroped with MeCN (3×5 mL). The residue was sonicated in water (10 mL) and ether (10 mL). The aqueous phase was separated, washed with ether (2×5 mL) and freeze dried to give 2-((3R,6S)-3-(benzyloxycarbonylamino)-2-hydroxy-1,2-oxaborinan-6-yl)acetic acid 69 as a fluffy solid (10 mg, 0.033 mmol, 29.6% yield). ESIMS found for $C_{14}H_{18}BNO_6S$ m/z 289.9 $(M-H_2O)^+$.

The following compound is prepared in accordance with the procedure described in the above Example 8.

2-((3R,6S)-2-hydroxy-3-(isobutoxycarbonylamino)-1,2-oxaborinan-6-yl)acetic acid 70 as a off-white solid (20 mg, 0.073 mmol, 27% yield). $^1$H NMR ($CD_3OD$) δ ppm 0.95 (d, J=7 Hz, 6H), 1.62-1.67 (m, 1H), 1.70-1.75 (m, 2H), 1.87-1.90 (m, 2H), 2.42-2.60 (m, 3H), 3.77-3.86 (m, 2H), 4.35-4.38 (m, 1H); ESIMS found for $C_{11}H_{20}BNO_6S$ m/z 256 $(M-H_2O)^+$.

Synthesis of 2-((3R,6S)-2-hydroxy-3-(phenylsulfonamido)-1,2-oxaborinan-6-yl)acetic acid 71

An example synthesis of 71 is depicted in Scheme 17 and Example 9.

Scheme 17

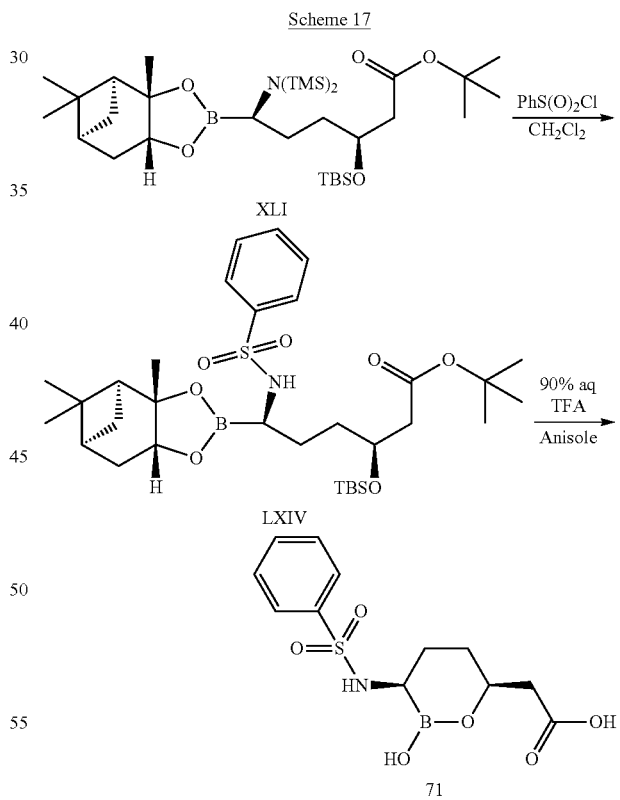

Example 9

Step 1-2

Prepared in accordance with the procedure described in the above Steps 1-2 of Example 8.

Off-white solid (30 mg, 0.096 mmol, 43% yield). $^1$H NMR ($CD_3OD$) δ ppm 1.57-1.83 (series of m, 4H), 2.49-

2.71 (series of m, 3H), 4.35-4.89 (m, 1H), 7.51-7.59 (m, 3H), 7.85-7.89 (m, 2H); ESIMS found for $C_{12}H_{16}BNO_6S$ m/z 296.1 $(M-H_2O)^+$.

Synthesis of 2-((3R,6S)-2-hydroxy-3-(3-phenylureido)-1,2-oxaborinan-6-yl)acetic acid 72

An example synthesis of 72 is depicted in Scheme 18 and Example 10.

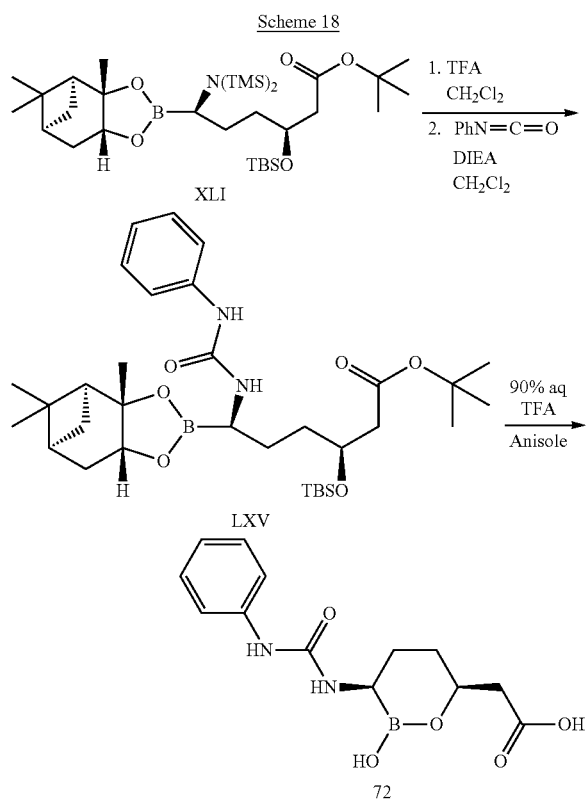

Example 10

Step 1

To a solution of bis-silyl amide XLI (0.2 mmol) in DCM (5 mL) at 0° C. was added a solution of TFA in hexane (0.6 mmol). The reaction was stirred at 0° C. for 20 min before adding phenyl isocyanate (0.04 mL, 0.4 mmol) followed by N,N-diisopropylethylamine (0.18 mL, 1 mmol). The cooling bath was then removed and the solution was stirred at ambient temperature for 16 h. The reaction was quenched with water and extracted twice with EtOAc. The organic layers were combined, washed with water, brine, dried ($Na_2SO_4$) and concentrated in vacuo to afford a pale yellow oil as crude product. The residue was chromatographed on a silica column (100% DCM→25% EtOAc/DCM) to afford the pure urea (50 mg, 0.081 mmol, 40.7% yield).

Step 2

Deprotection was performed following the procedure described above in step 2 of example 8 to give 2-((3R,6S)-2-hydroxy-3-(3-phenylureido)-1,2-oxaborinan-6-yl)acetic acid 72 as a white solid (20 mg, 0.068 mmol, 86% yield). $^1$H NMR ($CD_3OD$) δ ppm 1.24-1.31 (m, 1H), 1.56-1.64 (m, 2H) 1.78-1.81 (m, 1H), 2.36-2.40 (dd, J=15 Hz, J=6 Hz, 1H), 2.46-2.58 (dd, J=13 Hz, J=7 Hz, 1H), 2.68-2.71 (m, 1H), 4.07-4.12 (m, 1H), 7.15-7.18 (m, 1H), 7.34-7.37 (m, 4H); ESIMS found for $C_{13}H_{17}BN_2O_5$ m/z 275.1 $(M-H_2O)^+$.

Illustrative compounds of Formula (I) are shown in Table 1. Some structures are shown with defined configurations at selected stereocenters but the shown stereochemistries are not meant to be limiting and all possible stereoisomers of the shown structures are to be considered encompassed herein. Compounds of any absolute and relative configurations at the stereocenters as well as mixtures of enantiomers and diastereoisomers of any given structure are also encompassed herein.

TABLE 1

| Example | Structure |
|---------|-----------|
| 1 | 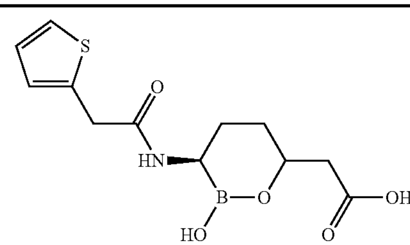 |
| 2 | 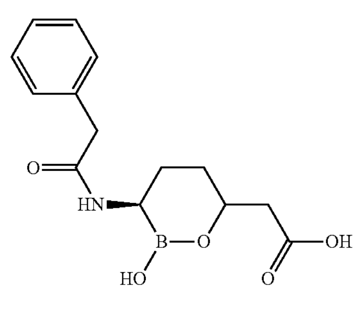 |

TABLE 1-continued

| Example | Structure |
|---|---|
| 3 | (acetamido boronate structure) |
| 4 | (cyclopropanecarboxamido boronate structure) |
| 5 | (2-thienylacetamido boronate structure) |
| 6 | (phenylacetamido boronate structure) |
| 7 | (ammonium chloride boronate structure) |
| 8 | (4-aminobutanamido boronate structure) |
| 9 | (2-amino-2-phenylacetamido boronate structure) |

TABLE 1-continued

| Example | Structure |
|---------|-----------|
| 10 | 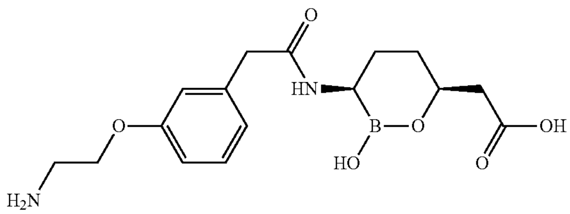 [SMILES: NCCOc1cccc(CC(=O)N[C@H]2CC[C@@H](CC(=O)O)OB2O)c1] |
| 11 | 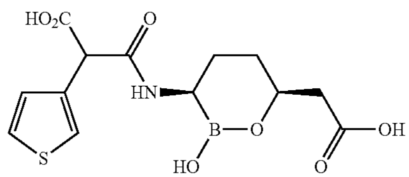 [SMILES: O=C(O)C[C@@H]1CC[C@H](NC(=O)C(C(=O)O)c2ccsc2)B(O)O1] |
| 12 | 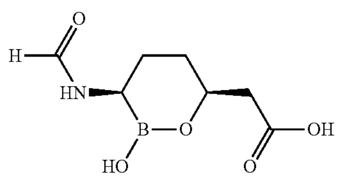 [SMILES: O=CN[C@H]1CC[C@@H](CC(=O)O)OB1O] |
| 13 | 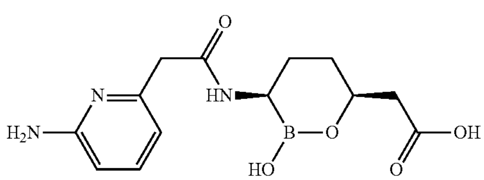 [SMILES: Nc1cccc(CC(=O)N[C@H]2CC[C@@H](CC(=O)O)OB2O)n1] |
| 14 | 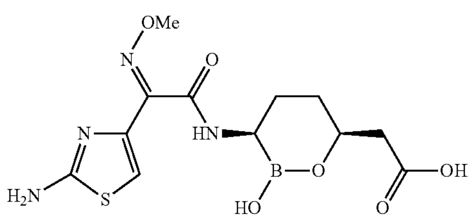 [SMILES: CO/N=C(\C(=O)N[C@H]1CC[C@@H](CC(=O)O)OB1O)c1csc(N)n1] |
| 15 | 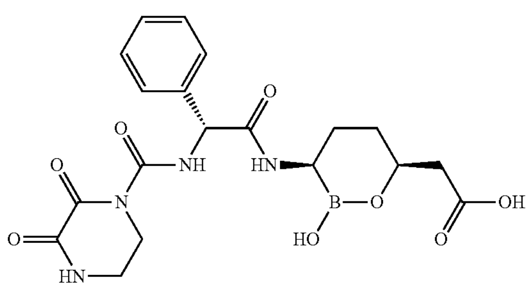 [SMILES: O=C(O)C[C@@H]1CC[C@H](NC(=O)[C@H](NC(=O)N2CCNC(=O)C2=O)c2ccccc2)B(O)O1] |
| 16 | 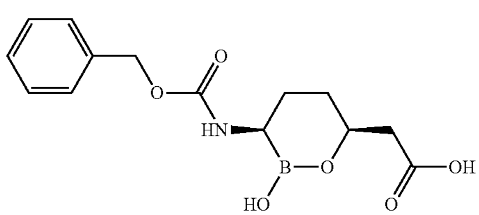 [SMILES: O=C(O)C[C@@H]1CC[C@H](NC(=O)OCc2ccccc2)B(O)O1] |

TABLE 1-continued

| Example | Structure |
|---|---|
| 17 | (phenylacetimidamide-NH linked to boronate tetrahydropyran with CH₂COOH) |
| 18 | (benzyl urea-NH linked to boronate tetrahydropyran with CH₂COOH) |
| 19 | (phenylsulfonamide-NH linked to boronate tetrahydropyran with CH₂COOH) |
| 20 | (pyridin-2-ylamino linked to boronate tetrahydropyran with CH₂COOH) |
| 21 | (pyridin-2-ylmethyl linked to boronate tetrahydropyran with CH₂COOH) |
| 22 | (2,3-dicarboxyphenyl-CH₂C(O)NH linked to boronate tetrahydropyran with CH₂COOH) |
| 23 | (2,3-dicarboxypyridin-4-yl-CH₂C(O)NH linked to boronate tetrahydropyran with CH₂COOH) |

TABLE 1-continued

| Example | Structure |
|---|---|
| 24 | (structure) |
| 25 | (structure) |
| 26 | (structure) |
| 27 | (structure) |
| 28 | (structure) |
| 29 | (structure) |
| 30 | (structure) |

TABLE 1-continued

| Example | Structure |
|---|---|
| 31 | 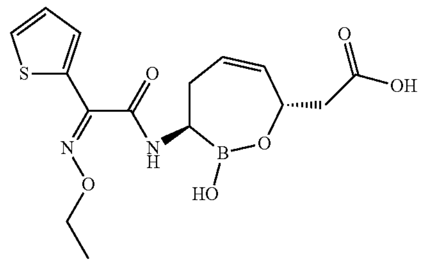 [SMILES: CCO/N=C(\C(=O)N[C@H]1CC=C[C@H](CC(=O)O)OB1O)c1cccs1] |
| 32 | 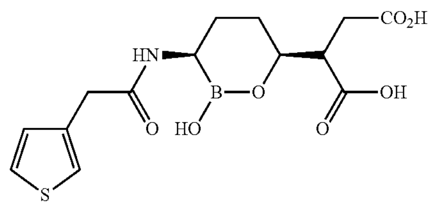 [SMILES: O=C(O)CC(C(=O)O)[C@@H]1CC[C@H](NC(=O)Cc2ccsc2)B(O)O1] |
| 33 | 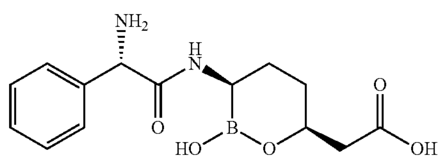 [SMILES: N[C@H](C(=O)N[C@H]1CC[C@@H](CC(=O)O)OB1O)c1ccccc1] |
| 34 | 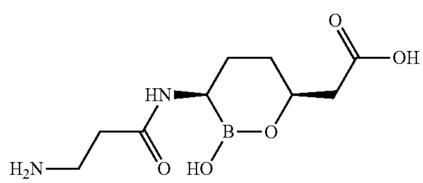 [SMILES: NCCC(=O)N[C@H]1CC[C@@H](CC(=O)O)OB1O] |
| 35 | 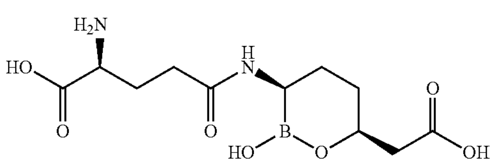 [SMILES: N[C@@H](CCC(=O)N[C@H]1CC[C@@H](CC(=O)O)OB1O)C(=O)O] |
| 36 | 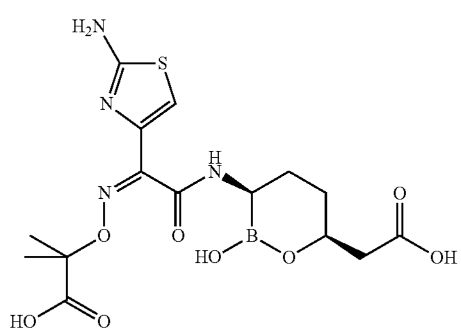 [SMILES: CC(C)(O/N=C(\C(=O)N[C@H]1CC[C@@H](CC(=O)O)OB1O)c1csc(N)n1)C(=O)O] |
| 37 | 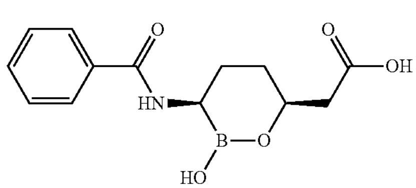 [SMILES: O=C(O)C[C@@H]1CC[C@H](NC(=O)c2ccccc2)B(O)O1] |

TABLE 1-continued
| Example | Structure |
|---|---|
| 38 | 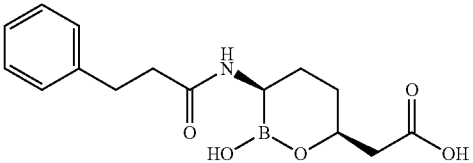 [SMILES: O=C(O)C[C@@H]1CC[C@H](NC(=O)CCc2ccccc2)B(O)O1] |
| 39 | 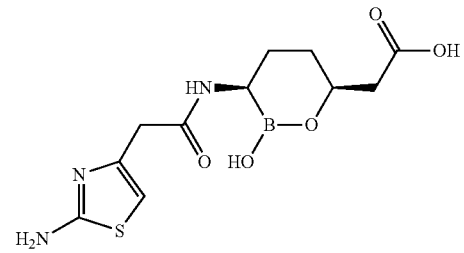 [SMILES: Nc1nc(CC(=O)N[C@H]2CC[C@@H](CC(=O)O)OB2O)cs1] |
| 40 | 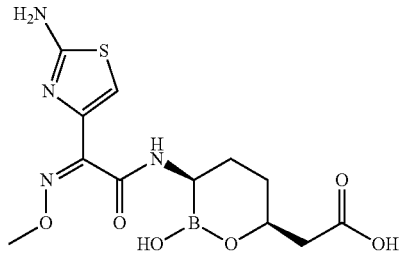 [SMILES: CO/N=C(\C(=O)N[C@H]1CC[C@@H](CC(=O)O)OB1O)c1csc(N)n1] |
| 41 | 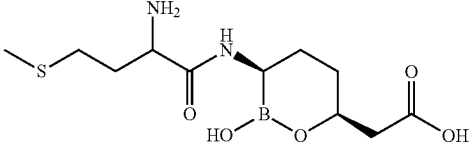 [SMILES: CSCCC(N)C(=O)N[C@H]1CC[C@@H](CC(=O)O)OB1O] |
| 42 | 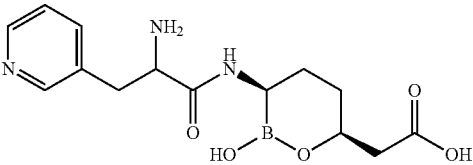 [SMILES: NC(Cc1cccnc1)C(=O)N[C@H]1CC[C@@H](CC(=O)O)OB1O] |
| 43 | 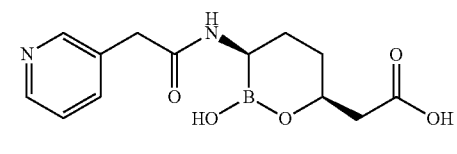 [SMILES: O=C(O)C[C@@H]1CC[C@H](NC(=O)Cc2cccnc2)B(O)O1] |
| 44 | 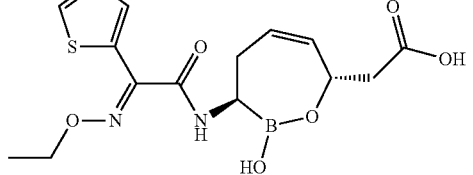 |
| 45 | 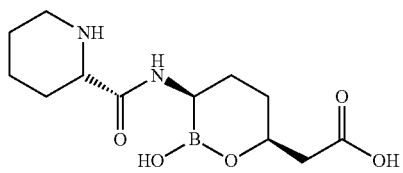 |

TABLE 1-continued

| Example | Structure |
|---------|-----------|
| 46 | 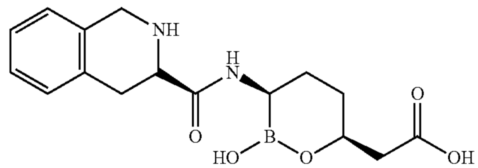 |
| 47 | 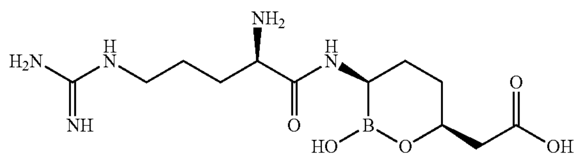 [SMILES: N=C(N)NCCC[C@@H](N)C(=O)N[C@H]1CC[C@@H](CC(=O)O)OB1O] |
| 48 | 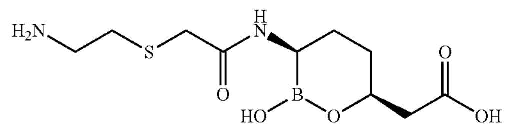 [SMILES: NCCSCC(=O)N[C@H]1CC[C@@H](CC(=O)O)OB1O] |
| 49 | 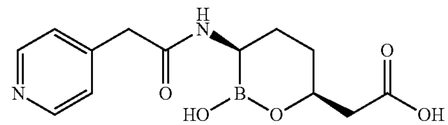 [SMILES: O=C(O)C[C@@H]1CC[C@H](NC(=O)Cc2ccncc2)B(O)O1] |
| 50 | 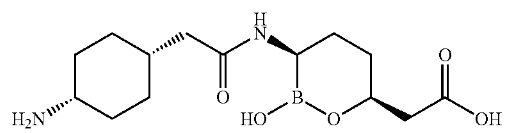 [SMILES: N[C@H]1CC[C@@H](CC(=O)N[C@H]2CC[C@@H](CC(=O)O)OB2O)CC1] |
| 51 | 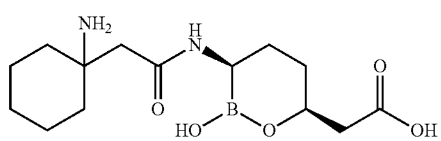 [SMILES: NC1(CC(=O)N[C@H]2CC[C@@H](CC(=O)O)OB2O)CCCCC1] |
| 52 | 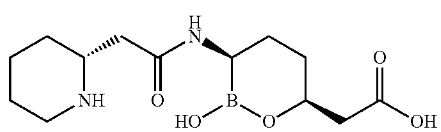 [SMILES: O=C(O)C[C@@H]1CC[C@H](NC(=O)C[C@H]2CCCCN2)B(O)O1] |
| 53 | 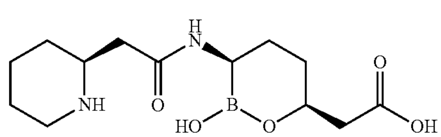 [SMILES: O=C(O)C[C@@H]1CC[C@H](NC(=O)C[C@@H]2CCCCN2)B(O)O1] |
| 54 | 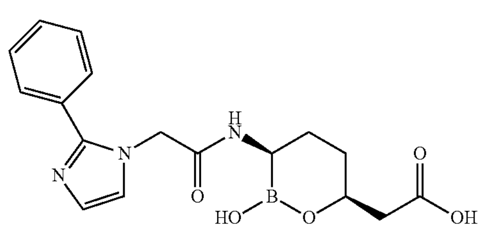 [SMILES: O=C(O)C[C@@H]1CC[C@H](NC(=O)Cn2ccnc2-c2ccccc2)B(O)O1] |

TABLE 1-continued

| Example | Structure |
|---|---|
| 55 | (2-methylbenzimidazol-1-yl)propanoyl-amino boronic acid cyclic ester with acetic acid side chain |
| 56 | 4-(tetrazol-1-ylmethyl)benzoyl-amino boronic acid cyclic ester with acetic acid side chain |
| 57 | (pyridin-2-yl)acetyl-amino boronic acid cyclic ester with acetic acid side chain |
| 58 | 1-cyclopropyl-6-fluoro-7-piperazinyl-4-oxoquinoline-3-carboxamide-amino boronic acid cyclic ester with acetic acid side chain |
| 59 | sulbactam-like sulfone β-lactam triazolylmethyl carboxamide-amino boronic acid cyclic ester with acetic acid side chain |
| 60 | (5-phenyl-1,3,4-oxadiazol-2-yl)propanoyl-amino boronic acid cyclic ester with acetic acid side chain |
| 61 | (2-aminopyridin-4-yl)acetyl-amino boronic acid cyclic ester with acetic acid side chain |

TABLE 1-continued

| Example | Structure |
|---|---|
| 62 | (structure) |
| 63 | (structure) |
| 64 | (structure) |
| 65 | (structure) |
| 66 | (structure) |

TABLE 1-continued
| Example | Structure |
|---|---|
| 67 | 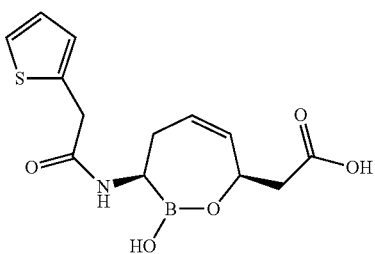 [SMILES: O=C(O)C[C@@H]1C=CC[C@H](NC(=O)Cc2cccs2)B(O)O1] |
| 68 | 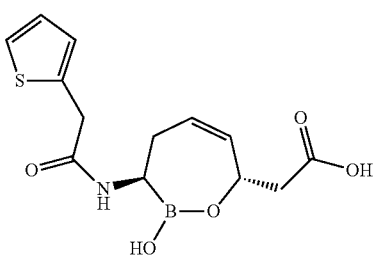 [SMILES: O=C(O)C[C@H]1C=CC[C@H](NC(=O)Cc2cccs2)B(O)O1] |
| 69 | 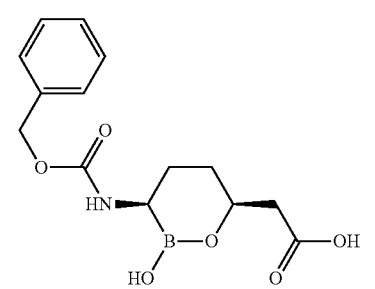 [SMILES: O=C(O)C[C@@H]1CC[C@H](NC(=O)OCc2ccccc2)B(O)O1] |
| 70 | 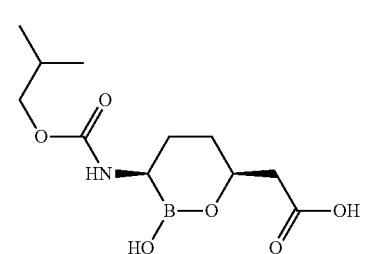 [SMILES: CC(C)COC(=O)N[C@H]1CC[C@@H](CC(=O)O)OB1O] |
| 71 | 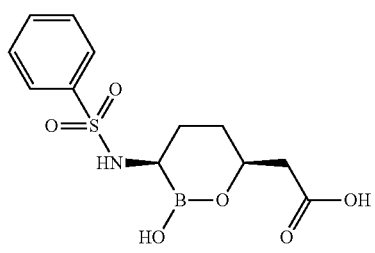 [SMILES: O=C(O)C[C@@H]1CC[C@H](NS(=O)(=O)c2ccccc2)B(O)O1] |
| 72 | 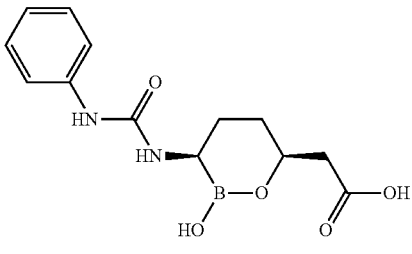 [SMILES: O=C(O)C[C@@H]1CC[C@H](NC(=O)Nc2ccccc2)B(O)O1] |

107 108

TABLE 1-continued

| Example | Structure |
|---|---|
| 73 | 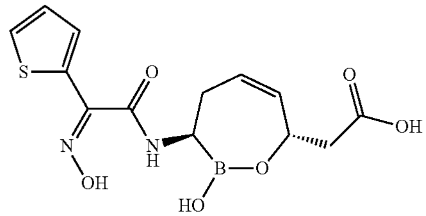 [SMILES: O=C(O)C[C@H]1C=CC[C@H](NC(=O)/C(=N\O)c2cccs2)B(O)O1] |
| 74 | 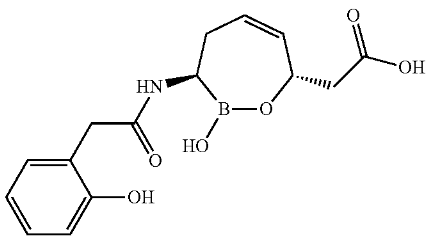 [SMILES: O=C(O)C[C@H]1C=CC[C@H](NC(=O)Cc2ccccc2O)B(O)O1] |
| 75 | 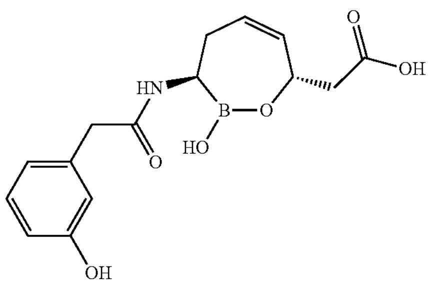 [SMILES: O=C(O)C[C@H]1C=CC[C@H](NC(=O)Cc2cccc(O)c2)B(O)O1] |
| 76 | 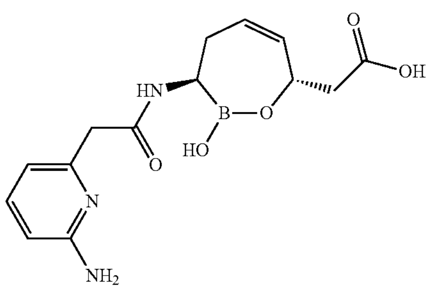 |
| 77 | 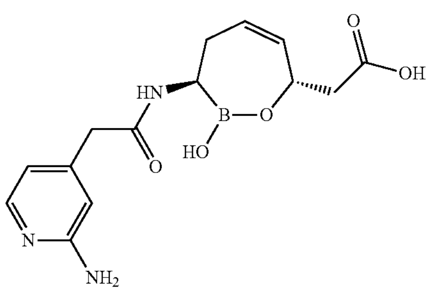 [SMILES: Nc1cc(CC(=O)N[C@H]2CC=C[C@H](CC(=O)O)OB2O)ccn1] |
| 78 | 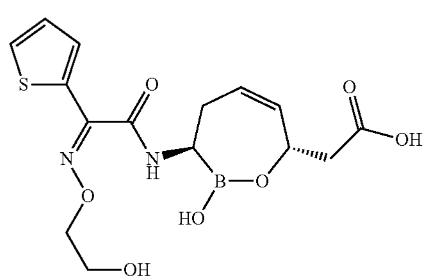 [SMILES: O=C(O)C[C@H]1C=CC[C@H](NC(=O)/C(=N\OCCO)c2cccs2)B(O)O1] |

TABLE 1-continued
| Example | Structure |
|---|---|
| 79 | 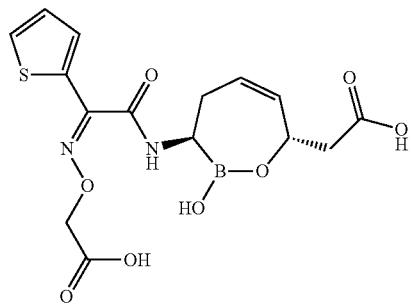 [SMILES: O=C(O)CO/N=C(\C(=O)N[C@H]1CC=C[C@H](CC(=O)O)OB1O)c1cccs1] |
| 80 | 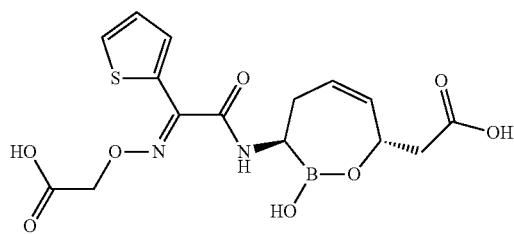 [SMILES: O=C(O)CO/N=C(/C(=O)N[C@H]1CC=C[C@H](CC(=O)O)OB1O)c1cccs1] |
| 81 | 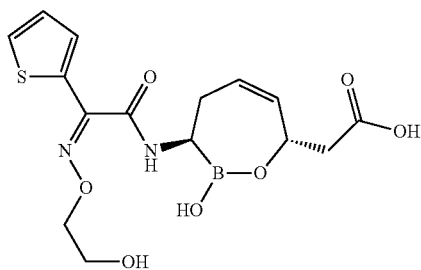 [SMILES: O=C(O)C[C@H]1C=CC[C@H](NC(=O)/C(=N\OCCO)c2cccs2)B(O)O1] |
| 82 | 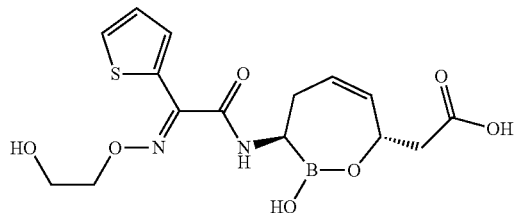 [SMILES: O=C(O)C[C@H]1C=CC[C@H](NC(=O)/C(=N/OCCO)c2cccs2)B(O)O1] |
| 83 | 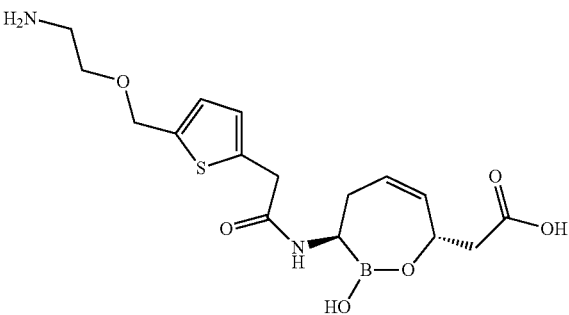 [SMILES: NCCOCc1ccc(CC(=O)N[C@H]2CC=C[C@H](CC(=O)O)OB2O)s1] |

TABLE 1-continued
| Example | Structure |
|---------|-----------|
| 84 | 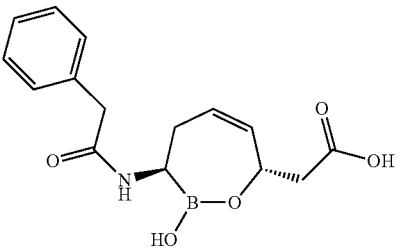 [SMILES: O=C(O)C[C@H]1C=CC[C@H](NC(=O)Cc2ccccc2)B(O)O1] |
| 85 | 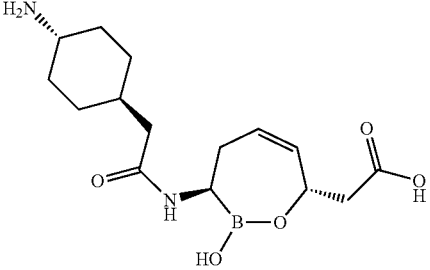 [SMILES: N[C@H]1CC[C@H](CC(=O)N[C@H]2CC=C[C@H](CC(=O)O)OB2O)CC1] |
| 86 | 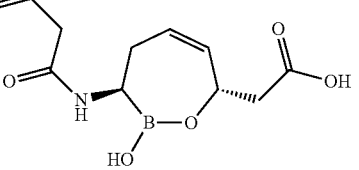 |
| 87 | 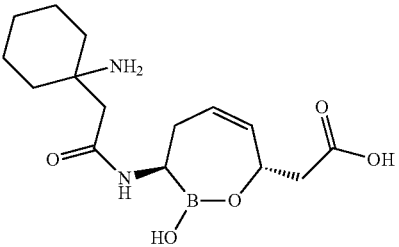 [SMILES: NC1(CC(=O)N[C@H]2CC=C[C@H](CC(=O)O)OB2O)CCCCC1] |
| 88 | 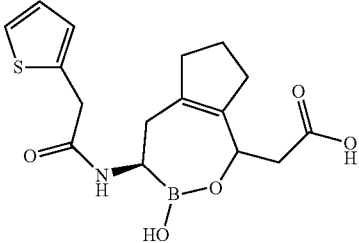 [SMILES: O=C(O)CC1OB(O)[C@@H](NC(=O)Cc2cccs2)CC2=C1CCC2] |
| 89 | 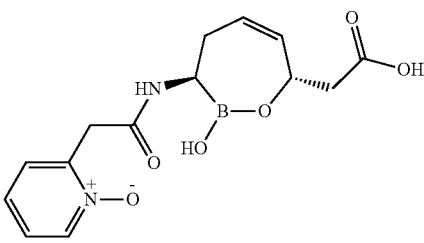 |

TABLE 1-continued

| Example | Structure |
|---|---|
| 90 | 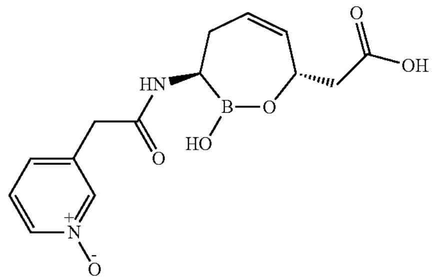 |
| 91 | 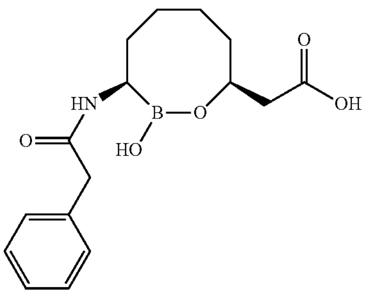 [SMILES: O=C(O)C[C@@H]1CCCC[C@H](NC(=O)Cc2ccccc2)B(O)O1] |
| 92 | 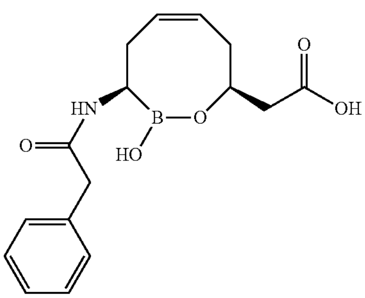 [SMILES: O=C(O)C[C@@H]1C/C=C\C[C@H](NC(=O)Cc2ccccc2)B(O)O1] |
| 93 | 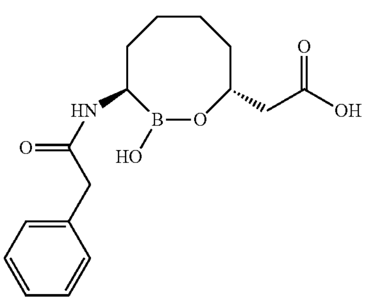 [SMILES: O=C(O)C[C@H]1CCCC[C@H](NC(=O)Cc2ccccc2)B(O)O1] |
| 94 | 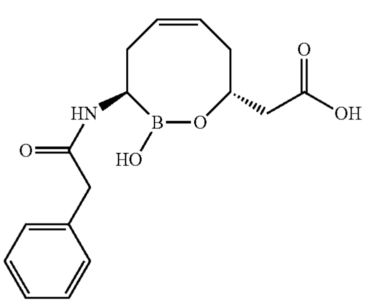 [SMILES: O=C(O)C[C@H]1C/C=C\C[C@H](NC(=O)Cc2ccccc2)B(O)O1] |

TABLE 1-continued
| Example | Structure |
|---|---|
| 95 | 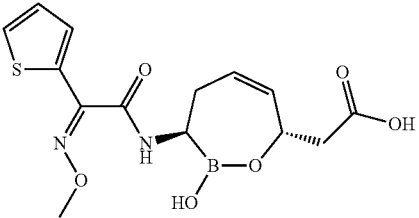 [SMILES: CO/N=C(\C(=O)N[C@H]1CC=C[C@H](CC(=O)O)OB1O)c1cccs1] |
| 96 | 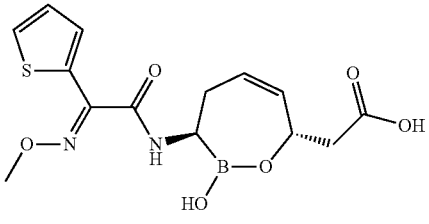 [SMILES: CO/N=C(/C(=O)N[C@H]1CC=C[C@H](CC(=O)O)OB1O)c1cccs1] |
| 97 | 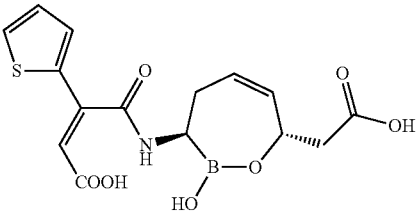 [SMILES: O=C(O)/C=C(\C(=O)N[C@H]1CC=C[C@H](CC(=O)O)OB1O)c1cccs1] |
| 98 | 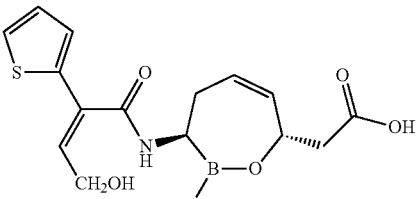 |
| 99 | 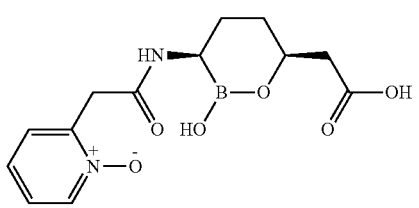 |
| 100 | 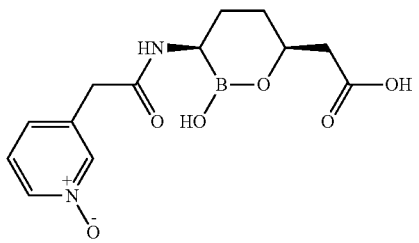 |
| 101 | 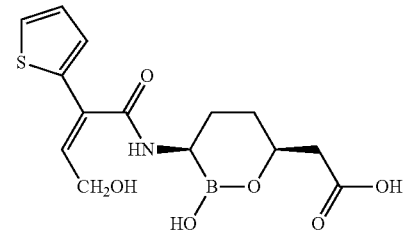 [SMILES: O=C(O)C[C@@H]1CC[C@H](NC(=O)/C(=C\CO)c2cccs2)B(O)O1] |

TABLE 1-continued
| Example | Structure |
|---------|-----------|
| 102 | 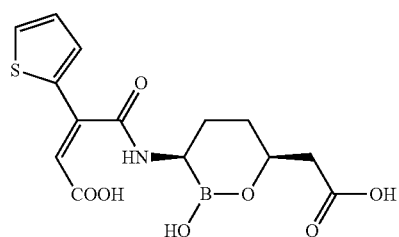 [SMILES: O=C(O)/C=C(\C(=O)N[C@H]1CC[C@@H](CC(=O)O)OB1O)c1cccs1] |
| 103 | 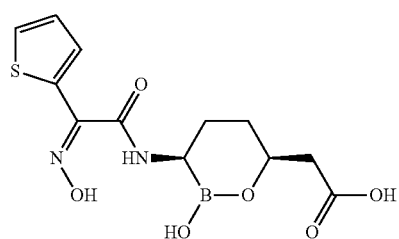 [SMILES: O=C(O)C[C@@H]1CC[C@H](NC(=O)/C(=N\O)c2cccs2)B(O)O1] |
| 104 | 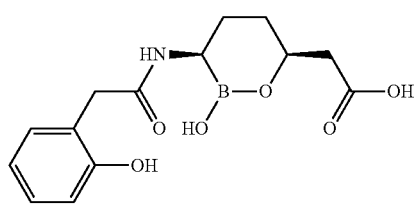 [SMILES: O=C(O)C[C@@H]1CC[C@H](NC(=O)Cc2ccccc2O)B(O)O1] |
| 105 | 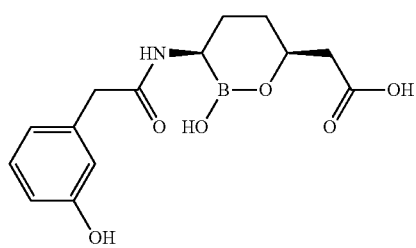 [SMILES: O=C(O)C[C@@H]1CC[C@H](NC(=O)Cc2cccc(O)c2)B(O)O1] |
| 106 | 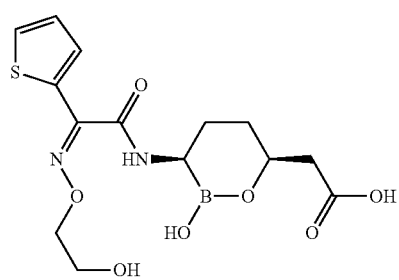 [SMILES: O=C(O)C[C@@H]1CC[C@H](NC(=O)/C(=N\OCCO)c2cccs2)B(O)O1] |
| 107 | 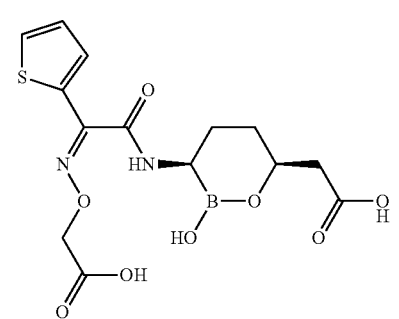 [SMILES: O=C(O)CO/N=C(\C(=O)N[C@H]1CC[C@@H](CC(=O)O)OB1O)c1cccs1] |

TABLE 1-continued
| Example | Structure |
|---|---|
| 108 | 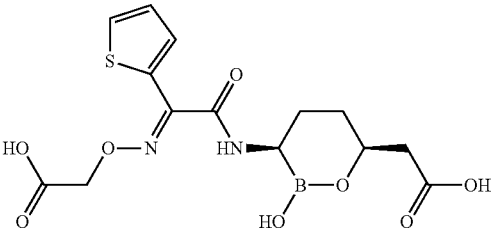 [SMILES: O=C(O)CO/N=C(/C(=O)N[C@H]1CC[C@@H](CC(=O)O)OB1O)c1cccs1] |
| 109 | 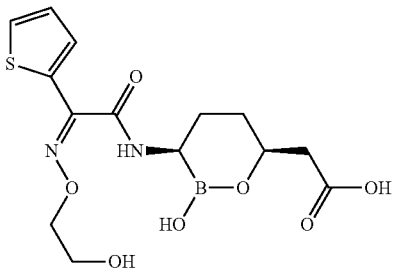 [SMILES: O=C(O)C[C@@H]1CC[C@H](NC(=O)/C(=N\OCCO)c2cccs2)B(O)O1] |
| 110 | 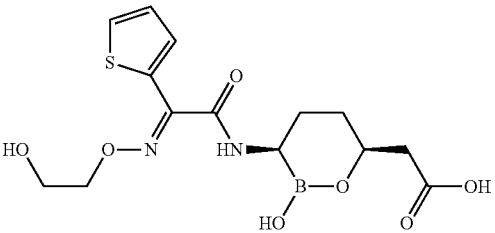 |
| 111 | 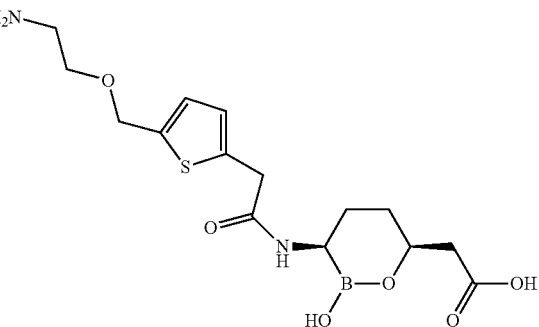 |
| 112 | 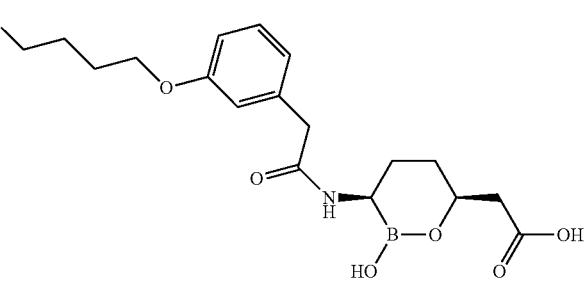 |
| 113 | 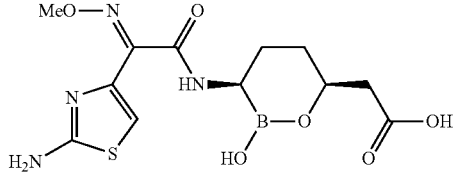 [SMILES: CO/N=C(/C(=O)N[C@H]1CC[C@@H](CC(=O)O)OB1O)c1csc(N)n1] |

TABLE 1-continued

| Example | Structure |
|---|---|
| 114 | 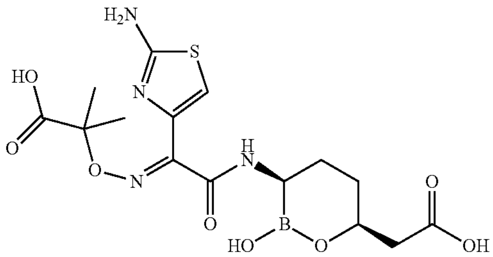 [SMILES: CC(C)(O/N=C(/C(=O)N[C@H]1CC[C@@H](CC(=O)O)OB1O)c1csc(N)n1)C(=O)O] |
| 115 | 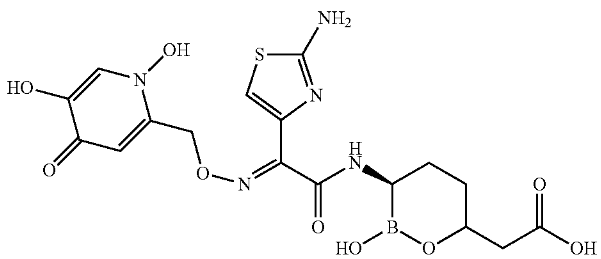 [SMILES: Nc1nc(/C(=N\OCc2cc(=O)c(O)cn2O)C(=O)N[C@H]2CCC(CC(=O)O)OB2O)cs1] |
| 116 | 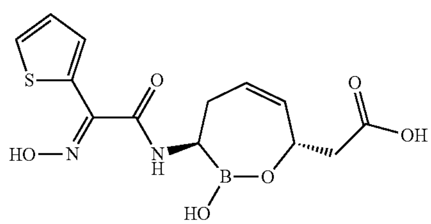 [SMILES: O=C(O)C[C@H]1C=CC[C@H](NC(=O)/C(=N/O)c2cccs2)B(O)O1] |
| 117 | 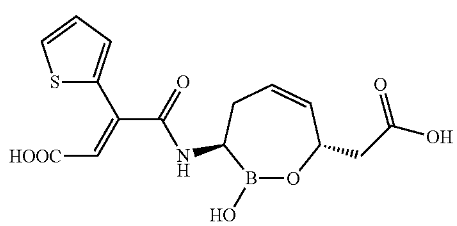 [SMILES: O=C(O)/C=C(/C(=O)N[C@H]1CC=C[C@H](CC(=O)O)OB1O)c1cccs1] |
| 118 | 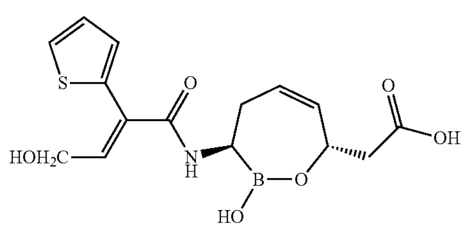 [SMILES: O=C(O)C[C@H]1C=CC[C@H](NC(=O)/C(=C/CO)c2cccs2)B(O)O1] |
| 119 | 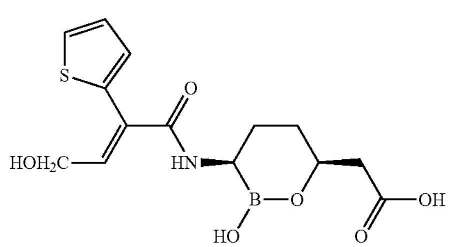 [SMILES: O=C(O)C[C@@H]1CC[C@H](NC(=O)/C(=C/CO)c2cccs2)B(O)O1] |

TABLE 1-continued

| Example | Structure |
|---------|-----------|
| 120 | (structure: thiophene-substituted acrylamide with HOOC group, linked via HN to a boron-containing cyclic structure with B—O, HO, and carboxylic acid group) |
| 121 | (structure: thiophene with HO—N= oxime, amide linked to boron-containing cyclic structure with B—O, HO, and carboxylic acid group) |

Example 11

The potency and spectrum of β-lactamase inhibitors was determined by assessing their antibiotic potentiation activity.

The potentiation effect is observed by the reduction of the minimum inhibitory concentration of β-lactam antibiotics in the presence of β-lactamase inhibitors (BLIs). The activity of BLIs in combination with ceftazidime or biapenem is assessed by the checkerboard assay (Antimicrobial Combinations. In Antibiotics in Laboratory Medicine, Ed. Victor Lorian, M.D., Fourth edition, 1996, pp 333-338) using broth microdilution method performed as recommended by the NCCLS (National Committee for Clinical Laboratory Standards (NCCLS). 1997. Methods for Dilution of Antimicrobial Susceptibility Tests for Bacteria That Grow Aerobically—Fourth Edition; Approved Standard. NCCLS Document M7-A4, Vol 17 No. 2). In this assay, multiple dilutions of two drugs, namely BLI and β-lactam (ceftazidime or biapenem), are being tested, alone and in combination, at concentrations equal to, above and below their respective minimal inhibitory concentrations (MICs). BLIs are solubilized in 10% DMSO at 10 mg/mL. Stock solutions are further diluted, according to the needs of a particular assay, in Mueller Hinton Broth (MHB). Stock solution can be stored at −80° C.

The checkerboard (CB) assay is performed in microtiter plates. Ceftazidime or biapenem are diluted in the x axis, each column containing a single concentration of antibiotic. BLIs are diluted in the y axis, each row containing an equal concentration of BLI. The result of these manipulations is that each well of the microtiter plate contains a unique combination of concentrations of the two agents. The assay is performed in MHB with a final bacterial inoculum of 5×10$^5$ CFU/mL (from an early-log phase culture). Microtiter plates are incubated during 20 h at 35° C. and are read using a microtiter plate reader (Molecular Devices) at 650 nm as well as visual observation using a microtiter plate reading mirror. The MIC is defined as the lowest concentration of antibiotics, within the combination, at which the visible growth of the organism is completely inhibited. Activity of BLIs is reported at MPC8, or the minimal potentiation concentration to reduce the MIC of antibiotic 8-fold.

Ceftazidime potentiation is studied in strains of various bacteria that are resistant to ceftazidime due to expression of β-lactamase hydrolyzing enzymes. The panel of strains used in checkerboard experiments contains β-lactamases that belong to all the known classes of these enzymes: A, B, C and D. Activity of Compound 1 is tested at the maximum concentration of 40 μg/mL. At this concentration it shows no inhibition of growth of any bacteria tested, however at concentration as low as 0.6 μg/mL it reduced MICs to ceftazidime 8-fold in some bacteria (Table 2). Based on CB results, 1 has a broad-spectrum β-lactam potentiation activity against the strains expressing β-lactamases. Compound 1 was the most potent against the strains expressing KPCs and other class A enzymes (CTX-M-3), and some class C (MIR-1, CMY-2), and class D (OXA-2) enzymes.

TABLE 2

| Strain | Organism | Description | PCR | Class | MPC8 |
|--------|----------|-------------|-----|-------|------|
| KP1005 | Klebsiella pneumoniae | ESBL | CTX-M-14 | A | Z |
| KP1009 | Klebsiella pneumoniae | ESBL | CTX-M-15 | A | Y |
| EC1008 | Escherichia coli | ESBL | CTX-M-3 | A | X |
| KP1004 | Klebsiella pneumoniae | Serine carbapenemase | KPC-2 | A | X |
| KP1008 | Klebsiella pneumoniae | Serine carbapenemase | KPC-2 | A | X |
| EC1007 | Escherichia coli | Serine carbapenemase | KPC-3 | A | X |
| KP1010 | Klebsiella pneumoniae | ESBL | SHV-12 | A | Y |
| KP1012 | Klebsiella pneumoniae | ESBL | SHV-18 | A | Y |
| ec306 | Escherichia coli | First ESBL described | SHV-2 | A | Y |
| ec307 | Escherichia coli | Common SHV ESBL | SHV-4 | A | Y |
| ec308 | Escherichia coli | Common SHV ESBL | SHV-5 | A | Y |
| EC1009 | Escherichia coli | ESBL | TEM-10 | A | Z |
| ec302 | Escherichia coli | Common ESBL in US | TEM-10 | A | Z |
| EC1012 | Escherichia coli | ESBL | TEM-12 | A | Y |
| ec303 | Escherichia coli | Common ESBL in US | TEM-12 | A | Y |
| EC1011 | Escherichia coli | ESBL | TEM-26 | A | Z |

TABLE 2-continued

| Strain | Organism | Description | PCR | Class | MPC8 |
|---|---|---|---|---|---|
| ec304 | Escherichia coli | Common ESBL in US | TEM-26 | A | Z |
| ec300 | Escherichia coli | Common ESBL in France | TEM-3 | A | Y |
| ec301 | Escherichia coli | ESBL | TEM-6 | A | Z |
| CF1000 | Citrobacter freundii | Hyper AmpC expression | | C | Y |
| ECL1003 | Enterobacter cloacae | Hyper AmpC expression | | C | Z |
| ec310 | Escherichia coli | E. cloacae-like Amp-C | ACT-1 | C | X |
| EC1004 | Escherichia coli | pAmpC | CMY-2 | C | X |
| EC1010 | Escherichia coli | pAmpC | CMY-6 | C | Y |
| EC1014 | Escherichia coli | pAmpC | DHA-1 | C | Z |
| EC1006 | Escherichia coli | pAmpC | FOX-5 | C | Y |
| EC1016 | Escherichia coli | pAmpC | FOX-5 | C | Z |
| ec309 | Escherichia coli | E. cloacae-like Amp-C | MIR-1 | C | X |
| KP1007 | Klebsiella pneumoniae | ESBL | OXA-10, qnrB4 | D | Y |
| KX1000 | Klebsiella oxytoca | ESBL | OXA-2 | D | X |

X = MPC8 of 2.5 μg/mL or less.
Y = MPC8 of greater than 2.5 μg/mL to 10 μg/mL.
Z = MPC8 of greater than 10 μg/mL.

Next, ceftazidime potentiation activity of several cyclic boronic acid ester derivatives was tested using a larger panel of strains expressing β-lactamase hydrolyzing enzymes. Ceftazidime MICs were determined alone and in the presence of fixed concentrations of various cyclic boronic acid ester derivatives. Most compounds were tested at 10 μg/mL. Cyclic boronic acid ester derivatives were capable of reducing ceftazidime MICs 4 to >64-fold depending on β-lactamase (Table 3).

TABLE 3

| | | | | | | Ceftazidime MIC (μg/mL) with or without cyclic boronic acid ester derivative | | | | | |
|---|---|---|---|---|---|---|---|---|---|---|---|
| Strain | Organism | Description | PCR | Class | Alone | 3 at 10 μg/mL | 4 at 10 μg/mL | 5 at 10 μg/mL | 6 at 10 μg/mL | 7 at 10 μg/mL |
| KP1005 | Klebsiella pneumoniae | ESBL | CTX-M-14 | A | Z | Z | Z | Z | Z | Z |
| KP1009 | Klebsiella pneumoniae | ESBL | CTX-M-15 | A | Z | Z | Z | Z | Z | Z |
| KP1006 | Klebsiella pneumoniae | ESBL | CTX-M2 | A | Y | X | X | X | X | ND |
| EC1008 | Escherichia coli | ESBL | CTX-M3 | A | Z | Y | Y | Y | Y | Z |
| pa 1063 | Pseudomonas aeruginosa | ESBL | GES-1 | A | Z | Z | Z | Z | Z | Z |
| KP1004 | Klebsiella pneumoniae | Serine carbapenemase | KPC-2 | A | Z | Y | Y | Y | Y | Z |
| KP1008 | Klebsiella pneumoniae | Serine carbapenemase | KPC-2 | A | Y | X | X | X | X | Z |
| EC1007 | Escherichia coli | Serine carbapenemase | KPC-3 | A | Z | X | X | X | X | Z |
| KP1010 | Klebsiella pneumoniae | ESBL | SHV-12 | A | Z | Z | Z | Y | Y | Z |
| KP1012 | Klebsiella pneumoniae | ESBL | SHV-18 | A | Z | Z | Z | Y | Y | Z |
| ec306 | Escherichia coli | First ESBL described | SHV-2 | A | Z | Z | Z | Z | Z | Z |
| ec307 | Escherichia coli | Common SHV ESBL | SHV-4 | A | Z | Z | Z | Y | Z | Z |
| ec308 | Escherichia coli | Common SHV ESBL | SHV-5 | A | Z | Z | Z | Z | Z | Z |
| KP1011 | Klebsiella pneumoniae | ESBL | SHV-5 | A | Y | X | X | X | X | ND |
| EC1009 | Escherichia coli | ESBL | TEM-10 | A | Z | Z | Z | Z | Z | Z |
| ec302 | Escherichia coli | Common ESBL in US | TEM-10 | A | Z | Z | Z | Z | Z | Z |
| EC1012 | Escherichia coli | ESBL | TEM-12 | A | Z | Z | Z | Y | Y | Z |
| ec303 | Escherichia coli | Common ESBL in US | TEM-12 | A | Z | Z | Z | Y | Y | Z |
| EC1011 | Escherichia coli | ESBL | TEM-26 | A | Z | Z | Z | Z | Z | Z |
| ec300 | Escherichia coli | Common ESBL in France | TEM-3 | A | Z | Z | Z | Y | Z | Z |
| ec301 | Escherichia coli | ESBL | TEM-6 | A | Z | Z | Z | Z | Z | Z |
| KP1014 | Klebsiella pneumoniae | Metallo β-lactamase | Vim-1 | B | Z | Z | Z | Z | Z | ND |
| CF1000 | Citrobacter freundii | Hyper AmpC expression | | C | Z | Z | Z | Y | Y | Z |
| CF1001 | Citrobacter freundii | Hyper AmpC expression | | C | Z | Z | Z | Y | Y | ND |

TABLE 3-continued

| | | | | | | Ceftazidime MIC (µg/mL) with or without cyclic boronic acid ester derivative | | | | | |
|---|---|---|---|---|---|---|---|---|---|---|---|
| Strain | Organism | Description | PCR | Class | Alone | 3 at 10 µg/mL | 4 at 10 µg/mL | 5 at 10 µg/mL | 6 at 10 µg/mL | 7 at 10 µg/mL | | |
| ECL1002 | Enterobacter cloacae | Hyper AmpC expression | | C | Z | Z | Z | Y | Y | Y | Z |
| ECL1003 | Enterobacter cloacae | Hyper AmpC expression | | C | Z | Z | Z | Z | Z | Z | ND |
| ec310 | Escherichia coli | E. cloacae-like Amp-C | ACT-1 | C | Z | Z | Y | Y | X | X | Z |
| EC1004 | Escherichia coli | pAmpC | CMY-2 | C | Z | Z | Y | Y | Y | Y | Z |
| SA1000 | Salmonella | pAmpC | CMY-2 | C | Z | Z | Z | Y | Y | X | ND |
| KP1013 | Klebsiella pneumoniae | pAmpC | CMY-2 | C | Z | Z | Z | Y | Y | Y | ND |
| EC1010 | Escherichia coli | pAmpC | CMY-6 | C | Z | Z | Z | Y | Y | Y | Z |
| EC1014 | Escherichia coli | pAmpC | DHA-1 | C | Z | Z | Y | Y | X | X | Z |
| EC1006 | Escherichia coli | pAmpC | FOX-5 | C | Z | Z | Y | Z | Y | Y | Z |
| EC1016 | Escherichia coli | pAmpC | FOX-5 | C | Z | Z | Z | Z | Z | Z | ND |
| ec309 | Escherichia coli | E. cloacae-like Amp-C | MIR-1 | C | Z | Z | Y | Y | X | X | Z |
| PAM2005 | Pseudomonas aeruginosa | ampC | | C | Z | Z | Z | Z | Z | Z | Z |
| PAM2035 | Pseudomonas aeruginosa | ampC mexA:tet | | C | Z | Z | Z | Z | Y | Y | Z |
| KP1007 | Klebsiella pneumoniae | ESBL | OXA-10 | D | Z | Z | Z | Z | Y | Y | Z |
| KX1000 | Klebsiella oxytoca | ESBL | OXA-2 | D | Z | Z | Y | Y | Y | Y | Y |
| AB1054 | Acinetobacter baumannii | OXA-carbapenemase | OXA-23 | D | Z | Z | Z | Z | Z | Z | Z |
| AB1052 | Acinetobacter baumannii | OXA-carbapenemase | OXA-24 | D | Z | Z | Z | Z | Z | Z | ND |
| AB1057 | Acinetobacter baumannii | OXA-carbapenemase | OXA-58 | D | Z | Z | Z | Z | Z | Z | Z |

X = MIC of 1 µg/mL or less.
Y = MIC of greater than 1 µg/mL to 8 µg/mL.
Z = MIC of greater than 8 µg/mL.
ND = Not Determined.

Biapenem is a carbapenem β-lactam; only selected β-lactamases confer resistance to this class of antibiotics. Among them are serine carbapemenases that belong to class A and class D. Biapenem potentiation is studied in strains expressing various carbapenemases from these classes using CB assays. Various cyclic boronic acid ester derivatives showed significant potentiation of biapenem against the strains expressing class A carbapenemases: MPC8 (minimal potentiation concentration of cyclic boronic acid ester derivative (µg/mL) to reduce the MIC of Biapenem 8-fold) varied from 0.02 µg/mL to 0.16 ng/mL (Table 4). Cyclic boronic acid ester derivatives were capable of reducing biapenem MICs up to 1000-fold (Table 4).

TABLE 4

| Strain | Organism | Description | PCR | Class | Compound | MPC8 |
|---|---|---|---|---|---|---|
| ECL1004 | Enterobacter cloacae | Serine carbapenemase | NMC-A | A | 1 | Y |
| EC1007 | Escherichia coli | Serine carbapenemase | KPC-3 | A | 1 | X |
| KP1004 | Klebsiella pneumoniae | Serine carbapenemase | KPC-2 | A | 1 | Y |
| SM1000 | Serratia marcescens | Serine carbapenemase | SME-2 | A | 1 | Y |
| ECL1004 | Enterobacter cloacae | Serine carbapenemase | NMC-A | A | 2 | Y |
| EC1007 | Escherichia coli | Serine carbapenemase | KPC-3 | A | 2 | X |
| KP1004 | Klebsiella pneumoniae | Serine carbapenemase | KPC-2 | A | 2 | X |
| SM1000 | Serratia marcescens | Serine carbapenemase | SME-2 | A | 2 | Y |
| ECL1004 | Enterobacter cloacae | Serine carbapenemase | NMC-A | A | 3 | X |
| EC1007 | Escherichia coli | Serine carbapenemase | KPC-3 | A | 3 | X |
| KP1004 | Klebsiella pneumoniae | Serine carbapenemase | KPC-2 | A | 3 | X |
| KP1008 | Klebsiella pneumoniae | Serine carbapenemase | KPC-2 | A | 3 | X |
| SM1000 | Serratia marcescens | Serine carbapenemase | SME-2 | A | 3 | Y |
| AB1052 | Acinetobacter baumannii | OXA-carbapenemase | OXA-24 | D | 3 | Z |
| AB1054 | Acinetobacter baumannii | OXA-carbapenemase | OXA-23 | D | 3 | Z |
| AB1057 | Acinetobacter baumannii | OXA-carbapenemase | OXA-58 | D | 3 | Z |
| ECL1004 | Enterobacter cloacae | Serine carbapenemase | NMC-A | A | 4 | X |
| EC1007 | Escherichia coli | Serine carbapenemase | KPC-3 | A | 4 | X |

TABLE 4-continued

| Strain | Organism | Description | PCR | Class | Compound | MPC8 |
|---|---|---|---|---|---|---|
| KP1004 | Klebsiella pneumoniae | Serine carbapenemase | KPC-2 | A | 4 | X |
| KP1008 | Klebsiella pneumoniae | Serine carbapenemase | KPC-2 | A | 4 | X |
| SM1000 | Serratia marcescens | Serine carbapenemase | SME-2 | A | 4 | X |
| AB1052 | Acinetobacter baumannii | OXA-carbapenemase | OXA-24 | D | 4 | Z |
| AB1054 | Acinetobacter baumannii | OXA-carbapenemase | OXA-23 | D | 4 | Z |
| AB1057 | Acinetobacter baumannii | OXA-carbapenemase | OXA-58 | D | 4 | Z |
| ECL1004 | Enterobacter cloacae | Serine carbapenemase | NMC-A | A | 5 | Y |
| EC1007 | Escherichia coli | Serine carbapenemase | KPC-3 | A | 5 | X |
| KP1004 | Klebsiella pneumoniae | Serine carbapenemase | KPC-2 | A | 5 | X |
| SM1000 | Serratia marcescens | Serine carbapenemase | SME-2 | A | 5 | Y |
| AB1052 | Acinetobacter baumannii | OXA-carbapenemase | OXA-24 | D | 5 | Z |
| AB1054 | Acinetobacter baumannii | OXA-carbapenemase | OXA-23 | D | 5 | Z |
| AB1057 | Acinetobacter baumannii | OXA-carbapenemase | OXA-58 | D | 5 | Z |
| ECL1004 | Enterobacter cloacae | Serine carbapenemase | NMC-A | A | 6 | Y |
| EC1007 | Escherichia coli | Serine carbapenemase | KPC-3 | A | 6 | X |
| KP1004 | Klebsiella pneumoniae | Serine carbapenemase | KPC-2 | A | 6 | X |
| SM1000 | Serratia marcescens | Serine carbapenemase | SME-2 | A | 6 | Y |
| AB1052 | Acinetobacter baumannii | OXA-carbapenemase | OXA-24 | D | 6 | Z |
| AB1054 | Acinetobacter baumannii | OXA-carbapenemase | OXA-23 | D | 6 | X |
| AB1057 | Acinetobacter baumannii | OXA-carbapenemase | OXA-58 | D | 6 | Z |

X = MPC8 of less than 0.16 µg/mL.
Y = MPC8 of 0.16 µg/mL to 1 µg/mL.
Z = MPC8 of greater than 1 µg/mL.

Example 12

The ability of β-lactamase inhibitors to inhibit hydrolysis of ceftazidime and biapenem was studied. Lysates were prepared from bacteria expressing various β-lactamases as a source of enzymes. Bacterial lysates were prepared as follows. A single colony from the fresh over-night plate was transferred to 5 mL of LB broth and grown to $OD_{600}$=0.6-0.8. Next, this culture was transferred to 500 mL of LB and grown to $OD_{600}$=0.7-0.9. Cells were pelleted by centrifugation at 5000 RPM (JA-14 rotor) for 15 minutes at room temperature. The pellet was resuspended in 10 mL of PBS. Five freeze-thaw cycles by putting cells at −20° C. and thawing them at the room temperature were next applied. After the last thaw step cells were spun down at 18K for 30 minutes and the supernatant was collected. This lysate was stored at −20° C.

Next, the activity of bacterial lysates was optimized for ceftazidime and biapenem cleavage as follows. 50 µl of buffer A (50 mM Sodium Phosphate pH=7; 0.5% glucose, 1 mM $MgCl_2$) was added to each well of 96-well UV-transparent plate. 50 µl of lysate was titrated vertically in 96-well plate column to generate 2-fold lysate dilutions. 100 µl of buffer A was added to each well, placed in plate reader at 37° C. and incubated for 15 minutes. 50 µl of 50 µg/mL solutions of ceftazidime or biapenem in buffer A (pre-incubated at 37° C. for 15 minutes) were added to each well. Hydrolysis of ceftazidime and biapenem was measured at 250 nm and 296 nm, respectively. This experiment was used to determine the optimal lysate dilution which produced a linear curve of relative UV signal that decreased to approximately OD=0.3-0.5 over 1 hour.

Finally, the potency of cyclic boronic acid ester derivative to inhibit the cleavage of ceftazidime and biapenem cleavage by bacterial lysates was determined. 100 µl of buffer A (50 mM Sodium Phosphate pH=7; 0.5% glucose, 1 mM $MgCl_2$) was added to each well of 96-well UV-transparent plate. 50 µl of 6× cyclic boronic acid ester derivative solution in buffer A was titrated vertically in 96-well plate column to generate 3-fold dilutions. 50 µl of diluted lysate in buffer A (optimal dilution is determined in experiment above) was added, and the plate was incubated in the plate reader at 37° C. for 15 minutes. 50 µl of 50 µg/mL solutions of ceftazidime or biapenem in buffer A (pre-incubated at 37° C. for 15 minutes) were next added to each well and hydrolysis of ceftazidime or biapenem was recorded at 250 nm and 296 nm, respectively. $EC_{50}$ of inhibition was determined by plotting the rate of ceftazidime or biapenem cleavage vs. cyclic boronic acid ester derivative concentration.

The results of these experiments are presented in Table 5 and Table 6. These experiments demonstrate that the described compounds are inhibitors with a broad-spectrum activity towards various β-lactamases.

TABLE 5

| | | | | | | $IC_{50}$ (µg/mL) of inhibition of Ceftazidime hydrolysis | | | | | |
|---|---|---|---|---|---|---|---|---|---|---|---|
| Strain | Organism | Description | PCR | Class | Tazobactam | 3 | 4 | 5 | 6 | 7 |
| KP1005 | Klebsiella pneumoniae | ESBL | CTX-M-14 | A | X | Z | Z | X | Y | Z |
| KP1009 | Klebsiella pneumoniae | ESBL | CTX-M-15 | A | X | Z | Z | X | Y | Y |
| pa 1063 | Pseudomonas aeruginosa | ESBL | GES-1 | A | Y | Z | Y | X | Y | Y |
| KP1004 | Klebsiella pneumoniae | Serine carbapenemase | KPC-2 | A | Z | X | X | X | X | Z |
| KP1008 | Klebsiella pneumoniae | Serine carbapenemase | KPC-2 | A | Z | Y | X | X | X | Z |

TABLE 5-continued

| | | | | | | IC$_{50}$ (μg/mL) of inhibition of Ceftazidime hydrolysis | | | | | |
|---|---|---|---|---|---|---|---|---|---|---|---|
| Strain | Organism | Description | PCR | Class | Tazobactam | 3 | 4 | 5 | 6 | 7 |
| EC1007 | *Escherichia coli* | Serine carbapenemase | KPC-3 | A | Z | Y | X | X | X | Z |
| KP1010 | *Klebsiella pneumoniae* | ESBL | SHV-12 | A | X | Z | Z | Y | Z | Z |
| KP1012 | *Klebsiella pneumoniae* | ESBL | SHV-18 | A | X | Z | Z | Y | Y | Z |
| ec306 | *Escherichia coli* | First ESBL described | SHV-2 | A | Y | Z | Z | Y | Y | Z |
| ec308 | *Escherichia coli* | Common SHV ESBL | SHV-5 | A | X | Z | Z | Z | Z | Z |
| ec302 | *Escherichia coli* | Common ESBL in US | TEM-10 | A | X | Y | Z | X | Y | Y |
| ec303 | *Escherichia coli* | Common ESBL in US | TEM-12 | A | X | Z | Z | Y | Z | Y |
| ec304 | *Escherichia coli* | Common ESBL in US | TEM-26 | A | X | Z | Z | Y | Y | Y |
| ec300 | *Escherichia coli* | Common ESBL in France | TEM-3 | A | X | Z | Z | Y | Z | Z |
| ec301 | *Escherichia coli* | ESBL | TEM-6 | A | X | Z | Z | Y | Y | Y |
| ECL1003 | *Enterobacter cloacae* | Hyper AmpC expression | | C | ND | Z | Z | Y | Z | Z |
| EC1014 | *Escherichia coli* | pAmpC | DHA-1 | C | ND | Z | Z | Y | Z | Z |
| KP1007 | *Klebsiella pneumoniae* | ESBL | OXA-10 | D | Y | Z | Z | Y | Z | Z |
| KX1000 | *Klebsiella oxytoca* | ESBL | OXA-2 | D | X | Z | Z | X | Y | Z |

X = IC$_{50}$ of less than 0.1 μg/mL.
Y = IC$_{50}$ of 0.1 μg/mL to 1 μg/mL.
Z = IC$_{50}$ of greater than 1 μg/mL.
ND = Not Determined.

TABLE 6

| | | | | | | IC$_{50}$ (μg/mL) of inhibition of biapenem hydrolysis | | | | | |
|---|---|---|---|---|---|---|---|---|---|---|---|
| Strain | Organism | Description | PCR | Class | Tazobactam | 3 | 4 | 5 | 6 | 7 |
| EC1007 | *Escherichia coli* | Serine carbapenemase | KPC-3 | A | Z | Y | Y | X | X | Z |
| KP1004 | *Klebsiella pneumoniae* | Serine carbapenemase | KPC-2 | A | Z | Z | Y | X | Y | ND |
| KP1008 | *Klebsiella pneumoniae* | Serine carbapenemase | KPC-2 | A | Z | Z | Z | Y | Y | ND |
| SM1000 | *Serratia marcescens* | Serine carbapenemase | SME-2 | A | Y | Z | Y | X | Y | Z |

X = IC$_{50}$ of less than 0.1 μg/mL.
Y = IC$_{50}$ of 0.1 μg/mL to 1 μg/mL.
Z = IC$_{50}$ of greater than 1 μg/mL.
ND = Not Determined.

The potency and spectrum of β-lactamase inhibitors is also determined by assessing their aztreonam potentiation activity in a dose titration potentiation assay using strains of various bacteria that are resistant to aztreonam due to expression of various β-lactamases. Aztreonam is a monobactam antibiotic and, similar to ceftazidime, is hydrolyzed by the majority of beta-lactamases that belong to class A, C or D (but not class B). The potentiation effect is observed as the ability of BLI compounds to inhibit growth in the presence of sub-inhibitory concentration of aztreonam. MIC of test strains vary from 32 μg/mL to >128 μg/mL. Aztreonam is present in the test medium at 4 μg/mL. Compounds were tested at the highest concentration of 40 μg/mL. In this assay potency of compounds is determined as a concentration of BLIs to inhibit growth of bacteria in the presence of 4 μg/mL of aztreonam (MPC$_{@4}$). Tables 7, 8 and 9 summarize BLI potency of aztreonam potentiation (MPC$_{@4}$) for various strains overexpressing class A (ESBLs), class A (KPCs), and class C and class D beta-lactamases, respectively. Aztreonam MIC for each strain is also shown. Table 7 summarizes activity of BLIs to potentiate aztreonam against strains expressing class A ESBLs. Table 8 summarizes activity of BLIs to potentiate aztreonam against strains expressing class A KPCs. Table 9 summarizes activity of BLIs to potentiate aztreonam against strains expressing class C and D enzymes.

TABLE 7

| | Aztreonam MIC (µg/mL) | | | | | | | |
|---|---|---|---|---|---|---|---|---|
| | >128 AZT MPC$_4$ CTX-M-14 KP1005 | >128 AZT MPC$_4$ CTX-M-15 KP1009 | 64 AZT MPC$_4$ SHV-5 ec308 | >128 AZT MPC$_4$ SHV-12 KP1010 | 32 AZT MPC$_4$ SHV-18 KP1012 | 128 AZT MPC$_4$ TEM-10 EC1009 | >128 AZT MPC$_4$ TEM-10 ec302 | 64 AZT MPC$_4$ TEM-26 ec304 |
| Clavulanic Acid | 1.25 | 1.25 | 0.08 | 0.04 | 0.04 | 0.16 | 0.3 | 0.04 |
| Tazobactam | 10 | 20 | 10 | 1.25 | 1.15 | 2.5 | 5 | 0.6 |
| 3 | Z | Z | Z | Z | Z | Z | Z | Z |
| 4 | Z | Z | Z | Z | Z | Z | Z | Z |
| 5 | Z | Y | Y | Y | X | Y | Z | Y |
| 6 | Z | Z | Z | Y | Y | Y | Z | Y |
| 7 | Z | Z | Z | Z | Y | X | Y | Y |
| 33 | Z | Z | Z | Z | Z | Z | Z | Z |
| 34 | Z | Z | Z | Z | Z | Z | Z | Z |
| 35 | Z | Z | Z | Z | Z | Z | Z | Z |
| 36 | Z | Z | Z | Y | Y | Z | Z | Y |
| 37 | Z | Z | Z | Y | X | Y | Z | Y |
| 38 | Z | Z | Z | Y | Z | Z | Z | Z |
| 39 | Z | Z | Z | Z | Y | Z | Z | Y |
| 40 | Z | Z | Z | Y | Z | Z | Z | Z |
| 41 | Z | Z | Z | Z | Z | Z | Z | Z |
| 42 | Z | Z | Z | Z | Z | Z | Z | Z |
| 43 | Z | Z | Z | Y | Y | Y | Z | Y |
| 45 | Z | Z | Z | Z | Z | Z | Z | Z |
| 46 | Z | Z | Z | Z | Z | Z | Z | Z |
| 47 | Z | Z | Z | Z | Z | Z | Z | Z |
| 48 | Z | Z | Z | Z | Z | Z | Z | Z |
| 49 | Z | Z | Z | Z | Y | Z | Z | Z |
| 50 | Z | Z | Z | Z | Z | Z | Z | Z |
| 51 | Z | Z | Z | Z | Y | Y | Z | Z |
| 52 | Z | Z | Z | Z | Z | Z | Z | Z |
| 53 | Z | Z | Z | Z | Z | Z | Z | Z |
| 54 | Z | Z | Z | Z | Z | Z | Z | Z |
| 55 | Z | Z | Z | Z | Z | Z | Z | Y |
| 56 | Z | Z | Z | Z | Z | Z | Z | Z |
| 57 | Z | Z | Z | Z | Y | Z | Z | Z |
| 58 | Z | Z | Z | Z | Z | Z | Z | Z |
| 59 | Z | Z | Z | Z | Z | Z | Z | Z |
| 60 | Z | Z | Z | Z | Z | Z | Z | Z |
| 61 | Z | Z | Z | Y | Y | Z | Z | Z |
| 62 | X | X | X | X | X | X | Y | X |
| 63 | Y | Y | Y | X | X | Y | Z | Y |
| 64 | Y | Y | X | X | X | Y | Y | X |
| 65 | Z | Z | Z | Z | Z | Z | Z | Z |
| 66 | Z | Z | Z | Z | Z | Z | Z | Z |

X = MPC$_{@4}$ of less than 5 µg/mL.
Y = MPC$_{@4}$ of 5 µg/mL to 20 µg/mL.
Z = MPC$_{@4}$ of greater than 20 µg/mL.
ND = Not Determined.

TABLE 8

| | Aztreonam MIC | | |
|---|---|---|---|
| | >128 AZT MPC$_4$ KPC-2 KP1004 | 64 AZT MPC$_4$ KPC-2 KP1008 | >128 AZT MPC$_4$ KPC-3 EC1007 |
| Clavulanic Acid | >40 | 20 | 40 |
| Tazobactam | >40 | >40 | >40 |
| 3 | X | X | X |
| 4 | X | X | X |
| 5 | X | X | X |
| 6 | X | X | X |
| 33 | X | X | X |
| 34 | X | X | X |
| 35 | Y | X | X |
| 36 | Z | Z | Z |
| 37 | X | X | X |
| 38 | Z | X | X |
| 39 | Y | X | X |
| 40 | Z | Y | Z |
| 41 | Y | X | X |
| 42 | Y | X | X |
| 43 | X | X | X |
| 45 | Z | Y | X |
| 46 | X | X | X |
| 47 | Z | Y | Y |
| 48 | X | X | X |
| 49 | X | X | X |
| 50 | X | X | X |
| 51 | X | X | X |
| 52 | Y | X | X |
| 53 | Y | X | X |
| 54 | Z | X | Y |
| 55 | Y | X | X |
| 56 | Y | X | X |

TABLE 8-continued

| | Aztreonam MIC | | |
|---|---|---|---|
| | >128 AZT MPC$_4$ KPC-2 KP1004 | 64 AZT MPC$_4$ KPC-2 KP1008 | >128 AZT MPC$_4$ KPC-3 EC1007 |
| 57 | X | X | X |
| 58 | Z | Z | Z |
| 59 | Z | Z | Z |
| 60 | Z | Y | Y |
| 61 | X | X | X |
| 62 | Y | X | Y |
| 63 | Z | Y | Y |
| 64 | Z | X | Y |
| 65 | Z | Z | Z |
| 66 | Y | X | X |

X = MPC$_{@4}$ of less than 5 µg/mL.
Y = MPC$_{@4}$ of 5 µg/mL to 20 µg/mL.
Z = MPC$_{@4}$ of greater than 20 µg/mL.
ND = Not Determined.

TABLE 9

| Class | C | C | C | D | D |
|---|---|---|---|---|---|
| Aztreonam MIC | 64 AZT MPC$_{@4}$ ECL1002 | >128 AZT MPC$_{@4}$ CMY-6 EC1010 | 32 AZT MPC$_{@4}$ PAM2035 | 128 AZT MPC$_{@4}$ OXA-10, qnrB4 KP1007 | 128 AZT MPC$_{@4}$ OXA-2 KPX1001 |
| Clavulanic Acid | >40 | 40 | >40 | 0.08 | 5 |
| Tazobactam | >40 | 20 | 20 | 5 | >40 |
| 3 | Z | Z | Z | Z | Z |
| 4 | Y | Y | Z | Z | Z |
| 5 | Y | Y | X | X | Y |
| 6 | Y | Z | Y | Y | Z |
| 33 | Z | Z | Z | Z | Z |
| 34 | Z | Z | Z | Z | Z |
| 35 | Z | Z | Z | Z | Z |
| 36 | Z | Z | Z | Y | Z |
| 37 | Z | Z | Z | Z | X |
| 38 | Z | Z | Z | Z | Z |
| 39 | Z | Z | Z | Z | Z |
| 40 | Z | Z | Z | Z | Z |
| 41 | Z | Z | Z | Z | Z |
| 42 | Z | Z | Z | Z | Z |
| 43 | Y | Y | Y | Z | Y |
| 45 | Z | Z | Z | Z | Z |
| 46 | Z | Z | Z | Z | Z |
| 47 | Z | Z | Z | Z | Z |
| 48 | Z | Z | Z | Z | Z |
| 49 | Z | Z | Y | Z | Y |
| 50 | Z | Z | Z | Z | Y |
| 51 | Z | Z | Z | Z | Y |
| 52 | Z | Z | Z | Z | Z |
| 53 | Z | Z | Z | Y | Y |
| 54 | Z | Z | Z | Z | Z |
| 55 | Z | Z | Z | Z | Z |
| 56 | Z | Z | Z | Z | Y |
| 57 | Z | Z | Z | Z | Z |
| 58 | Z | Z | Z | Z | Z |
| 59 | Z | Z | Z | Z | Z |
| 60 | Z | Z | Z | Z | Z |
| 61 | Y | Y | Y | Y | Y |
| 62 | Z | X | X | X | Y |
| 63 | Y | Y | Y | Y | Y |
| 64 | Y | Z | Y | X | Y |
| 65 | Z | Z | Z | Z | Z |
| 66 | Z | Z | Z | Z | Z |

X = MPC$_{@4}$ of less than 5 µg/mL.
Y = MPC$_{@4}$ of 5 µg/mL to 20 µ/mL.
Z = MPC$_{@4}$ of greater than 20 µg/mL.
ND = Not Determined.

The potency and spectrum of β-lactamase inhibitors is also determined by assessing their biapenem potentiation activity in a dose titration potentiation assay using strains expressing serine carbapemenases (such as KPC). The potentiation effect is observed as the ability of BLI compounds to inhibit growth in the presence of sub-inhibitory concentration of biapenem. MIC of test strains vary from 4 µg/mL to >1 µg/mL. Biapenem is present in the test medium at 1 µg/mL. Compounds tested at the highest concentration of 40 µg/mL. In this assay potency of compounds is determined as a concentration of BLIs to inhibit growth of bacteria in the presence of 1 µg/mL of biapenem (MPC$_{@1}$). Table 10 summarizes BLI potency of biapenem potentiation (MPC$_{@1}$). Biapenem MIC for each strain is also shown.

TABLE 10

| | Biapenem MIC | | | |
|---|---|---|---|---|
| | >8 BPM MPC$_{@1}$ KP1004 KPC-2 | 8 BPM MPC$_{@1}$ KP1008 KPC-2 | 4 BPM MPC$_{@1}$ EC1007 KPC-3 | 8 BPM MPC$_{@1}$ ECL1004 NMC-A |
| Tazobactam | 40 | 0.3 | 5 | 0.6 |
| 3 | X | X | X | Y |
| 4 | X | X | X | X |
| 5 | X | X | X | X |
| 6 | X | X | X | X |
| 33 | X | X | X | X |
| 34 | X | X | X | Y |
| 35 | X | X | X | Y |
| 36 | Z | X | Y | X |
| 37 | X | X | X | X |
| 38 | X | X | X | X |
| 39 | X | X | X | X |
| 40 | Y | X | Y | Y |
| 41 | X | X | X | Y |
| 42 | X | X | X | Y |
| 43 | X | X | X | X |
| 45 | Y | X | X | Z |
| 46 | X | X | X | X |
| 47 | Y | X | X | Z |
| 48 | X | X | X | X |
| 49 | X | X | X | X |
| 50 | X | X | X | X |
| 51 | X | X | X | Y |
| 52 | X | X | X | Y |
| 53 | X | X | X | Y |
| 54 | X | X | X | X |
| 55 | X | X | X | X |
| 56 | X | X | X | X |
| 57 | X | X | X | X |
| 58 | Z | Z | Z | Z |
| 59 | Y | X | X | X |
| 60 | X | X | X | X |
| 61 | X | X | X | X |
| 62 | X | X | X | X |
| 63 | Y | X | Y | Y |
| 64 | Y | X | X | X |
| 65 | Y | X | Y | Z |
| 66 | X | X | X | X |

X = MFC$_{@1}$ of less than 1 µg/mL.
Y = MFC$_{@1}$ of 1 µg/mL to 5 µg/mL.
Z = MFC$_{@1}$ of greater than 5 µg/mL.
ND = Not Determined.

Some bacterial lysates were also optimized for the cleavage of aztreonam and nitrocefin. EC$_{50}$ of inhibition was determined by plotting the rate of aztreonam or nitrocefin cleavage vs. BLI concentration. The results of these experiments are presented in Table 11. These experiments confirmed that the described compounds are inhibitors with a broad-spectrum activity towards various β-lactamases.

TABLE 11

| | AZT IC$_{50}$ KP1005 CTX-M-14 | AZT IC$_{50}$ KP1009 CTX-M-15 | AZT IC$_{50}$ ec302 TEM-10 | AZT IC$_{50}$ ec304 TEM-26 | AZT IC$_{50}$ KP1004 KPC-2 | AZT IC$_{50}$ KP1008 KPC-2 | AZT IC$_{50}$ EC1007 KPC-3 | AZT IC$_{50}$ KP1007 OXA-10 | AZT IC$_{50}$ KPX1001 OXA-2 | NCF IC$_{50}$ EC1010 pAmpC (CMY-6) |
|---|---|---|---|---|---|---|---|---|---|---|
| Clavulanic Acid | 0.0548 | 0.247 | 0.027 | 0.027 | 0.74 | 2.22 | 1.48 | 1.48 | 0.08 | ND |
| Tazobactam | <0.0274 | 0.027 | 0.055 | 0.027 | 0.74 | 2.22 | 0.74 | 4.44 | 0.0274 | ND |
| 3 | X | Z | Y | Z | X | Y | X | Z | Z | Z |
| 4 | X | Y | Z | Z | X | X | X | Z | Z | Z |
| 5 | X | Y | Z | Z | X | X | X | Z | X | Z |
| 6 | X | X | Z | Z | X | X | X | Z | Y | Z |
| 33 | X | Z | Z | Z | Y | Y | X | Z | Y | Z |
| 34 | Z | Z | Z | Z | Y | Y | X | Z | Z | Z |
| 35 | Z | Z | Z | Z | Z | Z | X | Z | Z | Z |
| 36 | X | X | X | X | Y | Y | X | Z | Z | Z |
| 37 | X | X | Z | Z | X | X | X | Y | Y | X |
| 38 | X | Y | Z | Y | X | X | X | Z | Y | Y |
| 39 | Y | Y | Z | Y | X | Y | X | Z | Y | Z |
| 40 | X | X | Z | Y | Y | Z | Y | Y | X | Y |
| 41 | Z | Z | Z | Z | X | X | X | Z | Z | Z |
| 42 | Z | Z | Z | Z | X | X | X | Z | Z | Z |
| 43 | Y | Z | Z | Z | X | X | X | Z | Y | Z |
| 45 | Z | Z | Z | Z | Y | Y | X | Z | Z | Z |
| 46 | Z | Z | Z | Z | X | X | X | Z | Z | Z |
| 47 | Z | Z | Z | Z | Y | Y | X | Z | Z | Z |
| 48 | Y | Z | Z | Z | X | Y | X | Z | Y | Z |
| 49 | Y | Z | Z | Z | X | X | X | Z | Y | Z |
| 50 | Y | Z | Z | Z | X | X | X | Z | Z | Z |
| 51 | Z | Z | Z | Z | X | X | X | Z | Y | Y |
| 52 | Z | Z | Z | Z | X | Y | Y | Z | Z | Z |
| 53 | Z | Z | Z | Z | X | Y | Y | Z | Y | Z |
| 54 | X | Z | Z | Z | X | X | X | Z | Y | Y |
| 55 | Y | Z | Z | Y | X | X | X | Z | Y | Z |
| 56 | X | Y | Z | Z | X | X | X | Z | Y | Y |
| 57 | X | Z | Z | Z | X | X | X | Z | Z | Z |
| 58 | Y | Z | Z | Z | X | X | X | Z | Z | Z |
| 59 | Z | Z | Z | Z | Y | X | Y | Z | Y | Z |
| 60 | Y | Y | Z | Z | X | X | X | Z | Y | Y |
| 61 | Y | Z | Z | Z | X | X | X | Z | Y | Z |
| 62 | Y | Y | Z | Y | Y | X | X | Z | Z | Z |
| 63 | Y | Y | Z | Z | Y | Y | Y | Z | Y | Y |
| 65 | Y | Z | Z | Z | Y | Y | Z | Z | Y | Z |
| 66 | Y | Z | Z | Z | X | X | X | Z | X | Z |

X = IC$_{50}$ of less than 0.5 µg/mL.
Y = IC$_{50}$ of 0.5 µg/mL to 2 µg/mL.
Z = IC$_{50}$ of greater than 2 µg/mL.
ND = Not Determined.

Example 13

Selected β-lactamase inhibitors were also tested for their ability to potentiate the monobactam tigemonam. The potentiation effect is observed as the ability of BLI compounds to inhibit growth in the presence of sub-inhibitory concentration of tigemonam. MIC of test strains vary from 8 µg/mL to >128 µg/mL. Tigemonam is present in the test medium at 4 µg/mL. Compounds tested at the highest concentration of 40 µg/mL. In this assay potency of compounds is determined as a concentration of BLIs to inhibit growth of bacteria in the presence of 4 µg/mL of aztreonam (MPC$_{@4}$). Tables 12 and 13 summarize BLI potency of tigemonam potentiation (MPC$_{@4}$) for various strains overexpressing class A (ES-BLs), class C and class D beta-lactamases, respectively. Tigemonam MIC for each strain is also shown. Table 12 summarizes activity of BLIs to potentiate tigemonam against strains expressing class A ESBLs. Table 13 summarizes activity of BLIs to potentiate aztreonam against strains expressing class C and D enzymes.

TABLE 12

| | Tigemonam MIC (µg/mL) | | | | | | | |
|---|---|---|---|---|---|---|---|---|
| | 512 MPC$_4$ CTX-M-14 KP1005 | 256 MPC$_4$ CTX-M-15 KP1009 | >512 MPC$_4$ SHV-5 ec308 | 256 MPC$_4$ SHV-12 KP1010 | 64 MPC$_4$ SHV-18 KP1012 | 256 MPC$_4$ TEM-10 EC1009 | >512 MPC$_4$ TEM-10 ec302 | 512 MPC$_4$ TEM-26 ec304 |
| Tazobactam | 10 | 10 | 5 | 1.25 | 1.25 | 2.5 | 5 | 1.25 |
| Clavulanic Acid | 2.5 | 1.25 | <=0.6 | <=0.6 | <=0.6 | <=0.6 | 2.5 | <=0.6 |
| 5 | Z | Z | Z | Z | Z | Z | Z | Z |
| 9 | Z | Z | Z | Z | Z | Z | Z | Z |
| 18 | X | X | Y | X | X | X | Y | Y |
| 37 | Z | Z | Z | Z | Z | Z | Z | Z |

TABLE 12-continued

| | \multicolumn{8}{c}{Tigemonam MIC (µg/mL)} | | | | | | | |
|---|---|---|---|---|---|---|---|---|
| | 512 MPC$_4$ CTX-M-14 KP1005 | 256 MPC$_4$ CTX-M-15 KP1009 | >512 MPC$_4$ SHV-5 ec308 | 256 MPC$_4$ SHV-12 KP1010 | 64 MPC$_4$ SHV-18 KP1012 | 256 MPC$_4$ TEM-10 EC1009 | >512 MPC$_4$ TEM-10 ec302 | 512 MPC$_4$ TEM-26 ec304 |
| 48 | Z | Z | Z | Z | Z | Z | Z | Z |
| 63 | Z | Y | Z | Y | Y | Z | Z | Z |
| 64 | Z | Y | Y | X | Y | Y | Z | Z |
| 67 | Z | Y | Z | Y | Y | Z | Z | Z |
| 68 | Y | Y | Y | X | X | Y | Y | Y |

X = MPC$_{@4}$ of less than 2 µg/mL.
Y = MPC$_{@4}$ of 2 µg/mL to 10 µg/mL.
Z = MPC$_{@4}$ of greater than 10 µg/mL.
ND = Not Determined.

TABLE 13

| Class | C | C | C | D | S |
|---|---|---|---|---|---|
| Tigemonam MIC (µg/mL) | 32 | 16 | 8 | 256 | 8 |
| | MPC$_4$ ECL1002 | MPC$_4$ CMY-6, EC1010 | MPC$_4$ PAM2035 | MPC$_4$ OXA-10, KP1007 | MPC$_4$ OXA-2, KPX1001 |
| Tazobactam | 10 | 2.5 | 5 | 5 | 40 |
| Clavulanic Acid | >40 | 40 | >40 | <=0.6 | 1.25 |
| 5 | Y | X | X | Z | X |
| 9 | Y | Y | Y | Z | X |
| 18 | Y | X | X | Y | Y |
| 37 | X | X | X | Z | X |
| 48 | Y | X | Y | Z | X |
| 63 | Y | X | Y | Y | X |
| 64 | X | X | Y | X | Y |
| 67 | Y | X | X | Z | X |
| 68 | Y | X | Y | X | X |

X = MPC$_{@4}$ of less than 2 µg/mL.
Y = MPC$_{@4}$ of 2 µg/mL to 10 µg/mL.
Z = MPC$_{@4}$ of greater than 10 µg/mL.
ND = Not Determined.

Example 14

Checkerboard assays were used to evaluate the ability of Compound 5 to potentiate various carbapenems (biapenem, doripenem, ertapenem, imipenem, and meropenem) against the strains expressing KPC alone or in combination with additional beta-lactamases. The highest concentration of Compound 5 was 10 mg/L. The results are present in the Table 14. Compound 5 was capable to significantly potentiate multiple carbapenems.

TABLE 14

| | | | | \multicolumn{8}{c}{Concentration of Compound 5 (mg/L) to Potentiate Carbapenem (mg/L)} | | | | | | | |
|---|---|---|---|---|---|---|---|---|---|---|---|
| Organism | Strain | Enzymes | Antibiotic | 0 | 0.16 | 0.31 | 0.625 | 1.25 | 2.5 | 5 | 10 |
| Klebsiella pneumoniae | KP1004 | KPC-2 | Biapenem | Z | X | X | X | X | X | X | X |
| Klebsiella pneumoniae | KP1004 | KPC-2 | Doripenem | Y | Y | X | X | X | X | X | X |
| Klebsiella pneumoniae | KP1004 | KPC-2 | Ertapenem | Z | Z | Y | Y | X | X | X | X |
| Klebsiella pneumoniae | KP1004 | KPC-2 | Imipenem | Z | X | X | X | X | X | X | X |
| Klebsiella pneumoniae | KP1004 | KPC-2 | Meropenem | Z | Y | Y | X | X | X | X | X |
| Klebsiella pneumoniae | KP1008 | KPC-2 | Biapenem | Z | X | X | X | X | X | NG | NG |
| Klebsiella pneumoniae | KP1008 | KPC-2 | Doripenem | Y | X | X | X | X | X | NG | NG |
| Klebsiella pneumoniae | KP1008 | KPC-2 | Ertapenem | Z | X | X | X | X | X | NG | NG |
| Klebsiella pneumoniae | KP1008 | KPC-2 | Imipenem | Y | X | X | X | X | X | NG | NG |
| Klebsiella | KP1008 | KPC-2 | Meropenem | Y | X | X | X | X | X | NG | NG |

TABLE 14-continued

| | | | | Concentration of Compound 5 (mg/L) to Potentiate Carbapenem (mg/L) | | | | | | | |
|---|---|---|---|---|---|---|---|---|---|---|---|
| Organism | Strain | Enzymes | Antibiotic | 0 | 0.16 | 0.31 | 0.625 | 1.25 | 2.5 | 5 | 10 |
| pneumoniae | | | | | | | | | | | |
| Klebsiella pneumoniae | KP1082 | KPC-2, SHV-1 | Biapenem | Y | X | X | X | X | X | X | X |
| Klebsiella pneumoniae | KP1082 | KPC-2, SHV-1 | Doripenem | Y | X | X | X | X | X | X | X |
| Klebsiella pneumoniae | KP1082 | KPC-2, SHV-1 | Ertapenem | Y | X | X | X | X | X | X | X |
| Klebsiella pneumoniae | KP1082 | KPC-2, SHV-1 | Imipenem | Y | X | X | X | X | X | X | X |
| Klebsiella pneumoniae | KP1082 | KPC-2, SHV-1 | Meropenem | Y | X | X | X | X | X | X | X |
| Klebsiella pneumoniae | KP1087 | KPC-2, CTX-M-15, SHV-11, TEM-1 | Biapenem | Z | Z | Z | Z | Y | Y | X | X |
| Klebsiella pneumoniae | KP1087 | KPC-2, CTX-M-15, SHV-11, TEM-1 | Doripenem | Z | Z | Z | Z | Z | Y | Y | X |
| Klebsiella pneumoniae | KP1087 | KPC-2, CTX-M-15, SHV-11, TEM-1 | Ertapenem | Z | Z | Z | Z | Z | Z | Y | Y |
| Klebsiella pneumoniae | KP1087 | KPC-2, CTX-M-15, SHV-11, TEM-1 | Imipenem | Z | Y | Y | Y | Y | Y | X | X |
| Klebsiella pneumoniae | KP1087 | KPC-2, CTX-M-15, SHV-11, TEM-1 | Meropenem | Z | Z | Z | Z | Z | Y | Y | X |
| Klebsiella oxytoca | KX1019 | KPC-2, OXA-2 | Biapenem | Z | Y | Y | Y | Y | Y | X | X |
| Klebsiella oxytoca | KX1019 | KPC-2, OXA-2 | Doripenem | Y | Y | Y | Y | X | X | X | X |
| Klebsiella oxytoca | KX1019 | KPC-2, OXA-2 | Ertapenem | Z | Y | Y | Y | Y | Y | X | X |
| Klebsiella oxytoca | KX1019 | KPC-2, OXA-2 | Imipenem | Y | Y | Y | X | X | X | X | X |
| Klebsiella oxytoca | KX1019 | KPC-2, OXA-2 | Meropenem | Y | Y | Y | X | X | X | X | X |
| Klebsiella oxytoca | KX1017 | KPC-2, OXA-2, SHV-30 | Biapenem | Y | Y | Y | X | X | X | X | X |
| Klebsiella oxytoca | KX1017 | KPC-2, OXA-2, SHV-30 | Doripenem | Y | Y | Y | Y | X | X | X | X |
| Klebsiella oxytoca | KX1017 | KPC-2, OXA-2, SHV-30 | Ertapenem | Z | Y | Y | Y | Y | X | X | X |
| Klebsiella oxytoca | KX1017 | KPC-2, OXA-2, SHV-30 | Imipenem | Z | Y | X | X | X | X | X | X |
| Klebsiella oxytoca | KX1017 | KPC-2, OXA-2, SHV-30 | Meropenem | Y | Y | Y | X | X | X | X | X |
| Klebsiella oxytoca | KX1018 | KPC-2, SHV-40, OXY-1 | Biapenem | Z | X | X | X | X | X | NG | NG |
| Klebsiella oxytoca | KX1018 | KPC-2, SHV-40, OXY-1 | Doripenem | Y | X | X | X | X | X | NG | NG |
| Klebsiella oxytoca | KX1018 | KPC-2, SHV-40, OXY-1 | Ertapenem | Z | X | X | X | X | X | NG | NG |
| Klebsiella oxytoca | KX1018 | KPC-2, SHV-40, OXY-1 | Imipenem | Y | X | X | X | X | X | NG | NG |
| Klebsiella oxytoca | KX1018 | KPC-2, SHV-40, OXY-1 | Meropenem | Y | X | X | X | X | X | NG | NG |
| Escherichia coli | EC1007 | KPC-3 | Biapenem | Z | X | X | X | X | X | X | X |
| Escherichia coli | EC1007 | KPC-3 | Doripenem | Y | X | X | X | X | X | X | X |

TABLE 14-continued

| | | | | Concentration of Compound 5 (mg/L) to Potentiate Carbapenem (mg/L) | | | | | | | |
|---|---|---|---|---|---|---|---|---|---|---|---|
| Organism | Strain | Enzymes | Antibiotic | 0 | 0.16 | 0.31 | 0.625 | 1.25 | 2.5 | 5 | 10 |
| *Escherichia coli* | EC1007 | KPC-3 | Ertapenem | Z | X | X | X | X | X | X | X |
| *Escherichia coli* | EC1007 | KPC-3 | Imipenem | Z | X | X | X | X | X | X | X |
| *Escherichia coli* | EC1007 | KPC-3 | Meropenem | Y | X | X | X | X | X | X | X |
| *Enterobacter cloacae* | ECL1058 | KPC-3, SHV-11, TEM-1 | Biapenem | Z | Y | Y | Y | X | X | X | X |
| *Enterobacter cloacae* | ECL1058 | KPC-3, SHV-11, TEM-1 | Doripenem | Z | Y | Y | Y | Y | X | X | X |
| *Enterobacter cloacae* | ECL1058 | KPC-3, SHV-11, TEM-1 | Ertapenem | Z | Z | Z | Z | Y | Y | X | X |
| *Enterobacter cloacae* | ECL1058 | KPC-3, SHV-11, TEM-1 | Imipenem | Z | Y | Y | Y | X | X | X | X |
| *Enterobacter cloacae* | ECL1058 | KPC-3, SHV-11, TEM-1 | Meropenem | Z | Y | Y | Y | Y | X | X | X |
| *Enterobacter cloacae* | ECL1059 | KPC-3, SHV-12, TEM-1 | Biapenem | Y | X | X | X | X | X | X | X |
| *Enterobacter cloacae* | ECL1059 | KPC-3, SHV-12, TEM-1 | Doripenem | Y | X | X | X | X | X | X | X |
| *Enterobacter cloacae* | ECL1059 | KPC-3, SHV-12, TEM-1 | Ertapenem | Y | X | X | X | X | X | X | X |
| *Enterobacter cloacae* | ECL1059 | KPC-3, SHV-12, TEM-1 | Imipenem | Y | X | X | X | X | X | X | X |
| *Enterobacter cloacae* | ECL1059 | KPC-3, SHV-12, TEM-1 | Meropenem | Y | X | X | X | X | X | X | X |
| *Klebsiella pneumoniae* | KP1083 | KPC-3, SHV-1, TEM-1 | Biapenem | Z | Y | X | X | X | X | X | X |
| *Klebsiella pneumoniae* | KP1083 | KPC-3, SHV-1, TEM-1 | Doripenem | Z | Y | X | X | X | X | X | X |
| *Klebsiella pneumoniae* | KP1083 | KPC-3, SHV-1, TEM-1 | Ertapenem | Z | Y | X | X | X | X | X | X |
| *Klebsiella pneumoniae* | KP1083 | KPC-3, SHV-1, TEM-1 | Imipenem | Z | Y | X | X | X | X | X | X |
| *Klebsiella pneumoniae* | KP1083 | KPC-3, SHV-1, TEM-1 | Meropenem | Z | Y | X | X | X | X | X | X |
| *Klebsiella pneumoniae* | KP1084 | KPC-3, SHV-11, TEM-1 | Biapenem | Z | Z | Z | Z | Z | Y | X | X |
| *Klebsiella pneumoniae* | KP1084 | KPC-3, SHV-11, TEM-1 | Doripenem | Z | Z | Z | Z | Y | Y | Y | X |
| *Klebsiella pneumoniae* | KP1084 | KPC-3, SHV-11, TEM-1 | Ertapenem | Z | Z | Z | Z | Z | Z | Y | Y |
| *Klebsiella pneumoniae* | KP1084 | KPC-3, SHV-11, TEM-1 | Imipenem | Z | Z | Z | Z | Y | Y | X | X |
| *Klebsiella pneumoniae* | KP1084 | KPC-3, SHV-11, TEM-1 | Meropenem | Z | Z | Z | Z | Z | Y | Y | X |
| *Klebsiella pneumoniae* | KP1088 | KPC-3, SHV-11, TEM-1 | Biapenem | Z | Y | X | X | X | X | X | X |
| *Klebsiella pneumoniae* | KP1088 | KPC-3, SHV-11, TEM-1 | Doripenem | Y | Y | Y | X | X | X | X | X |
| *Klebsiella pneumoniae* | KP1088 | KPC-3, SHV-11, TEM-1 | Ertapenem | Z | Z | Y | X | X | X | X | X |

TABLE 14-continued

| Organism | Strain | Enzymes | Antibiotic | \multicolumn{8}{c}{Concentration of Compound 5 (mg/L) to Potentiate Carbapenem (mg/L)} |
|---|---|---|---|---|---|---|---|---|---|---|---|
| | | | | 0 | 0.16 | 0.31 | 0.625 | 1.25 | 2.5 | 5 | 10 |
| Klebsiella pneumoniae | KP1088 | KPC-3, SHV-11, TEM-1 | Imipenem | Z | Y | X | X | X | X | X | X |
| Klebsiella pneumoniae | KP1088 | KPC-3, SHV-11, TEM-1 | Meropenem | Z | Y | Y | X | X | X | X | X |

X = MIC of less than 0.5 mg/L.
Y = MIC of 0.5 mg/L to 4 mg/L.
Z = MIC of greater than 4 mg/L.
NG = No Growth.

Example 15

An in vivo model can be used to evaluate the single dose pharmacokinetic properties and absolute oral bioavailability of a test compound. As described more specifically below, a test compound is administered to Sprague-Dawley (SD) rats either intravenously or orally in a crossover study design and the resulting pharmacokinetic properties and oral bioavailability are measured.

For intravenous administration, male rats were given a 30 minutes intravenous infusion dose of 20 or 50 mg/kg of Compound 5 via femoral vein cannula. Plasma samples (0.3 ml) were collected from jugular vein cannula at 0.17, 0.33, 0.47, 0.58, 0.68, 0.75, 1, 2, 3, 4, and 6 hrs after the dosing. For oral administration, male rats were given 50 mg/kg of Compound 5 (in saline) or Compound 62 (in 100% ethanol) orally using an oral gavage tip. Plasma samples were collected from each rat at 0.08, 0.17, 0.25, 0.33, 0.50, 0.75, 1, 2, 3, 4, and 6 hrs after the dosing.

Plasma concentrations of the compounds were tested using LC/MS/MS method with a lower limit of quantification of 10 ng/mL for Compound 5 and 100 ng/mL for Compound 62. Extraction: 50 μL volumes of plasma from samples and standards were extracted using 200 μL of methanol with 100 mM ammonium acetate, 2 μg/mL gatifloxacin (internal standard for Compound 62) and 2 μg/mL Compound 38 (internal standard for Compound 5). The samples were mixed and centrifuged for 30 min at 3000×g. 150 μL of supernatant was removed and added to 450 μL of water.

HPLC—mass spectrometry: An Agilent 1100HPLC pump, HTC PAL autosampler and a Sciex 3200Q mass spectrometer were used for separation and quantification. Compound 62 and its internal standard were detected using +ESI. Compound 5 and its internal standard were detected using −ESI. LC/MS/MS: 1) Column: Chromolith FastGradient RP-18e, 50×2 mm; 2) Mobile phase A: Aqueous Water with 0.1% TFA, Orgainic phase B: Acetonitrile with 0.1% TFA; Flow Rate: 600 μL/min; Injection volume: 10 μL; HPLC gradient: 5% B→60% B, 0.01→1.5 min; 60% B, 1.5→1.6 min; 60% B→5% B, 1.6→1.7 min; 5% B, 1.7→2.7 min.

Plasma concentrations were modeled using WinNonlin® (Pharsight Corp, Mountain View, Calif.).

In this experiment, three male Sprague Dawley rats were given Compound 5 by intravenous or oral route. At designated time points, bloods were collected and analyzed. As shown in the above Table 15 and FIG. 1, Compound 5 has a linear PK in rats. However, Compound 5 it is not orally absorbed.

TABLE 15

| Route of Adm | Dose/ (mg/kg) | $T_{1/2}$ (hr) | Cmax (mg/L) | CL/F (L/h/kg) | AUC (mg*h/L) |
|---|---|---|---|---|---|
| IV | 20 | 1.56 | 19.82 | 1.65 | 12.15 |
| IV | 50 | 4.53 | 45.93 | 1.77 | 28.19 |
| PO | 50 | 1.55 | 0.29 | 60.38 | 0.81 |

Figure 2:
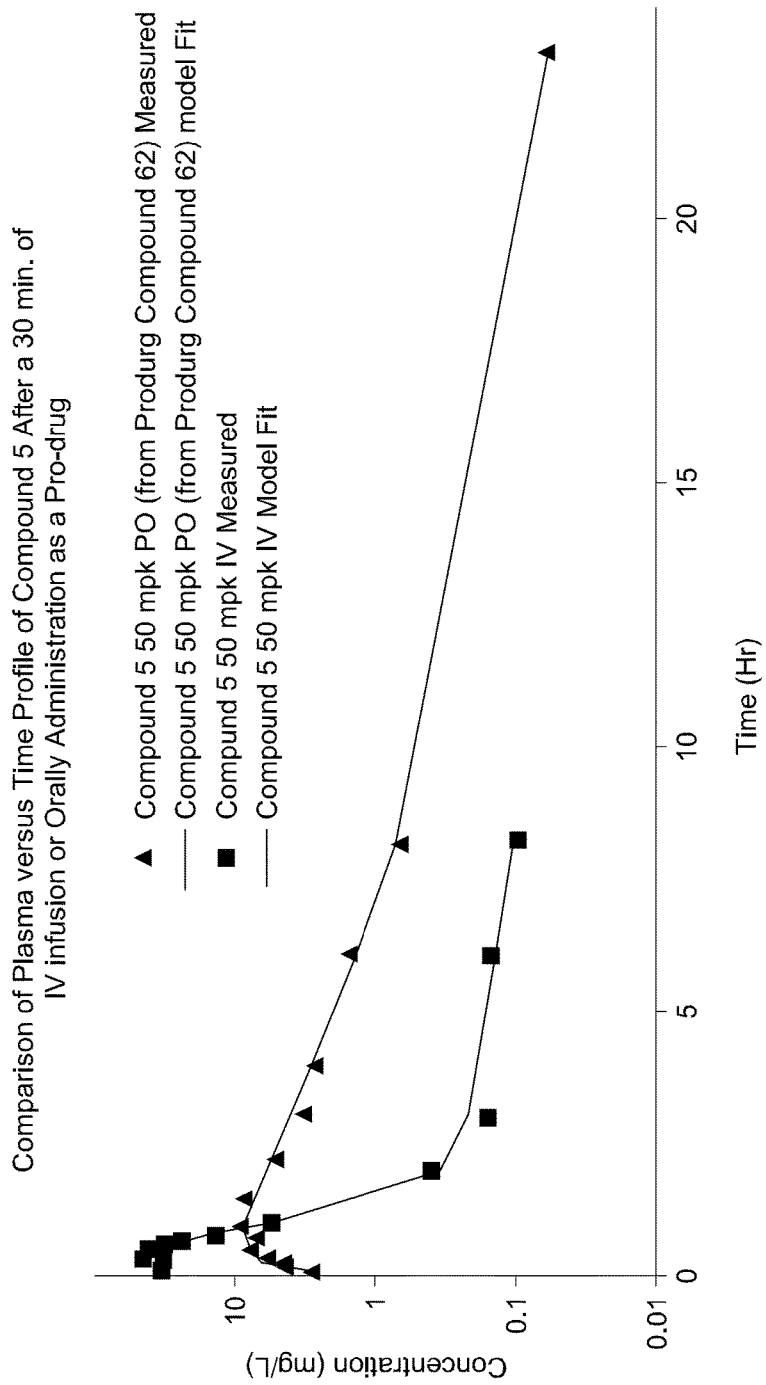
FIG. 2 is a graph depicting the plasma concentration profile of a prodrug of the cyclic boronic acid ester derivative of FIG. 1 as a function of time after administration to Sprague Dawley rats.

In this experiment, three male Sprague dawley rats were given Compound 5 by intravenous or Compound 62 orally (pro-drug for Compound 5). Plasma samples were collected at designated time points and analyzed for the presence of Compound 5. This study was designed to determine the oral bioavailability of Compound 62 a pro-drug of Compound 5. Male rats (non-fasted) were orally administered 50 mg/kg of the prodrug Compound 62. As shown in FIG. 2, the pro-drug of Compound 5 has oral bioavailability of greater than 80%.

Polymorphs can be detected, identified, classified and characterized using well-known techniques such as, but not limited to, differential scanning calorimetry (DSC), thermogravimetry (TGA) and powder X-ray diffractometry (PXRD).

Example 16

The crystal structure of Compound 5 was analyzed using X-ray powder diffraction ("PXRD"). The X-ray diffraction data were collected at room temperature using a PANalytical X'Pert Pro diffractometer (Cu Kα radiation) fitted with an automatic sample changer, a theta-theta goniometer, automatic beam divergence slits, a secondary monochromator and a scintillation counter. Samples were prepared for analysis by packing the powder into a 12 mm diameter, 0.25 mm deep cavity that had been cut into a Si zero-background wafer specimen mount. The sample was rotated while being irradiated with copper K-alpha 1 X-rays (wavelength=1.5406 Angstroms) with the X-ray tube operated at 45 kV/40 mA. The analyses were performed with the goniometer running in continuous mode set for a 5 second count per 0.02° step over a two theta range of 2° to 55°. The illustrative PXRD pattern for Compound 5 is shown in FIG. 3.

Figure 3:
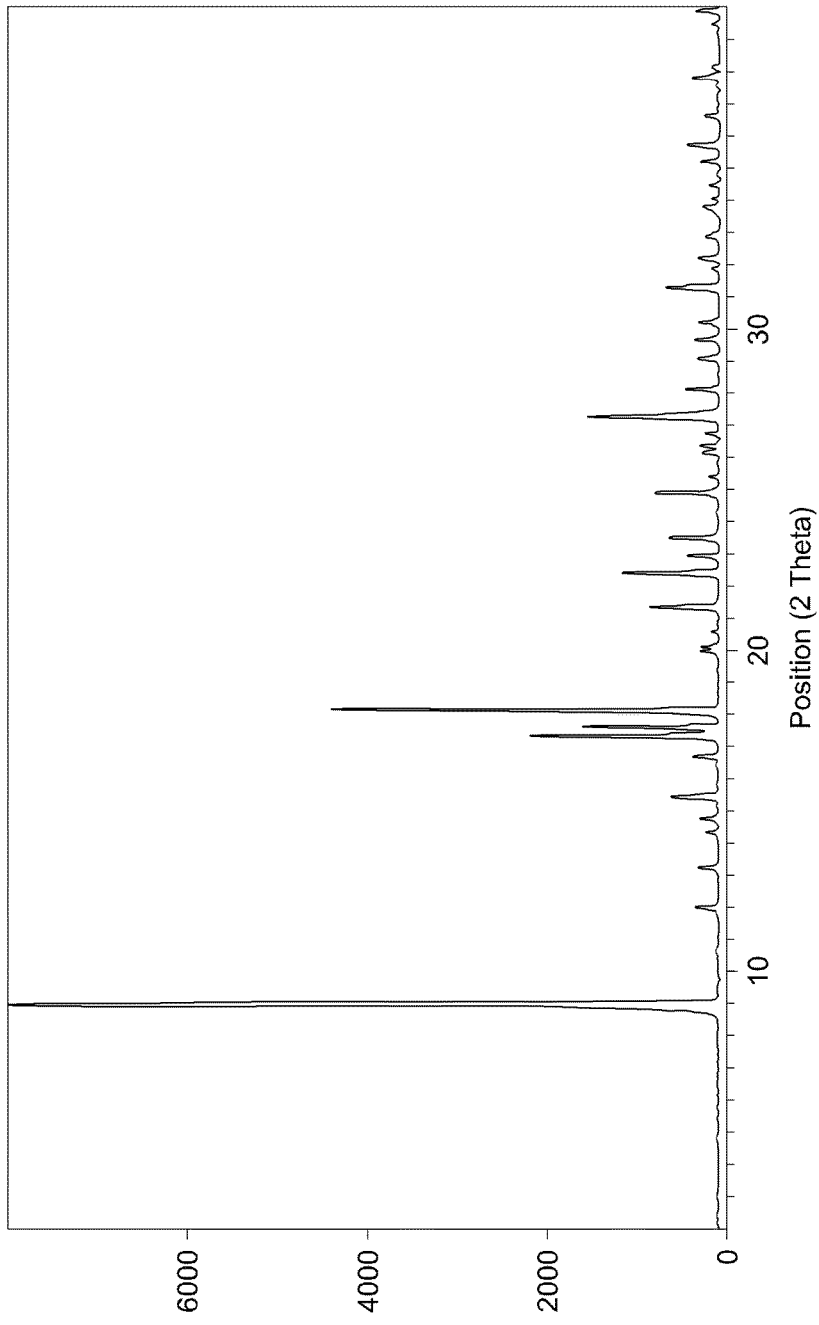
FIG. 3 is an X-ray powder diffraction of a crystalline form of a cyclic boronic acid ester derivative.

As will be appreciated by the skilled crystallographer, the relative intensities of the various peaks reported in FIG. 3 may vary due to a number of factors such as orientation effects of crystals in the X-ray beam or the purity of the material being analyzed or the degree of crystallinity of the sample. The peak positions may also shift for variations in sample height but the peak positions will remain substantially as defined in FIG. 3. The skilled crystallographer also will appreciate that measurements using a different wavelength will result in different shifts according to the Bragg equation −nλ=2 d sin θ. Such further PXRD patterns generated by use of alternative wavelengths are considered to be alternative representations of the PXRD patterns of the crystalline materials of the present invention and as such are within the scope of the present invention.

Table 16 lists peak positions and relative intensities for the PXRD pattern of FIG. 3. Accordingly, some embodiments include a crystalline form of Compound 5 having three or more, four or more, five or more, six or more, seven or more, eight or more, nine or more, or ten or more characteristic PXRD (wavelength=1.5406 Å) peaks selectede from 9.0°, 15.7°, 17.3°, 17.6°, 18.1°, 21.3°, 22.4°, 23.5°, 24.9°, 27.2°, 27.4°, 28.1°, 29.1°, 31.2°, and 35.7° 2θ. Some embodiments include a crystalline form of Compound 5 having three or more, four or more, five or more, or six characterstic PXRD (wavelength=1.5406 Å) peaks selected from 9.0°, 17.3°, 17.6°, 18.1°, 22.4°, and 27.2° 2θ. Some embodiments include a crystalline form of Compound 5 having characteristic PXRD (wavelength=1.5406 Å) peaks at 9.1°, 17.3°, 17.6°, and 18.1° 2θ.

TABLE 16

| °2θ | Area [cts °2θ] | d-spacing [Å] |
| --- | --- | --- |
| 9.0088 | 870.8 | 9.80831 |
| 12.0132 | 29.19 | 7.36118 |
| 13.2369 | 19.12 | 6.68332 |
| 15.4527 | 55.73 | 5.72961 |
| 16.6911 | 41.97 | 5.30719 |
| 17.3464 | 285.76 | 5.10815 |
| 17.59 | 171.25 | 5.03794 |
| 18.1212 | 475.59 | 4.89145 |
| 19.9585 | 23.95 | 4.4451 |
| 20.1214 | 18.12 | 4.40949 |
| 21.3328 | 84.5 | 4.16175 |
| 22.4035 | 147.38 | 3.96521 |
| 22.9212 | 39.45 | 3.87681 |
| 23.48 | 60.99 | 3.78579 |
| 24.8881 | 77.52 | 3.5747 |
| 26.1352 | 20.92 | 3.40689 |
| 26.3458 | 20.23 | 3.38013 |
| 27.2278 | 162.9 | 3.27261 |
| 27.357 | 50.29 | 3.25744 |
| 28.0871 | 54.62 | 3.17441 |
| 29.0644 | 51.29 | 3.06985 |
| 29.63 | 30.23 | 3.01253 |
| 30.1989 | 19.34 | 2.95706 |
| 31.2457 | 65.66 | 2.86033 |
| 32.1641 | 32.04 | 2.78073 |
| 33.7983 | 19.84 | 2.64992 |
| 35.1614 | 21.23 | 2.55025 |
| 35.6871 | 57.8 | 2.51388 |
| 36.5979 | 22 | 2.45338 |
| 37.7599 | 33.73 | 2.3805 |
| 39.8439 | 31.99 | 2.26066 |

As is well understood in the art, because of the experimental variability when X-ray diffraction patterns are measured on different instruments, the peak positions are assumed to be equal if the two theta (2θ) values agree to within 0.2° (i.e., ±0.2°). For example, the United States Pharmacopeia states that if the angular setting of the 10 strongest diffraction peaks agree to within ±0.2° with that of a reference material, and the relative intensities of the peaks do not vary by more than 20%, the identity is confirmed. Accordingly, peak positions within 0.2° of the positions recited herein are assumed to be identical.

Example 17

DSC measure thermal transition temperatures at which a crystalline form absorbs or releases heat when its crystal structure changes or it melts. TGA is used to measure thermal stability and the fraction of volatile components of a sample by monitoring the weight change as the sample is heated. If infrared spectroscopy is conducted on the volatile components outgassed during TGA analysis of a pseudopolymorph (TGA-IR), then the molecular composition of the pseudopolymorph can be determined. These techniques are thus useful for characterizing solid state forms existing as solvates and/or hydrates.

Figure 4:
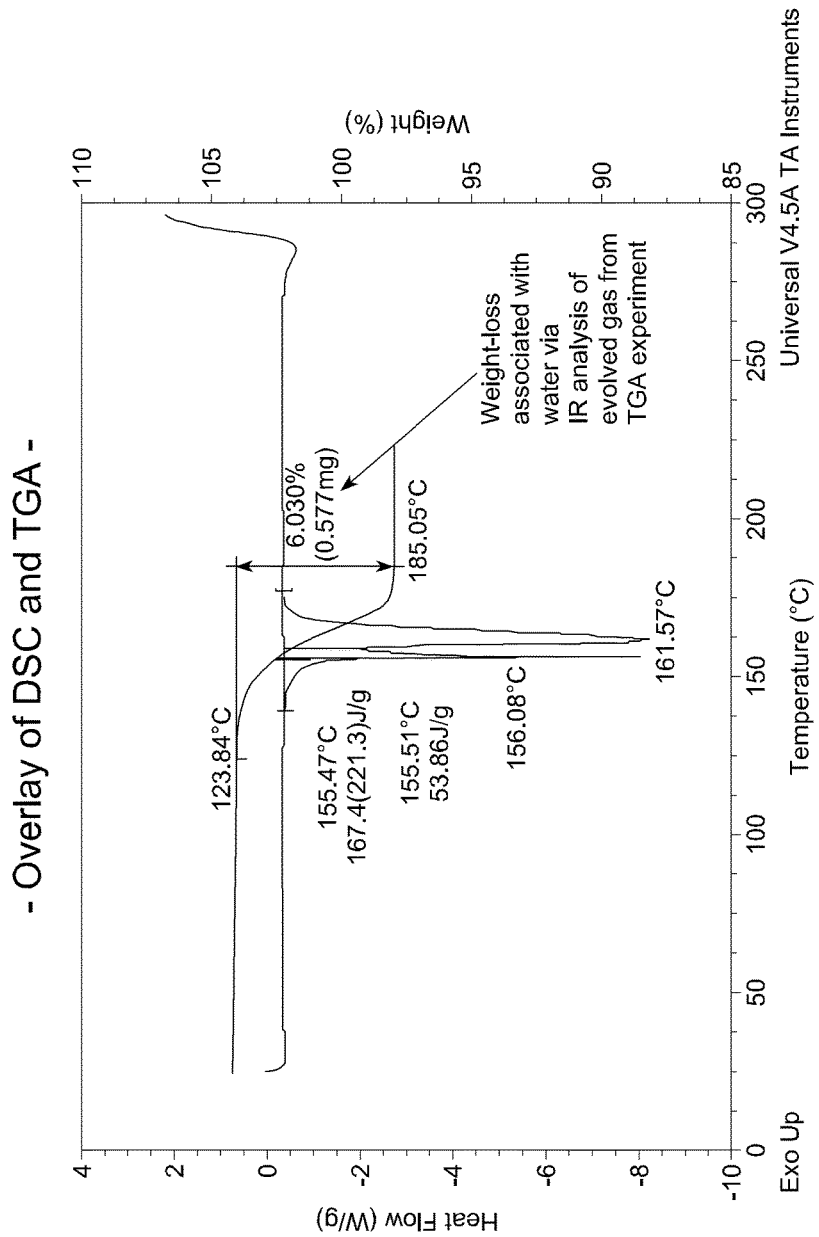
FIG. 4 is a graph depicting an overlay of differential scanning calorimetry and thermogravimetric results for the crystalline form of FIG. 3.

Compound 5 was analyzed using differential scanning calorimetry (DSC). A TA Instruments Q100 differential scanning calorimeter equipped with an autosampler and a refrigerated cooling system under 40 mL/min $N_2$ purge was used to perform the analysis. Each sample was heated from 25 to 300° C. at 15° C. per minute in an aluminium pan with the lid laid on top, with a nitrogen purge gas. The data from DSC analyses are dependent on several factors, including the rate of heating, the purity of the sample, crystal size, and sample size. The DSC thermogram obtained for the sample of Compound 5 is shown in FIG. 4 overlayed with the TGA thermogram. These data reveal a single endothermic transition at 155° C.

Thermogravimetric-infrared (TG-IR) Analysis was performed on a TA Instruments Q5000 thermogravimetric analyzer interfaced to a Nicolet 6700 FT-IR spectrometer (Thermo Electron) equipped with an external TGA-IR module with a gas flow cell and DTGS detector. The FT-IR wavelength verification was performed using polystyrene, and the TG calibration standards were nickel and Alumel™. The sample was placed in a platinum or aluminium sample pan, and the pan was inserted into the TG furnace. The TG instrument was started first, immediately followed by the FT-IR instrument. The TG instrument was operated under a flow of helium at 90 and 10 cc/min for the purge and balance, respectively. The furnace was heated under nitrogen at a rate of 15° C./minute to a final temperature of 230° C. IR spectra were collected approximately every 32 seconds for approximately 13 minutes. Each IR spectrum used 32 co-added scans collected at a spectral resolution of 4 $cm^{-1}$. The TGA thermogram obtained for the sample of Compound 5 is shown in FIG. 4 overlayed with the DSC thermogram. These TGA data with IR analysis of the evolved gas indicate that the input material is non-solvated but loses one mole-equivalent of water between 135 and 181° C.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials that are susceptible to modifications, as well as alterations in the fabrication methods and equipment. Such modifications will become apparent to those skilled in the art from a consideration of this disclosure or practice of the methods disclosed herein. Consequently, it is not intended that this invention be limited to the specific embodiments disclosed herein, but that it cover all modifications and alternatives coming within the true scope and spirit of the invention.

What is claimed is:

1. A pharmaceutical composition comprising a compound of Formula (I) and an additional medicament selected from the group consisting of an antibacterial agent, antifungal agent, an antiviral agent, an anti-inflammatory agent, and an anti-allergic agent, wherein Formula (I) has the structure:

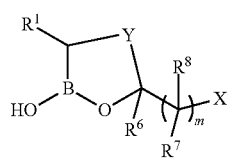

I or a pharmaceutically acceptable salt thereof, wherein:
Y is a 1-4 atom alkylene or 2-4 atom alkenylene linker, optionally substituted by one or more substituents selected from the group consisting of Cl, F, CN, $CF_3$, $-R^9$, $-OR^9$, $-C(=O)NR^9R^{10}$, and $-C(=O)OR^9$, wherein said alkylene or alkenylene linker is optionally fused to an optionally substituted aryl, optionally substituted heteroaryl, optionally substituted carbocyclyl, or optionally substituted heterocyclyl;

$R^1$ is selected from a group consisting of $-C_{1-9}$alkyl, $-C_{2-9}$alkenyl, $-C_{2-9}$alkynyl, $-NR^9R^{10}$, $-C_{1-9}$alkyl$R^{11}$, $-C_{2-9}$alkenyl$R^{11}$, $-C_{2-9}$alkynyl$R^{11}$, -carbocyclyl-$R^{11}$, $-CH(OH)C_{1-9}$alkyl$R^9$, $-CH(OH)C_{2-9}$alkenyl$R^9$, $-CH(OH)C_{2-9}$alkynyl$R^9$, $-CH(OH)$carbocyclyl-$R^9$, $-C(=O)R^9$, $-C(=O)C_{1-9}$alkyl$R^9$, $-C(=O)C_{2-9}$alkenyl$R^9$, $-C(=O)C_{2-9}$alkynyl$R^9$, $-C(=O)C_{2-9}$carbocyclyl-$R^9$, $-C(=O)NR^9R^{10}$, $-N(R^9)C(=O)R^9$, $-N(R^9)C(=O)NR^9R^{10}$, $-N(R^9)C(=O)OR^9$, $-N(R^9)C(=O)C(=NR^{11})R^9$, $-N(R^9)C(=O)C(=CR^9R^{10})R^9$, $-N(R^9)C(=O)C_{1-4}$alkylN$(R^9)C(=O)R^9$, $-N(R^9)C(=NR^{10})R^9$, $-C(=NR)NR^9R^{10}$, $-N=C(R^9)NR^9R^{10}$, $-N(R^9)SO_2R^9$, $-N(R^9)SO_2NR^9R^{10}$, $-N=CHR^9$, optionally substituted aryl, optionally substituted heteroaryl, optionally substituted carbocyclyl, and optionally substituted heterocyclyl;

$R^6$ is selected from a group consisting of H, $-C_{1-9}$alkyl, $C_{2-9}$alkenyl, $-C_{2-9}$alkynyl, carbocyclyl, $-C_{1-9}$alkyl$R^{11}$, $-C_{2-9}$alkenyl$R^{11}$, $-C_{2-9}$alkynyl$R^{11}$, carbocyclyl-$R^{11}$, $-C(=O)OR^9$, $-C_{1-9}$alkyl$CO_2R^9$, $-C_{2-9}$alkenyl$CO_2R^9$, $-C_{2-9}$alkynyl$CO_2R^9$, and -carbocyclyl-$CO_2R^9$, or alternatively:
(i) $R^6$ and an $R^7$ are taken together with the atoms to which they are attached to form an optionally substituted carbocyclyl or optionally substituted heterocyclyl, or
(ii) $R^6$ is absent when the carbon to which it is attached is a ring atom in an aryl or heteroaryl ring;

each $R^7$ is independently selected from a group consisting of H, halo, $-C_{1-9}$alkyl, $-C_{2-9}$alkenyl, $-C_{2-9}$alkynyl, $-NR^9R^{10}$, $-OR^9$, $-C_{1-9}$alkyl$CO_2R^9$, $-C_{2-9}$alkenyl$CO_2R^9$, $-C_{2-9}$alkynyl$CO_2R^9$, and -carbocyclyl-$CO_2R^9$, or independently:
(i) $R^6$ and an $R^7$ are taken together with the atoms to which they are attached to form an optionally substituted carbocyclyl or optionally substituted heterocyclyl, or
(ii) $R^7$ and an $R^8$ are taken together with the atoms to which they are attached to form an optionally substituted carbocyclyl or optionally substituted heterocyclyl;

each $R^8$ is independently selected from a group consisting of H, halo, $-C_{1-9}$alkyl, $-C_{2-9}$alkenyl, $-C_{2-9}$alkynyl, $-NR^9R^{10}$, $-OR^9$, $-C_{1-9}$alkyl$CO_2R^9$, $-C_{2-9}$alkenyl$CO_2R^9$, $-C_{2-9}$alkynyl$CO_2R^9$, -carbocyclyl-$CO_2R^9$, or independently:
(i) an $R^7$ and an $R^8$ are taken together with the atoms to which they are attached to form an optionally substituted carbocyclyl or optionally substituted heterocyclyl,
(ii) a geminal $R^7$ and $R^8$ together form $-C_{2-9}$alkenylenyl$CO_2R^9$, or
(iii) each $R^8$ attached to a ring atom forming part of an optionally substituted aryl is absent;

each $R^9$ is independently selected from a group consisting of H, $-C_{1-9}$alkyl, $C_{2-9}$alkenyl, $-C_{2-9}$alkynyl, carbocyclyl, $-C_{1-9}$alkyl$R^{11}$, $-C_{2-9}$alkenyl$R^{11}$, $-C_{2-9}$alkynyl$R^{11}$, -carbocyclyl-$R^{11}$, optionally substituted aryl, optionally substituted heteroaryl, optionally substituted carbocyclyl, and optionally substituted heterocyclyl;

each $R^{10}$ is independently selected from a group consisting of H, $-C_{1-9}$alkyl, $-OR^9$, $-CH(=NH)$, $-C(=O)OR^9$, optionally substituted aryl, optionally substituted heteroaryl, optionally substituted carbocyclyl, and optionally substituted heterocyclyl;

each $R^{11}$ is independently selected from a group consisting of optionally substituted aryl, optionally substituted heteroaryl, optionally substituted carbocyclyl, and optionally substituted heterocyclyl;

X is selected from a group consisting of $-CO_2R^{12}$, and a carboxylic acid isostere;

$R^{12}$ is selected from a group consisting of H, $C_{1-9}$alkyl, $-(CH_2)_{0-3}-R_{11}$, $-C(R^{13})_2OC(O)C_{1-9}$alkyl, $-C(R^{13})_2OC(O)R^{11}$, $-C(R^{13})_2OC(O)OC_{1-9}$alkyl and $-C(R^{13})_2OC(O)OR^{11}$;

each $R^{13}$ is independently selected from a group consisting of H and $C_{1-4}$alkyl; and m is independently zero or an integer from 1 to 2, wherein each $C_{1-9}$alkyl, $C_{2-9}$alkenyl, and $C_{2-9}$alkynyl is independently optionally substituted.

2. The pharmaceutical composition of claim 1, having the structure of formula II:

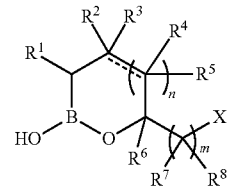

II or a pharmaceutically acceptable salt thereof, wherein:

the bond represented by a dashed and solid line represents a bond selected from the group consisting of a single bond and a double bond with the proviso that the dashed and solid line can only be a double bond when n is 1;

$R^1$ is selected from a group consisting of $-NR^9R^{10}$, $-C_{1-9}alkylR^{11}$, $-C_{2-9}alkenylR^{11}$, $-C_{2-9}alkynylR^{11}$, -carbocyclyl-$R^{11}$, $-CH(OH)C_{1-9}alkylR^9$, $-CH(OH)C_{2-9}alkenylR^9$, $-CH(OH)C_{2-9}alkynylR^9$, $-CH(OH)$carbocyclyl-$R^9$, $-C(=O)R^9$, $-C(=O)C_{1-9}alkylR^9$, $-C(=O)C_{2-9}alkenylR^9$, $-C(=O)C_{2-9}alkynylR^9$, $-C(=O)C_{2-9}$carbocyclyl-$R^9$, $-C(=O)NR^9R^{10}$, $-N(R^9)C(=O)R^9$, $-N(R^9)C(=O)NR^9R^{10}$, $-N(R^9)C(=O)OR^9$, $-N(R^9)C(=O)C(=NR^{10})R^9$, $-N(R^9)C(=O)C(=CR^9R^{10})R^9$, $-N(R^9)C(=O)C_{1-4}$ alkylN$(R^9)C(=O)R^9$, $-N(R^9)C(=NR^{10})R^9$, $-C(NR^{10})NR^9R^{10}$, $-N=C(R^9)NR^9R^{10}$, $-N(R^9)SO_2R^9$, $-N(R^9)SO_2NR^9R^{10}$, $-N=CHR^9$, optionally substituted aryl, optionally substituted heteroaryl, optionally substituted carbocyclyl, and optionally substituted heterocyclyl;

$R^2$ and $R^4$ are independently selected from a group consisting of H, Cl, F, CN, $CF_3$, $-R^9$, $-OR^9$, $-C(=O)NR^9R^{10}$, and $-C(=O)OR^9$;

$R^3$ and $R^5$ are independently selected from a group consisting of H, Cl, F, CN, $CF_3$, $-R^9$, $-OR^9$, $-C(=O)NR^9R^{10}$, and $-C(=O)OR^9$, with the proviso that if the bond represented by a dashed and solid line is a double bond then $R^3$ and $R^5$ are absent;

$R^6$ is selected from a group consisting of H, $-C_{1-9}$alkyl, $C_{2-9}$alkenyl, $-C_{2-9}$alkynyl, $-C_{1-9}$alkylR$^{11}$, $-C_{2-9}$alkenylR$^{11}$, $-C_{2-9}$alkynylR$^{11}$, $-C(=O)OR^9$, and $-C_{1-9}$alkylCO$_2R^9$, $-C_{2-9}$alkenylCO$_2R^9$, and $-C_{2-9}$alkynylCO$_2R^9$;

each $R^7$ is independently selected from a group consisting of H, $-NR^9R^{10}$, $-OR^9$, and $-C_{1-9}$alkylCO$_2R^9$, $-C_{2-9}$alkenylCO$_2R^9$, and $-C_{2-9}$alkynylCO$_2R^9$;

each $R^8$ is independently selected from a group consisting of H, $-NR^9R^{10}$, $-OR^9$, and $-C_{1-9}$alkylCO$_2R^9$, $-C_{2-9}$alkenylCO$_2R^9$, and $-C_{2-9}$alkynylCO$_2R^9$;

each $R^9$ is independently selected from a group consisting of H, $-C_{1-9}$alkyl, $C_{2-9}$alkenyl, $-C_{2-9}$alkynyl, $-C_{1-9}$alkylR$^{11}$, $-C_{2-9}$alkenylR$^{11}$, $-C_{2-9}$alkynylR$^{11}$, optionally substituted aryl, optionally substituted heteroaryl, optionally substituted $-(CH_2)_{0-3}$carbocyclyl, and optionally substituted heterocyclyl;

each $R^{10}$ is independently selected from a group consisting of H, $-C_{1-9}$alkyl, $-OR^9$, $-CH(=NH)$, optionally substituted aryl, optionally substituted heteroaryl, optionally substituted carbocyclyl, and optionally substituted heterocyclyl;

X is $-CO_2H$; and n is independently zero or an integer from 1 to 2.

3. The pharmaceutical composition of claim 2, wherein n is 1.

4. The pharmaceutical composition of claim 2, wherein $R^2$, $R^3$, $R^4$, and $R^5$ are hydrogen.

5. The pharmaceutical composition of claim 1, wherein the compound has the structure of formula IIIa, IIIb, IVa, IVb, or IVc:

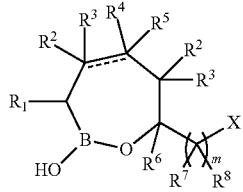

IIIa

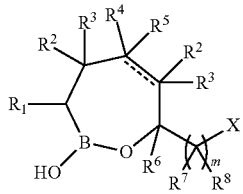

IIIb

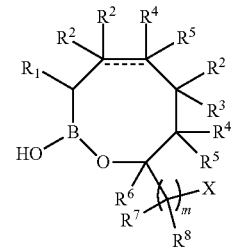

IVa

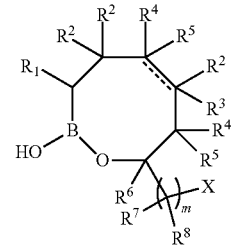

IVb

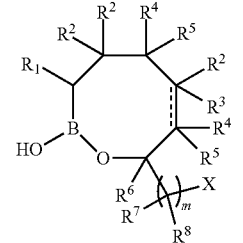

IVc or a pharmaceutically acceptable salt thereof, wherein:

the bond represented by a dashed and solid line represents a bond selected from the group consisting of a single bond and a double bond;

each $R^2$ and $R^4$ are independently selected from a group consisting of H, Cl, F, CN, $CF_3$, $-R^9$, $-OR^9$, $-C(=O)NR^9R^{10}$, and $-C(=O)OR^9$; and each $R^3$ and $R^5$ are independently selected from a group consisting of H, Cl, F, CN, $CF_3$, $-R^9$, $-OR^9$, $-C(=O)NR^9R^{10}$, and $-C(=O)OR^9$, with the proviso that if the bond represented by a dashed and solid line is a double bond then $R^3$ and $R^5$ are absent.

6. The pharmaceutical composition of claim 1, wherein $R^1$ is $-NHC(=O)C_{1-9}$alkylR$^{11}$.

7. The pharmaceutical composition of claim 6, wherein $R^{11}$ is optionally substituted aryl or optionally substituted heteroaryl.

8. The pharmaceutical composition of claim 7, wherein $R^{11}$ is thien-2-yl.

9. The pharmaceutical composition of claim 1, wherein m is 1.

10. The pharmaceutical composition of claim 1, wherein $R^6$ and each $R^7$ and $R^8$ is hydrogen.

11. The pharmaceutical composition of claim 1, wherein X is —$CO_2H$.

12. The pharmaceutical composition of claim 1, having a structure selected from the group consisting of:

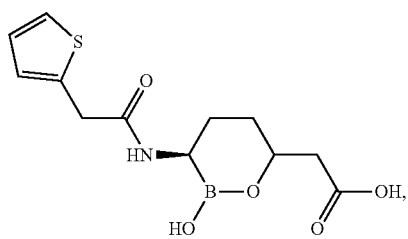

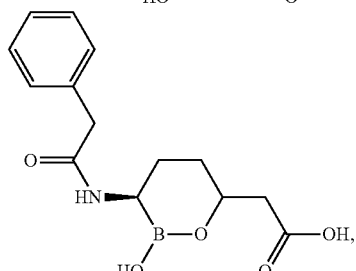

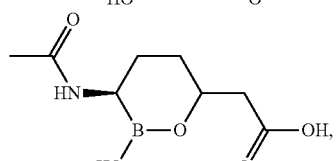

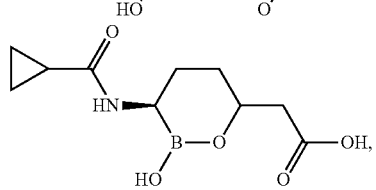

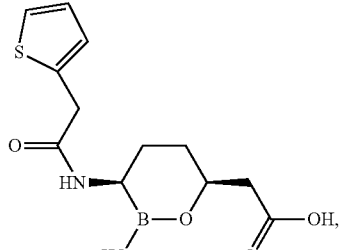

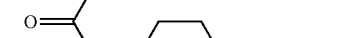

-continued

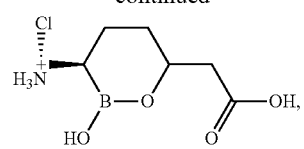

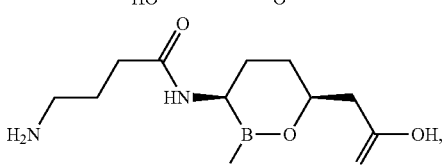

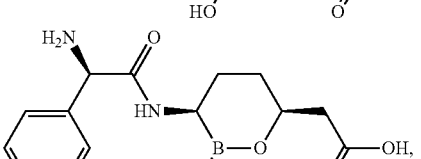

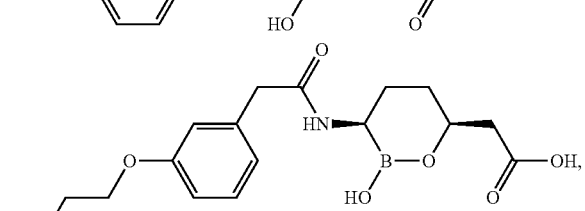

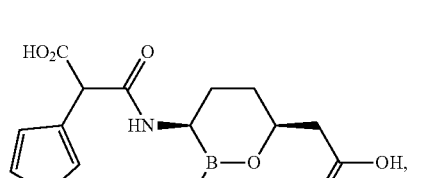

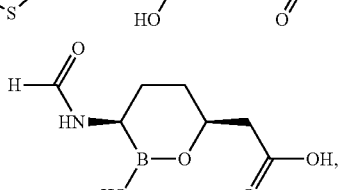

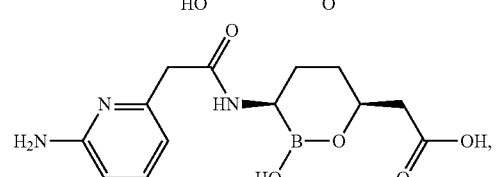

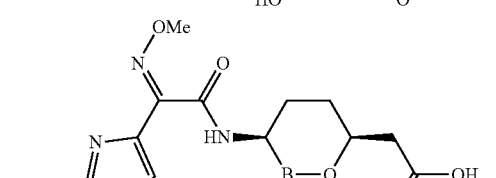

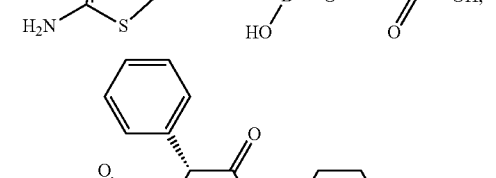

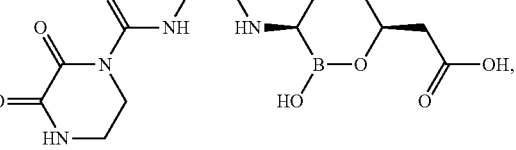

155
-continued
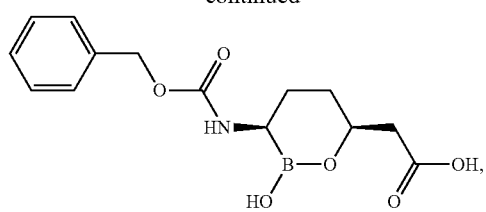
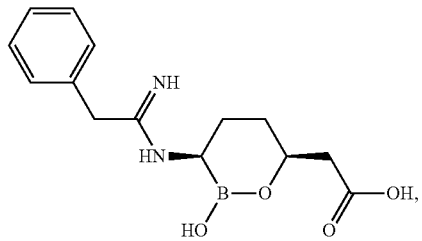
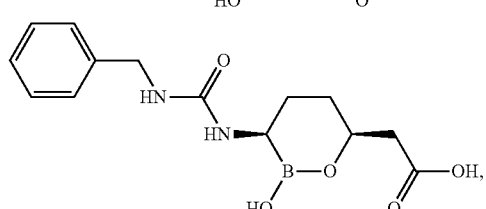
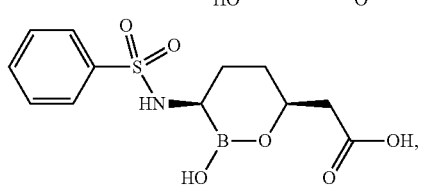
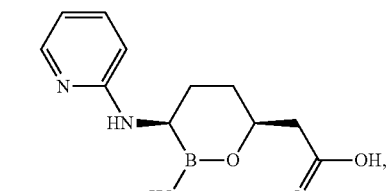
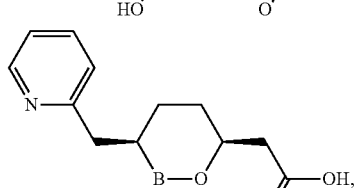
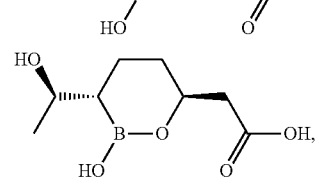
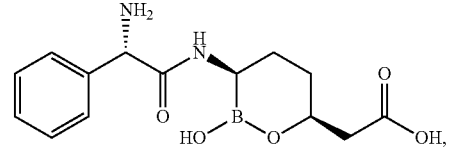
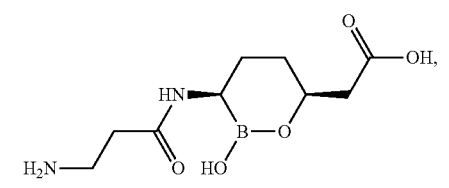
156
-continued
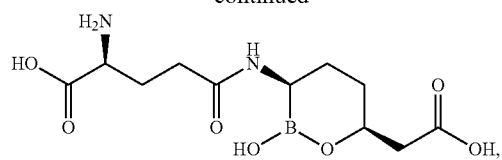
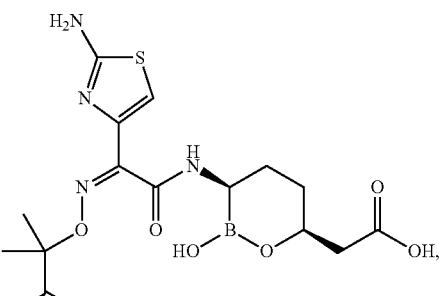
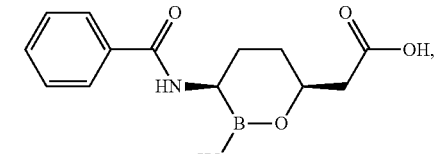
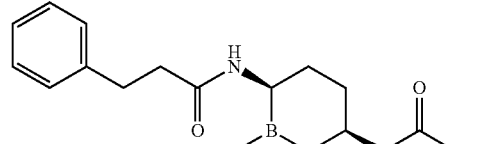
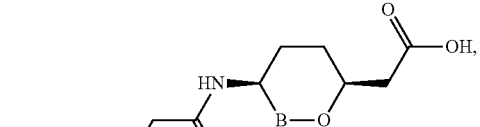
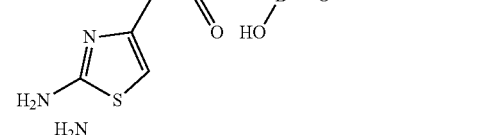
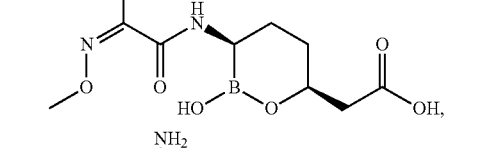
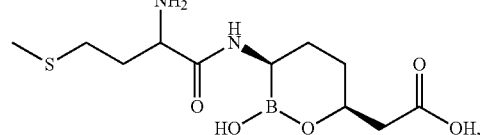
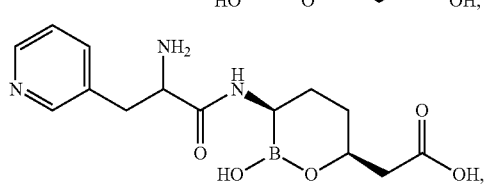

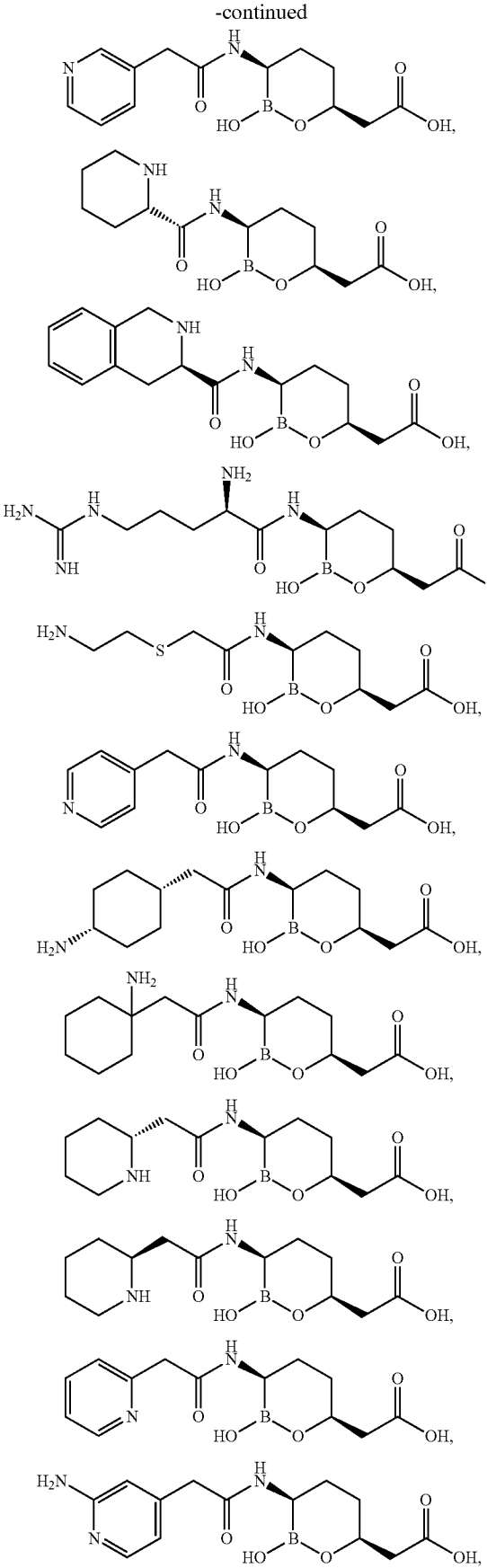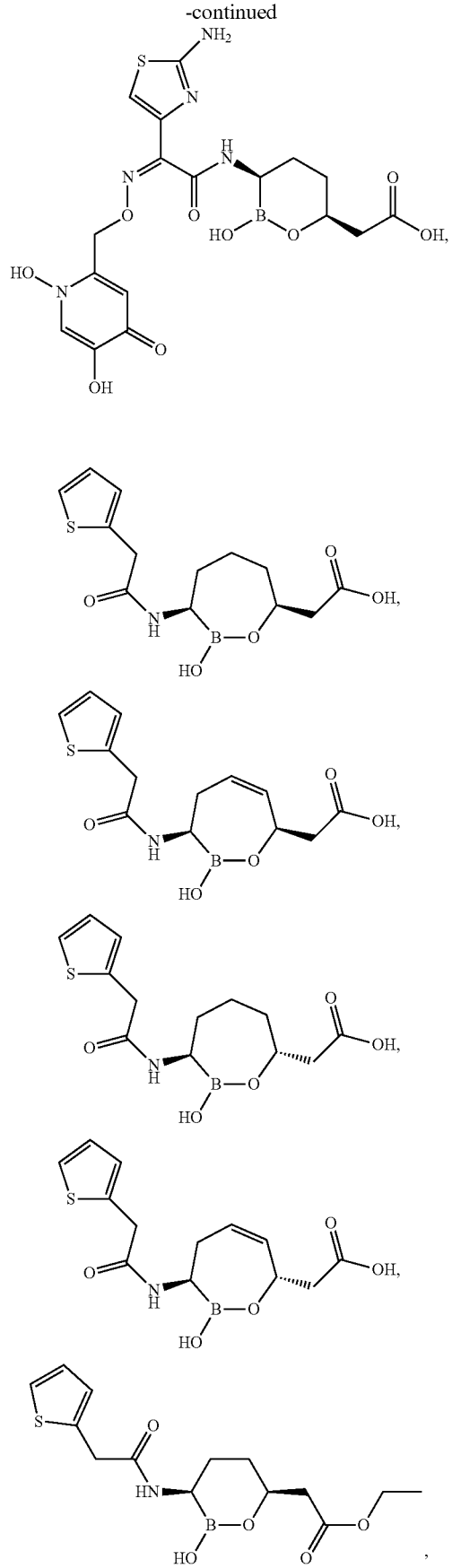

159
-continued
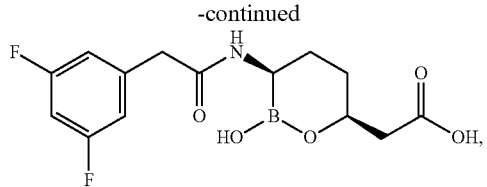
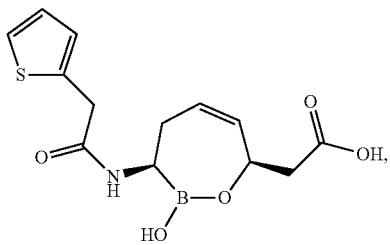
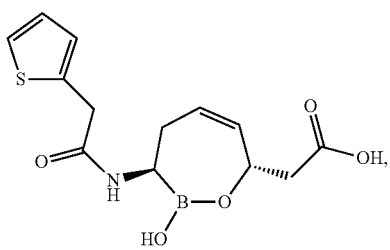
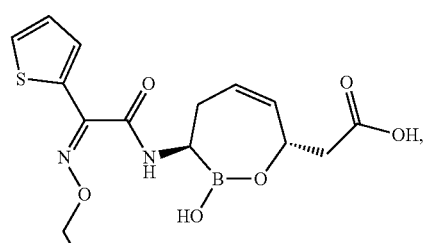
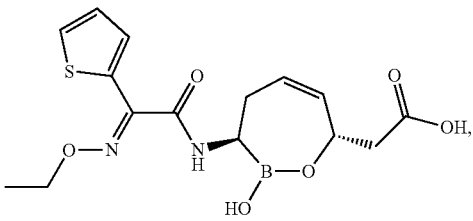
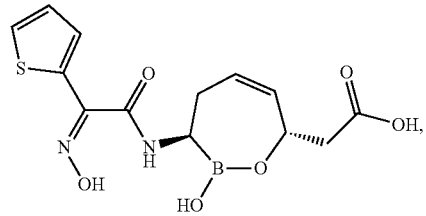
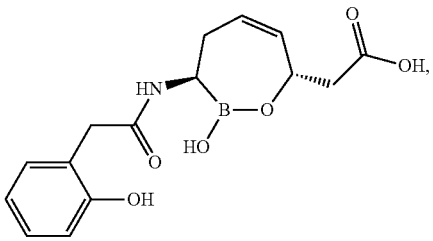
160
-continued
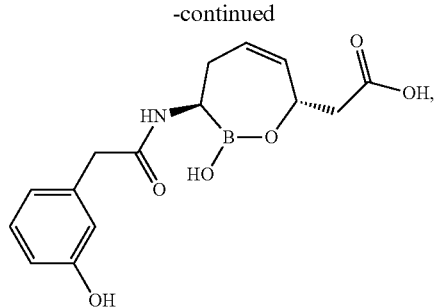
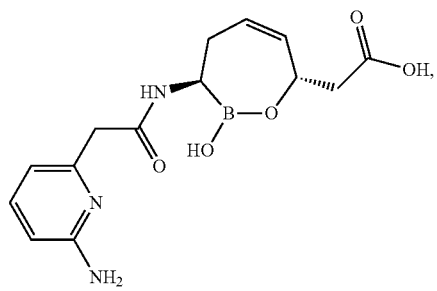
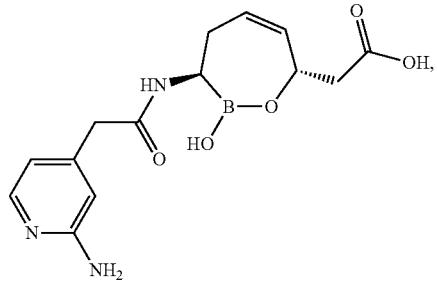
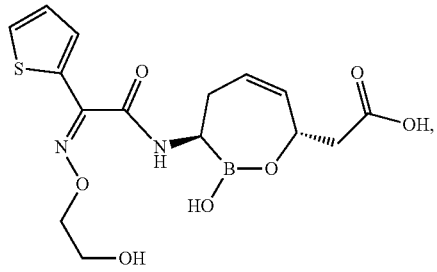
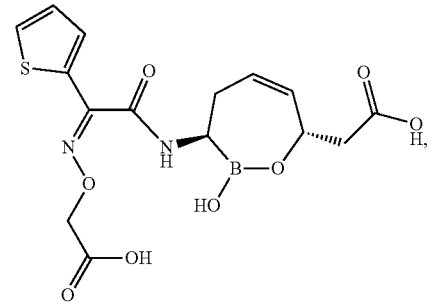
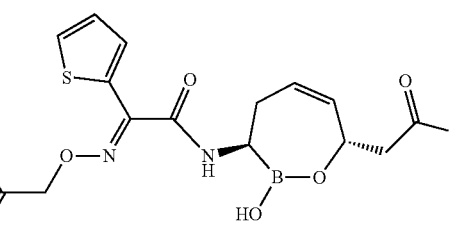

161
-continued
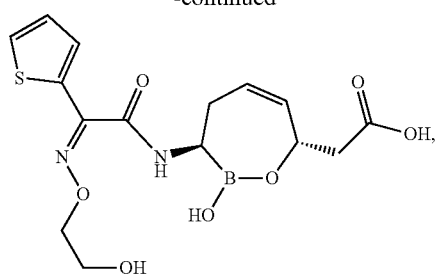
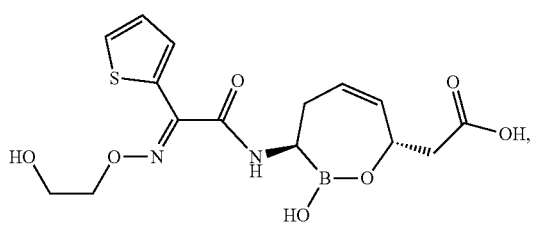
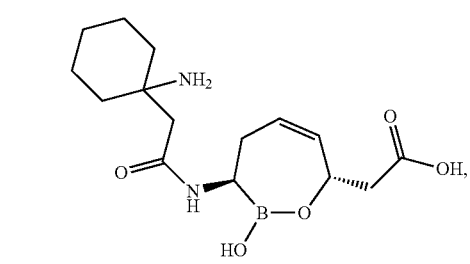
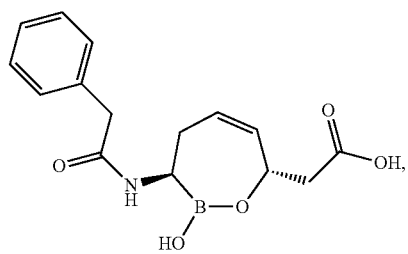
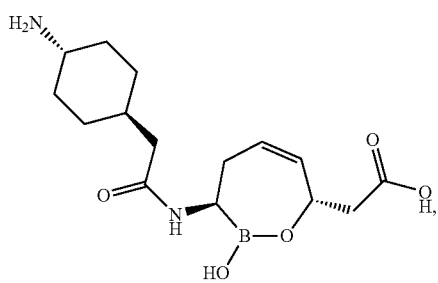
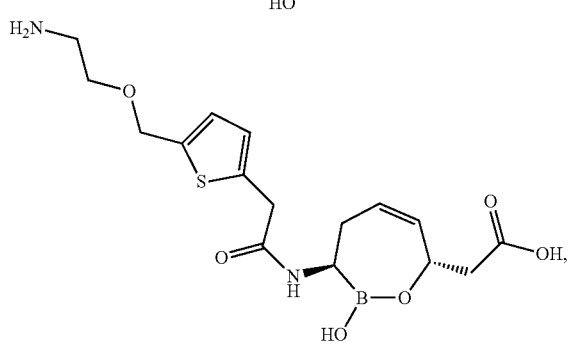
162
-continued
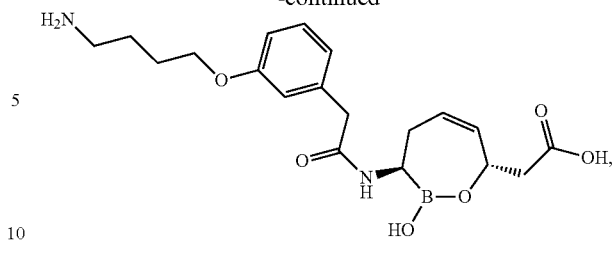
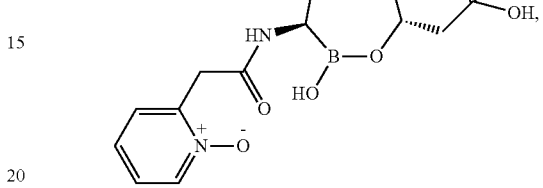
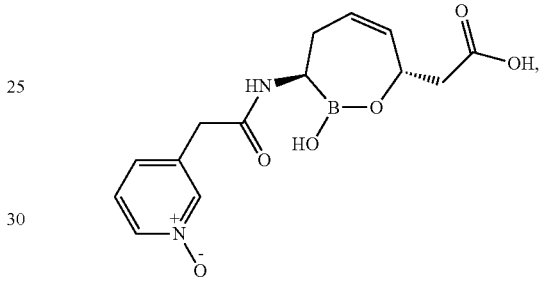
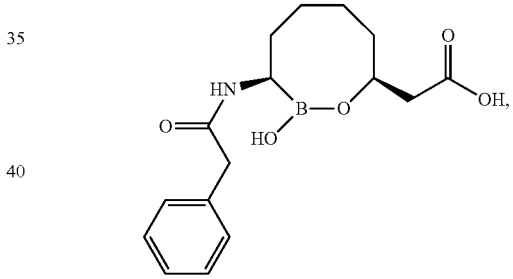
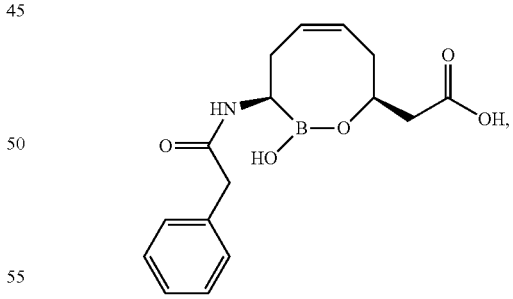
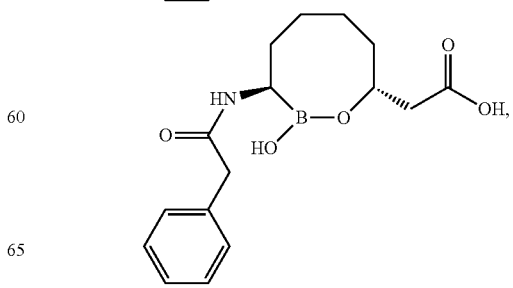

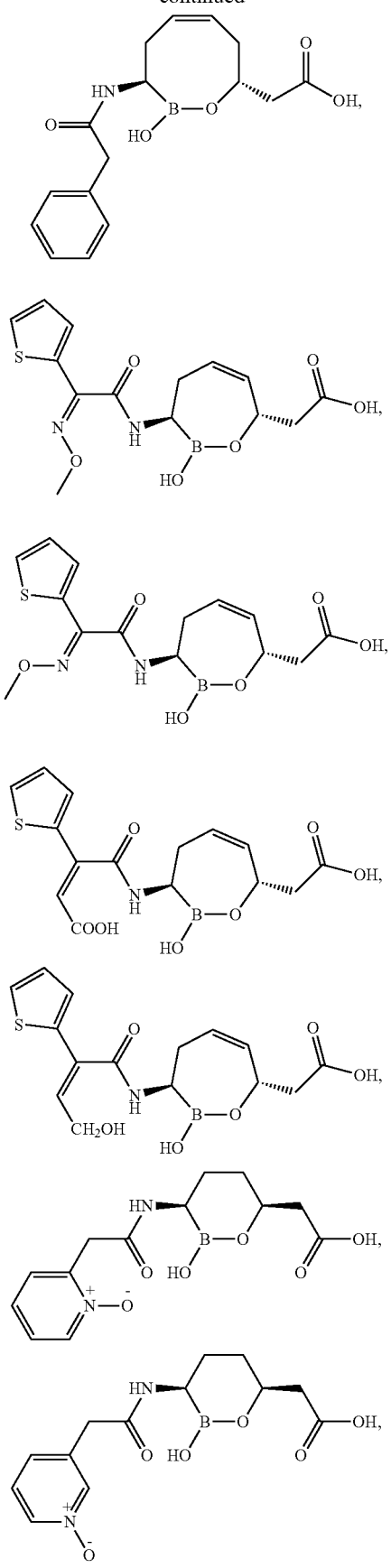
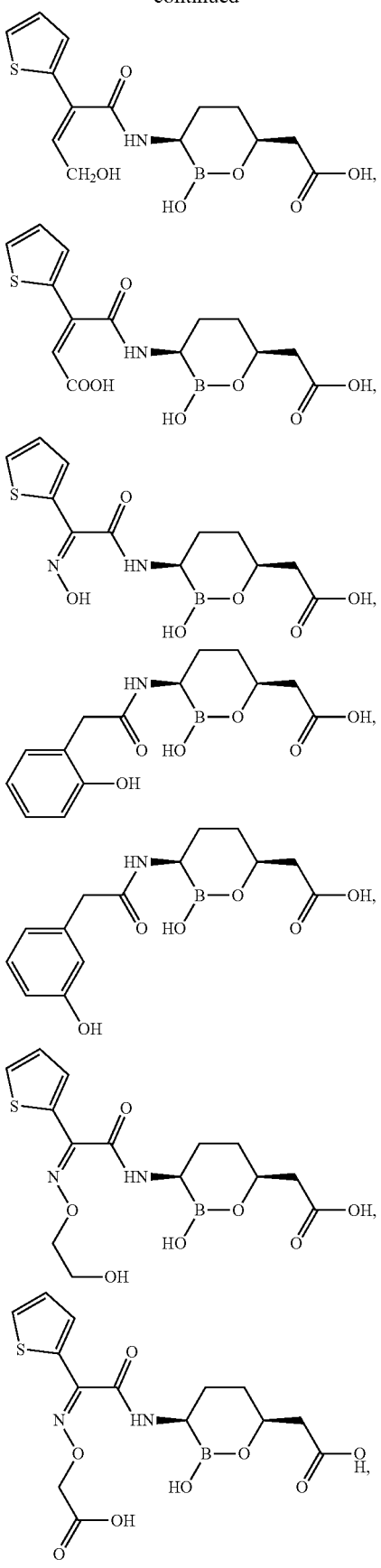

165
-continued
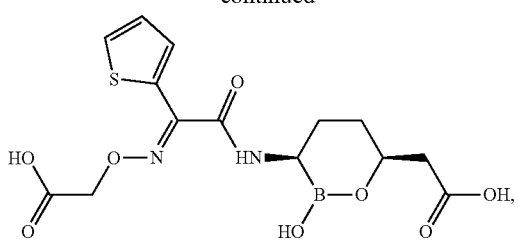
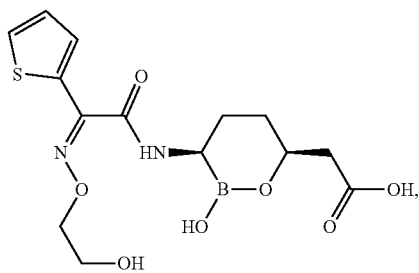
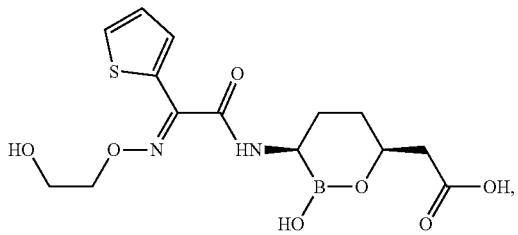
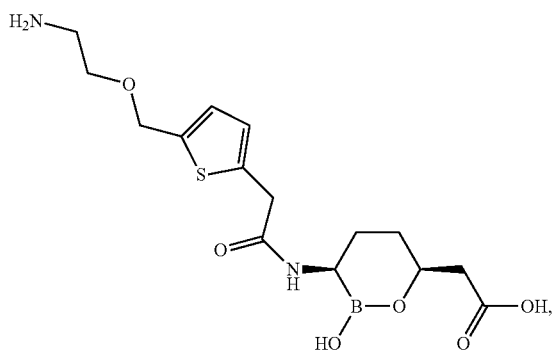
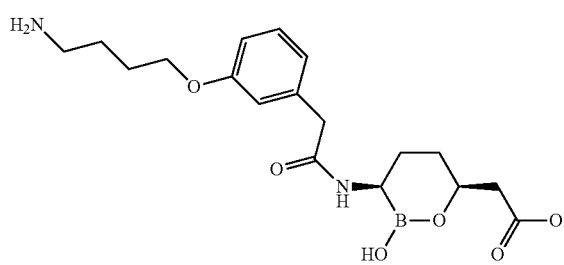
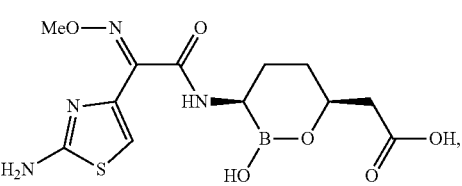
166
-continued
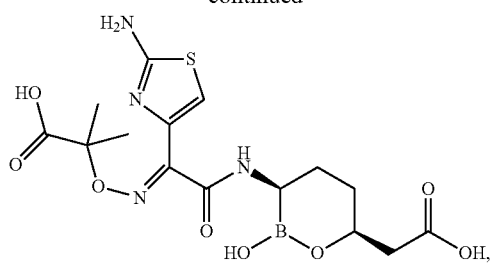
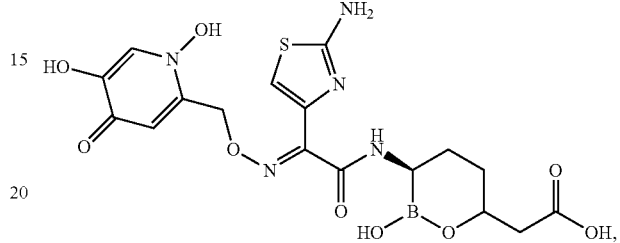
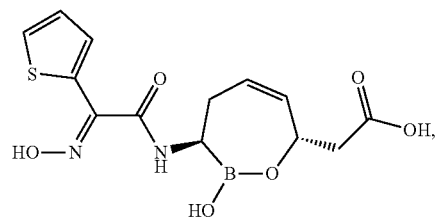
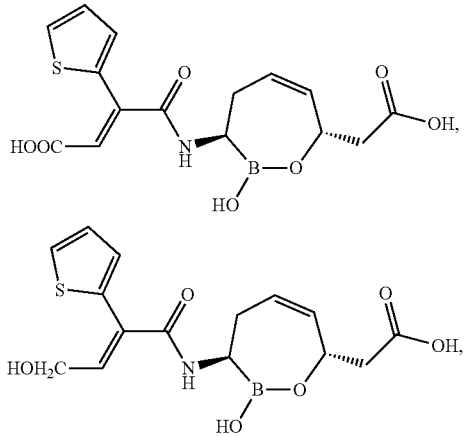
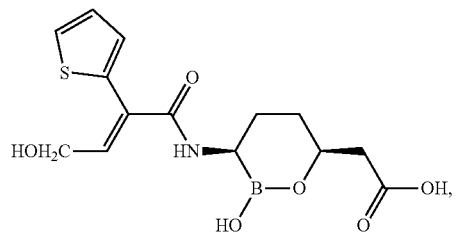
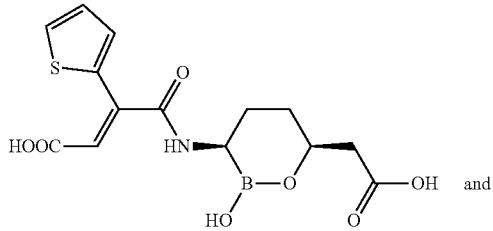
and -continued

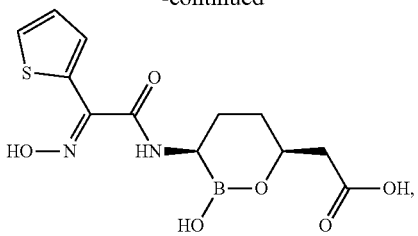

or a pharmaceutically acceptable salt thereof.

13. The pharmaceutical composition of claim 1, wherein the compound is:

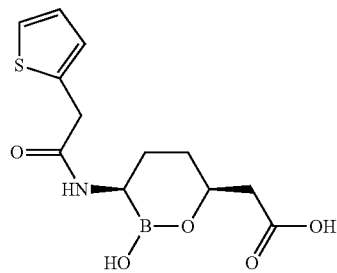 [SMILES: O=C(O)C[C@@H]1CC[C@H](NC(=O)Cc2cccs2)B(O)O1]

or a pharmaceutically acceptable salt thereof.

14. The pharmaceutical composition of claim 1, wherein the additional medicament is a β-lactam antibacterial agent.

15. The pharmaceutical composition of claim 14, wherein the β-lactam antibacterial agent is a carbapenem selected from the group consisting of simipenem, biapenem, doripenem, meropenem, and ertapenem.

16. The pharmaceutical composition of claim 15, wherein the carbapenem is meropenem.

17. The pharmaceutical composition of claim 14, wherein the β-lactam antibacterial agent is selected from the group consisting of Amoxicillin, Ampicillin, Pivampicillin, Hetacillin, Bacampicillin, Metampicillin, Talampicillin, Epicillin, Carbenicillin, Carindacillin, Ticarcillin, Temocillin, Azlocillin, Piperacillin, Mezlocillin, Mecillinam, Pivmecillinam, Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin, Dicloxacillin, Flucloxacillin, Oxacillin, Meticillin, Nafcillin, Faropenem, Biapenem, Doripenem, Ertapenem, Imipenem, Meropenem, Panipenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, RWJ-333441, ME1036, BAL30072, BAL19764, Ceftiofur, Cefquinome, Cefovecin, Aztreonam, Tigemonam, Carumonam, RWJ-442831, RWJ-333441, and RWJ-333442.

18. The pharmaceutical composition of claim 1, in a solid form.

19. The pharmaceutical composition of claim 1, further comprising sodium carbonate.

20. The pharmaceutical composition of claim 1, further comprising saline.

21. A pharmaceutical composition in a solid form comprising a compound and meropenem, the compound having the structure:

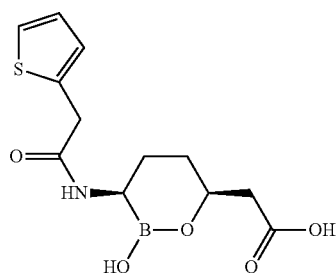 [SMILES: O=C(O)C[C@@H]1CC[C@H](NC(=O)Cc2cccs2)B(O)O1]

or a pharmaceutically acceptable salt thereof.

22. The pharmaceutical composition of claim 21, further comprising sodium carbonate.

23. A pharmaceutical composition comprising a compound, meropenem, sodium carbonate and saline, the compound having the structure:

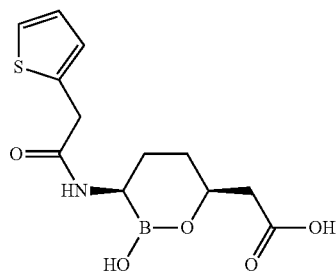 [SMILES: O=C(O)C[C@@H]1CC[C@H](NC(=O)Cc2cccs2)B(O)O1]

or a pharmaceutically acceptable salt thereof.

24. A pharmaceutical composition comprising a compound and meropenem, the compound having the structure:

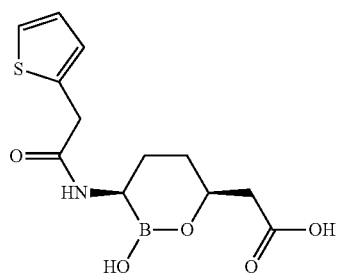 [SMILES: O=C(O)C[C@@H]1CC[C@H](NC(=O)Cc2cccs2)B(O)O1]

or a pharmaceutically acceptable salt thereof.

* * * * *